United States Patent
Hatakeyama et al.

(10) Patent No.: US 10,265,693 B2
(45) Date of Patent: Apr. 23, 2019

(54) PARTICLES, PARTICLE DISPERSION, PARTICLE-DISPERSED RESIN COMPOSITION, PRODUCING METHOD THEREFOR, RESIN MOLDED ARTICLE, PRODUCING METHOD THEREFOR, CATALYST PARTICLES, CATALYST SOLUTION, CATALYST COMPOSITION, CATALYST MOLDED ARTICLE, TITANIUM COMPLEX, TITANIUM OXIDE PARTICLES AND PRODUCING METHOD THEREFOR

(71) Applicant: NITTO DENKO CORPORATION, Ibaraki-shi, Osaka (JP)

(72) Inventors: Yoshiharu Hatakeyama, Osaka (JP); Takahiro Fukuoka, Osaka (JP); Junichi Nagase, Osaka (JP); Shusaku Shibata, Osaka (JP); Tatsuki Nagatsuka, Osaka (JP); Saori Yamamoto, Osaka (JP)

(73) Assignee: NITTO DENKO CORPORATION, Ibaraki-shi, Osaka (JP)

( * ) Notice: Subject to any disclaimer, the term of this patent is extended or adjusted under 35 U.S.C. 154(b) by 0 days.

(21) Appl. No.: 15/466,279

(22) Filed: Mar. 22, 2017

(65) Prior Publication Data
US 2017/0189895 A1 Jul. 6, 2017

Related U.S. Application Data

(62) Division of application No. 13/640,911, filed as application No. PCT/JP2011/059040 on Apr. 11, 2011.

(30) Foreign Application Priority Data

Apr. 12, 2010 (JP) ................................. 2010-091577
Jul. 30, 2010 (JP) ................................. 2010-172309

(Continued)

(51) Int. Cl.
C01F 11/18 (2006.01)
B01J 31/38 (2006.01)
(Continued)

(52) U.S. Cl.
CPC ............... B01J 31/38 (2013.01); B01J 31/06 (2013.01); B01J 31/2208 (2013.01);
(Continued)

(58) Field of Classification Search
CPC ...... C08K 9/04; C01F 5/24; C01F 1/18–1/188
See application file for complete search history.

(56) References Cited

U.S. PATENT DOCUMENTS 4,192,792 A 3/1980 Sugerman et al.
4,874,806 A 10/1989 Kay et al.
(Continued)

FOREIGN PATENT DOCUMENTS

CN 1389527 A 1/2003
CN 1455933 A 11/2003
(Continued)

OTHER PUBLICATIONS

Shokoohi, S.; Arefazar, A. "Coupling Agents: Basics and Classifications". Wiley Encyclopedia of Composites, Second Edition. Edited by Luigi Nicolais and Assunta Borzacchiello. 2012 John Wiley & Sons, Inc. Published 2012 by John Wiley & Sons, Inc. (Year : 2012).*

(Continued)

Primary Examiner — Michael M Dollinger
Assistant Examiner — Christina H Wales
(74) Attorney, Agent, or Firm — Sughrue Mion, PLLC

(57) ABSTRACT

Organic-inorganic composite particles that can be dispersed in a solvent and/or a resin as primary particles having an organic group on the surface of inorganic particles, the organic-inorganic composite particles having negative birefringence.

10 Claims, 18 Drawing Sheets

FE-SEM micrograph of Example 1-1

(30) Foreign Application Priority Data

| | | | |
|---|---|---|---|
| Jul. 30, 2010 | (JP) | ................................ | 2010-172310 |
| Apr. 8, 2011 | (JP) | ................................ | 2011-086371 |
| Apr. 8, 2011 | (JP) | ................................ | 2011-086701 |
| Apr. 8, 2011 | (JP) | ................................ | 2011-086803 |

(51) Int. Cl.

| | |
|---|---|
| *C07F 3/00* | (2006.01) |
| *C07F 5/00* | (2006.01) |
| *C07F 7/28* | (2006.01) |
| *C07F 19/00* | (2006.01) |
| *B01J 31/22* | (2006.01) |
| *B01J 31/28* | (2006.01) |
| *C08K 9/04* | (2006.01) |
| *B01J 31/06* | (2006.01) |
| *B01J 31/26* | (2006.01) |

(52) U.S. Cl.
CPC ........... *B01J 31/2221* (2013.01); *B01J 31/26* (2013.01); *B01J 31/28* (2013.01); *C07F 3/00* (2013.01); *C07F 3/003* (2013.01); *C07F 5/00* (2013.01); *C07F 5/003* (2013.01); *C07F 7/28* (2013.01); *C07F 19/00* (2013.01); *C08K 9/04* (2013.01); *B01J 2231/005* (2013.01); *B01J 2531/46* (2013.01); *B01J 2531/66* (2013.01); *C01F 11/183* (2013.01)

(56) References Cited

U.S. PATENT DOCUMENTS

| | | | |
|---|---|---|---|
| 5,022,990 | A | 6/1991 | Doi et al. |
| 5,712,045 | A | 1/1998 | Miyai |
| 5,746,916 | A | 5/1998 | Kamo et al. |
| 5,969,087 | A | 10/1999 | Maeda |
| 6,479,029 | B1* | 11/2002 | Mingels ................ C01F 11/181 423/165 |
| 6,761,879 | B1 | 7/2004 | Finidori |
| 6,986,943 | B1 | 1/2006 | Cook et al. |
| 7,169,832 | B2 | 1/2007 | Poppe et al. |
| 8,541,591 | B2 | 9/2013 | Kato et al. |
| 2001/0046944 | A1 | 11/2001 | Ito |
| 2002/0069790 | A1 | 6/2002 | Hayashi et al. |
| 2003/0056693 | A1 | 3/2003 | Hayashi et al. |
| 2003/0116758 | A1 | 6/2003 | Morii et al. |
| 2003/0151032 | A1 | 8/2003 | Ito et al. |
| 2004/0101626 | A1 | 5/2004 | Kanada et al. |
| 2004/0191549 | A1 | 9/2004 | Ahn et al. |
| 2006/0020099 | A1 | 1/2006 | Stengel et al. |
| 2007/0003463 | A1 | 1/2007 | Ajiri |
| 2007/0030417 | A1* | 2/2007 | Kubo ..................... B29C 41/28 349/96 |
| 2007/0072815 | A1 | 4/2007 | Yoon et al. |
| 2008/0085441 | A1 | 4/2008 | Lee et al. |
| 2008/0152933 | A1 | 6/2008 | Mizuno et al. |
| 2008/0160374 | A1 | 7/2008 | Takagi et al. |
| 2008/0213646 | A1 | 9/2008 | Takekawa et al. |
| 2008/0247937 | A1* | 10/2008 | Kawano ................ C01F 11/186 423/432 |
| 2008/0260614 | A1* | 10/2008 | Tetsuo .................. C01F 11/183 423/430 |
| 2008/0292527 | A1* | 11/2008 | Kawano ................ B82Y 30/00 423/430 |
| 2009/0124744 | A1* | 5/2009 | Ishizaka ................ B82Y 30/00 524/424 |
| 2009/0208806 | A1 | 8/2009 | Izuhara et al. |
| 2009/0220840 | A1 | 9/2009 | Yamaguchi et al. |
| 2010/0092663 | A1 | 4/2010 | Ajiri |
| 2010/0304110 | A1 | 12/2010 | Iida et al. |
| 2011/0144061 | A1 | 6/2011 | Kato et al. |

FOREIGN PATENT DOCUMENTS

| | | |
|---|---|---|
| CN | 1543433 A | 11/2004 |
| EP | 1 975 136 | 10/2008 |
| JP | 63-278944 A | 11/1988 |
| JP | 64-003002 A | 1/1989 |
| JP | 64-40490 A | 2/1989 |
| JP | 3-215535 A | 9/1991 |
| JP | 5-31341 A | 2/1993 |
| JP | 7-232044 A | 9/1995 |
| JP | 9-67405 A | 3/1997 |
| JP | 10-330482 A | 12/1998 |
| JP | 2000-185916 A | 7/2000 |
| JP | 2000-351787 A | 12/2000 |
| JP | 2002-331244 A | 11/2002 |
| JP | 2003-26850 A | 1/2003 |
| JP | 2003-513011 A | 4/2003 |
| JP | 2003-261329 A | 9/2003 |
| JP | 2003-292497 A | 10/2003 |
| JP | 2004-018477 A | 1/2004 |
| JP | 2004-035347 A | 2/2004 |
| JP | 2005-82756 A | 3/2005 |
| JP | 2005-170757 | 6/2005 |
| JP | 2005-193237 | 7/2005 |
| JP | 2005-194148 A | 7/2005 |
| JP | 2006-21988 A | 1/2006 |
| JP | 2006-506416 A | 2/2006 |
| JP | 2006-131881 A | 5/2006 |
| JP | 2006-297209 A | 11/2006 |
| JP | 2007-099611 | 4/2007 |
| JP | 2007-125821 A | 5/2007 |
| JP | 2007-206061 A | 8/2007 |
| JP | 2008-44835 A | 2/2008 |
| JP | 2008-091342 | 4/2008 |
| JP | 2008-156390 A | 7/2008 |
| JP | 2008-303299 | 12/2008 |
| JP | 2009-067949 | 4/2009 |
| JP | 2009-073699 | 4/2009 |
| JP | 2009-73994 A | 4/2009 |
| JP | 2009-080440 | 4/2009 |
| JP | 2009-149713 A | 7/2009 |
| JP | 2009-167315 A | 7/2009 |
| JP | 2009-191167 A | 8/2009 |
| JP | 2009-268943 A | 11/2009 |
| JP | 2009-298945 A | 12/2009 |
| JP | 2010-23017 A | 2/2010 |
| JP | 2010-051952 | 3/2010 |
| JP | 2011-515569 A | 5/2011 |
| WO | 2007/083786 | 7/2007 |
| WO | 2008-010533 A1 | 1/2008 |
| WO | 2009/119899 A1 | 10/2009 |
| WO | 2009/120846 A2 | 10/2009 |
| WO | 2009-127000 A1 | 10/2009 |
| WO | 2010/013822 A1 | 2/2010 |

OTHER PUBLICATIONS

Feng, S.H.; Li, G.H. "Hydrothermal ans Solvothermal Synthesis" Modern Inorganic Synthetic Chemistry. 2017. pp. 73-104 (Year: 2017).*

Tagaya, A.; Ohkita, H.; Mukoh, M.; Sakaguchi, R.; Koike, Y. "Compensation of the Birefringence of a polymer by a birefringent crystal". Science vol. 301, 2003. pp. 812-814. (Year: 2003).*

Third Office Action dated Jun. 13, 2017, from the State Intellectual Property Office of the P.R.C., in Chinese application No. 201410542267.3, which corresponds to U.S. Appl. No. 15/097,400.

"Study on Preparation of Strontium Carbonate Particles and Controlling of Shapes by Homogeneous Precipitation Method", Haibin Wang et al., pp. 45-48.

Non-Final Office Action dated Feb. 10, 2017, which issued by thU.S. Appl. No. 13/640,434.

Cancelation of Pretrial Proceedings dated Dec. 1, 2015 from the Japanese Patent Office in counterpart application No. 2010-172309, which corresponds to U.S. Appl. No. 13/640,911.

Non-Final Office Action dated Apr. 1, 2016 from the U.S. Patent and Trademark Office in U.S. Appl. No. 13/640,434.

(56) References Cited

OTHER PUBLICATIONS

First Office Action dated Apr. 14, 2016 from the State Intellectual Property Office of the P.R.C in application No. 201410542267.3, which corresponds to U.S. Appl. No. 13/640,911.
Communication dated Apr. 6, 2015, issued by the United States Patent and Trademark Office in U.S. Appl. No. 13/640,434.
Non-Final Office Action dated Jan. 14, 2016 from the U.S. Patent and Trademark Office in U.S. Appl. No. 14/535,478.
Fourth Notification of Office Action dated Jun. 25, 2015, issued by the State Intellectual Property Office of the People's Republic of China in Application No. 201110092651.4, which corresponds to U.S. Appl. No. 13/084,843.
Decision of Refusal dated Mar. 10, 2015 from the Japanese Patent Office in counterpart application No. 2010-172309, which corresponds to U.S. Appl. No. 13/640,911.
Communication dated Mar. 5, 2014, issued by the State Intellectual Property Office of the People's Republic of China in corresponding Application No. 201180018234.3.
Second Office Action dated Nov. 21, 2016, from the State Intellectual Property Office of People's Republic of China in corresponding Application No. 201410542267.3.
Notification of Reasons for Refusal dated Oct. 13, 2015 from the Japanese Patent Office in application No. 2011-086371, which corresponds to 13/640,084,843 and U.S. Appl. No. 13/640,911.
Notification of Reasons for Refusal dated Oct. 7, 2014 from the Japanese Patent Office in counterpart Japanese Patent Application No. 2010-172309.
Final Office Action from the U.S. Patent and Trademark Office dated Sep. 19, 2016 U.S. Appl. No. 13/640,434.
Non-Final Office Action from United States Patent and Trademark Office dated Sep. 6, 2016 in U.S. Appl. No. 13/640,911.
Final Office Action dated Feb. 18, 2016 from the U.S. Patent and Trademark Office in U.S. Appl. No. 13/640,911.
K. Tomita et al., "A Water-Soluble Titanium Complex for the Selective Synthesis of Nanocrystalline Brookite, Rutile, and Anatase by a Hydrothermal Method", Angewandte Chemie International Edition, Apr. 3, 2006, vol. 45, Issue 15, 2378-2381.
Notification Notifying a Submission of Publications dated Jan. 27, 2015 from the Japanese Patent Office in application No. 2010-172309, which corresponds to U.S. Appl. No. 13/640,911.
Notification of Reasons for Refusal dated Feb. 3, 2015, issued by the Japanese Patent Office in Japanese application No. 2011-086371, which corresponds to U.S. Appl. No. 13/640,911.
Pretrial Report dated Nov. 20, 2015 from the Japanese Patent Office in counterpart application No. 2010-172309.
Request form for inspection for a Submission of Publications dated May 14, 2015 to the Japanese Patent Office in application No. 2010-172309, which corresponds to U.S. Appl. No. 13/640,911.
Submission of Publications dated Dec. 24, 2014 to the Japanese Patent Office in application No. 2010-172309, which corresponds to U.S. Appl. No. 13/640,911.
The Complete Book of Dispersion Techniques (Publisher) Akitoshi Taniguchi (Publishing office) Johokiko Co., Ltd. (Issue date) Jul. 15, 2005, Corresponding sections (Chapter 2, Section 1 and 5).
U.S. Final Office Action issued in U.S. Appl. No. 13/084,843, dated Oct. 10, 2013.
Zhao et al., "Surface modification of TiO2 by Phosphate: Effect on Photocatalytic Activity and Mechanism Implication", J. Phys. Chem. C 2008, 112, 5993-6001.
Decision of Rejection dated Dec. 1, 2015 from the State Intellectual Property Office of P.R. China in application No. 201110092651.4, which corresponds to U.S. Appl. No. 13/084,843.
Pretrial Report dated Dec. 1, 2015 from the Japanese Patent Office in application No. 2010-172309, which corresponds to U.S. Appl. No. 13/640,911.
Final Office Action dated Dec. 14, 2015 from the U.S. Patent and Trademark Office in U.S. Appl. No. 13/084,843.
Notification of Reasons for Refusal dated Nov. 10, 2015, from the Japanese patent Office in application No. 2014-23685, which corresponds to U.S. Appl. No. 13/084,843.
Notification of Reasons for Refusal dated Aug. 25, 2015 from the Japanese Patent Office in counterpart application No. 201-086803, which corresponds to U.S. Appl. No. 13/640,911.
Final Office Action from US Patent and Trademark Office Action dated Jul. 15, 2015 in U.S. Appl. No. 13/084,843.
Final Office Action from US Patent and Trademark Office dated Jul. 16, 2016 in U.S. Appl. No. 13/640,434.
Non-Final Office Action from US Patent and Trademark Office dated Jun. 30, 2015 in U.S. Appl. No. 13/640,911.
Third Office Action dated May 11, 2015 from the State Intellectual Property Office of People's Republic of China in Application No. 201180018234.3, which corresponds to U.S. Appl. No. 13/640,434.
Notification of Reasons for Refusal dated Feb. 10, 2015, from the Japanese Patent Office in application No. 2012-510649, which corresponds to U.S. Appl. No. 13/640,434.
Notification of Reasons for Refusal dated Feb. 10, 2015, issued by the Japanese Patent Office in Japanese application No. 2011-086803, which corresponds to U.S. Appl. No. 13/640,911.
Second Office Action dated Feb. 13, 2015, issued by the State Intellectual Property Office of P.R. China in Chinese application No. 201180017265.7, which corresponds to U.S. Appl. No. 13/640,911.
Non-Final Office Action dated Dec. 22 2014, issued by the U.S Patent and Trademark Office in U.S. Appl. No. 13/084,843.
Notification of the Third Office Action dated Jan. 4, 2015, issued by the State Intellectual Property Office of the People's Republic of China in Chinese Application No. 201110092651.4, which corresponds to U.S. Appl. No. 13/084,843.
Notification of Reasons for Refusal dated Nov. 18, 2014 from the Japanese Patent Office in counterpart Japanese Patent Application No. 2011086701, which corresponds to U.S. Appl. No. 13/640,911.
Decision of Refusal dated Aug. 26, 2014, issued by the Japan Patent Office in Japanese Application No. 2010-172306, which corresponds to U.S. Appl. No. 13/084,943.
Final Office Action dated Jan. 12, 2015 from the United States Patent Office in U.S. Appl. No. 13/640,911.
Communication dated Nov. 4, 2014 from the State Intellectual Property Office of People's Republic of China in counterpart Chinese Patent Application No. 201180018234.3, which corresponds to U.S. Appl. No. 13/640,434.
Akihiro Tagaya et al., "Compensation of the Birefringence of a Polymer by a Birefringent Crystal", Science, Aug. 8, 2003, pp. 812-814, vol. 301.
International Search Report for PCT/JP2011/059040 dated Jul. 19, 2011.
U.S. Non-Final Office Action issued in U.S. Appl. No. 13/084,843, dated Apr. 12, 2013.
Notification of Reasons for Refusal issued in JP Application No. 2010-172306, dated Nov. 5, 2013.
Communication dated Dec. 18, 2013, issued by the State Intellectual Property Office of the People's Republic of China in Application No. 201110092651.4, which corresponds to U.S. Appl. No. 13/084,843.
Notification of Reasons for Refusal, dated Feb. 12, 2014, issued by the Japanese Patent Office, in counterpart Application No. 2010-172309.
Communication dated Mar. 5, 2014, issued by the State Intellectual Property Office of the People's Republic of China in Application No. 201180018234.3, which corresponds to U.S. Appl. No. 13/640,434.
U.S. Final Office Action dated Jun. 12, 2014, issued in corresponding U.S. Appl. No. 13/640,434.
Notification of Reasons for Refusal dated May 27, 2014, issued by the Japanese Patent Office in Application No. 2010-172310, which corresponds to U.S. Appl. No. 13/084,843.
First Office Action dated May 28, 2014, issued by the State Intellectual Property Office of the People's Republic of China in Application No. 201180017265.7, which corresponds to U.S. Appl. No. 13/640,911.
Communication dated Jun. 19, 2014, from the State Intellectual Property Office of the People's Republic of China in Chinese Application No. 201110092651.4, which corresponds to U.S. Appl. No. 13/084,843.
Decision of Refusal dated Aug. 26, 2014, issued by the Japan Patent Office in Japanese Application No. 2010-172306, which corresponds to U.S. Appl. No. 13/084,843.

(56) References Cited

OTHER PUBLICATIONS

U.S. Non-Final Office Action issued in U.S. Appl. No. 13/640,434, dated Dec. 5, 2013.
Imai, Y. et al., "Synthesis and characterization of high refractive index nanoparticle/poly (arylene ether ketone) nanocomposites", Polymer Journal 42, pp. 179-184, Published online Dec. 23, 2009.
Ohio State. "From Moles to Milliequivalents". http://www/vet.chio-state.edu/assets/courses/vm613/part7/party.html. Mar. 2015. p. 1-2.
Non-Final Office Action dated Jan. 22, 2018, issued by the USPTO in U.S. Appl. No. 15/097,400.
Final Office Action dated Aug. 10, 2018, issued by the USPTO in U.S. Appl. No. 15/097,400.

* cited by examiner

FE-SEM micrograph of Example 1-1

FE-SEM micrograph of Comparative Example 1-2

TEM micrograph of Example 1-17

FE-SEM micrograph of Example 1-29

FE-SEM micrograph of Comparative Example 1-3

FE-SEM micrograph of Example 1-47

TEM micrograph of Example 1-55

TEM micrograph of Comparative Example 1-4

FE-SEM micrograph of Example 1-56

Particle size distribution of particles in particle dispersion obtained in Preparation Example 1-1

FE-SEM micrograph of cross section of resin molded article in which particles obtained in Example 1-36 are dispersed FE-SEM micrograph of cross section of resin molded article in which particles obtained in Comparative Example 1-2 are dispersed FE-SEM micrograph of cross section of optical film in which particles obtained in Example 1-36 are dispersed FE-SEM micrograph of cross section of optical film in which particles obtained in Comparative Example 1-2 are dispersed TEM micrograph of Preparation Example 2-1

FIG.16 TEM micrograph of Example 2-1
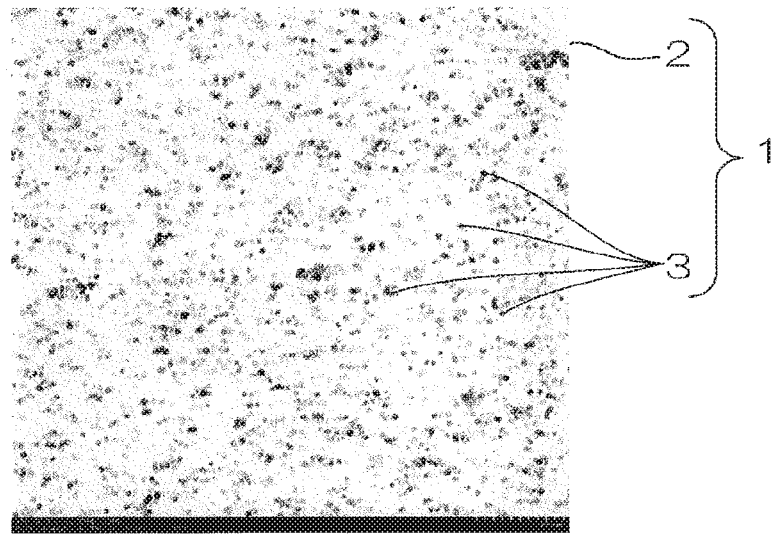
FIG.17 TEM micrograph of Example 2-2
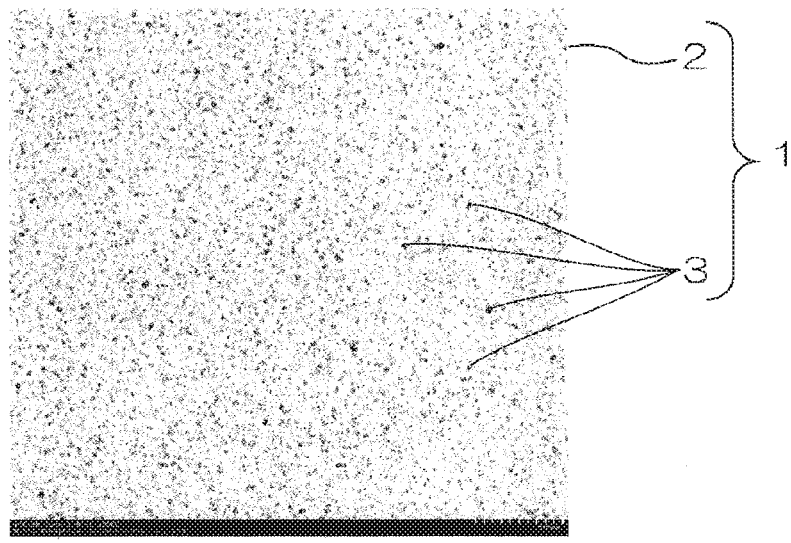

FIG.18  TEM micrograph of Example 2-3
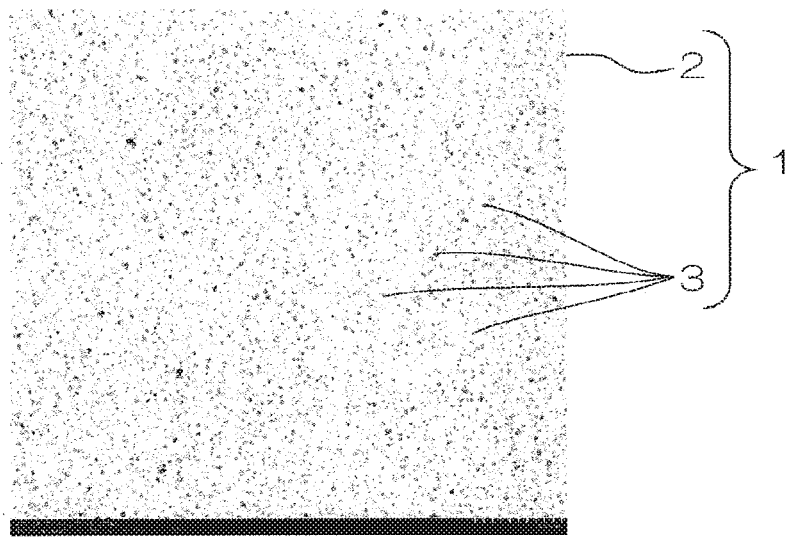
FIG.19  TEM micrograph of Example 2-4
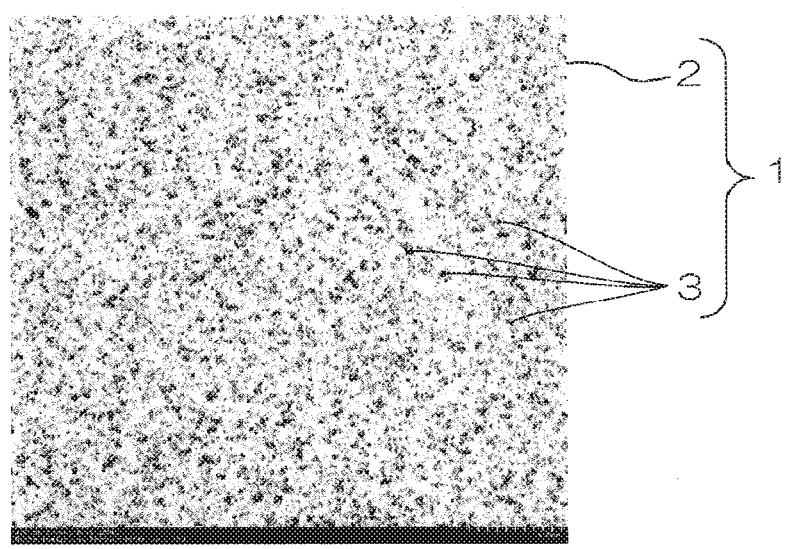

FIG.20  TEM micrograph of Example 2-7
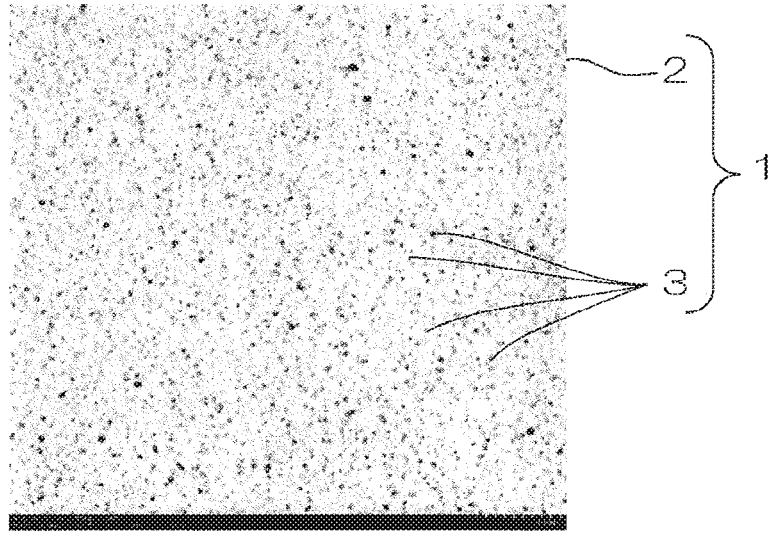
FIG.21  TEM micrograph of Example 2-8
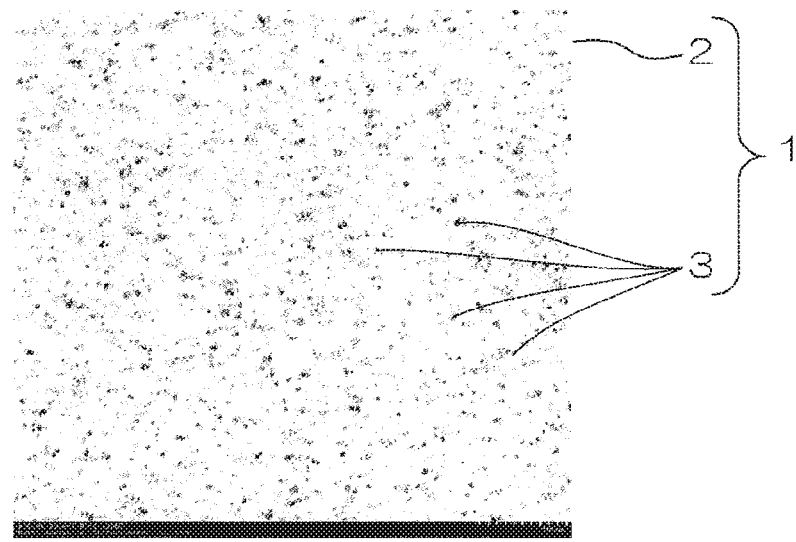

FIG.22  TEM micrograph of Example 2-11
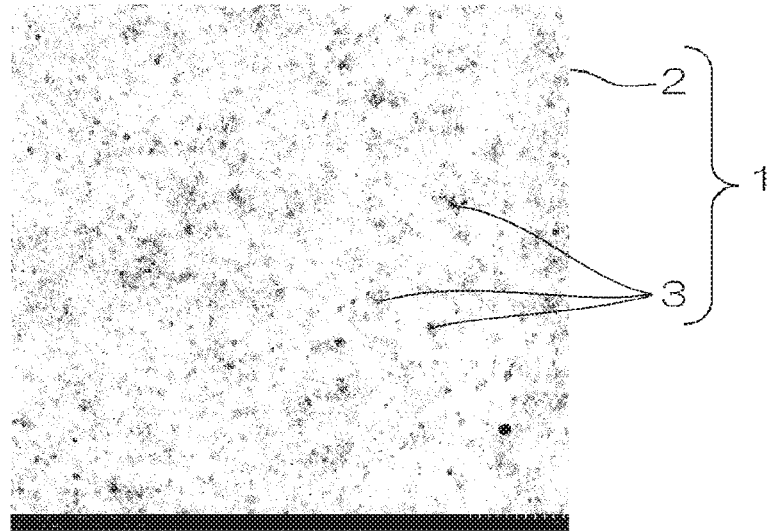
FIG.23  TEM micrograph of Example 2-13
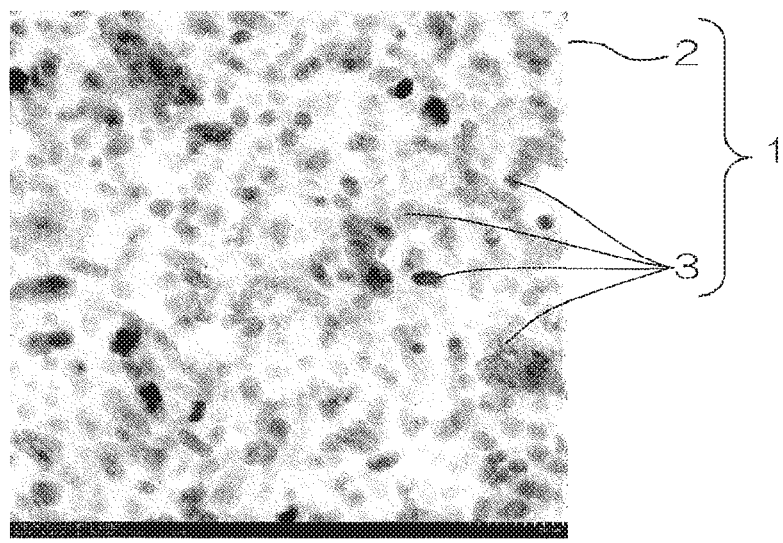

FIG.24  TEM micrograph of Example 2-14
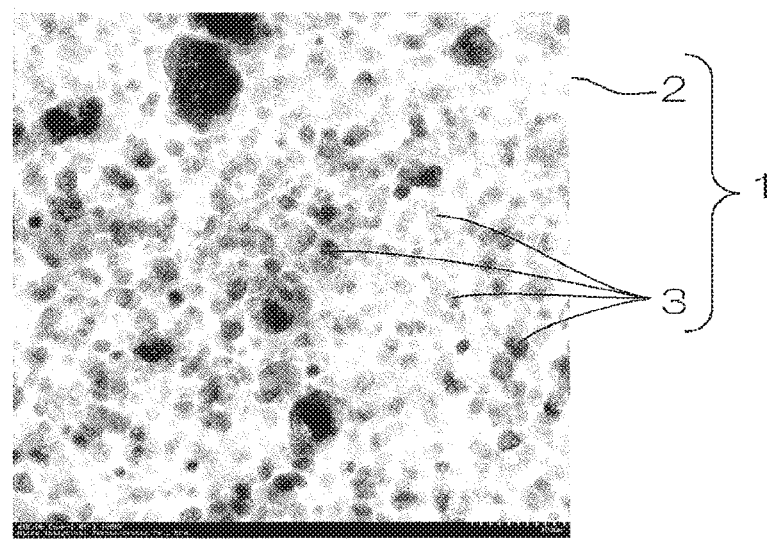

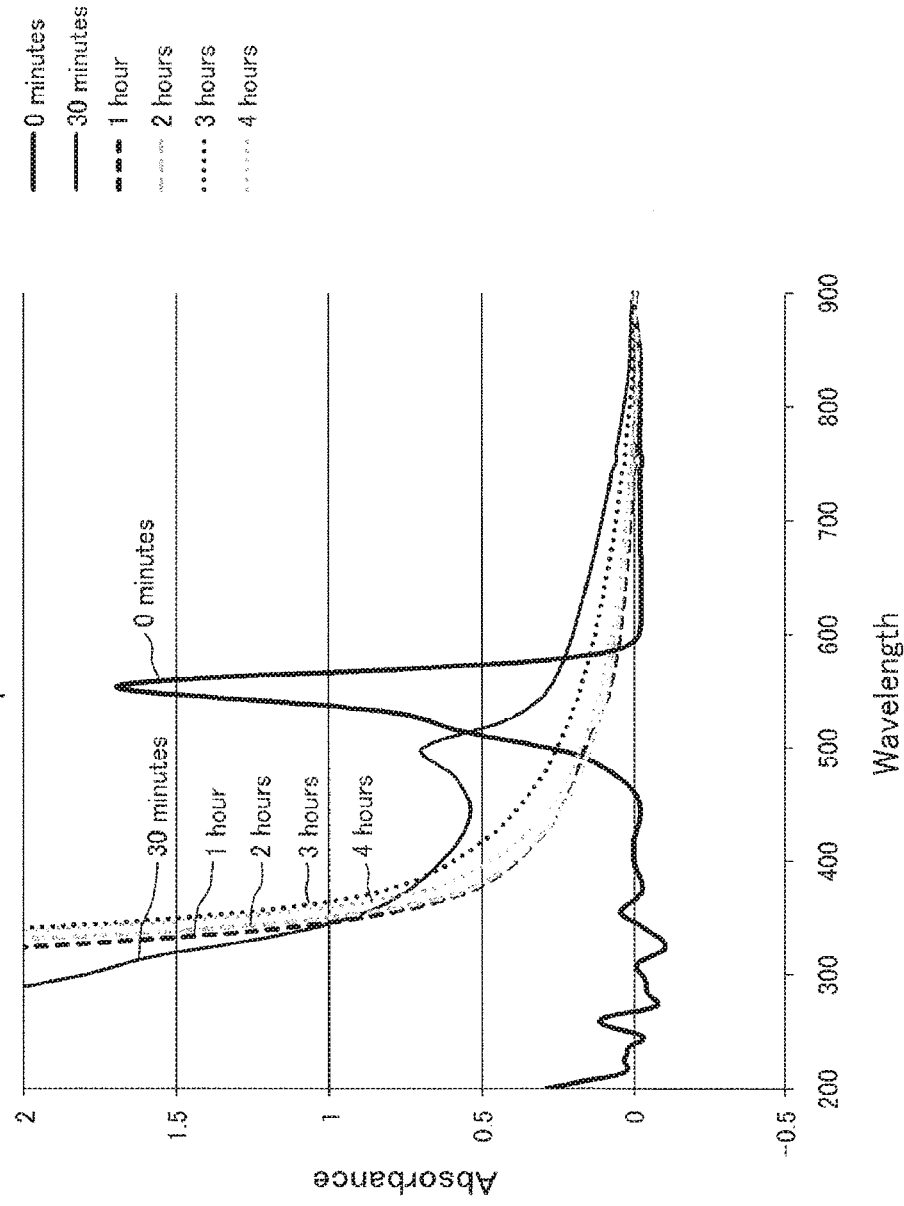

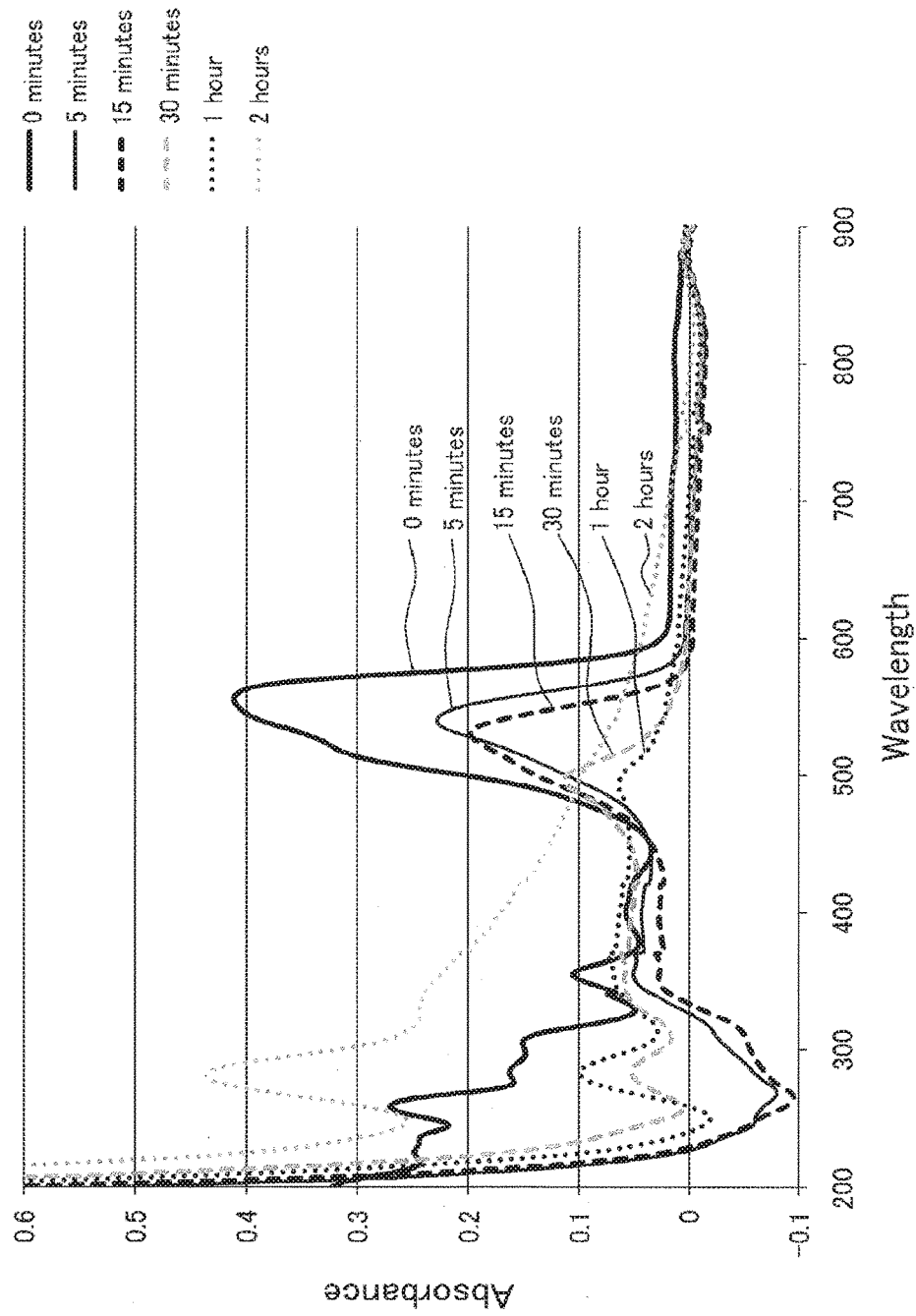

FIG.27    TEM micrograph of Example 4-6
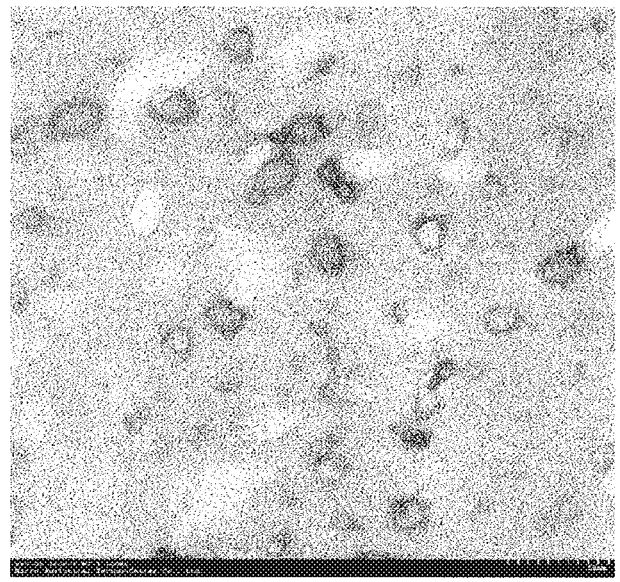
FIG.28    TEM micrograph of Example 4-7

FIG.29  TEM micrograph of Example 4-13

PARTICLES, PARTICLE DISPERSION, PARTICLE-DISPERSED RESIN COMPOSITION, PRODUCING METHOD THEREFOR, RESIN MOLDED ARTICLE, PRODUCING METHOD THEREFOR, CATALYST PARTICLES, CATALYST SOLUTION, CATALYST COMPOSITION, CATALYST MOLDED ARTICLE, TITANIUM COMPLEX, TITANIUM OXIDE PARTICLES AND PRODUCING METHOD THEREFOR

This is a divisional of U.S. application Ser. No. 13/640,911 filed Dec. 31, 2012, which is a national stage of PCT/JP2011/059040 filed Apr. 11, 2011, which claims priority from Japanese Patent Application Nos. 2010-091577, filed on Apr. 12, 2010; 2010-172310, filed on Jul. 30, 2010; 2010-172309 filed on Jul. 30, 2010; 2011-086371 filed Apr. 8, 2011; 2011-086701 filed Apr. 8, 2011; and 2011-086803 filed Apr. 8, 2011, the contents of all of which are hereby incorporated by reference into this application.

TECHNICAL FIELD

The present invention relates to particles, a particle dispersion, a particle-dispersed resin composition and a resin molded article, and more particularly to a particle dispersion, a particle-dispersed resin composition and a resin molded article that are for use in various applications including optical applications, and particles that can be dispersed therein.

The present invention also relates to a particle-dispersed resin composition, a particle-dispersed resin molded article, and producing methods therefor.

The present invention also relates to catalyst particles, a catalyst solution, a catalyst composition and a catalyst molded article, and more particularly to catalyst particles, a catalyst solution, a catalyst composition and a catalyst molded article that have a catalytic action.

The present invention also relates to a resin molded article and a producing method therefor.

The present invention also relates to a titanium complex, titanium oxide particles and a producing method therefor, and more particularly to a titanium oxide particle producing method, a titanium complex that can be used in the producing method, and titanium oxide particles prepared by the producing method.

BACKGROUND ART

It is conventionally known that nanometer-sized particles (nanoparticles) are used in optical materials.

For example, a method has been proposed in which organomodified fine particles are obtained by subjecting fine particles of a metal oxide such as $SiO_2$ or $TiO_2$ and an organic modifier to a hydrothermal synthesis (see, for example, Patent Document 1 listed below).

Also, it is long known that oxides such as titanium oxide exert a photocatalytic action.

For example, it is known that oxides such as titanium oxide, strontium titanate and tungsten oxide decompose organic substances by their photocatalytic action (see, for example, Non-Patent Document 1 listed below).

It is also long known that porous resin obtained by porosifying resin exhibits various physical properties due to porosification, in addition to the physical properties inherent to resin.

For example, a method has been proposed in which porous polyimide resin is obtained by blending polyethylene glycol dimethyl ether with a polyimide resin precursor so as to prepare a mixed resin solution, forming a coating and then bringing the coating into contact with hot high pressure carbon dioxide so as to extract polyethylene glycol dimethyl ether (see, for example, Patent Document 2 listed below).

The porous polyimide resin disclosed in Patent Document 2 has uniformly formed pores (cells), and the dielectric constant of the porous polyimide resin is set lower than that of non-porous polyimide resin.

It is also long known that titanium oxide particles for use in various industrial products are prepared in organic solvents or the like. Meanwhile, from a view point of reducing the environmental load in recent years, various methods are being studied to prepare titanium oxide particles in water, which imposes little load to the environment as compared to organic solvents or the like.

To produce such titanium oxide, for example, a titanium oxide particle producing method has been proposed in which titanium oxide particles are prepared by treating a titanium complex containing glycolic acid as a ligand in hot high pressure water (see, for example, Non-Patent Document 2 listed below).

CITATION LIST

Patent Documents

Patent Document 1: Japanese Unexamined Patent Publication No. 2005-194148
Patent Document 2: Japanese Unexamined Patent Publication No. 2003-26850

Non-Patent Documents

Non-Patent Document 1: Journal of Surface Science Society of Japan, vol. 24, No. 1, pp. 13 to 18, 2003
Non-Patent Document 2: Koji Tomita et al., "A Water-Soluble Titanium Complex for the Selective Synthesis of Nanocrystalline Brookite, Rutile, and Anatase by a Hydrothermal Method", Angewandte Chemie Int. Ed., 2006, vol. 45, pp. 2378 to 2381

DISCLOSURE OF THE INVENTION

Problems to be Solved

Particles for use in the above-described applications are required to have various characteristics, in addition to excellent optical characteristics.

Also, depending on the combination of organomodified fine particles and resin, a problem may arise in that the organomodified particles coagulate.

Also, depending on the application and purpose of catalysts, there are cases where after preparation of a catalyst resin composition by blending the oxide proposed in Non-Patent Document 1 mentioned above with a resin, a molded article is formed of the catalyst resin composition.

The molded article, however, is problematic in that it is easily degraded by the catalytic action of the oxide because the resin is in contact with the oxide in the molded article.

Also, there is another problem in that the oxide easily coagulates in the resin during preparation of the resin composition, resulting in poor clarity.

Meanwhile, in recent years, there is demand for porous resin having small-sized pores (cells). To address this demand, for example, attempts are made in which inorganic fine particles having a small particle size are blended with resin, and thereafter the inorganic fine particles are extracted.

However, blending inorganic fine particles with resin results in coagulation of the inorganic fine particles in the resin. Consequently, small-sized pores (cells) cannot be formed, and thus the porous resin will be opaque. Furthermore, the mechanical strength of the porous resin is insufficient and flexibility is poor, as a result of which a problem arises in that it is not possible to form a self-standing film.

Also, there is demand of wanting to design the arrangement of pores (cells) in porous resin.

Normally, titanium oxide particles are white, but the titanium oxide particles prepared by the titanium oxide particle producing method disclosed in Non-Patent Document 2 described above are colored (brown) due to a decomposition product of the ligand (decomposition product of glycolic acid) of the titanium complex that has been decomposed in hot high pressure water.

Also, in the case of preparing nano-sized titanium oxide particles, it is very difficult to separate the titanium oxide particles from the water-soluble ligand (glycolic acid) remaining from the production of the titanium complex.

For this reason, in the case of using such titanium oxide particles in optical applications, it is necessary to remove the color of the titanium oxide particles (the decomposition product of the ligand) and the residual ligand, which makes the titanium oxide particle producing process complex.

A first object of the present invention is to provide particles that have excellent optical characteristics and excellent dispersibility, a particle dispersion, a particle-dispersed resin composition and a resin molded article.

A second object of the present invention is to provide a particle-dispersed resin composition that contains organic-inorganic composite particles uniformly dispersed in a resin, a particle-dispersed resin molded article, and producing methods therefor.

A third object of the present invention is to provide catalyst particles that have excellent dispersibility in a solvent and/or a resin, a catalyst solution in which catalyst particles are dispersed in a solvent and that has excellent clarity, and a catalyst composition and a catalyst molded article in which degradation of the resin is suppressed and that have excellent clarity.

A fourth object of the present invention is to provide a resin molded article that has excellent clarity and excellent mechanical strength, and a producing method therefor.

A fifth object of the present invention is to provide a titanium oxide particle producing method with which the environmental load as well as coloring of titanium oxide particles can be reduced, a titanium complex that can be used in the producing method, and titanium oxide particles prepared by the producing method.

Means for Solving the Problem

A first group of inventions for achieving the first object is as follows.

Specifically, particles according to the present invention are organic-inorganic composite particles that can be dispersed in a solvent and/or a resin as primary particles having an organic group on the surface of inorganic particles, the organic-inorganic composite particles having negative birefringence.

Also, with the particles of the present invention, it is preferable that the inorganic particles are composed of a carbonate containing an alkaline earth metal and/or a composite oxide containing an alkaline earth metal.

Also, with the particles of the present invention, it is preferable that the primary particles are obtained by surface-treating the inorganic particles with an organic compound, and the organic compound contains a binding group capable of binding to the surface of the inorganic particles and a hydrophobic group and/or a hydrophilic group serving as the organic group.

Also, it is preferable that the particles of the present invention have an aspect ratio of 1000 or less.

Also, it is preferable that the particles of the present invention have a maximum length of 200 μm or less.

Also, it is preferable that the particles of the present invention are obtained by hydrothermal synthesis.

Also, with the particles of the present invention, it is preferable that an inorganic compound for forming inorganic particles and the organic compound are subjected to a hydrothermal synthesis.

Also, with the particles of the present invention, it is preferable that a metal hydroxide containing an alkaline earth metal, a carbonic acid source and the organic compound are subjected to a hydrothermal synthesis.

Also, with the particles of the present invention, it is preferable that the carbonic acid source is formic acid and/or urea.

Also, with the particles of the present invention, it is preferable that a metal hydroxide containing an alkaline earth metal, a metal complex and the organic compound are subjected to a hydrothermal synthesis.

Also, with the particles of the present invention, it is preferable that the hydrothermal synthesis is performed in the presence of a pH adjusting agent.

Also, it is preferable that the particles of the present invention are obtained by subjecting an inorganic compound for forming inorganic particles to a high temperature treatment in an organic compound containing the organic group.

Also, it is preferable that the particles of the present invention are subjected to wet classification using the solvent.

A particle dispersion according to the present invention contains a solvent and particles that are dispersed as primary particles in the solvent, and the particles are organic-inorganic composite particles having an organic group on the surface of inorganic particles and have negative birefringence.

A particle-dispersed resin composition according to the present invention contains a resin and particles that are dispersed as primary particles in the resin, and the particles are organic-inorganic composite particles having an organic group on the surface of inorganic particles and have negative birefringence.

A resin molded article according to the present invention is formed of a particle-dispersed resin composition containing a resin and particles that are dispersed as primary particles in the resin, and the particles are organic-inorganic composite particles having an organic group on the surface of inorganic particles and have negative birefringence.

Also, it is preferable that the resin molded article of the present invention is an optical film.

A second group of inventions for achieving the second object is as follows.

Specifically, a particle-dispersed resin composition according to the present invention contains a resin and organic-inorganic composite particles having an organic group on the surface of inorganic particles, and the organic-inorganic composite particles have at least a configuration that does not allow the inorganic particles to contact with each other by steric hindrance of the organic group and are dispersed as primary particles in the resin.

Also, with the particle-dispersed resin composition of the present invention, it is preferable that the resin has a functional group, and the organic group and the functional group both have a hydrophilic group or a hydrophobic group.

Also, with the particle-dispersed resin composition of the present invention, it is preferable that the resin contains a highly oriented resin.

Also, with the particle-dispersed resin composition of the present invention, it is preferable that the organic group contains a plurality of homologous organic groups.

Also, with the particle-dispersed resin composition of the present invention, it is preferable that the organic group contains a plurality of heterologous organic groups.

A particle-dispersed resin molded article according to the present invention is molded from a particle-dispersed resin composition containing a resin and organic-inorganic composite particles having an organic group on the surface of inorganic particles, and the organic-inorganic composite particles have at least a configuration that does not allow the inorganic particles to contact with each other by steric hindrance of the organic group and are dispersed as primary particles in the resin.

A method for producing a particle-dispersed resin composition according to the present invention includes blending a resin and organic-inorganic composite particles having an organic group on the surface of inorganic particles such that the organic-inorganic composite particles are dispersed as primary particles in the resin by steric hindrance of the organic group.

With the method for producing a particle-dispersed resin composition of the present invention, it is preferable that the organic-inorganic composite particles are produced in a hot solvent. It is also preferable that the organic-inorganic composite particles are produced in hot high pressure water.

A method for producing a particle-dispersed resin molded article according to the present invention includes producing a particle-dispersed resin molded article by molding a particle-dispersed resin composition obtained by blending a resin and organic-inorganic composite particles having an organic group on the surface of inorganic particles such that the organic-inorganic composite particles are dispersed as primary particles in the resin by steric hindrance of the organic group.

A third group of inventions for achieving the third object is as follows.

Specifically, catalyst particles according to the present invention contain inorganic particles with a catalytic action and an organic group that binds to the surface of the inorganic particles, and have a configuration that does not allow the inorganic particles to contact with each other by steric hindrance of the organic group.

It is preferable that the catalyst particles of the present invention have a catalytic action for a gas and/or a liquid.

Also, it is preferable that the catalyst particles of the present invention have a photocatalytic action for a gas and/or a liquid.

Also, it is preferable that the catalyst particles of the present invention are dispersed as primary particles in a solvent and/or a resin.

Also, it is preferable that the catalyst particles of the present invention contain a plurality of mutually different types of organic groups.

Also, with the catalyst particles of the present invention, it is preferable that the organic group is bound to the surface of the inorganic particles via a binding group, and the binding group contains a phosphoric acid group and/or a phosphoric acid ester group.

Also, with the catalyst particles of the present invention, it is preferable that the inorganic particles contain an oxide.

Also, with the catalyst particles of the present invention, it is preferable that the inorganic particles contain at least one oxide selected from the group consisting of $TiO_2$, $WO_3$ and $SrTiO_3$, and also contain at least one inorganic substance selected from the group consisting of Pt, Pd, Cu, CuO, $RuO_2$ and NiO.

Also, with the catalyst particles of the present invention, it is preferable that the catalyst particles have an average maximum length of 450 nm or less.

Also, it is preferable that the catalyst particles of the present invention are obtained by surface-treating an inorganic substance and/or a complex thereof with an organic compound containing the organic group. It is also preferable that the inorganic substance and/or the complex are surface-treated with the organic compound in hot high pressure water, or that the inorganic substance and/or the complex are surface-treated in the organic compound heated to a high temperature.

A catalyst solution according to the present invention contains a solvent and catalyst particles dispersed in the solvent, the catalyst particles contain inorganic particles with a catalytic action and an organic group that binds to the surface of the inorganic particles, and the catalyst particles have a configuration that does not allow the inorganic particles to contact with each other by steric hindrance of the organic group.

A catalyst composition according to the present invention contains a resin and catalyst particles dispersed in the resin, the catalyst particles contain inorganic particles with a catalytic action and an organic group that binds to the surface of the inorganic particles, and the catalyst particles have a configuration that does not allow the inorganic particles to contact with each other by steric hindrance of the organic group.

A catalyst molded article according to the present invention is formed of a catalyst composition containing a resin and catalyst particles dispersed in the resin, the catalyst particles contain inorganic particles with a catalytic action and an organic group that binds to the surface of the inorganic particles, and the catalyst particles have a configuration that does not allow the inorganic particles to contact with each other by steric hindrance of the organic group.

It is preferable that the catalyst molded article of the present invention is an optical film.

A fourth group of inventions for achieving the fourth object is as follows.

Specifically, a resin molded article according to the present invention has micropores formed by removing organic-inorganic composite particles from a particle-containing resin molded article containing a resin and the organic-inorganic composite particles that contain inorganic particles and an organic group that binds to the surface of the inorganic particles and have a configuration that does not allow the inorganic particles to contact with each other by steric hindrance of the organic group.

With the resin molded article of the present invention, it is preferable that the organic-inorganic composite particles have an average maximum length of 400 nm or less.

Also, with the resin molded article of the present invention, it is preferable that in the particle-containing resin molded article, the organic-inorganic composite particles are dispersed as primary particles in the resin, or that the particle-containing resin molded article has a phase separated structure formed of a resin phase composed of the resin and a particle phase that is composed of the organic-inorganic composite particles and phase-separated from the resin phase, and the phase separated structure is a bicontinuous phase separated structure in which the particle phase is three-dimensionally continuous.

Also, with the resin molded article of the present invention, it is preferable that the organic-inorganic composite particles partially remain, and the proportion of remaining organic-inorganic composite particles increases toward one side of the resin molded article.

Also, with the resin molded article of the present invention, it is preferable that the organic group contains a plurality of mutually different organic groups.

A method for producing a resin molded article according to the present invention includes the steps of: preparing organic-inorganic composite particles that contain inorganic particles and an organic group that binds to the surface of the inorganic particles and have a configuration that does not allow the inorganic particles to contact with each other by steric hindrance of the organic group; blending the organic-inorganic composite particles with a resin so as to prepare a particle-containing resin composition and forming a particle-containing resin molded article from the particle-containing resin composition; and forming micropores formed by removing the organic-inorganic composite particles from the particle-containing resin molded article.

With the method for producing a resin molded article of the present invention, it is preferable that the step of preparing organic-inorganic composite particles involves surface-treating an inorganic material with an organic compound in hot high pressure water, or that the step of preparing organic-inorganic composite particles involves surface-treating an inorganic material in a hot organic compound.

A fifth group of inventions for achieving the fifth object is as follows.

Specifically, a titanium complex according to the present invention contains a titanium atom as a central atom and a hydroxycarboxylic acid having a total of 7 or more carbon atoms as a ligand.

With the present invention, it is preferable that the hydroxycarboxylic acid is a hydroxyalkanoic acid having a total of 7 or more carbon atoms.

Also, with the present invention, it is preferable that the hydroxyalkanoic acid is linear.

Also, with the present invention, it is preferable that the hydroxycarboxylic acid is a hydroxymonocarboxylic acid.

Also, with the present invention, it is preferable that the hydroxycarboxylic acid is a monohydroxycarboxylic acid.

Also, with the present invention, it is preferable that the hydroxycarboxylic acid has a total of 13 or fewer carbon atoms.

Also, with the present invention, it is preferable that the hydroxycarboxylic acid is 2-hydroxycarboxylic acid and/or 3-hydroxycarboxylic acid.

Titanium oxide particles according to the present invention are obtained by treating a titanium complex containing a titanium atom as a central atom and a hydroxycarboxylic acid having a total of 7 or more carbon atoms as a ligand in hot high pressure water.

A method for producing titanium oxide particles according to the present invention includes treating a titanium complex containing a titanium atom as a central atom and a hydroxycarboxylic acid having a total of 7 or more carbon atoms as a ligand in hot high pressure water.

Effect of the Invention

The particles of the present invention can be dispersed as primary particles in a solvent and/or a resin, and therefore have excellent dispersibility in a solvent and/or a resin.

Accordingly, in the particle dispersion, particle-dispersed resin composition and resin molded article of the present invention, the particles are dispersed with good uniformity.

As a result, the resin molded article of the present invention can reliably have excellent optical characteristics.

The method for producing a particle-dispersed resin composition and the method for producing a particle-dispersed resin molded article of the present invention enable organic-inorganic composite particles to be dispersed in a resin with ease and uniformity by using a simple method in which the resin and the organic-inorganic composite particles are blended such that the organic-inorganic composite particles are dispersed as primary particles in the resin by steric hindrance of the organic group.

Accordingly, because the organic-inorganic composite particles are uniformly dispersed in the resin, the particle-dispersed resin composition and particle-dispersed resin molded article of the present invention have excellent clarity and are suitably used in various industrial applications including optical applications.

The catalyst particles of the present invention have a configuration that does not allow the inorganic particles to contact with each other by steric hindrance of the organic group, and therefore can be uniformly dispersed in a solvent and/or a resin.

Also, the catalyst solution of the present invention in which the catalyst particles of the present invention are dispersed in a solvent can enhance clarity because the catalyst particles are uniformly dispersed.

Furthermore, with the catalyst composition of the present invention in which the catalyst particles of the present invention are dispersed in a resin, as well as the catalyst molded article of the present invention formed of the catalyst composition, the inorganic particles cannot easily come into direct contact with the resin due to the configuration based on the steric hindrance of the organic group of the catalyst particles. Accordingly, the catalytic action for a gas or a liquid can be exerted while degradation of the resin of the catalyst composition and the catalyst molded article is suppressed.

As a result, the catalyst composition of the present invention and the catalyst molded article of the present invention can exert various catalytic actions such as a detoxification action, a deodorization action, a disinfectant (or in other words, antimicrobial or germicidal) action, a dirt repellent action and a decomposition action while having excellent durability.

Also, the catalyst composition of the present invention and the catalyst molded article of the present invention can enhance clarity because the catalyst particles are uniformly dispersed.

As a result, the catalyst molded article of the present invention can be used in various optical applications and various construction material applications.

The resin molded article of the present invention obtained by the method for producing a resin molded article of the present invention has excellent clarity and excellent mechanical strength.

Accordingly, the resin molded article of the present invention can be used in various industrial applications including optical applications as a resin molded article having excellent clarity and excellent reliability.

Also, the titanium complex of the present invention contains a hydroxycarboxylic acid having a total of 7 or more carbon atoms as a ligand. For this reason, even when titanium oxide particles are prepared in hot high pressure water, decomposition of the ligand is suppressed, and thus coloring of the titanium oxide particles can be reduced.

Therefore, according to the present invention, it is possible to reduce coloring of titanium oxide particles while reducing the environmental load.

BRIEF DESCRIPTION OF THE DRAWINGS

FIG. 16 shows an image-processed TEM micrograph of a cut surface of a film obtained in Example 2-1;

FIG. 17 shows an image-processed TEM micrograph of a cut surface of a film obtained in Example 2-2;

FIG. 18 shows an image-processed TEM micrograph of a cut surface of a film obtained in Example 2-3;

FIG. 19 shows an image-processed TEM micrograph of a cut surface of a film obtained in Example 2-4;

FIG. 20 shows an image-processed TEM micrograph of a cut surface of a film obtained in Example 2-7;

FIG. 21 shows an image-processed TEM micrograph of a cut surface of a film obtained in Example 2-8;

FIG. 22 shows an image-processed TEM micrograph of a cut surface of a film obtained in Example 2-11;

FIG. 23 shows an image-processed TEM micrograph of a cut surface of a film obtained in Example 2-13;

FIG. 24 shows an image-processed TEM micrograph of a cut surface of a film obtained in Example 2-14;

FIG. 25 shows UV-visible absorption spectra at the start of irradiation with light and 30 minutes, 1 hour, 2 hours, 3 hours and 4 hours after the irradiation, obtained in Example 3-10;

FIG. 26 shows UV-visible absorption spectra at the start of irradiation with light and 5 minutes, 10 minutes, 15 minutes, 30 minutes, 1 hour and 2 hours after the irradiation, obtained in Example 3-66;

FIG. 27 shows an image-processed TEM micrograph of a porous film obtained in Example 4-6;

FIG. 28 shows an image-processed TEM micrograph of a porous film obtained in Example 4-7; and FIG. 29 shows an image-processed TEM micrograph of a porous film obtained in Example 4-13.

EMBODIMENT OF THE INVENTION

Figure 1:
FIG. 1 shows an image-processed FE-SEM micrograph obtained in Example 1-1.

Hereinafter, first to fifth embodiments will be sequentially described that respectively correspond to the first to fifth groups of inventions that are included in the present invention and related to each other.

First Embodiment

Embodiment corresponding to the inventions of particles, a particle dispersion, a particle-dispersed resin composition and a resin molded article, which are included in the first group of inventions The particles of the present invention are organic-inorganic composite particles that can be dispersed in a solvent and/or a resin as primary particles having an organic group on the surface of inorganic particles, and have negative birefringence.

Specifically, the primary particles are obtained as organic-inorganic composite particles obtained by surface-treating inorganic particles with an organic compound.

That is, the inorganic compound (inorganic material) for forming inorganic particles has negative birefringence (minus birefringence) and can be, for example, a carbonate containing an alkaline earth metal and/or a composite oxide containing an alkaline earth metal.

Examples of the alkaline earth metal include beryllium (Be), magnesium (Mg), calcium (Ca), strontium (Sr), barium (B a), radium (Ra) and the like. Magnesium and strontium are preferable. The alkaline earth metals can be used singly or in a combination of two or more.

Specific examples of the carbonate containing an alkaline earth metal include beryllium carbonate, magnesium carbonate, calcium carbonate, strontium carbonate, barium carbonate, radium carbonate and the like. These carbonates can be used singly or in a combination of two or more.

Examples of the composite oxide containing an alkaline earth metal include alkaline earth metal salts of metal acids such as alkaline earth metal titanates, alkaline earth metal ferrates, alkaline earth metal stannates and alkaline earth metal zirconates. The composite oxides can be used singly or in a combination of two or more. Alkaline earth metal titanates are preferable.

Examples of alkaline earth metal titanates include beryllium titanate ($BeTiO_3$), magnesium titanate ($MgTiO_3$), calcium titanate ($CaTiO_3$), strontium titanate ($SrTiO_3$), barium titanate (BaTiO$_3$), radium titanate (RaTiO$_3$) and the like. The alkaline earth metal titanates can be used singly or in a combination of two or more.

The organic compound is, for example, a hydrophobic organic compound and/or a hydrophilic organic compound that imparts hydrophobicity and/or hydrophilicity to the surface of the inorganic particles. Specifically, the organic compound contains a binding group capable of binding to the surface of the inorganic particles and a hydrophobic group and/or a hydrophilic group.

The binding group is selected as appropriate according to the type of inorganic particles, and examples thereof include functional groups such as carboxyl group, phosphoric acid group (—PO(OH)$_2$, phosphono group), amino group and sulfo group.

One or more of these binding groups may be contained in the organic compound.

The hydrophobic group contained in the hydrophobic organic compound can be, for example, a hydrocarbon group having 4 to 20 carbon atoms, and examples thereof include alkyl group, alkenyl group, alkynyl group, cycloalkyl group, cycloalkenylalkylene group, aryl group, aralkyl group and the like.

Examples of the alkyl group include linear or branched alkyl groups having 4 to 20 carbon atoms such as butyl, isobutyl, sec-butyl, t-butyl, pentyl, isopentyl, neopentyl, hexyl, heptyl, octyl, 2-ethylhexyl, 3,3,5-trimethylhexyl, isooctyl, nonyl, isononyl, decyl, isodecyl, undecyl, dodecyl, tridecyl, tetradecyl, pentadecyl, hexadecyl, heptadecyl, octadecyl, nonadecyl and icosyl. A linear or branched alkyl group having 6 to 18 carbon atoms is preferable.

Examples of the alkenyl group include alkenyl groups having 4 to 20 carbon atoms such as hexenyl, octenyl, nonenyl, decenyl, undecenyl, dodecenyl, tetradecenyl, hexadecenyl, octadecenyl and icosenyl.

Examples of the alkynyl group include alkynyl groups having 4 to 20 carbon atoms such as hexynyl, heptynyl, octynyl, decynyl, undecynyl, dodecynyl, tridecynyl, tetradecynyl, pentadecynyl, hexadecynyl, heptadecynyl and octadecynyl.

Examples of the cycloalkyl group include cycloalkyl groups having 4 to 20 carbon atoms such as cyclohexyl, cycloheptyl, cyclooctyl, cyclononyl, cyclodecyl, cycloundecyl and cyclododecyl.

Examples of the cycloalkenylalkylene group include norbornene decyl (norboneryl decyl, bicyclo[2.2.1]hepta-2-enyl-decyl) and the like.

Examples of the aryl group include aryl groups having 6 to 20 carbon atoms such as phenyl, xylyl, naphthyl and biphenyl.

Examples of the aralkyl group include aralkyl groups having 7 to 20 carbon atoms such as benzyl, phenylethyl, phenylpropyl, diphenylmethyl, phenylbutyl, phenylpentyl, phenylhexyl and phenylheptyl.

The hydrophobic group is preferably an alkyl group, an alkenyl group, a cycloalkyl group, a cycloalkenylalkylene group or an aralkyl group.

Specific examples of the hydrophobic organic compound include alkyl group-containing compounds such as hexanoic acid, 3,3,5-trimethylhexanoic acid, decanoic acid, decylamine, lauric acid, decylphosphonic acid, trioctylphosphinoxide; alkenyl group-containing compounds such as 10-undecenoic acid, oleic acid; cycloalkyl group-containing compounds such as cyclohexanepentanoic acid (cyclohexylpentanoic acid), cyclopentanedecanoic acid; cycloalkenylalkylene group-containing compounds such as norbornene decanoic acid; aralkyl group-containing compounds such as 6-phenylhexanoic acid, and the like.

The hydrophilic group contained in the hydrophilic organic compound can be a hydroxyl group, a carbonyl groups or the like. One or more of the hydrophilic groups may be contained in the hydrophilic organic compound.

Specific examples of the hydrophilic organic compound include hydroxyl group-containing compounds (monohydroxycarboxylic acids or esters thereof) such as ethyl 6-hydroxyhexanoate, 4-hydroxyphenylacetic acid and 3-(4-hydroxyphenyl)propionic acid; carbonyl group-containing compounds (or in other words, monocarbonylcarboxylic acids) such as 4-oxovaleric acid; and the like.

The hydrophobic group and/or the hydrophilic group serve as the organic group that is present on the surface of the inorganic particles of the organic-inorganic composite particles.

The particles of the present invention can be obtained by subjecting the inorganic compound and the organic compound to a reaction treatment, preferably, a high temperature treatment.

Specifically, the particles of the present invention can be obtained by subjecting the inorganic compound and the organic compound to a high temperature treatment in water under high pressure (hydrothermal synthesis: hydrothermal reaction) or by subjecting the inorganic compound to a high temperature treatment in the organic compound (high temperature treatment in the organic compound). In short, the particles of the present invention can be obtained by surface-treating the surface of inorganic particles formed by the inorganic compound with the organic group.

In the hydrothermal synthesis, for example, the inorganic compound and the organic compound are reacted under high-temperature and high-pressure conditions in the presence of water (first hydrothermal synthesis).

Specifically, first, a reaction system is prepared under high-temperature and high-pressure conditions by placing the inorganic compound, the organic compound and water in a pressure-resistant airtight container and heating them.

The proportions of respective components per 100 parts by weight of the inorganic compound are as follows: the proportion of the organic compound is, for example, 5 to 160 parts by weight and preferably 10 to 110 parts by weight; and the proportion of water is, for example, 200 to 1000 parts by weight and preferably 400 to 700 parts by weight.

If the proportion of the organic compound is below the above range, the degree of progress of the surface modification reaction will be small, which may result in poor dispersibility in a solvent and/or a resin. If, on the other hand, the proportion of the organic compound exceeds the above range, the surface modification reaction will proceed sufficiently, but due to the excessive use of organic compound, the cost may increase.

If the proportion of water is below the above range, although the reaction will proceed, coarse particles (for example, with a maximum length of approximately 0.2 to 0.8 mm) which may be unsuitable for optical applications will be obtained.

If, on the other hand, the proportion of water exceeds the above range, the concentration of the inorganic compound will be excessively high, and the intended particles may not be produced.

The density of the organic compound is usually 0.8 to 1.1 g/mL, and thus the proportion of the organic compound in terms of volume is, for example, 10 to 150 mL and preferably 20 to 100 mL per 100 g of the inorganic compound.

Also, the number of moles of the organic compound can be, for example, 0.01 to 1000 mol and preferably 0.1 to 10 mol per mol of metal contained in the inorganic compound.

Also, the density of water is usually approximately 1 g/mL, and thus the proportion of water in terms of volume is, for example, 200 to 1000 mL and preferably 400 to 700 mL per 100 g of the inorganic compound.

If the proportions of the organic compound and water fall within the above ranges, the surface of inorganic particles can be reliably surface-treated.

Specific reaction conditions for the hydrothermal reaction are as follows. The heating temperature is, for example, 100 to 500° C. and preferably 200 to 400° C.

If the heating temperature is below the above range, the hydrothermal reaction will not proceed sufficiently, as a result of which the inorganic compound may remain. If, on the other hand, the heating temperature exceeds the above range, although the hydrothermal reaction will proceed, an excessive amount of heat will be generated, and thus the cost and the environmental load may increase.

The pressure is, for example, 10 to 50 MPa, and preferably 20 to 40 MPa.

If the pressure is below the above range, the hydrothermal reaction will not proceed sufficiently, as a result of which the inorganic compound may remain. If, on the other hand, the pressure falls within the above range, the hydrothermal reaction will proceed and the level of safety can be enhanced.

The reaction time is, for example, 1 to 200 minutes and preferably 3 to 150 minutes.

If the reaction time is below the above range, the hydrothermal reaction will not proceed sufficiently, as a result of which the inorganic compound may remain. If, on the other hand, the reaction time exceeds the above range, although the hydrothermal reaction will proceed, the particle growth will also proceed to give coarse particles which may be unsuitable for optical applications. Also, due to the long reaction time, the cost may increase.

After the hydrothermal reaction, the airtight container is cooled, and then, for example, a precipitate precipitated on the bottom wall of the airtight container or a deposit adhering to the inner wall of the airtight container is recovered.

The precipitate is obtained by, for example, sedimentation separation in which the reaction product is settled by gravity or a centrifugal field. Preferably, the precipitate is obtained as a precipitate of the reaction product by centrifugal sedimentation (centrifugal separation) in which the reaction product is settled by a centrifugal field.

The deposit is recovered by, for example, a scraper (spatula) or the like.

The reaction product can also be recovered (separated) by adding a solvent to wash away an unreacted organic compound (or in other words, dissolving the organic compound in the solvent) and thereafter removing the solvent.

As the solvent, for example, an alcohol such as methanol, ethanol, propanol or isopropanol or a ketone such as acetone or methyl ethyl ketone can be used, and an alcohol is preferably used.

The washed reaction product is separated from the solvent (supernatant liquid) by, for example, filtration, decantation or the like, and recovered.

In this manner, the particles are obtained.

The particles of the present invention can also be obtained by subjecting a metal hydroxide containing an alkaline earth metal, a carbonic acid source and an organic compound to a hydrothermal synthesis (second hydrothermal synthesis).

Examples of the alkaline earth metal contained in the metal hydroxide containing an alkaline earth metal include the same alkaline earth metals as those of the carbonates listed above.

Specific examples of the metal hydroxide include beryllium hydroxide, magnesium hydroxide, calcium hydroxide, strontium hydroxide, barium hydroxide, radium hydroxide and the like.

The carbonic acid source is, for example, formic acid and/or urea.

Examples of the organic compound include the same organic compounds as those used in the first hydrothermal synthesis described above.

In the second hydrothermal synthesis, the metal hydroxide, the carbonic acid source and the organic compound are reacted under high-temperature and high-pressure conditions in the presence of water.

The proportions of respective components per 100 parts by weight of the metal hydroxide are as follows: the proportion of the carbonic acid source is, for example, 5 to 140 parts by weight and preferably 10 to 70 parts by weight; the proportion of the organic compound is, for example, 4 to 550 parts by weight and preferably 15 to 330 parts by weight; and the proportion of water is, for example, 150 to 2500 parts by weight and preferably 300 to 500 parts by weight.

If the proportion of the carbonic acid source is below the above range, the concentration of the metal hydroxide will be excessively low, and the particles may not be obtained. If, on the other hand, the proportion of the carbonic acid source exceeds the above range, although the reaction will proceed, coarse particles which may be unsuitable for optical applications will be obtained.

If the proportion of the organic compound is below the above range, the surface modification reaction will not proceed sufficiently, which may result in poor dispersibility in a solvent and/or a resin. If, on the other hand, the proportion of the organic compound exceeds the above range, the surface modification reaction will proceed sufficiently, but due to the excessive use of organic compound, the cost may increase.

If the proportion of water is below the above range, although the reaction will proceed, coarse particles which may be unsuitable for optical applications will be obtained. If, on the other hand, the proportion of water exceeds the above range, the concentration of the metal hydroxide will be excessively high, and the intended particles may not be produced.

The density of the carbonic acid source is usually 1.1 to 1.4 g/mL, and thus the proportion of the carbonic acid source in terms of volume is, for example, 5 to 100 mL and preferably 10 to 50 mL per 100 g of the metal hydroxide. Also, the number of moles of the carbonic acid source may be, for example, 0.4 to 100 mol, preferably 1.01 to 10.0 mol and more preferably 1.05 to 1.30 mol per mol of the metal hydroxide.

Also, the proportion of the organic compound in terms of volume is, for example, 5 to 500 mL, and preferably 20 to 300 mL per 100 g of the metal hydroxide, and the number of moles of the organic compound may be, for example, 0.01 to 10000 mol and preferably 0.1 to 10 mol per mol of the metal hydroxide.

Also, the proportion of water in terms of volume is, for example, 150 to 2500 mL and preferably 300 to 500 mL per 100 g of the metal hydroxide.

If the proportions of the organic compound and water fall within the above ranges, the surface of inorganic particles can be reliably surface-treated.

The reaction conditions for the second hydrothermal synthesis are the same as those for the first hydrothermal synthesis described above.

Furthermore, in the present invention, the particles of the present invention can also be obtained by subjecting a metal hydroxide containing an alkaline earth metal, a metal complex and an organic compound to a hydrothermal synthesis (third hydrothermal synthesis).

Examples of the metal hydroxide containing an alkaline earth metal include the same metal hydroxides containing an alkaline earth metal as those used in the second hydrothermal synthesis described above.

The metal element contained in the metal complex is a metal element that constitutes a composite oxide with the alkaline earth metal contained in the metal hydroxide, and examples thereof include elemental titanium, elemental iron, elemental tin, elemental zirconium and the like. Elemental titanium is preferable.

Examples of the ligand of the metal complex include monohydroxycarboxylic acids such as 2-hydroxyoctanoic acid and the like.

Examples of the metal complex include 2-hydroxyoctanoic acid titanate and the like. The metal complex can be obtained by preparation from the metal element and the ligand.

Examples of the organic compound include the same organic compounds as those used in the first hydrothermal synthesis described above.

In the third hydrothermal synthesis, the metal hydroxide, the metal complex and the organic compound are reacted under high-temperature and high-pressure conditions in the presence of water.

The proportions of respective components per 100 parts by weight of the metal complex are as follows: the proportion of the metal hydroxide is, for example, 1 to 50 parts by weight and preferably 5 to 30 parts by weight; the proportion of the organic compound is, for example, 4 to 550 parts by weight and preferably 15 to 330 parts by weight; and the proportion of water is, for example, 200 to 1000 parts by weight and preferably 300 to 700 parts by weight.

If the proportion of the metal hydroxide is below the above range, the concentration of the metal hydroxide will be excessively low, and the particles may not be obtained. If, on the other hand, the proportion of the metal hydroxide exceeds the above range, although the surface modification reaction will proceed, coarse particles which may be unsuitable for optical applications will be obtained.

If the proportion of the organic compound is below the above range, the surface modification reaction will not proceed sufficiently, which may result in poor dispersibility in a solvent and/or a resin. If, on the other hand, the proportion of the organic compound exceeds the above range, the surface modification reaction will proceed sufficiently, but due to the excessive use of organic compound, the cost may increase.

If the proportion of water is below the above range, although the reaction will proceed, coarse particles which may be unsuitable for optical applications will be obtained. If, on the other hand, the proportion of water exceeds the above range, the concentration of the metal hydroxide will be excessively high, and the intended particles may not be produced.

The proportion of the organic compound in terms of volume is, for example, 5 to 500 mL and preferably 20 to 300 mL per 100 g of the metal complex, and the number of moles of the organic compound may be 0.01 to 1000 per mol of the organic compound.

The proportion of water in terms of volume is, for example, 200 to 1000 mL and preferably 300 to 700 mL per 100 g of the metal complex.

If the proportions of the organic compound and water fall within the above ranges, the surface of inorganic particles can be reliably surface-treated.

The reaction conditions for the third hydrothermal synthesis are the same as those for the first hydrothermal synthesis described above.

Furthermore, the above hydrothermal syntheses (first, second and third hydrothermal syntheses) may also be carried out in the presence of a pH adjusting agent.

Preferably, the second hydrothermal synthesis is carried out in the presence of a pH adjusting agent.

The pH adjusting agent can be an alkali or acid.

Examples of the alkali include inorganic alkalis such as potassium hydroxide and sodium hydroxide; organic alkalis such as ammonia; and the like. Examples of the acid include inorganic acids such as sulfuric acid, nitric acid and hydrochloric acid; organic acids such as formic acid and acetic acid; and the like.

Preferably, an alkali is used.

The pH of the reaction system is set to, for example, 8 to 12 by using the pH adjusting agent.

It is thereby possible to set the average particle size of the resulting particles in the desired range, more specifically, to a smaller value. Accordingly, the particles having a small average particle size (or lengthwise length LL and sideways length SL, which will be described later) can be suitably used in optical applications.

Examples of the inorganic compound subjected to the high temperature treatment in the organic compound include the same inorganic compounds as those listed above.

In the high temperature treatment in the organic compound, the inorganic compound and the organic compound are blended and heated under, for example, normal atmospheric pressure conditions.

The proportion of the organic compound is, for example, 10 to 10000 parts by weight and preferably 100 to 1000 parts by weight per 100 parts by weight of the inorganic compound. The proportion of the organic compound in terms of volume is, for example, 10 to 10000 mL and preferably 100 to 1000 mL per 100 g of the inorganic compound.

The heating temperature is, for example, a temperature above 100° C., preferably 125° C. or higher and more preferably 150° C. or higher, and usually for example, 300° C. or lower, and preferably 275° C. or lower.

The heating time is, for example, 1 to 60 minutes and preferably 3 to 30 minutes.

The particles (primary particles) thus obtained are mostly acicular, with a lengthwise length (maximum length) LL of, for example, 200 μm or less, preferably 5 nm to 200 μm, more preferably 10 nm to 50 μm and even more preferably 40 nm to 10 μm and a sideways length (minimum length) SL of, for example, 1 nm to 20 μm, preferably 3 nm to 10 μm and more preferably 5 nm to 5 μm.

In particular, the particles (primary particles) obtained by hydrothermal synthesis in the presence of a pH adjusting agent have a lengthwise length LL of, for example, 1 nm to 20 μm and preferably 10 nm to 10 μm and a sideways length SL of, for example, 0.5 nm to 2 μm and preferably 1 nm to 1 μm.

If the lengthwise length LL is below the above range, the particles will be too small, which may result in poor physical strength. If, on the other hand, the lengthwise length LL exceeds the above range, good optical characteristics will be obtained, but the particles may be crushed when mixed with a resin or the like.

If the sideways length SL is below the above range, the particles will be too small, which may result in poor physical strength. If, on the other hand, the sideways length SL exceeds the above range, a sufficient aspect ratio may not be obtained.

The particles have an aspect ratio of, for example, 1000 or less, specifically, 1 to 1000, preferably 3 to 100 and more preferably 5 to 30.

If the aspect ratio is below the above range, poor optical characteristics will be obtained. If, on the other hand, the aspect ratio exceeds the above range, good optical characteristics will be obtained, but the particles may be crushed when mixed with a resin or the like.

The particles thus obtained are unlikely to coagulate in a dry state, and even if the particles appear coagulated in a dry state, the coagulation (formation of secondary particles) will be reliably prevented in a particle dispersion and/or a particle-dispersed resin composition, which will be described next, and therefore the particles are dispersed as primary particles substantially uniformly in a solvent and/or a resin.

The particles obtained in the above-described manner can be subjected to wet classification.

Specifically, a solvent is added to the particles, and the resulting mixture is stirred and allowed to stand still, and thereafter separated into a supernatant and a precipitate. As the solvent, the same solvents as those listed above can be used.

After that, the supernatant is recovered to give particles having a small particle size.

With the wet classification, the lengthwise length LL of the resulting particles can be adjusted to, for example, 10 nm to 400 nm and preferably 20 nm to 200 nm, and the sideways length SL can be adjusted to, for example, 1 nm to 100 nm and preferably 5 nm to 50 nm.

If the lengthwise length LL is below the above range, the particle will be too small, which may result in poor physical strength. If, on the other hand, the lengthwise length LL exceeds the above range, good optical characteristics will be obtained, but the particles may be crushed when mixed with a resin or the like.

If the sideways length SL is below the above range, the particles will be too small, which may result in poor physical strength. If, on the other hand, the sideways length SL exceeds the above range, a sufficient aspect ratio may not be obtained.

There is no particular limitation on the solvent for dispersing the particles obtained above. Examples thereof include the solvents used in washing described above, and other examples include halogenated hydrocarbons such as chloroform, dichloromethane, 1,1,1-trichloroethane, chlorobenzene and dichlorobenzene; alkanes such as pentane, hexane and heptane; cycloalkanes such as cyclopentane and cyclohexane; esters such as ethyl acetate; polyols such as ethylene glycol and glycerin; aromatic hydrocarbons such as benzene, toluene and xylene; ethers such as tetrahydrofuran; nitrogen-containing compounds such as N-methylpyrrolidone, pyridine, acetonitrile and dimethylformamide; and the like.

These solvents can be used singly or in a combination of two or more.

The proportion of the solvent is not particularly limited, and the concentration of the particles in the particle dispersion is adjusted to, for example, 0.1 to 70 wt % and preferably 1 to 50 wt %.

If the concentration of the particles in the particle dispersion is below the above range, the particle dispersion will be too dilute, and thus sufficient optical characteristics may not be obtained when mixed with a resin or the like. If, on the other hand, the concentration of the particles in the particle dispersion exceeds the above range, the dispersibility will be low.

In order to disperse the particles in the solvent, the particles and the solvent are blended, and the resulting mixture is stirred.

As a result, in the particle dispersion, the particles are uniformly dispersed as primary particles in the solvent, or in other words, without coagulation of the particles.

There is no particular limitation on the resin for dispersing the particles, and examples thereof include thermosetting resins, thermoplastic resins and the like.

Examples of thermosetting resins include epoxy resin, polyimide resin (thermosetting polyimide resin), phenol resin, urea resin, melamine resin, diallyl phthalate resin, silicone resin, urethane resin (thermosetting urethane resin) and the like.

Examples of thermoplastic resins include polyolefin (for example, polyethylene, polypropylene, ethylene-propylene copolymer and the like), acrylic resin (for example, polymethyl methacrylate and the like), polyvinyl acetate, ethylene-vinylacetate copolymer (EVA), polyvinyl chloride, polystyrene, polyacrylonitrile, polyamide (PA; nylon), polycarbonate, polyacetal, polyester (for example, polyarylate, polyethylene terephthalate (PET) and the like), polyphenylene oxide, polyphenylene sulfide, polysulfone, polyether sulfone, polyether ether ketone (PEEK), polyallylsulfone, thermoplastic polyimide resin, thermoplastic urethane resin, polyaminobismaleimide, polyamideimide, polyetherimide, bismaleimidetriazine resin, polymethylpentene, fluorine resin, liquid crystal polymer, olefin-vinyl alcohol copolymer, ionomer, polyarylate, acrylonitrile-ethylene-styrene copolymer (AES), acrylonitrile-butadiene-styrene copolymer (ABS), acrylonitrile-styrene copolymer (AS) and the like.

These resins can be used singly or in a combination of two or more.

Among the resins, a thermoplastic resin is preferable, and polyetherimide and polyester are more preferable.

The resin (specifically, thermoplastic resin) has a melting temperature of, for example, 200 to 300° C. and a softening temperature of, for example, 150 to 280° C.

In order to disperse the particles in the resin, for example, at least the particles and the resin are blended, and the resulting mixture is stirred.

Preferably, the particles, the solvent and the resin are blended, the resulting mixture is stirred to prepare a particle-dispersed resin solution, and thereafter the solvent in the particle-dispersed resin solution is removed. Blending a solvent allows the particles to be more uniformly dispersed in the resin.

Specifically, a resin solution and/or a resin dispersion that has been dissolved and/or dispersed in a solvent are/is blended with the particle dispersion.

As the solvent used in preparation of the resin solution and/or the resin dispersion, the same solvents as those listed above can be used. The proportion of the solvent is adjusted to, for example, 40 to 2000 parts by weight and preferably 50 to 1000 parts by weight per 100 parts by weight of the resin solution and/or the resin dispersion.

If the proportion of the solvent is below the above range, the resin solution or the resin dispersion will be too viscous, making its application difficult, and also the dispersibility of the particles will be low. If, on the other hand, the proportion of the solvent exceeds the above range, the resin solution or the resin dispersion will be too dilute and the viscosity is too small, making it difficult to apply the resin solution or the resin dispersion so as to be thick.

The proportion between the resin solution and/or the resin dispersion and the particle dispersion is adjusted such that the proportion of the particles is, for example, 0.1 to 240 parts by weight and preferably 5 to 100 parts by weight per 100 parts by weight of the resin (solids content). In other words, the concentration of the particles in the particle-dispersed resin composition is adjusted to 0.1 to 70 wt % and preferably 1 to 50 wt %.

If the proportion of the particles is below the above range, the particle-dispersed resin composition will be too dilute, and thus sufficient optical characteristics may not be obtained in the particle-dispersed resin composition. If, on the other hand, the proportion of the particles exceeds the above range, the dispersibility of the particles will be low.

After that, the particle-dispersed resin composition is dried by application of heat at, for example, 40 to 60° C. to remove the solvent, and thereby a particle-dispersed resin composition is obtained.

After that, the particle-dispersed resin composition is injected into a metal mold or the like and then subjected to, for example, heat molding such as heat pressing, whereby the resin molded article of the present invention can be obtained.

As heat pressing, for example, vacuum pressing is used. The conditions are as follows: the temperature is greater than or equal to the melting temperature or softening temperature of the resin, specifically, 100 to 300° C. and preferably 150 to 250° C.; and the pressing pressure is, for example, 20 to 1000 MPa and preferably 40 to 80 MPa.

If the heating temperature is below the above range, it may not be possible to soften the resin. If, on the other hand, the heating temperature exceeds the above range, the resin may be thermally decomposed, and also the cost may increase due to an excessive amount of heat generated.

If the pressing pressure is below the above range, the resin may not be sufficiently deformed (molded). If, on the other hand, the pressing pressure exceeds the above range, the resin can be sufficiently molded, but the pressing pressure will be excessively high, which may increase the cost.

The resin molded article of the present invention can be obtained by (application method) applying the particle-dispersed resin solution onto a support plate by using, for example, an application method such as spin coating or roll coating, subsequently removing the solvent at the same temperature as described above, and then if necessary curing the resultant by application of heat so as to form a coating that is made of the particle-dispersed resin composition, and if necessary further drying the coating.

Furthermore, the resin molded article of the present invention can also be obtained by an extrusion method in which the particle-dispersed resin composition is extruded by an extruding machine or the like.

As a result, in the resin molded article, the particles are uniformly dispersed as primary particles in the resin, or in other words, without coagulation of the particles.

The resin molded article of the present invention has various applications including, for example, optical applications, electronic and electrical applications and mechanical applications. In the case of electronic and electrical applications, for example, the resin molded article of the present invention is used as a flexible substrate or the like.

Preferably, the resin molded article of the present invention is used in optical applications, specifically, as an optical fiber, an optical disc, a light guide plate, an optical film or the like.

The thickness of the optical film is, for example, 1 to 100 μm and preferably 5 to 50 μm.

If the thickness of the optical film is below the above range, sufficient optical characteristics may not be obtained. If, on the other hand, the thickness of the optical film exceeds the above range, although sufficient optical characteristics can be obtained, it may be difficult to form a uniform film and the cost may increase.

In the case where the resin molded article is used as an optical film, the resin molded article is formed into a film suitable for optical applications by the application method, or in other words, an optical film is obtained.

The particles of the present invention can be dispersed as primary particles in a solvent and/or a resin, and therefore have excellent dispersibility in a solvent and/or a resin.

Accordingly, in the particle dispersion and the particle-dispersed resin composition of the present invention, the particles are dispersed with good uniformity.

Moreover, the particles of the present invention have negative birefringence.

Accordingly, the resin molded article of the present invention can reliably have excellent optical characteristics and thus is useful as an optical member, in particular, as an optical film.

More specifically, the particles of the present invention have a particle size (lengthwise length LL and sideways length SL) that is smaller than the wavelength of light (for example, 380 to 800 nm in the case of visible light) and are dispersed in the resin molded article of the present invention, and therefore negative birefringence can be imparted to the optical film with excellent reliability.

For this reason, the optical film of the present invention can be suitably used in phase difference plates or polarizing plates for plasma display panels or liquid crystal televisions, or the like.

Second Embodiment

Embodiment corresponding to the inventions of a particle-dispersed resin composition, a particle-dispersed resin molded article and producing methods therefor, which are included in the second group of inventions The particle-dispersed resin composition of the present invention contains a resin and organic-inorganic composite particles.

Examples of the resin include thermosetting resins, thermoplastic resins and the like.

Examples of thermosetting resins include polycarbonate resin, epoxy resin, thermosetting polyimide resin (including thermosetting fluorine-based polyimide resin), phenol resin, urea resin, melamine resin, diallyl phthalate resin, silicone resin, thermosetting urethane resin and the like.

Examples of thermoplastic resins include olefin resin, acrylic resin, polystyrene resin, polyester resin, polyacrylonitrile resin, maleimide resin, polyvinyl acetate resin, ethylene-vinylacetate copolymer, polyvinyl alcohol resin, polyamide resin, polyvinyl chloride resin, polyacetal resin, polyphenylene oxide resin, polyphenylene sulfide resin, polysulfone resin, polyether sulfone resin, polyether ether ketone resin, polyallylsulfone resin, thermoplastic polyimide resin (including thermoplastic fluorine-based polyimide resin), thermoplastic urethane resin, polyetherimide resin, polymethylpentene resin, cellulose resin, liquid crystal polymer, ionomer and the like.

These resins can be used singly or in a combination of two or more.

In the case where excellent mechanical strength needs to be imparted to the particle-dispersed resin molded article molded from a particle-dispersed resin composition, the resin is preferably a highly oriented resin having high orientation, and specific examples thereof include olefin resin, acrylic resin, polystyrene resin, polyester resin, polyvinyl alcohol resin, thermoplastic polyimide resin, polyetherimide resin, liquid crystal polymer and the like.

Examples of the olefin resin include cyclic olefin resin, chain olefin resin and the like. Cyclic olefin resin is preferable.

Examples of the cyclic olefin resin include polynorbornene, ethylene-norbornene copolymers, and derivative thereof.

Examples of the chain olefin resin include polyethylene, polypropylene, ethylene-propylene copolymer and the like.

Examples of the acrylic resin include polymethyl methacrylate and the like.

Examples of the polyester resin include polyarylate, polyethylene terephthalate, polyethylene naphthalate and the like.

The polyvinyl alcohol resin is obtained by, for example, complete or partial saponification of polyvinyl acetate resin obtained by polymerizing vinyl monomers containing vinyl acetate as a primary component by an appropriate method. The saponification degree of polyvinyl alcohol resin is, for example, 70 to 99.99 mol % and preferably 70 to 99.9 mol %.

The resin preferably has a functional group. Examples of the functional group include hydrophilic groups such as carboxyl group and hydroxyl group; hydrophobic groups such as hydrocarbon group; and the like.

The organic-inorganic composite particles are particles that can be dispersed as primary particles in a solvent (described later) and/or a resin and that have an organic group on the surface of the inorganic particles. Specifically, the organic-inorganic composite particles are obtained by surface-treating inorganic particles with an organic compound. The organic-inorganic composite particles can be used singly or in a combination of two or more.

The inorganic substance for forming inorganic particles can be a metal composed of a metal element such as a main group element or a transition element, a nonmetal composed of a nonmetal element such as boron or silicon, an inorganic compound containing a metal element and/or a nonmetal, or the like.

Examples of the metal element and the nonmetal element include elements that are located on the left side and the lower side of a border line that is assumed to pass through boron (B) of the IIIB group, silicon (Si) of the IVB group, arsenic (As) of the VB group, tellurium (Te) of the VIB group and astatine (At) of the VIIB group on the long-form periodic table (IUPAC, 1989), as well as the elements that are located on the border line. Specific examples thereof include the group IIIA elements such as Sc and Y; the group IVA elements such as Ti, Zr, and Hf; the group VA elements such as V, Nb, and Ta; the group VIA elements such as Cr, Mo, and W; the group VIIA elements such as Mn and Re; the group VIIIA elements such as Fe, Co, Ni, Ru, Rh, Pd, Os, Ir, and Pt; the group IB elements such as Cu, Ag, and Au; the group IIB elements such as Zn, Cd, and Hg; the group IIIB elements such as B, Al, Ga, In, and Tl; the group IVB elements such as Si, Ge, Sn, and Pb; the group VB elements such as As, Sb, and Bi; the group VIB elements such as Te and Po; the lanthanide series elements such as La, Ce, Pr, and Nd; the actinium series elements such as Ac, Th, and U; and the like.

The inorganic compound can be, for example, a hydrogen compound, a hydroxide, a nitride, a halide, an oxide, a carbonate, a sulfate, a nitrate, a metal complex, a sulfide, a carbide, a phosphorus compound, or the like. The inorganic compound may be a composite compound such as, for example, an oxynitride or a composite oxide.

The inorganic substance is preferably an inorganic compound, and more preferable examples include an oxide, a composite oxide, a carbonate, a sulfate and the like.

Examples of the oxide include metal oxides, and preferable examples include titanium oxide (titanium dioxide, titanium oxide (IV), titania: $TiO_2$), cerium oxide (cerium dioxide, cerium oxide (IV), ceria: $CeO_2$) and the like.

The oxides can be used singly or in a combination of two or more.

The composite oxide is a compound consisting of oxygen and a plurality of elements, and the plurality of elements may be a combination of at least two elements selected from the elements other than oxygen contained in the oxides listed above, the group I elements, and the group II elements.

Examples of the group I elements include alkali metals such as Li, Na, K, Rb, and Cs. Examples of the group II elements include the same alkaline earth metals as those listed in the first embodiment.

Preferable examples of the combination of a plurality of elements include combinations that contain at least a group II element such as a combination of a group II element and a group IVB element, a combination of a group II element and a group VIIIB element, and a combination of a group II element and a group IVA element.

Examples of the composite oxide containing at least a group II element include alkaline earth metal titanates, alkaline earth metal zirconates, alkaline earth metal ferrates, alkaline earth metal stannates, and the like.

Preferable composite oxides are alkaline earth metal titanates.

Examples of alkaline earth metal titanates include the same alkaline earth metal titanates as those listed in the first embodiment.

The composite oxides can be used singly or in a combination of two or more.

In the carbonate, the element that combines with carbonic acid can be, for example, an alkali metal, an alkaline earth metal or the like. The alkali metal and the alkaline earth metal can be the same alkali metals and alkaline earth metals as those listed above.

The element that combines with carbonic acid is preferably an alkaline earth metal.

Specifically, the carbonate is preferably a carbonate containing an alkaline earth metal, and examples of such a carbonate include the same carbonates as those listed in the first embodiment. These carbonates can be used singly or in a combination of two or more.

The sulfate is a compound consisting of a sulfate ion ($SO_4^{2-}$) and a metal cation (more specifically, a compound formed by substitution of the hydrogen atoms of sulfuric acid ($H_2SO_4$) with a metal), and the metal contained in the sulfate can be, for example, an alkali metal, an alkaline earth metal or the like. The alkali metal and the alkaline earth metal can be the same alkali metals and alkaline earth metals as those listed above.

The metal is preferably an alkaline earth metal.

Specifically, preferable sulfates are sulfates containing an alkaline earth metal, and examples of such sulfates include beryllium sulfate, magnesium sulfate, calcium sulfate, strontium sulfate, barium sulfate, radium sulfate and the like. Barium sulfate is preferable.

These sulfates can be used singly or in a combination of two or more.

The organic compound is, for example, an organic group-introducing compound that introduces (disposes) an organic group on the surface of inorganic particles. Specifically, the organic compound contains a binding group capable of binding to the surface of inorganic particles and an organic group.

The binding group may be selected as appropriate according to the type of inorganic particles, and examples thereof include functional groups such as carboxyl group, phosphoric acid group (—PO(OH)$_2$, phosphono group), amino group, sulfo group, hydroxyl group, thiol group, epoxy group, isocyanate group (cyano group), nitro group, azo group, silyloxy group, imino group, aldehyde group (acyl group), nitrile group, vinyl group (polymerizable group), and the like. Preferable examples include carboxyl group, phosphoric acid group, amino group, sulfo group, hydroxyl group, thiol group, epoxy group, azo group, vinyl group, and the like. More preferable examples include carboxyl group and phosphoric acid group.

The carboxyl group includes a carboxylic acid ester group (carboxy ester group).

The phosphoric acid group includes a phosphoric acid ester group (phosphonate group).

One or more of these binding groups are contained in the organic compound. Specifically, the binding group is bound to a terminal or a side chain of the organic group.

The binding group is selected as appropriate according to the type of inorganic particles. Specifically, when the inorganic particles contain cerium oxide, strontium carbonate and/or barium sulfate, for example, a carboxyl group is selected. When the inorganic particles contain titanium oxide, for example, a phosphoric acid group is selected.

The organic group includes, for example, a hydrocarbon group such as an aliphatic group, an alicyclic group, an araliphatic group or an aromatic group, or the like.

The aliphatic group includes, for example, a saturated aliphatic group, an unsaturated aliphatic group and the like.

Examples of the saturated aliphatic group include alkyl groups having 1 to 20 carbon atoms and the like.

Examples of the alkyl group include linear or branched alkyl groups (paraffin hydrocarbon groups) having 1 to 20 carbon atoms such as methyl, ethyl, propyl, isopropyl, butyl, isobutyl, sec-butyl, t-butyl, pentyl, isopentyl, neopentyl, hexyl, heptyl, octyl, 2-ethylhexyl, 3,3,5-trimethylhexyl, isooctyl, nonyl, isononyl, decyl, isodecyl, undecyl, dodecyl, tridecyl, tetradecyl, pentadecyl, hexadecyl, heptadecyl, octadecyl, nonadecyl and icosyl, and the like. A linear or branched alkyl group having 4 to 18 carbon atoms is preferable.

Examples of the unsaturated aliphatic group include alkenyl groups having 2 to 20 carbon atoms, alkynyl groups having 2 to 20 carbon atoms, and the like.

Examples of the alkenyl group include alkenyl groups (olefin hydrocarbon groups) having 2 to 20 carbon atoms such as ethenyl, propenyl, butenyl, pentenyl, hexenyl, octenyl, nonenyl, decenyl, undecenyl, dodecenyl, tetradecenyl, hexadecenyl, octadecenyl (oleyl) and icosenyl.

Examples of the alkynyl group include alkynyl groups (acetylene hydrocarbon groups) having 2 to 20 carbon atoms such as ethynyl, propynyl, butynyl, pentynyl, hexynyl, heptynyl, octynyl, decynyl, undecynyl, dodecynyl, tridecynyl, tetradecynyl, pentadecynyl, hexadecynyl, heptadecynyl and octadecynyl.

Examples of the alicyclic group include cycloalkyl groups having 4 to 20 carbon atoms, cycloalkenylalkylene groups having 7 to 20 carbon atoms, and the like.

Examples of the cycloalkyl group include cyclobutyl, cyclopentyl, cyclohexyl, cycloheptyl, cyclooctyl, cyclononyl, cyclodecyl, cycloundecyl, cyclododecyl and the like.

Examples of the cycloalkenylalkylene group include norbornene decyl (norboneryl decyl, bicyclo[2.2.1]hept-2-enyl-decyl) and the like.

Examples of the araliphatic group include aralkyl groups having 7 to 20 carbon atoms such as benzyl, phenylethyl, phenylpropyl, phenylbutyl, phenylpentyl, phenylhexyl, phenylheptyl and diphenylmethyl.

Examples of the aromatic group include aryl groups having 6 to 20 carbon atoms such as phenyl, xylyl, naphthyl and biphenyl.

The organic group is used as a hydrophobic group for imparting hydrophobicity to the surface of inorganic particles.

Accordingly, the organic compounds containing a hydrophobic group described above are used as hydrophobic organic compounds for hydrophobic treatment of inorganic particles.

Specific examples of such hydrophobic organic compounds in the case where the binding group is a carboxyl group include aliphatic group-containing carboxylic acids including saturated aliphatic group-containing carboxylic acids (saturated fatty acids) such as hexanoic acid and decanoic acid and unsaturated aliphatic group-containing carboxylic acids (unsaturated fatty acids) such as oleic acid, and the like. Other specific examples of hydrophobic organic compounds in the case where the binding group is a carboxyl group include alicyclic group-containing carboxylic acids (alicyclic carboxylic acids) such as cyclohexyl monocarboxylic acid, araliphatic group-containing carboxylic acids (araliphatic carboxylic acids) such as 6-phenylhexanoic acid, aromatic group-containing carboxylic acids (aromatic carboxylic acids) such as benzoic acid and toluenecarboxylic acid, and the like.

Specific examples of hydrophobic organic compounds in the case where the binding group is a phosphoric acid group (including phosphoric acid ester group), aliphatic group-containing phosphate esters including saturated aliphatic group-containing phosphate esters such as ethyl octylphosphonate and ethyl decylphosphonate.

The organic compound can also be used as a hydrophilic organic compound for hydrophilic treatment of inorganic particles. In this case, the organic group contained in the hydrophilic organic compound includes any of the above hydrocarbon groups and a hydrophilic group that binds to the hydrocarbon group.

That is, in the hydrophilic organic compound, the hydrophilic group is bound to a terminal (the terminal (the other terminal) opposite the terminal that is bound to the binding group (one terminal)) or a side chain of the hydrocarbon group.

The hydrophilic group is a functional group having a polarity (or in other words, polar group), and examples thereof include a carboxyl group, a hydroxyl group, a phosphoric acid group, an amino group, a sulfo group, a carbonyl group, a cyano group, a nitro group, an aldehyde group, a thiol group and the like. One or more of the hydrophilic groups are contained in the hydrophilic organic compound.

Examples of the organic group containing a carboxyl group (carboxyl group-containing organic group) include carboxyaliphatic groups including carboxysaturated aliphatic groups such as 3-carboxypropyl, 4-carboxybutyl, 6-carboxyhexyl, 8-carboxyoctyl and 10-carboxydecyl and carboxyunsaturated aliphatic groups such as carboxybutenyl, and the like. Other examples of the organic group containing a carboxyl group include carboxyalicyclic groups such as carboxycyclohexyl, carboxyaraliphatic groups such as carboxyphenylhexyl, carboxyaromatic groups such as carboxyphenyl, and the like.

Examples of the organic group containing a hydroxyl group (hydroxyl group-containing organic group) include hydroxysaturated aliphatic groups (hydroxy aliphatic groups) such as 4-hydroxybutyl, 6-hydroxylhexyl and 8-hydroxyoctyl, hydroxyaraliphatic groups such as 4-hydroxybenzyl, 2-(4-hydroxyphenyl)ethyl, 3-(4-hydroxyphenyl)propyl and 6-(4-hydroxyphenyl)hexyl, hydroxyaromatic groups such as hydroxy phenyl, and the like.

Examples of the organic group containing a phosphoric acid group (phosphoric acid group-containing organic group) include phosphonosaturated aliphatic groups (phosphonoaliphatic groups) such as 6-phosphonohexyl, phosphonoaraliphatic groups such as 6-phosphonophenylhexyl, and the like.

Examples of the organic group containing an amino group (amino group-containing organic group) include aminosaturated aliphatic groups (aminoaliphatic groups) such as 6-aminohexyl, aminoaraliphatic groups such as 6-aminophenylhexyl, and the like.

Examples of the organic group containing a sulfo group (sulfo group-containing organic group) include sulphosaturated aliphatic groups (sulphoaliphatic groups) such as 6-sulphohexyl, sulphoaraliphatic groups such as 6-sulphophenylhexyl, and the like.

Examples of the organic group containing a carbonyl group (carbonyl group-containing organic group) include oxosaturated aliphatic groups (oxoaliphatic groups) such as 3-oxopentyl, and the like.

Examples of the organic group containing a cyano group (cyano group-containing organic group) include cyanosaturated aliphatic groups (cyanoaliphatic groups) such as 6-cyanohexyl, and the like.

Examples of the organic group containing a nitro group (nitro group-containing organic group) include nitrosaturated aliphatic groups (nitroaliphatic groups) such as 6-nitrohexyl, and the like.

Examples of the organic group containing an aldehyde group (aldehyde group-containing organic group) include aldehydesaturated aliphatic groups (aldehydealiphatic groups) such as 6-aldehydehexyl, and the like.

Examples of the organic group containing a thiol group (thiol group-containing organic group) include thiolsaturated aliphatic groups (thiolaliphatic groups) such as 6-thiolhexyl, and the like.

Specifically, the organic compound containing a hydrophilic group can be, for example, a carboxyl group-containing organic compound, a hydroxyl group-containing organic compound, a phosphoric acid group-containing organic compound, an amino group-containing organic compound, a sulfo group-containing organic compound, a carbonyl group-containing organic compound, a cyano group-containing organic compound, a nitro group-containing organic compound, an aldehyde group-containing organic compound, a thiol group-containing organic compound, and the like.

The carboxyl group-containing organic compound can be, for example, a dicarboxylic acid or the like in the case where both the binding group and the hydrophilic group are carboxyl groups. Examples of the dicarboxylic acid include aliphatic dicarboxylic acids including saturated aliphatic dicarboxylic acids such as propanedioic acid (malonic acid), butanedioic acid (succinic acid), hexanedioic acid (adipic acid), octanedioic acid, decanedioic acid (sebacic acid) and unsaturated aliphatic dicarboxylic acids such as itaconic acid; alicyclic dicarboxylic acids such as cyclohexyl dicarboxylic acid; araliphatic dicarboxylic acids such as 6-carboxyphenyl hexanoic acid; aromatic dicarboxylic acids such as phthalic acid, terephthalic acid and isophthalic acid; and the like. Also, the carboxyl group-containing organic compound can be a carboxyl group-containing phosphate ester or the like in the case where the binding group is a carboxyl group and the hydrophilic group is a phosphoric acid ester group (in the case where the inorganic particles include, for example, cerium oxide, strontium carbonate or barium sulfate), or in the case where the binding group is a phosphoric acid ester group and the hydrophilic group is a carboxyl group (in the case where the inorganic particles include, for example, zinc oxide or barium sulfate). Specific examples thereof include ethyl carboxydecylphosphate, ethyl carboxyoctylphosphate, and the like.

The hydroxyl group-containing organic compound can specifically be, for example, a monohydroxyl carboxylic acid in the case where the binding group is a carboxyl group and the hydrophilic group is a hydroxyl group (in the case where the inorganic particles include, for example, cerium oxide, strontium carbonate or barium sulfate). Specific examples of the monohydroxyl carboxylic acid include 4-hydroxybutanoic acid, 6-hydroxyhexanoic acid, 8-hydroxyoctanoic acid, 4-hydroxyphenylacetic acid, 3-(4-hydroxyphenyl)propionic acid, 6-(4-hydroxyphenyl)hexanoic acid, hydroxybenzoic acid, and the like.

The phosphoric acid group-containing organic compound can be, for example, a monophosphonocarboxylic acid in the case where the binding group is a carboxyl group and the hydrophilic group is a phosphoric acid group (in the case where the inorganic particles include, for example, cerium oxide, strontium carbonate or barium sulfate). Specific examples thereof include 6-phosphonohexanoic acid, 6-phosphonophenylhexanoic acid, as well as the carboxyl group-containing phosphate esters listed above.

The amino group-containing organic compound can specifically be, for example, a monoaminocarboxylic acid in the case where the binding group is a carboxyl group and the hydrophilic group is an amino group (in the case where the inorganic particles include, for example, cerium oxide, strontium carbonate or barium sulfate). Specific examples thereof include 6-aminohexanoic acid, 6-aminophenylhexanoic acid, and the like.

The sulfo group-containing organic compound can specifically be, for example, a monosulfocarboxylic acid in the case where the binding group is a carboxyl group and the hydrophilic group is a sulfo group (in the case where the inorganic particles include, for example, cerium oxide, strontium carbonate or barium sulfate). Specific examples thereof include 6-sulfohexanoic acid, 6-sulfophenylhexanoic acid, and the like.

The carbonyl group-containing organic compound can specifically be, for example, a monocarbonylcarboxylic acid in the case where the binding group is a carboxyl group and the hydrophilic group is a carbonyl group (in the case where the inorganic particles include, for example, cerium oxide, strontium carbonate or barium sulfate). Specific examples thereof include 4-oxovaleric acid, and the like.

The cyano group-containing organic compound can specifically be, for example, a monocyanocarboxylic acid in the case where the binding group is a carboxyl group and the hydrophilic group is a cyano group (in the case where the inorganic particles include, for example, cerium oxide, strontium carbonate or barium sulfate). Specific examples thereof include 6-cyano hexanoic acid, and the like.

The nitro group-containing organic compound can specifically be, for example, a mononitrocarboxylic acid in the case where the binding group is a carboxyl group and the hydrophilic group is a nitro group (in the case where the inorganic particles include, for example, cerium oxide, strontium carbonate or barium sulfate). Specific examples thereof include 6-nitro hexanoic acid, and the like.

The aldehyde group-containing organic compound can specifically be, for example, a monoaldehydecarboxylic acid in the case where the binding group is a carboxyl group and the hydrophilic group is an aldehyde group (in the case where the inorganic particles include, for example, cerium oxide, strontium carbonate or barium sulfate). A specific example is 6-aldehydehexanoic acid.

The thiol group-containing organic compound can specifically be, for example, a monothiolcarboxylic acid in the case where the binding group is a carboxyl group and the hydrophilic group is a thiol group (in the case where the inorganic particles include, for example, cerium oxide, strontium carbonate or barium sulfate). Specific examples include 6-thiolhexanoic acid, and the like.

The same or mutually different organic groups may be used.

In the case where mutually different organic groups are used, or in other words, the organic group contains a plurality of different types of organic groups, a plurality of homologous organic groups and/or a plurality of heterologous organic groups are contained.

Examples of the homologous organic groups include a combination of a plurality of aliphatic groups, a combination of a plurality of alicyclic groups, a combination of a plurality of araliphatic groups and a combination of a plurality of aromatic groups. Other examples of the homologous organic groups include a combination of a plurality of carboxyaliphatic groups, a combination of a plurality of carboxyalicyclic groups, a combination of a plurality of carboxyaraliphatic groups, a combination of a plurality of carboxyaromatic groups, a combination of a plurality of hydroxy aliphatic groups, a combination of a plurality of hydroxyaraliphatic groups, a combination of a plurality of hydroxyaromatic groups, a combination of a plurality of phosphonoaliphatic groups, a combination of a plurality of phosphonoaraliphatic groups, a combination of a plurality of aminoaliphatic groups, a combination of a plurality of aminoaraliphatic groups, a combination of a plurality of sulphoaliphatic groups, a combination of a plurality of sulphoaraliphatics, a combination of a plurality of oxoaliphatic groups, a combination of a plurality of cyanoaliphatic groups, a combination of a plurality of nitroaliphatic groups, a combination of a plurality of aldehydealiphatic groups, a combination of a plurality of thiolaliphatic groups, and the like.

As the homologous organic groups, a preferable example is a combination of a plurality of aliphatic groups, a more preferable example is a combination of a plurality of saturated aliphatic groups, and a particularly preferable example is a combination of a saturated aliphatic group having less than 10 carbon atoms and a saturated aliphatic group having 10 or more carbon atoms, specifically, a combination of hexyl and decyl.

When the organic group contains a plurality of homologous organic groups, a plurality of organic groups having different sizes (lengths or/and dimensions, or in other words, the number of carbon atoms) are contained in the organic group. Accordingly, in a space between adjacent larger organic groups, a resin molecule enters a gap (pocket) formed in accordance with the smaller organic group, and the interaction between the larger organic group and the resin molecule can be enhanced. As a result, the dispersibility of the organic-inorganic composite particles can be enhanced.

Examples of the heterologous organic groups include a combination of at least two different groups selected from the group consisting of an aliphatic group, an alicyclic group, an araliphatic group, an aromatic group, a carboxyaliphatic group, a carboxyalicyclic group, a carboxyaraliphatic group, a carboxyaromatic group, a hydroxy aliphatic group, a hydroxyaraliphatic group, a hydroxyaromatic group, a phosphonoaliphatic group, a phosphonoaraliphatic group, an aminoaliphatic group, an aminoaraliphatic group, a sulphoaliphatic group, a sulphoaraliphatic group, an oxoaliphatic group, a cyanoaliphatic group, a nitroaliphatic group, an aldehydealiphatic group and a thiolaliphatic group.

A preferable example of the heterologous organic groups is a combination of an araliphatic group and an aromatic group, and a more preferable example is a combination of an araliphatic group having 7 to 15 carbon atoms and an aromatic group having 6 to 12 carbon atoms, specifically, a combination of phenylhexyl and phenyl.

Another preferable example of the heterologous organic groups is a combination of an aliphatic group and a hydroxy aliphatic group, a more preferable example is a combination of a saturated aliphatic group and a hydroxysaturated aliphatic group, and a particularly preferable example is a combination of a saturated aliphatic group having 10 or more carbon atoms and a hydroxysaturated aliphatic group having less than 10 carbon atoms, specifically, a combination of decyl and 6-hydroxyhexyl.

As long as the organic group contains a plurality of heterologous organic groups, when the resin is prepared as a mixture of a plurality of resin components, the organic group can exert excellent compatibility with the resin molecules of the respective resin components having excellent compatibility with the organic groups of the respective groups. Accordingly, the interaction between the organic groups and the resin molecules of the resin components can be enhanced. As a result, the dispersibility of the organic-inorganic composite particles can be enhanced.

The organic groups are present on the surface of inorganic particles in the organic-inorganic composite particles. Specifically, the organic groups are bound to the surface of inorganic particles via a binding group. Also, the organic groups extend from the surface of inorganic particles toward the outside of the inorganic particles via the binding group.

The organic-inorganic composite particles are produced by subjecting an inorganic substance and an organic compound to a reaction treatment, preferably to a high temperature treatment.

The high temperature treatment is carried out in a solvent. As the solvent, for example, water and any of the organic compounds listed above can be used.

Specifically, the organic-inorganic composite particles are obtained by subjecting an inorganic substance and an organic compound to a high temperature treatment in water under high pressure conditions (hydrothermal synthesis: hydrothermal reaction), or subjecting an inorganic substance to a high temperature treatment in an organic compound (high temperature treatment in an organic compound). In other words, the organic-inorganic composite particles are obtained by surface-treating the surface of inorganic particles formed by an inorganic substance with an organic compound.

In the hydrothermal synthesis, for example, the inorganic substance and the organic compound are reacted under high-temperature and high-pressure conditions in the presence of water (first hydrothermal synthesis).

The inorganic substance subjected to the first hydrothermal synthesis is preferably a carbonate or a sulfate.

Specifically, first, a reaction system is prepared under high-temperature and high-pressure conditions by placing the inorganic substance, the organic compound and water in a pressure-resistant airtight container and heating them.

The proportions of respective components per 100 parts by mass of the inorganic substance are as follows: the proportion of the organic compound is, for example, 1 to 1500 parts by mass, preferably 5 to 500 parts by mass and more preferably 5 to 250 parts by mass; and the proportion of water is, for example, 50 to 8000 parts by mass, preferably 80 to 6600 parts by mass and more preferably 100 to 4500 parts by mass.

The density of the organic compound is usually 0.8 to 1.1 g/mL, and thus the proportion of the organic compound is, for example, 1 to 1500 mL, preferably 5 to 500 mL and more preferably 5 to 250 mL per 100 g of the inorganic substance.

Also, the number of moles of the organic compound may be, for example, 0.01 to 1000 mol, preferably 0.02 to 50 mol, and more preferably 0.1 to 10 mol per mol of the inorganic substance.

In the case where the organic compound contains a plurality of (for example, two) different types of organic groups, specifically, the molar ratio between an organic compound containing one type of organic groups and an organic compound containing the other type of organic group is, for example, 10:90 to 99.9:0.1 and preferably 20:80 to 99:1.

Also, the density of water is usually approximately 1 g/mL, and thus the proportion of water is, for example, 50 to 8000 mL, preferably 80 to 6600 mL, and more preferably 100 to 4500 mL per 100 g of the inorganic substance.

Specific reaction conditions for the hydrothermal reaction are as follows. The heating temperature is, for example, 100 to 500° C. and preferably 200 to 400° C. The pressure is, for example, 0.2 to 50 MPa, preferably 1 to 50 MPa and more preferably 10 to 50 MPa. The reaction time is, for example, 1 to 200 minutes and preferably 3 to 150 minutes. In the case where a continuous reactor is used, the reaction time can be set to one minute or less.

The reaction product obtained by the above reaction includes a precipitate that mostly precipitates in water and a deposit that adheres to the inner wall of the airtight container.

The precipitate is obtained by, for example, sedimentation separation in which the reaction product is settled by gravity or a centrifugal field. Preferably, the precipitate is obtained as a precipitate of the reaction product by centrifugal sedimentation (centrifugal separation) in which the reaction product is settled by a centrifugal field.

The deposit is recovered by, for example, a scraper (spatula) or the like.

The reaction product can also be recovered (separated) by adding a solvent to wash away an unreacted organic compound (or in other words, dissolving the organic compound in the solvent) and thereafter removing the solvent.

The solvent can be, for example, an alcohol (hydroxyl group-containing aliphatic hydrocarbon) such as methanol, ethanol, propanol or isopropanol, a ketone (carbonyl group-containing aliphatic hydrocarbon) such as acetone, methyl ethyl ketone, cyclohexanone or cyclopentanone, an aliphatic hydrocarbon such as pentane, hexane or heptane, a halogenated aliphatic hydrocarbon such as dichloromethane, chloroform or trichloroethane, a halogenated aromatic hydrocarbon such as chlorobenzene or dichlorobenzene, an ether such as tetrahydrofuran, an aromatic hydrocarbon such as benzene, toluene or xylene, an aqueous pH adjusting solution such as aqueous ammonia, or the like. An alcohol is preferable.

The washed reaction product is separated from the solvent (supernatant liquid) by, for example, filtration, decantation or the like, and recovered. After that, the reaction product is dried by, for example, application of heat, an air stream or the like if necessary.

In this manner, the organic-inorganic composite particles having an organic group on the surface of inorganic particles are obtained.

In the first hydrothermal synthesis, the inorganic substance before reaction and the inorganic substance after reaction that forms inorganic particles are the same.

Alternatively, by subjecting an inorganic substance (starting material) and an organic compound to a hydrothermal synthesis, it is also possible to obtain organic-inorganic composite particles containing inorganic particles formed of an inorganic substance that is different from the inorganic substance serving as the starting material (second hydrothermal synthesis).

The inorganic substance subjected to the second hydrothermal synthesis can be, for example, a hydroxide, a metal complex, a nitrate, a sulfate or the like. A hydroxide and a metal complex are preferable.

In the hydroxide, the element (element that constitutes a cation that combines with a hydroxyl ion ($OH^-$)) contained in the hydroxide can be the same as the element that combines with oxygen in an oxide listed above.

Specifically, the hydroxide can be, for example, titanium hydroxide ($Ti(OH)_4$) or cerium hydroxide ($Ce(OH)_4$).

In the metal complex, the metal element contained in the metal complex is a metal element that constitutes a composite oxide with the metal contained in the hydroxide, and examples thereof include titanium, iron, tin, zirconium and the like. Titanium is preferable.

The ligand of the metal complex can be, for example, a monohydroxycarboxylic acid such as 2-hydroxyoctanoic acid, or the like.

Examples of the metal complex include 2-hydroxyoctanoic acid titanate and the like. The metal complex can be obtained by preparation from a metal element and a ligand described above.

As the organic compound, for example, the same organic compounds as those that can be used in the first hydrothermal synthesis described above can be used.

In the second hydrothermal synthesis, the inorganic substance and the organic compound are reacted under high-temperature and high-pressure conditions in the presence of water.

The proportions of respective components per 100 parts by mass of the inorganic compound are as follows: the proportion of the organic compound is, for example, 1 to 1500 parts by mass, preferably 5 to 500 parts by mass, and more preferably 5 to 250 parts by mass; and the proportion of water is, for example, 50 to 8000 parts by mass, preferably 80 to 6600 parts by mass, and more preferably 80 to 4500 parts by mass.

The proportion of the organic compound is, for example, 0.9 to 1880 mL, preferably 4.5 to 630 mL, and more preferably 4.5 to 320 mL per 100 g of the hydroxide, and the number of moles of the organic compound may be, for example, 0.01 to 10000 mol, and preferably 0.1 to 10 mol per mol of the hydroxide.

The proportion of water is, for example, 50 to 8000 mL, preferably 80 to 6600 mL, and more preferably 5 to 4500 mL per 100 g of the hydroxide.

The reaction conditions for the second hydrothermal synthesis are the same as those for the first hydrothermal synthesis described above.

In this manner, the organic-inorganic composite particles containing an organic group on the surface of inorganic particles formed of an inorganic substance that is different from the inorganic substance serving as a starting material are obtained.

In the formulation used in the second hydrothermal synthesis, a carbonic acid source or a hydrogen source can be blended with the components described above.

The carbonic acid source can be, for example, carbon dioxide (carbonic acid gas), formic acid and/or urea.

The hydrogen source can be, for example, hydrogen (hydrogen gas), an acid such as formic acid or lactic acid, a hydrocarbon such as methane or ethane, or the like.

The proportion of the carbonic acid source or hydrogen source is, for example, 5 to 140 parts by mass and preferably 10 to 70 parts by mass per 100 parts by mass of the inorganic substance.

The proportion of the carbonic acid source can be, for example, 5 to 100 mL and preferably 10 to 50 mL per 100 g of the inorganic substance. The number of moles of the carbonic acid source can be, for example, 0.4 to 100 mol, preferably 1.01 to 10.0 mol and more preferably 1.05 to 1.30 mol per mol of the inorganic substance.

The proportion of the hydrogen source can be, for example, 5 to 100 mL and preferably 10 to 50 mL per 100 g of the inorganic substance. The number of moles of the hydrogen source can be, for example, 0.4 to 100 mol, preferably 1.01 to 10.0 mol and more preferably 1.05 to 2.0 mol per mol of the inorganic substance.

In the high temperature treatment in an organic compound, an inorganic substance and an organic compound are blended and heated under, for example, normal atmospheric pressure conditions. The organic compound is subjected to the high-temperature treatment while serving as an organic group-introducing compound as well as a solvent for dispersing or dissolving the inorganic substance.

The proportion of the organic compound is, for example, 10 to 10000 parts by mass and preferably 100 to 1000 parts by mass per 100 parts by mass of the inorganic substance. The proportion of the organic compound in terms of volume is, for example, 10 to 10000 mL and preferably 100 to 1000 mL per 100 g of the inorganic substance.

The heating temperature is, for example, a temperature above 100° C., preferably 125° C. or higher, and more preferably 150° C. or higher, and, usually for example, 300° C. or lower, and preferably 275° C. or lower. The heating time is, for example, 1 to 60 minutes and preferably 3 to 30 minutes.

There is no particular limitation on the shape of the organic-inorganic composite particles (primary particles) obtained in the above-described manner, and for example the organic-inorganic composite particles may be anisotropic or isotropic, with an average particle size (maximum length in the case where they are anisotropic) of, for example, 200 μm or less, preferably 1 nm to 200 μm, more preferably 3 nm to 50 μm and particularly preferably 3 nm to 10 μm.

As will be described in detail in the examples given below, the average particle size of the organic-inorganic composite particles is determined by measurement by dynamic light scattering (DLS) and/or calculated from a transmission electron microscopic (TEM) or scanning electron microscopic (SEM) image analysis.

If the average particle size is below the above range, the proportion of the volume of the organic group relative to the surface of the organic-inorganic composite particles will be high, and the function of the inorganic particles is unlikely to be obtained.

If, on the other hand, the average particle size exceeds the above range, the organic-inorganic composite particles may be crushed when mixed with the resin or the like.

The organic-inorganic composite particles thus obtained are unlikely to coagulate in a dry state, and even if the organic-inorganic composite particles appear coagulated in a dry state, the coagulation (formation of secondary particles) will be reliably prevented in the particle-dispersed resin composition and the particle-dispersed resin molded article, and therefore the organic-inorganic composite particles are dispersed substantially uniformly in the resin as primary particles.

In other words, the organic-inorganic composite particles have at least a configuration that does not allow the inorganic particles to contact with each other by steric hindrance of the organic group.

In the organic-inorganic composite particles, the proportion of the surface area of the organic group relative to the surface area of the inorganic particles, or in other words, the surface coverage by the organic group in the organic-inorganic composite particles (=(surface area of organic group/surface area of inorganic particles)×100) is, for example, 30% or greater and preferably 60% or greater and usually 200% or less.

To calculate the surface coverage, first, the shape of the inorganic particles is checked with a transmission electron microscope (TEM), the average particle size is then calculated, and the specific surface area of the particles is calculated from the shape of the inorganic particles and the average particle size. Alternatively, the proportion of the organic group in the organic-inorganic composite particles is calculated from the weight change as a result of the organic-inorganic composite particles being heated to 800° C. with a differential thermal balance (TG-DTA). After that, the amount of the organic group per particle is calculated from the molecular weight of the organic group, the particle density and the average volume. Then, the surface coverage is determined from the calculated results.

In the case where at least the surface coverage is high and the organic group of the organic-inorganic composite particles has a length sufficient to cancel the electric charge of the inorganic particles, the type of solvent (medium) for dispersing the organic-inorganic composite particles can be controlled (designed or managed) according to the type of organic group.

The organic-inorganic composite particles obtained in the above-described manner can be subjected to wet classification.

That is, a solvent is added to the organic-inorganic composite particles, and the resulting mixture is stirred and allowed to stand still, and thereafter separated into a supernatant and a precipitate. The solvent varies depending on the type of organic groups, but for example, the same solvents as those listed above can be used. Preferably, the solvent is a hydroxyl group-containing aliphatic hydrocarbon, a carbonyl group-containing aliphatic hydrocarbon, an aliphatic hydrocarbon, a halogenated aliphatic hydrocarbon or an aqueous pH adjusting solution.

After that, the supernatant is recovered, and it is thereby possible to obtain organic-inorganic composite particles having a small particle size.

With the wet classification, the average particle size of the resulting organic-inorganic composite particles (primary particles) can be adjusted to, for example, 1 nm to 450 nm, preferably 3 nm to 200 nm and more preferably 3 nm to 100 nm.

It is also possible to select the resin and the organic-inorganic composite particles such that the solubility parameters (SP values) thereof satisfy a predetermined relationship.

Specifically, the resin and the organic-inorganic composite particles are selected so as to attain a predetermined SP difference (ASP, specifically, the absolute value of the difference between the solubility parameter of resin ($SP_{RESIN}$ value) and the solubility parameter of organic-inorganic composite particles ($SP_{PARTICLE}$ value)).

Preferable hydrophilic groups included in both the functional group and the organic group are a carboxyl group and a hydroxyl group, and preferable hydrophobic groups included in both the functional group and the organic group are a hydrocarbon group and the like. The affinity between the organic-inorganic composite particles and the resin can be enhanced as a result of both the functional group and the organic group having any of the above groups having the same property (hydrophilicity or hydrophobicity).

Specifically, in order to prepare a particle-dispersed resin composition, for example, a solvent, organic-inorganic composite particles and a resin are blended, and the resulting mixture is stirred (solution preparation). The thus-prepared particle-dispersed resin composition is a varnish (solution) containing a solvent.

There is no particular limitation on the solvent, and the solvent can be any of the solvents used in washing described above. Other examples include alicyclic hydrocarbons such as cyclopentane and cyclohexane; esters such as ethyl acetate; polyols such as ethylene glycol and glycerol; nitrogen-containing compounds such as N-methylpyrrolidone, pyridine, acetonitrile and dimethylformamide; acryl-based monomers such as isostearyl acrylate, lauryl acrylate, isoboronyl acrylate, butyl acrylate, methacrylate, acrylic acid, tetrahydrofurfuryl acrylate, 1,6-hexanediol diacrylate, 2-hydroxyethyl acrylate, 4-hydroxybutyl acrylate, phenoxyethyl acrylate, and acryloylmorpholine; vinyl group-containing monomers such as styrene and ethylene; epoxy-containing monomers such as bisphenol A epoxy; and the like.

These solvents can be used singly or in a combination of two or more. A halogenated aliphatic hydrocarbon and an aqueous pH adjusting solution are preferable.

Specifically, in order to prepare a particle-dispersed resin composition, first, the above solvent and a resin are blended so as to dissolve the resin in the solvent to prepare a resin solution. After that, the resin solution is blended with organic-inorganic composite particles, and the resulting mixture is stirred to prepare a particle-dispersed resin composition (first preparation method).

The proportion of resin per 100 parts by mass of the resin solution is, for example, 40 parts by mass or less, preferably 35 parts by mass or less, and more preferably 30 parts by mass or less, and usually 1 part by mass or greater. If the proportion of resin exceeds the above range, the solubility of resin may be low.

The proportion of the organic-inorganic composite particles per 100 parts by mass of the solids content (resin) of the resin solution is, for example, 1 to 1000 parts by mass, preferably 5 to 500 parts by mass and more preferably 10 to 300 parts by mass. Also, the proportion of the organic-inorganic composite particles per 100 parts by mass of the total amount of the resin solution (the total amount of the resin and the solvent) is, for example, 0.1 to 300 parts by mass, preferably 1 to 200 parts by mass and more preferably 3 to 100 parts by mass.

Also, the particle-dispersed resin composition can also be prepared by blending a solvent and organic-inorganic composite particles to disperse the organic-inorganic composite particles in the solvent to prepare a particle dispersion, and then blending the particle dispersion with a resin and stirring the resulting mixture (second preparation method).

In the particle dispersion, the organic-inorganic composite particles are dispersed in the solvent as primary particle.

The proportion of the organic-inorganic composite particles per 100 parts by mass of the particle dispersion is, for example, 0.1 to 70 parts by mass, preferably 0.2 to 60 parts by mass, and more preferably 0.5 to 50 parts by mass.

The proportion of resin per 100 parts by mass of the solids content (organic-inorganic composite particles) of the particle dispersion is, for example, 10 to 10000 parts by mass, preferably 20 to 2000 parts by mass and more preferably 40 to 1000 parts by mass.

Furthermore, the particle-dispersed resin composition can also be prepared by, for example, blending a solvent, organic-inorganic composite particles and a resin simultaneously and stirring the resulting mixture (third preparation method).

The proportions of respective components per 100 parts by mass of the total amount of the particle-dispersed resin composition are as follows: the proportion of the organic-inorganic composite particles is, for example, 0.1 to 50 parts by mass, preferably 1 to 40 parts by mass and more preferably 3 to 30 parts by mass; and the proportion of resin is, 40 parts by mass or less, preferably 35 parts by mass or less and more preferably 30 parts by mass or less, and unusually 1 part by mass or greater. The proportion of the solvent is the remainder obtained by excluding the organic-inorganic composite particles and the resin from the particle-dispersed resin composition.

The particle-dispersed resin composition can also be prepared by, first, preparing a resin solution and a particle dispersion in a separate manner, and then blending and stirring the resin solution and the particle dispersion (fourth preparation method).

The proportion of resin in the resin solution is the same as those shown in the first preparation method described above.

The proportion of the organic-inorganic composite particles in the particle dispersion is the same as those shown in the second preparation method described above.

The resin solution and the particle dispersion are blended such that the proportion of resin relative to the organic-inorganic composite particles in terms of mass is, for example, 99:1 to 10:90, preferably 95:5 to 20:80 and more preferably 90:10 to 30:70.

Furthermore, the particle-dispersed resin composition can also be prepared without the use of a solvent by, for example, melting a resin by application of heat and blending the resin with organic-inorganic composite particles (fifth preparation method).

The thus-prepared particle-dispersed resin composition is a melt of the particle-dispersed resin composition which does not include a solvent.

The heating temperature is, in the case where the resin is a thermoplastic resin, greater than or equal to the melting temperature of the resin, specifically, 200 to 350° C. In the case where the resin is a thermosetting resin, the heating temperature is a temperature at which the resin is B-staged, for example, 85 to 140° C.

The proportion of resin relative to the organic-inorganic composite particles in terms of mass is, for example, 99:1 to 10:90, preferably 95:5 to 20:80 and more preferably 90:10 to 30:70.

In the particle-dispersed resin composition obtained by any of the above-described preparation methods, the organic-inorganic composite particles are uniformly dispersed in the resin. Specifically, in the particle-dispersed resin composition, the organic-inorganic composite particles are dispersed as primary particles in the resin (without substantial coagulation).

After that, the obtained particle-dispersed resin composition is applied to, for example, a known support plate to form a coating, and the coating is dried, whereby a particle-dispersed resin molded article as a film is molded.

The particle-dispersed resin composition is applied by using, for example, a known application method such as spin coating or bar coating. Simultaneously with or immediately after application of the particle-dispersed resin composition, the solvent is removed by volatilization. If necessary, the solvent can be dried by application of heat after application of the particle-dispersed resin composition.

The thickness of the obtained film can be set as appropriate according to the use and purpose, and the thickness is, for example, 0.1 to 2000 µm, preferably 0.5 to 1000 µm and more preferably 1.0 to 500 µm.

The particle-dispersed resin molded article as a film can also be molded by a melt molding method in which the particle-dispersed resin composition is extruded by an extruding machine or the like.

The particle-dispersed resin molded article can also be molded as a block (mass) by injecting the particle-dispersed resin composition into a metal mold or the like and thereafter subjecting the resultant to, for example, heat molding such as heat pressing.

In any of the particle-dispersed resin molded articles molded in the above-described manner, the organic-inorganic composite particles are dispersed as primary particles in the resin.

That is, with a simple method in which a resin and organic-inorganic composite particles are blended such that the organic-inorganic composite particles are dispersed as primary particles in the resin by steric hindrance of the organic group, the organic-inorganic composite particles can be easily and uniformly dispersed in the resin in the particle dispersion and the particle-dispersed resin molded article. In short, with such a very simple operation, the organic-inorganic composite particles can be dispersed as primary particles in the resin. Also, the organic-inorganic composite particles can be dispersed as primary particles in the resin regardless of the type of inorganic particles with the above-described simple operation.

Accordingly, the particle-dispersed resin compositions and the particle-dispersed resin molded articles obtained by the above-described methods have excellent clarity because the organic-inorganic composite particles are uniformly dispersed in the resin, and therefore they can be suitably used in various industrial applications including optical applications.

Third Embodiment

Embodiment corresponding to the inventions of catalyst particles, a catalyst solution, a catalyst composition and a catalyst molded article, which are included in the third group of inventions The catalyst particles of the present invention contain inorganic particles with a catalytic action and an organic group that binds to the surface of the inorganic particles.

The inorganic particles preferably have a photocatalytic action that exerts a catalytic action for a gas and/or a liquid (described later) by absorbing light.

Such catalyst particles can be obtained by, for example, surface-treating an inorganic substance and/or a complex thereof with an organic compound.

The inorganic substance include a metal composed of a metal element such as a main group element or a transition element, a nonmetal composed of a nonmetal element such as boron or silicon, an inorganic compound containing a metal element and/or a nonmetal, or the like.

Examples of the metal element and the nonmetal element include elements that are located on the left side and the lower side of a border line that is assumed to pass through boron (B) of the IIIB group, silicon (Si) of the IVB group, arsenic (As) of the VB group, tellurium (Te) of the VIB group and astatine (At) of the VIIB group on the long-form periodic table (IUPAC, 1989), as well as the elements that are located on the border line, and the same elements as those listed in the second embodiment.

The inorganic compound can be, for example, a hydrogen compound, a hydroxide, a nitride, a halide, an oxide, a carbonate, a sulfate, a nitrate, an acetate, a formate, a sulfide, a carbide, a phosphorus compound, or the like. The inorganic compound may be a composite compound such as, for example, an oxynitride or a composite oxide.

Among the inorganic substances listed above, a preferable example is an inorganic compound, and more preferable examples are an oxide, a sulfate, a nitrate, an acetate, a formate and a composite oxide. An oxide is particularly preferable.

Examples of the oxide include metal oxides, and preferable examples include titanium oxide (titanium dioxide, titanium oxide (IV), titania: $TiO_2$), tungsten oxide (tungsten trioxide, tungsten oxide (VI), $WO_3$), cerium oxide (cerium dioxide, cerium oxide (IV), ceria: $CeO_2$), zirconium oxide (zirconium dioxide, zirconium oxide (IV), zirconia: $ZrO_2$), tantalum oxide (tantalum dioxide, tantalum oxide (IV), $TaO_2$) and the like.

The arrangement of atoms in an oxide is not particularly limited, and can be, for example, either crystalline or non-crystalline (amorphous).

The oxides can be used singly or in a combination of two or more

The sulfate is a compound consisting of a sulfate ion ($SO_4^{2-}$) and a metal cation (more specifically, a compound formed by substitution of the hydrogen atoms of sulfuric acid ($H_2SO_4$) with a metal), and the metal element contained in the sulfate can be, for example, a group IVA element or a group IB element. Ti and Cu are preferable.

Specifically, the sulfate is preferably titanium sulfate, zirconium sulfate, hafnium sulfate, copper sulfate, silver sulfate or the like. Titanium sulfate and copper sulfate are more preferable.

The sulfates can be used singly or in a combination of two or more.

The nitrate is a compound consisting of a nitrate ion ($NO_3^-$) and a metal cation (more specifically, a compound formed by substitution of the hydrogen atom of nitric acid ($HNO_3$) with a metal), and the metal element contained in the nitrate can be, for example, a group VIII element. Pd and Pt are preferable.

Specifically, preferable nitrates are iron nitrate, cobalt nitrate, nickel nitrate, ruthenium nitrate, rhodium nitrate, palladium nitrate, osmium nitrate, iridium nitrate and the like. Palladium nitrate and platinum nitrate are more preferable.

The nitrates can be used singly or in a combination of two or more.

The acetate is a compound consisting of an acetate ion ($CH_3COO^-$) and a metal cation (more specifically, a compound formed by substitution of the hydrogen atom of the carboxyl group (—COOH) in acetic acid with a metal), and the metal element contained in the acetate can be, for example, a group VIII element. Ni is preferable.

Specifically, a preferable acetate is nickel acetate.

The acetates can be used singly or in a combination of two or more.

The formate is a compound consisting of a formate ion ($HCOO^-$) and a metal cation (more specifically, a compound formed by substitution of the hydrogen atom of the carboxyl group (—COOH) in formic acid with a metal), and the metal element contained in the formate can be, for example, a group IB element. Cu is preferable.

Specifically, a preferable formate is copper formate.

The formates can be used singly or in a combination of two or more.

The composite oxide is a compound consisting of oxygen and a plurality of elements, and the plurality of elements is a combination of at least two elements selected from the elements other than oxygen contained in the oxides listed above, the group I elements, and the group II elements.

Examples of the group I elements include alkali metals such as Li, Na, K, Rb, and Cs. Examples of the group II elements include the same alkaline earth metals as those listed in the second embodiment.

Examples of the combination of a plurality of elements include combinations that include at least a group II element such as a combination of a group II element and a group IVB element, a combination of a group II element and a group VIII element, a combination of a group II element and a group IVA element, and a combination of a group II element and a group VA element; combinations that include at least a group I element such as a combination of a group I element and a group IVA element, a combination of a group I element, a group IVA element and a lanthanide series element, and a combination of a group I element and a group VA element; a combination of a group VA element and a group IIB element; and the like.

Examples of the composite oxide containing at least a group II element include alkaline earth metal titanates, alkaline earth metal zirconates, alkaline earth metal ferrates, alkaline earth metal stannates, alkaline earth metal niobates and the like.

Examples of the composite oxide containing at least a group I element include alkali metal titanates, alkali metal zirconates, alkali metal vanadates, alkali metal niobates and the like.

Examples of the composite oxide containing a group VA element and a group IIB group element include metal niobates and the like.

Preferable composite oxides are alkaline earth metal titanates, alkali metal titanates, alkaline earth metal niobates, alkali metal niobates and metal niobates.

Examples of alkaline earth metal titanates include beryllium titanate ($BeTiO_3$), magnesium titanate ($MgTiO_3$), calcium titanate ($CaTiO_3$), strontium titanate ($SrTiO_3$), barium titanate ($BaTiO_3$), barium tetratitinate ($BaTi_4O_9$), radium titanate ($RaTiO_3$) and the like.

Examples of alkali metal titanates include sodium hexatitanate ($Na_2Ti_6O_{13}$), potassium lanthanum titanate ($K_2La_2Ti_3O_{10}$) and the like.

Examples of alkaline earth metal niobates include strontium diniobate ($Sr_2Nb_2O_7$) and the like.

Examples of alkali metal niobates include potassium hexaniobate ($K_4Nb_6O_{17}$) and the like.

Examples of metal niobates include zinc diniobate ($ZnNb_2O_6$) and the like.

The composite oxides can be used singly or in a combination of two or more.

The complex contains a central atom and/or a central ion and a ligand that coordinates thereto.

Examples of the central atom include the same metal elements as those listed above. Preferable examples include a group IVA element, a group VIII element and a group IVB element. More preferable examples include Ti, Zr, Fe, Ni, Ru, Sn and the like.

Examples of the central ion include cations of the metal elements listed above.

Examples of the ligand include coordinating compounds such as carboxylic acid, hydroxycarboxylic acid and acetylacetone; coordinating ions such as cations and hydroxide ions of the above coordinating compounds; and the like.

Examples of the carboxylic acid include dicarboxylic acids such as oxalic acid, succinic acid, phthalic acid, and the like.

Examples of the hydroxycarboxylic acid include monohydroxymonocarboxylic acids (specifically, α-monohydroxycarboxylic acids) such as 2-hydroxyoctanoic acid, lactic acid and glycolic acid; monohydroxydicarboxylic acids such as malic acid; monohydroxytricarboxylic acids such as citric acid; and the like.

The coordination number is, for example, 1 to 6 and preferably 1 to 3.

The complex can be obtained by preparation from a metal element and a ligand described above.

The inorganic substance (specifically, oxide, composite oxide) and the complex can be formed (prepared) as salts and/or hydrates. Examples of the salts include salts with cations such as ammonium ions.

The inorganic substances and the complexes listed above can be used singly or in a combination of two or more.

In the case where an inorganic substance and/or a complex are used in combination, the combination of an inorganic substance and/or a complex can be, for example, a combination of a plurality of types of inorganic substances (first combination) or a combination of an inorganic substance and a complex (second combination).

The first combination can be, for example, a combination of a plurality of types of inorganic substances. Specific examples include a combination of an oxide (first inorganic substance) and at least one inorganic substance (second inorganic substance) selected from the group consisting of metals, sulfates, nitrates and formates.

More specifically, examples of the first combination include a combination of a metal oxide and a metal (group VIII element), a combination of a metal oxide and a sulfate, and a combination of a metal oxide and a formate. Specific examples of the first combination include a combination of tungsten oxide and palladium, a combination of tungsten oxide and platinum, a combination of tungsten oxide and copper sulfate, and a combination of tungsten oxide and copper formate.

Examples of the second combination include a combination of a complex whose ligand is hydroxycarboxylic acid and a metal, a combination of a complex whose ligand is hydroxycarboxylic acid, a hydroxide and an acetate, and a combination of a complex whose ligand is hydroxycarboxylic acid, a hydroxide and a complex whose ligand is acetylacetone.

Specific examples of the second combination include a combination of a titanium complex whose central atom is titanium and whose ligand is 2-hydroxyoctanoic acid and platinum, a combination of a titanium complex whose central atom is titanium and whose ligand is 2-hydroxyoctanoic acid, strontium hydroxide and nickel acetate, and a combination of a titanium complex whose central atom is titanium and whose ligand is 2-hydroxyoctanoic acid, strontium hydroxide and a ruthenium complex whose central atom is ruthenium and ligand is acetylacetone.

The organic compound is, for example, an organic group-introducing compound that introduces (disposes) an organic group on the surface of inorganic particles. Specifically, the organic compound contains a binding group capable of binding to the surface of inorganic particles and an organic group. In other words, the organic group is bound to the surface of inorganic particles via a binding group.

The binding group is selected as appropriate according to the type of inorganic particles and examples thereof include functional groups such as phosphoric acid group (—PO(OH)$_2$, phosphono group), phosphoric acid ester group (phosphonate group), carboxyl group, carboxylic acid ester group (carboxy ester group), amino group, sulfo group, hydroxyl group, thiol group, epoxy group, isocyanate group, nitro group, azo group, silyloxy group, imino group, aldehyde group (acyl group), nitrile group and vinyl group (polymerizable group). Preferable examples include phosphoric acid group, phosphoric acid ester group, carboxyl group, amino group, sulfo group, hydroxyl group, thiol group, epoxy group, azo group, vinyl group and the like. More preferable examples include phosphoric acid group, phosphoric acid ester group, carboxyl group, amino group and hydroxyl group.

Phosphoric acid ester groups are, for example, alkyl ester groups of phosphoric acid (specifically, orthophosphoric acid), or in other words, alkoxy phosphonyls, and can be represented by the following formula (1):

$$—PO(OR)_n H_{2-n} \qquad (1)$$

where R is an alkyl group having 1 to 3 carbon atoms, and n is an integer of 1 or 2.

In the above formula (1), the alkyl group represented by R is preferably methyl or ethyl.

n is preferably 2.

Examples of phosphoric acid ester groups include dialkyl phosphate esters such as dimethyl phosphate esters (dimethoxy phosphonyl: —PO(OCH$_3$)$_2$), diethyl phosphate esters (diethoxy phosphonyl: —PO(OC$_2$H$_5$)$_2$), dipropyl phosphate esters (dipropoxy phosphonyl: —PO(OC$_3$H$_7$)$_2$); monoalkyl phosphate esters such as monomethyl phosphate esters (monomethoxy phosphonyl: —PO(OCH$_3$)H), monoethyl phosphate esters (monoethoxy phosphonyl: —PO(O$_2$CH$_5$)H) and monopropyl phosphate esters (monopropoxy phosphonyl: —PO(O$_3$CH$_7$)H); and the like. Dialkyl phosphate esters are preferable.

The binding group is selected as appropriate according to the type of inorganic particles. Specifically, when the inorganic particles contain titanium oxide, for example, a phosphoric acid group and/or a phosphoric acid ester group are selected. When the inorganic particles contain tungstic acid (described later), for example, an amino group is selected. When the inorganic particles contain strontium titanate, for example, a carboxylic acid, a phosphoric acid group and/or a phosphoric acid ester group are selected.

One or more of these binding groups are contained in the organic compound. Specifically, the binding group is bound to a terminal or a side chain of the organic group.

The organic group includes, for example, a hydrocarbon group such as an aliphatic group, an alicyclic group, an araliphatic group or an aromatic group, or the like. Examples of the hydrocarbon group include the same hydrocarbon groups as those listed in the second embodiment.

The organic group is a hydrophobic group for imparting hydrophobicity to the surface of inorganic particles.

Accordingly, the organic compounds containing a hydrophobic group described above are used as hydrophobic organic compounds for hydrophobic treatment of inorganic particles.

Specific examples of such hydrophobic organic compounds in the case where the binding group is a phosphoric acid group include aliphatic group-containing phosphonic acids including saturated aliphatic group-containing phosphonic acids (saturated phosphonic acids) such as methylphosphonic acid, hexyl phosphonic acid, octylphosphonic acid and decylphosphonic acid, and the like. Other examples of the hydrophobic organic compounds include alicyclic group-containing phosphonic acids (alicyclic phosphonic acids) such as cyclohexyl phosphonic acid; araliphatic group-containing phosphonic acids (araliphatic phosphonic acids) such as 6-phenylhexyl phosphonic acid; aromatic group-containing phosphonic acids (aromatic phosphonic acids) such as phenyl phosphonic acid and toluenephosphonic acid; and the like.

Specific examples of hydrophobic organic compounds in the case where the binding group is a phosphoric acid ester group include aliphatic group-containing phosphonate esters including saturated aliphatic group-containing phosphonate esters (saturated phosphonic acid dialkyl esters) such as hexyl phosphonic acid diethyl ester, octylphosphonic acid diethyl ester and decylphosphonic acid diethyl ester, and the like. Other examples of the hydrophobic organic compounds include alicyclic group-containing phosphonic acid alkyl esters (alicyclic phosphonic acid dialkyl esters) such as cyclohexanephosphonic acid diethyl ester; araliphatic group-containing phosphonate esters (araliphatic phosphonic acid dialkyl esters) such as 6-phenylhexyl phosphonic acid diethyl ester; aromatic group-containing phosphonic acid alkyl esters (aromatic phosphonic acid dialkyl esters) such as phenyl phosphonic acid diethyl ester and toluenephosphonic acid diethyl ester; and the like.

Specific examples of hydrophobic organic compounds in the case where the binding group is a carboxyl group include aliphatic group-containing carboxylic acids (fatty acids) such as hexanoic acid, octanoic acid and decanoic acid; araliphatic group-containing carboxylic acids such as 6-phenylhexanoic acid; and the like.

Specific examples of hydrophobic organic compounds in the case where the binding group is an amino group include aliphatic group-containing amines such as hexylamine, octylamine and decylamine; and the like.

Alternatively, the organic compound can also be used as a hydrophilic organic compound for hydrophilic treatment of inorganic particles. In this case, the organic group contained in the hydrophilic organic compound includes any of the above hydrocarbon groups and a hydrophilic group that binds to the hydrocarbon group.

Specifically, in the hydrophilic organic compound, the hydrophilic group is bound to a terminal (the terminal (the other terminal) opposite the terminal that is bound to the binding group (one terminal)) or a side chain of the hydrocarbon group.

The hydrophilic group is a functional group having a polarity (or in other words, polar group), and examples thereof include a phosphoric acid group, a phosphoric acid ester group, a hydroxyl group, a carboxyl group, an amino group, a sulfo group, a carbonyl group, a cyano group, a nitro group, an aldehyde group, a thiol group and the like.

Preferable examples of the hydrophilic group include a phosphoric acid group, phosphoric acid ester group, a hydroxyl group, a carboxyl group, a carboxylic acid ester group (carboxy ester group), an amino group, and a sulfo group. More preferable examples include a phosphoric acid group and a phosphoric acid ester group.

One or more of the hydrophilic groups are contained in the hydrophilic organic compound. In the case where a plurality of hydrophilic groups are contained in the hydrophilic organic compound, for example, an amino group and a sulfo group are used in combination.

Examples of the organic group containing a phosphoric acid group (phosphoric acid group-containing organic group) include phosphonosaturated aliphatic groups (phosphonoaliphatic groups) such as 3-phosphonopropyl, 6-phosphonohexyl and 10-phosphonodecyl; phosphonoaraliphatic groups such as 6-phosphonophenylhexyl; and the like.

Examples of the organic group containing a phosphoric acid ester group (phosphoric acid ester group-containing organic group) include alkoxyphosphonyl hydrocarbon groups including alkoxyphosphonyl saturated aliphatic groups (alkoxyphosphonyl aliphatic groups) such as 3-(diethoxy-phosphonyl)propyl, 6-(diethoxy-phosphonyl)hexyl and 10-(diethoxy-phosphonyl)decyl; and alkoxyphosphonyl araliphatic groups such as 6-(diethoxy-phosphonyl)phenylhexyl.

Examples of the organic group containing a hydroxyl group (hydroxy group-containing organic group) include hydroxy aliphatic groups such as 10-hydroxydecyl; and the like.

Examples of the organic group containing a carboxyl group (carboxyl group-containing organic group) include carboxysaturated aliphatic groups (carboxyaliphatic groups) such as 2-carboxyethyl, 3-carboxypropyl, 4-carboxybutyl, 5-carboxypentyl, 6-carboxyhexyl, 7-carboxyheptyl, 8-carboxyoctyl, 9-carboxynonyl and 10-carboxydecyl; and the like.

Examples of the organic group containing a carboxylic acid ester group (carboxy ester group-containing organic group) include carboxy ester aliphatic groups such as 2-(methoxy-carbonyl)ethyl, 3-(methoxy-carbonyl)propyl, 4-(methoxy-carbonyl)butyl, 5-(methoxy-carbonyl)pentyl, 6-(methoxy-carbonyl)hexyl, 7-(methoxy-carbonyl)heptyl, 8-(methoxy-carbonyl)octyl, 9-(methoxy-carbonyl)nonyl and 10-(methoxy-carbonyl)decyl.

Examples of the organic group containing an amino group and a sulfo group (amino group- and sulfo group-containing organic group) include amino/sulphoaliphatic groups such as 2-amino-3-sulfopropyl.

Specifically, examples of the organic compound containing a hydrophilic group include a phosphoric acid group-containing organic compound, a phosphoric acid ester group-containing organic compound, a hydroxyl group-containing organic compound, a carboxyl ester group-containing organic compound, an amino group-containing organic compound, a sulfo group-containing organic compound, a carbonyl group-containing organic compound, a cyano group-containing organic compound, a nitro group-containing organic compound, an aldehyde group-containing organic compound, a thiol group-containing organic compound and the like.

Preferable examples include a phosphoric acid group-containing organic compound, a phosphoric acid ester group-containing organic compound, a hydroxyl group-containing organic compound and a carboxy ester group-containing organic compound.

Examples of the phosphoric acid group-containing organic compound in the case where the binding group is a phosphoric acid group and the polar group is a carboxyl group (more specifically, in the case where the phosphoric acid group is bound to the inorganic particles containing titanium oxide) include monophosphonocarboxylic acids, and specific examples include 3-phosphono propionic acid, 6-phosphonohexanoic acid, 10-phosphono decanoic acid, 6-phosphonophenylhexanoic acid, and the like.

Examples of the phosphoric acid ester group-containing organic compound in the case where the binding group is a phosphoric acid ester group and the polar group is a carboxy ester group (more specifically, in the case where the phosphoric acid ester group is bound to the inorganic particles containing titanium oxide) include 3-(diethoxy-phosphonyl)ethyl propionic acid ester, 6-(diethoxy-phosphonyl)hexanoic acid ethyl ester, 10-(diethoxy-phosphonyl)decanoic acid ethyl ester and the like. The above-listed phosphoric acid ester group-containing organic compounds are also regarded as carboxy ester group-containing organic compounds.

Examples of the phosphoric acid ester group-containing organic compound in the case where the binding group is a phosphoric acid ester group and the polar group is a hydroxyl group (more specifically, in the case where the phosphoric acid ester group is bound to the inorganic particles containing titanium oxide) include phosphoric acid ester group- and hydroxyl group-containing compounds such as 10-(diethoxy-phosphonyl)decanol; and the like. The phosphoric acid ester group- and hydroxyl group-containing compounds are also regarded as hydroxyl group-containing compounds.

The same or mutually different organic groups may be used.

In the case where mutually different organic groups are used, or in other words, the organic group contains a plurality of different types of organic groups, a plurality of homologous organic groups and/or a plurality of heterologous organic groups are contained.

Examples of the homologous organic groups include a combination of a plurality of aliphatic groups, a combination of a plurality of phosphonoaliphatic groups, a combination of a plurality of alkoxyphosphonyl aliphatic groups, a combination of a plurality of carboxyaliphatic groups, a combination of a plurality of carboxy ester aliphatic groups, and the like.

The combination of a plurality of aliphatic groups can be, for example, a combination of a saturated aliphatic group having less than 10 carbon atoms and a saturated aliphatic group having 10 or more carbon atoms. Specific examples include a combination of octyl and decyl, and a combination of methyl and decyl. Another example of the combination of a plurality of aliphatic groups is a combination of a saturated aliphatic group having less than 7 carbon atoms and a saturated aliphatic group having 7 or more carbon atoms. Specific examples include a combination of methyl and octyl, a combination of hexyl and decyl, and a combination of hexyl and octyl. Another example is a combination of a saturated aliphatic group having less than 5 carbon atoms and a saturated aliphatic group having 5 or more carbon atoms. A specific example is a combination of methyl and hexyl.

Examples of the combination of a plurality of phosphonoaliphatic groups include a combination of a phosphonoaliphatic group having less than 5 carbon atoms and a phosphonoaliphatic group having 5 or more carbon atoms. A specific example is a combination of 3-phosphonopropyl and 6-phosphonohexyl.

Examples of the combination of a plurality of alkoxyphosphonyl aliphatic groups include a combination of an alkoxyphosphonyl aliphatic group having less than 10 carbon atoms and an alkoxyphosphonyl aliphatic group having 10 or more carbon atoms. Specific examples include a combination of 3-(diethoxy-phosphonyl)propyl and 6-(diethoxy-phosphonyl)hexyl, and a combination of 3-(diethoxy-phosphonyl)propyl and 10-(diethoxy-phosphonyl)decyl.

Examples of the combination of a plurality of carboxyaliphatic groups include a carboxyaliphatic group having less than 5 carbon atoms and a carboxyaliphatic group having 5 or more carbon atoms. A specific example is a combination of 2-carboxyethyl and 5-carboxypropyl.

The combination of a plurality of carboxy ester aliphatic groups can be, for example, a combination of a carboxy ester aliphatic group having less than 7 carbon atoms and a carboxy ester aliphatic group having 7 or more carbon atoms. Specific examples include a combination of 2-(methoxy-carbonyl)ethyl and 5-(methoxy-carbonyl)heptyl, and a combination of 2-(methoxy-carbonyl)ethyl and 9-(methoxy-carbonyl)nonyl.

When the organic group contains a plurality of homologous organic groups, a plurality of organic groups having different sizes (lengths or/and dimensions, or in other words, the number of carbon atoms) are contained in the organic group. Accordingly, in a space between adjacent larger organic groups, a resin molecule enters a gap (pocket) formed in accordance with the smaller organic group, and the interaction between the larger organic group and the resin molecule can be enhanced. As a result, the dispersibility of the catalyst particles can be enhanced.

Examples of the heterologous organic groups include a combination of two different groups selected from the group consisting of an aliphatic group, an alicyclic group, an araliphatic group, an aromatic group, a phosphonoaliphatic group, a phosphonoaraliphatic group, an alkoxyphosphonyl aliphatic group, an alkoxyphosphonyl araliphatic group, a hydroxy aliphatic group, a carboxyaliphatic group, a carboxyaraliphatic group, a carboxyaromatic group, a carboxy ester aliphatic group and an amino/sulphoaliphatic group.

Preferable examples of the heterologous organic groups include a combination of an aliphatic group and an araliphatic group, a combination of an aliphatic group and a carboxyaliphatic group, a combination of an aliphatic group and a carboxy ester aliphatic group, and a combination of a carboxyaliphatic group and a carboxy ester aliphatic group.

The combination of an aliphatic group and an araliphatic group can be, for example, a combination of a saturated aliphatic group having 6 to 12 carbon atoms and an araliphatic group having 7 to 15 carbon atoms, and a specific example is a combination of octyl and phenylhexyl.

The combination of an aliphatic group and a carboxyaliphatic group can be, for example, a combination of an aliphatic group having less than 6 carbon atoms and a carboxyaliphatic group having less than 6 carbon atoms. Specific examples include a combination of methyl and 2-carboxyethyl and a combination of methyl and 5-carboxypentyl. Another example is a combination of an aliphatic group having 6 or more carbon atoms and a carboxyaliphatic group having less than 6 carbon atoms, and specific examples include a combination of octyl and 2-carboxyethyl and a combination of octyl and 5-carboxypentyl.

The combination of an aliphatic group and a carboxy ester aliphatic group can be, for example, a combination of an aliphatic group having less than 6 carbon atoms and a carboxy ester aliphatic group having less than 6 carbon atoms, and a specific example is a combination of methyl and 2-(methoxy-carbonyl)ethyl.

Also, the combination of an aliphatic group and a carboxy ester aliphatic group can be, for example, a combination of an aliphatic group having less than 6 carbon atoms and a carboxy ester aliphatic group having 6 or more carbon atoms, and a specific example is a combination of methyl and 9-(methoxy-carbonyl)nonyl.

Another example of the combination of an aliphatic group and a carboxy ester aliphatic group is a combination of an aliphatic group having 7 or more carbon atoms and a carboxy ester aliphatic group having 7 or more carbon atoms, and specific examples include a combination of octyl and 9-(methoxy-carbonyl)nonyl and a combination of decyl and 9-(methoxy-carbonyl)nonyl.

Another example of the combination of an aliphatic group and a carboxy ester aliphatic group is a combination of an aliphatic group having 6 or more carbon atoms and a carboxy ester aliphatic group having less than 6 carbon atoms, and a specific example is a combination of decyl and 2-(methoxy-carbonyl)ethyl.

The combination of a carboxyaliphatic group and a carboxy ester aliphatic group can be, for example, a combination of a carboxyaliphatic group having less than 5 carbon atoms and a carboxy ester aliphatic group having 6 or more carbon atoms, and a specific example is a combination of 2-carboxyethyl and 9-(methoxy-carbonyl)nonyl.

As long as the organic group contains a plurality of heterologous organic groups, when the resin is prepared as a mixture of a plurality of resin components, the organic group can exert excellent compatibility with the resin molecules of the respective resin components having excellent compatibility with the organic groups of the respective groups. Accordingly, the interaction between the organic groups and the resin molecules of the resin components can be enhanced. As a result, the dispersibility of the catalyst particles can be enhanced.

The organic groups are present on the surface of inorganic particles in the catalyst particles. Specifically, the organic groups extend from the surface of inorganic particles toward the outside of the inorganic particles via a binding group.

The catalyst particles are produced by subjecting an inorganic substance and/or a complex and an organic compound to a reaction treatment, preferably to a high temperature treatment.

The high temperature treatment is carried out in a solvent. As the solvent, for example, water and any of the organic compounds listed above can be used.

Specifically, the catalyst particles are obtained by surface-treating (hydrothermal synthesis: hydrothermal reaction) an inorganic substance and/or a complex with an organic compound in hot high pressure water, or surface-treating an inorganic substance and/or a complex in a hot organic compound. In other words, the catalyst particles are obtained by surface-treating the surface of (inorganic particles formed of) the inorganic substance and/or the complex with any of the organic compounds containing an organic group listed above.

In the hydrothermal synthesis, for example, the inorganic substance and the organic compound are reacted under high-temperature and high-pressure conditions in the presence of water (first hydrothermal synthesis).

Preferable examples of the inorganic substance subjected to the first hydrothermal synthesis include an oxide, a sulfate, a nitrate, a formate, a hydroxide and a metal.

The inorganic substances subjected to the first hydrothermal synthesis can be used singly or in combination. In the case where the inorganic substances are used in combination, the first combination mentioned above is used.

To carry out the first hydrothermal synthesis, first, a reaction system is prepared under high-temperature and high-pressure conditions by placing an inorganic substance, an organic compound and water in a pressure-resistant airtight container and heating them.

The proportions of respective components are the same as those (in terms of mass, volume, mol, and the like) shown in the second embodiment.

Particularly when the inorganic substances are used in combination, specifically, when the first combination is used, the amount of the first inorganic substance is greater than that of the second inorganic substance when they are blended. Specifically, the proportion of the second inorganic substance per 100 parts by mass of the first inorganic substance is, for example, 20 parts by mass or less, preferably 10 parts by mass or less, and more preferably 5 parts by mass or less, and usually 0.01 parts by mass or greater. In other words, the proportion of the second inorganic substance per mol of the first inorganic substance is, for example, 0.2 mol or less, preferably 0.1 mol or less, and more preferably 0.05 mol or less, and usually 0.0001 mol or greater.

Specific reaction conditions for the hydrothermal reaction are as follows. The heating temperature is, for example, 100 to 600° C., and preferably 200 to 500° C. The pressure is, for example, 0.2 to 50 MPa, preferably 1 to 50 MPa, and more preferably 10 to 50 MPa. The reaction time is, for example, 1 to 2000 minutes, preferably 2 to 1000 minutes, and more preferably 3 to 500 minutes. In the case where a continuous reactor is used, the reaction time is set to, for example, one minute or less.

The reaction product obtained by the above reaction includes a precipitate that mostly precipitates in water and a deposit that adheres to the inner wall of the airtight container.

The precipitate is obtained by, for example, sedimentation separation in which the reaction product is settled by gravity or a centrifugal field. Preferably, the precipitate is obtained as a precipitate of the reaction product by centrifugal sedimentation (centrifugal separation) in which the reaction product is settled by a centrifugal field.

The deposit is recovered by, for example, a scraper (spatula) or the like.

The reaction product can also be recovered (separated) by adding a solvent to wash away an unreacted organic compound (or in other words, dissolving the organic compound in the solvent) and thereafter removing the solvent.

As the solvent, the same solvents as those listed in the second embodiment can be used.

The washed reaction product is separated from the solvent (supernatant liquid) by, for example, filtration, decantation or the like, and recovered. After that, the reaction product is dried by, for example, application of heat, an air stream or the like if necessary.

In this manner, the catalyst particles containing inorganic particles and an organic group that binds to the surface of the inorganic particles are obtained.

Alternatively, unlike the first hydrothermal synthesis, by subjecting an inorganic substance and/or a complex (starting material) and an organic compound to a hydrothermal synthesis, it is possible to obtain catalyst particles containing inorganic particles formed of an inorganic substance and/or a complex that is/are different from the starting material (second hydrothermal synthesis).

Examples of the inorganic substance subjected to the second hydrothermal synthesis include a hydroxide, a sulfate, an acetate, a metal, hydrates thereof and the like.

In the hydroxide, the element (element that constitutes a cation that combines with a hydroxyl ion ($OH^-$)) contained in the hydroxide can be the same as the element that combines with oxygen in an oxide listed above.

Specifically, the hydroxide can be, for example, strontium hydroxide ($Sr(OH)_2$) or the like.

The complex subjected to the second hydrothermal synthesis can be, for example, titanium complex or the like.

Examples of the hydrates subjected to the second hydrothermal synthesis include tungstic acid ($WO_3 \cdot H_2O$), ammonium tungstate pentahydrate ($(NH_4)_2WO_4 \cdot 5H_2O$) and the like. These hydrates produce tungsten oxide as a result of elimination of water of hydration in the second hydrothermal synthesis.

Such inorganic substances and complexes (raw materials) can be used singly or in a combination of two or more.

In the case where the raw materials subjected to the second hydrothermal synthesis are used in combination, the first combination and the second combination mentioned above are used.

In the case where the first combination is used, and the second inorganic substance is a metal, the second inorganic substance does not cause a change in the chemical composition before and after the reaction (second hydrothermal synthesis).

Specific examples of the second inorganic substance subjected to the second hydrothermal synthesis in the first combination include palladium, platinum and the like. These elements do not cause a change in the chemical composition before and after the reaction (second hydrothermal synthesis).

After the second hydrothermal synthesis, the metal or oxide forming the second inorganic substance is supported on the first inorganic substance.

The term "supported" as used herein is defined as the state in which the metal or oxide is present substantially uniformly inside of and/or on the surface of the first inorganic substance.

Specifically, a metal (copper) forming a sulfate (copper) is supported on an oxide (tungsten oxide) after the second hydrothermal synthesis. Also, a group VIII element (palladium or platinum) is supported on an oxide (tungsten oxide) after the second hydrothermal synthesis. Furthermore, a metal (copper) forming a formate (copper formate) is supported on tungsten oxide after the second hydrothermal synthesis.

The proportions of respective components in the second hydrothermal synthesis per 100 parts by mass of the inorganic substance and the complex are as follows: the proportion of the organic compound is, for example, 1 to 1500 parts by mass, preferably 5 to 500 parts by mass and more preferably 5 to 250 parts by mass; and the proportion of water is, for example, 50 to 8000 parts by mass, preferably 80 to 6600 parts by mass and more preferably 80 to 4500 parts by mass.

The proportion of the organic compound is, for example, 0.9 to 1880 mL, preferably 4.5 to 630 mL and more preferably 4.5 to 320 mL per 100 g of the inorganic substance and the complex, and the number of moles of the organic compound may be, for example, 0.01 to 10000 mol and preferably 0.1 to 10 mol per mol of the inorganic substance and the complex.

The proportion of water is, for example, 50 to 8000 mL, preferably 80 to 6600 mL and more preferably 100 to 4500 mL per 100 g of the inorganic substance and the complex.

In the case where an inorganic substance and a complex are used in combination, the second combination mentioned above is used. More specifically, when a combination of a complex and an inorganic substance is used, the proportion of the inorganic substance per 100 parts by mass of the complex is, for example, 10 parts by mass or less, preferably 8 parts by mass or less and more preferably 5 parts by mass or less, and usually 0.001 parts by mass or greater. In other words, the proportion of the inorganic substance per mol of the complex is, for example, 0.1 mol or less, preferably 0.08 mol or less and more preferably 0.05 mol or less, and usually 0.00001 mol or greater.

In the case where a plurality of complexes are used, specifically, in the case where a combination of a titanium complex and a ruthenium complex is used, the proportion of the ruthenium complex per 100 parts by mass of the titanium complex is, for example, 50 parts by mass or less, preferably 25 parts by mass or less and usually 0.1 parts by mass or greater. In other words, the proportion of the ruthenium complex per mol of the titanium complex is, for example, 0.5 mol or less, preferably 0.25 mol or less, and usually 0.0001 mol or greater.

The reaction conditions for the second hydrothermal synthesis are the same as those for the first hydrothermal synthesis described above.

In the case where a combination of a titanium complex and platinum is used as the second combination, the titanium complex produces titanium oxide as a result of the reaction (second hydrothermal synthesis) while platinum does not cause a change in the chemical reaction in the chemical composition before and after the reaction. Also, in the case where a combination of a titanium complex, strontium hydroxide and nickel acetate is used as the second combination, the titanium complex and strontium hydroxide produce strontium titanate ($SrTiO_3$) as a result of the reaction (second hydrothermal synthesis) while nickel acetate produces nickel oxide (NiO). Furthermore, in the case where a combination of a titanium complex, strontium hydroxide and a ruthenium complex is used as the second combination, the titanium complex and strontium hydroxide produce strontium titanate ($SrTiO_3$) as a result of the reaction (second hydrothermal synthesis), while the ruthenium complex produces ruthenium oxide ($RuO_2$).

In this manner, the catalyst particles containing inorganic particles formed of an inorganic substance that is different from the inorganic substance serving as a starting material and a complex, and an organic group that binds to the surface of the inorganic particles are obtained.

In the formulations used in the first hydrothermal synthesis and the second hydrothermal synthesis, a pH adjusting agent can be blended with the components in an appropriate proportion.

The pH adjusting agent can be, for example, an aqueous ammonia solution, an aqueous sodium hydroxide solution or the like.

In the surface treatment performed in a hot organic compound, an inorganic substance and/or a complex and an organic compound are blended and heated, for example, under normal atmospheric pressure conditions. The organic compound is subjected to the high temperature treatment while serving as an organic group-introducing compound as well as a solvent for dispersing or dissolving the inorganic substance and/or the complex.

The proportion of the organic compound is, for example, 1 to 10000 parts by mass, preferably 10 to 5000 parts by mass, and more preferably 20 to 1000 parts by mass per 100 parts by mass of the inorganic substance and the complex. The proportion of the organic compound in terms of volume is, for example, 1 to 10000 mL, preferably 10 to 5000 mL, and more preferably 20 to 1000 mL per 100 g of the inorganic substance and the complex.

The heating temperature is, for example, a temperature above 100° C., preferably 125° C. or higher, and more preferably 150° C. or higher, and usually for example, 600° C. or lower. The heating time is, for example, 1 to 2000 minutes, preferably 2 to 1000 minutes, and more preferably 3 to 500 minutes. In the case where a continuous reactor is used, the reaction time is set to, for example, one minute or less.

Also, heating can be carried out under, for example, high pressure. As for the high pressure conditions, the same pressures as those used in the hydrothermal synthesis shown above can be used.

Through the surface treatment in a hot organic compound, the catalyst particles containing inorganic particles formed of a metal oxide forming an inorganic substance and/or a complex, and an organic group that binds to the surface of the inorganic particles are obtained.

The high temperature treatment (surface treatment) described above can be carried out once, or can be carried out a plurality of times from a view point of enhancing treatment efficiency.

As the method for carrying out the high temperature treatment a plurality of times, for example, a method in which each of the first hydrothermal synthesis, the second hydrothermal synthesis and the surface treatment in a hot organic compound is repeated, or a method in which the above treatments are carried out in combination is used. Preferably, the method in which the above treatments are carried out in combination is used. More preferably, a method in which the surface treatment in a hot organic compound is performed after the second hydrothermal synthesis is used.

Specifically, organic-inorganic composite particles in which a carboxyaliphatic group is bound to titanium oxide via a phosphoric acid group are obtained by subjecting a titanium complex to a high temperature treatment in any of the phosphoric acid ester group-containing organic compounds (carboxy ester group-containing organic compounds) listed above. After that, the obtained organic-inorganic composite particles are subjected to a high temperature treatment in an alcohol, whereby in the organic group, a carboxy ester group-containing organic group is produced from the carboxyaliphatic group. In other words, a carboxyl group binding to a terminal of an aliphatic group is esterified by the alcohol.

There is no particular limitation on the configuration of the catalyst particles (primary particles) obtained in the above-described manner, and for example the catalyst particles may be anisotropic or isotropic, with an average particle size (average maximum length in the case where they are anisotropic) of, for example, 450 nm or less, preferably 1 to 450 nm, more preferably 1 to 200 nm and particularly preferably 1 to 100 nm from a view point of clarity.

As will be described in detail in the examples given below, the average particle size of the catalyst particles is determined by measurement by dynamic light scattering (DLS) or calculated from a transmission electron microscopic (TEM) or scanning electron microscopic (SEM) image analysis or with the Scherrer's equation based on data of X-ray diffractometry (XRD).

If the average particle size exceeds the above range, the clarity of the catalyst solution, the catalyst resin composition or the catalyst molded article will be low, or the particles may be crushed when mixed with a resin or the like.

If, on the other hand, the average particle size is below the above range, the proportion of the volume of the organic group relative to the surface of the catalyst particles will be high, and the inorganic particles may be unlikely to exert its catalytic action.

The catalyst particles thus obtained are unlikely to coagulate in a dry state, and even if the catalyst particles appear coagulated in a dry state, the coagulation (formation of secondary particles) will be reliably prevented in a catalyst composition and a catalyst molded article, and therefore the catalyst particles are dispersed substantially uniformly in a resin as primary particles.

In the catalyst particles, the proportion of the surface area of the organic group relative to the surface area of the inorganic particles, or in other words, the surface coverage by the organic group in the catalyst particles (=(surface area of organic group/surface area of inorganic particles)×100) is, for example, 30% or greater and preferably 60% or greater and usually 200% or less.

The surface coverage is determined by the same method as that described in the second embodiment.

In the case where at least the surface coverage is high and the organic group of the catalyst particles has a length sufficient to cancel the electric charge of the inorganic particles, the type of solvent (medium) for dispersing the catalyst particles can be controlled (designed or managed) according to the type of organic group.

The catalyst particles obtained in the above-described manner can be subjected to wet classification.

Specifically, a solvent is added to the catalyst particles, and the resulting mixture is stirred and allowed to stand still, and thereafter separated into a supernatant and a precipitate. The solvent varies depending on the type of organic group, but for example, the same solvents as those listed above can be used, and preferable examples include a hydroxyl group-containing aliphatic hydrocarbon, a carbonyl group-containing aliphatic hydrocarbon, an aliphatic hydrocarbon, a halogenated aliphatic hydrocarbon and an aqueous pH adjusting solution.

After that, the supernatant is recovered, and it is thereby possible to obtain catalyst particles having a small average particle size.

With the wet classification, the average particle size of the resulting catalyst particles (primary particles) can be adjusted to, for example, 400 nm or less, 1 nm to 400 nm, preferably 1 nm to 200 nm and more preferably 1 nm to 100 nm.

The catalyst particles obtained in the above-described manner can be dispersed in a solvent or a resin to prepare a catalyst solution or a catalyst composition.

The catalyst solution contains a solvent and catalyst particles described above.

In order to prepare such a catalyst solution, a solvent and catalyst particles are blended, and the resulting mixture is stirred so as to disperse the catalyst particles in the solvent.

There is no particular limitation on the solvent, and examples thereof include solvents used in washing described above. Other examples include alicyclic hydrocarbons such as cyclopentane and cyclohexane; esters such as ethyl acetate; polyols such as ethylene glycol and glycerol; nitrogen-containing compounds such as N-methylpyrrolidone, pyridine, acetonitrile and dimethylformamide; acrylic monomers such as isostearyl acrylate, lauryl acrylate, isoboronyl acrylate, butyl acrylate, methacrylate, acrylic acid, tetrahydrofurfuryl acrylate, 1,6-hexanediol diacrylate, 2-hydroxyethyl acrylate, 4-hydroxybutyl acrylate, phenoxyethyl acrylate and acryloylmorpholine; vinyl group-containing monomers such as styrene and ethylene; epoxy-containing monomers such as bisphenol A epoxy; and the like.

These solvents can be used singly or in a combination of two or more. A halogenated aliphatic hydrocarbon is preferable.

The proportion of the catalyst particles is, for example, 0.1 to 70 parts by mass, preferably 0.2 to 60 parts by mass and more preferably 0.5 to 50 parts by mass per 100 parts by mass of the catalyst solution.

In the catalyst solution obtained in this manner, the catalyst particles have a configuration that does not allow the inorganic particles to contact with each other, and therefore are uniformly dispersed as primary particles in the solvent. Accordingly, the clarity of the catalyst solution can be enhanced.

Also, the catalyst composition contains a resin and catalyst particles described above.

As the resin, the same resins as those listed in the second embodiment can be used. These resins can be used singly or in a combination of two or more.

It is also possible to select the catalyst particles and the resin such that the solubility parameters (SP values) thereof satisfy a predetermined relationship.

Specifically, the catalyst particles and the resin are selected so as to attain a predetermined SP difference (ASP, specifically, the absolute value of the difference between the solubility parameter of resin ($SP_{RESIN}$ value) and the solubility parameter of catalyst particles ($SP_{PARTICLE}$ value)).

Among the resins listed above, in the case where excellent mechanical strength needs to be imparted to the catalyst molded article molded from a catalyst composition, a highly oriented resin having high orientation is preferable. As the highly oriented resin, the same highly oriented resins as those listed in the second embodiment can be used. Also, the resin has, for example, a hydrophilic group such as a carboxyl group or a hydroxyl group, a hydrophobic group such as a hydrocarbon group, and the like.

In order to prepare a catalyst composition, first, a solvent and a resin described above are blended so as to dissolve the resin in the solvent to prepare a resin solution. After that, the resin solution is blended with catalyst particles, and the resulting mixture is stirred to prepare a catalyst composition (first preparation method).

The proportion of resin relative to the resin solution is the same as those shown in the second embodiment.

The proportion of the catalyst particles is, for example, 1 to 1000 parts by mass, preferably 5 to 500 parts by mass and more preferably 10 to 300 parts by mass per 100 parts by mass of the solids content (resin) of the resin solution. The proportion of the catalyst particles is also, for example, 0.1 to 300 parts by mass, preferably 1 to 200 parts by mass and more preferably 3 to 100 parts by mass per 100 parts by mass of the total amount of the resin solution (the total amount of the resin and the solvent).

Also, the catalyst composition can also be prepared by, first, preparing a catalyst solution described above, and then blending the catalyst solution with a resin and stirring the resulting mixture (second preparation method).

In the catalyst solution, the catalyst particles are dispersed as primary particles in the solvent.

The proportion of resin is, for example, 10 to 10000 parts by mass, preferably 20 to 2000 parts by mass and more preferably 40 to 1000 parts by mass per 100 parts by mass of the solids content (catalyst particle) of the catalyst solution.

Furthermore, the catalyst composition can also be prepared by, for example, blending a solvent, catalyst particles and a resin simultaneously and stirring the resulting mixture (third preparation method).

The proportions of respective components per 100 parts by mass of the total amount of the catalyst composition are as follows: the proportion of the catalyst particles is, for example, 0.1 to 50 parts by mass, preferably 1 to 40 parts by mass and more preferably 3 to 30 parts by mass; and the proportion of resin is, 40 parts by mass or less, preferably 35 parts by mass or less, more preferably 30 parts by mass or less, and usually 1 part by mass or greater. The proportion of the solvent is the remainder obtained by excluding the catalyst particles and the resin from the catalyst composition.

Also, the catalyst composition can also be prepared by, first, preparing a resin solution and a catalyst solution in a separate manner and then blending and stirring the resin solution and the catalyst solution (fourth preparation method).

The proportion of resin in the resin solution is the same as those shown in the first preparation method described above.

The proportion of the catalyst particles in the catalyst solution is the same as those shown in the preparation method for a catalyst solution described above.

The resin solution and the catalyst solution are blended such that the proportion of resin relative to the catalyst particles in terms of mass is, for example, 99:1 to 10:90, preferably 95:5 to 20:80 and more preferably 90:10 to 30:70.

Furthermore, the catalyst composition can also be prepared without the use of a solvent by, for example, melting a resin by application of heat and blending the resin with catalyst particles (fifth preparation method).

The thus-prepared catalyst composition is a melt of the catalyst composition without a solvent.

The heating temperature is, in the case where the resin is a thermoplastic resin, greater than or equal to the melting temperature of the resin, specifically, 200 to 350° C. In the case where the resin is a thermosetting resin, the heating temperature is a temperature at which the resin is B-staged, for example, 85 to 140° C.

The proportion of resin relative to the catalyst particles in terms of mass is, for example, 99:1 to 10:90, preferably 95:5 to 20:80 and more preferably 90:10 to 30:70.

In the catalyst composition obtained by any of the above-described preparation methods, the catalyst particles are uniformly dispersed in the resin. Specifically, in the catalyst composition, the catalyst particles are dispersed as primary particles in the resin (without substantial coagulation).

After that, the obtained catalyst composition is applied to, for example, a known support plate to form a coating, and the coating is dried, whereby a catalyst molded article as a film is molded.

The catalyst composition is applied by using, for example, a known application method such as spin coating or bar coating. Simultaneously with or immediately after application of the catalyst composition, the solvent is removed by volatilization. If necessary, the solvent can be dried by application of heat after application of the catalyst composition.

The thickness of the obtained film can be set as appropriate according to the use and purpose, and the thickness is, for example, 0.1 to 2000 µm, preferably 0.1 to 1000 µm and more preferably 0.1 to 500 µm.

The catalyst molded article as a film can also be molded by a melt molding method in which the catalyst composition is extruded by an extruding machine or the like.

The catalyst molded article can also be molded as a block (mass) by injecting the catalyst composition into a metal mold or the like and thereafter subjecting the resultant to, for example, heat molding such as heat pressing.

The catalyst molded article is formed of the catalyst composition in which the catalyst particles are dispersed in the resin, and the inorganic particles cannot easily come into direct contact with the resin due to the configuration based on the steric hindrance of the organic group of the catalyst particles. Accordingly, the catalyst molded article can, while suppressing degradation of the resin, exert a catalytic action for a gas or a liquid.

Specifically, the catalyst molded article can exert a detoxification action, a deodorization action, a disinfectant (or in other words, antimicrobial or germicidal) action and a decomposition action for toxins, odor (malodor), fungi and organic substances contained in a gas such as the air by absorbing light, specifically, for example, light having a wavelength of 1000 nm or less, preferably light having a wavelength of 900 nm or less and more preferably light having a wavelength of 800 nm or less. Furthermore, the catalyst molded article can exert a detoxification action, a disinfectant action, a dirt repellent action and a decomposition action for toxins, fungi, excrements and organic substances contained in a liquid such as water.

As a result, the catalyst molded article can be used as a catalyst molded article having various catalytic actions (photocatalytic actions) such as a detoxification action, a deodorization action, a disinfectant action, a dirt repellent action and a decomposition action while maintaining excellent durability.

Furthermore, in the catalyst molded article, the catalyst particles are uniformly dispersed, and thus clarity can be enhanced.

As a result, the catalyst molded article can be used in various optical applications and various construction material applications where clarity is required.

Specifically, the catalyst molded article can be used as, in the case where it is molded as a film, for example, an optical film for use in an image display apparatus (liquid crystal display, organic electroluminescent apparatus or the like) such as a polarizing film, a phase difference film, a brightness enhancing film, a viewing angle enhancing film, a high-refractive index film or a light diffusing film.

The catalyst molded article can also be used as, in the case where it is molded as a film, for example, a construction material (construction) film such as an ultraviolet absorbing film, a dirt repellent film, an antimicrobial film, a deodorizing film, a super-hydrophilic film, a germicidal film, a detoxification film or a chemical substance decomposing film.

Fourth Embodiment

Embodiment corresponding to the inventions of a resin molded article and a producing method therefor, which are included in the fourth group of inventions The resin molded article of the present invention can be obtained by removing organic-inorganic composite particles from a particle-containing resin molded article containing a resin and the organic-inorganic composite particles.

The resin is a matrix component forming the resin molded article and can be, for example, a thermosetting resin, a thermoplastic resin or the like. Examples of the thermosetting resin and the thermoplastic resin include the same thermosetting resins and thermoplastic resins as those listed in the second embodiment. These resins can be used singly or in a combination of two or more.

In the case where excellent mechanical strength and excellent clarity needs to be imparted to the particle-containing resin molded article that is molded from a particle-containing resin composition (described later), the resin is preferably a polyester resin, a thermoplastic polyimide resin, a polyetherimide resin or the like.

Also, the resin preferably has a functional group. Examples of the functional group include hydrophilic groups such as a carboxyl group and a hydroxyl group; hydrophobic groups such as a hydrocarbon group; and the like.

Also, the resin has a refractive index for light having a wavelength of 633 nm of, for example, greater than 1 and 3 or less, preferably 1.2 to 2.5, and more preferably 1.3 to 2.0. The refractive index is measured by, for example, a refractometer.

Also, the resin has a reflectance for light having a wavelength of 550 nm of, for example, 1 to 10%, preferably 2 to 9% and more preferably 3 to 8%. The reflectance is measured by, for example, a spectrophotometer.

Also, the resin has a dielectric constant of, for example, 1.5 to 1000, preferably 2 to 100 and more preferably 2 to 10. The dielectric constant is measured by, for example, an automatic dielectric loss measurement apparatus at a frequency of 1 MHz.

The organic-inorganic composite particles are particles that can be dispersed as primary particles in a solvent (described later) and/or a resin and extracted from the resin with an extraction solvent, and contain inorganic particles and an organic group that binds to the surface of the inorganic particles.

Specifically, the organic-inorganic composite particles are obtained by surface-treating an inorganic material form inorganic particles with an organic compound. The organic-inorganic composite particles can be used singly or in a combination of two or more.

The inorganic material form inorganic particles can be a metal composed of a metal element such as a main group element or a transition element, a nonmetal composed of a nonmetal element such as boron or silicon, an inorganic compound and/or a complex containing a metal element and/or a nonmetal.

Examples of the metal element and the nonmetal element include elements that are located on the left side and the lower side of a border line that is assumed to pass through boron (B) of the IIIB group, silicon (Si) of the IVB group, arsenic (As) of the VB group, tellurium (Te) of the VIB group and astatine (At) of the VIIB group on the long-form periodic table (IUPAC, 1989), as well as the elements that are located on the border line. Specific examples thereof include the group I elements (alkali metals) such as Li, Na, K, Rb and Cs; the group II elements (alkaline earth metals) such as Be, Mg, Ca, Sr, Ba and Ra; and the same elements as those listed in the second embodiment.

Examples of the inorganic compound include the same inorganic compounds as those listed in the second embodiment.

Preferable examples of the inorganic compound include an oxide, a carbonate, a sulfate and the like.

The oxide can be, for example, a metal oxide. Preferable examples include titanium oxide (titanium dioxide, titanium oxide (IV), titania: $TiO_2$), cerium oxide (cerium dioxide, cerium oxide (IV), ceria: $CeO_2$), zinc oxide (zinc oxide (II), flowers of zinc or zinc white, ZnO) and the like.

The oxides can be used singly or in a combination of two or more.

In the carbonate, the element that combines with carbonic acid can be, for example, an alkali metal, an alkaline earth metal or the like. The alkali metal and the alkaline earth metal can be the same alkali metals and alkaline earth metals as those listed above.

The element that combines with carbonic acid is preferably an alkaline earth metal.

Specifically, the carbonate is preferably a carbonate containing an alkaline earth metal, and examples of such a carbonate include beryllium carbonate, magnesium carbonate, calcium carbonate, strontium carbonate, barium carbonate, radium carbonate and the like. These carbonates can be used singly or in a combination of two or more.

The sulfate is a compound consisting of a sulfate ion ($SO_4^{2-}$) and a metal cation (more specifically, a compound formed by substitution of the hydrogen atoms of sulfuric acid ($H_2SO_4$) with a metal), and the metal contained in the sulfate can be, for example, an alkali metal, an alkaline earth metal or the like. The alkali metal and the alkaline earth metal can be the same alkali metals and alkaline earth metals as those listed above.

The metal is preferably an alkaline earth metal.

Specifically, the sulfate is preferably a sulfate containing an alkaline earth metal, and examples of such a sulfate include beryllium sulfate, magnesium sulfate, calcium sulfate, strontium sulfate, barium sulfate, radium sulfate and the like. Barium sulfate is preferable.

The sulfates can be used singly or in a combination of two or more.

The inorganic materials listed above can be used singly or in a combination of two or more.

The organic compound is, for example, an organic group-introducing compound that introduces (disposes) an organic group on the surface of inorganic particles. Specifically, the organic compound contains a binding group capable of binding to the surface of inorganic particles and an organic group.

The binding group may be selected as appropriate according to the type of inorganic particles, and examples thereof include functional groups such as carboxyl group, phosphoric acid group (—$PO(OH)_2$, phosphono group), amino group, sulfo group, hydroxyl group, thiol group, epoxy group, isocyanate group (cyano group), nitro group, azo group, silyloxy group, imino group, aldehyde group (acyl group), nitrile group, vinyl group (polymerizable group) and the like. Preferable examples include carboxyl group, phosphoric acid group, amino group, sulfo group, hydroxyl group, thiol group, epoxy group, azo group, vinyl group, and the like. More preferable examples include carboxyl group and phosphoric acid group.

The carboxyl group includes a carboxylic acid ester group (carboxy ester group).

The phosphoric acid group includes a phosphoric acid ester group (phosphonate group).

One or more of these binding groups are contained in the organic compound. Specifically, the binding group is bound to a terminal or a side chain of the organic group.

The binding group is selected as appropriate according to the type of inorganic particles. Specifically, when the inorganic particles contain cerium oxide, strontium carbonate and/or barium sulfate, for example, carboxyl group is selected. When the inorganic particles contain titanium oxide and/or zinc oxide, for example, a phosphoric acid group is selected.

The organic group includes, for example, a hydrocarbon group such as an aliphatic group, an alicyclic group, an araliphatic group or an aromatic group, or the like.

Examples of the hydrocarbon groups include the same hydrocarbon groups as those listed in the second embodiment.

The organic group is a hydrophobic group for imparting hydrophobicity to the surface of inorganic particles.

Accordingly, the organic compounds containing a hydrophobic group described above are used as hydrophobic organic compounds for hydrophobic treatment of inorganic particles. Specific examples of such hydrophobic organic compounds include the same hydrophobic organic compounds as those listed in the second embodiment.

Alternatively, the organic compound can also be used as a hydrophilic organic compound for hydrophilic treatment of inorganic particles. In this case, the organic group contained in the hydrophilic organic compound includes any of the above hydrocarbon groups and a hydrophilic group that binds to the hydrocarbon group.

Specifically, in the hydrophilic organic compound, the hydrophilic group is bound to a terminal (the terminal (the other terminal) opposite the terminal that is bound to the binding group (one terminal)) or a side chain of the hydrocarbon group.

The hydrophilic group is a functional group having a polarity (or in other words, polar group), and examples thereof include the same functional groups as those listed in the second embodiment. One or more of the hydrophilic groups are contained in the hydrophilic organic compound.

Specific examples of the organic compound containing a hydrophilic group include the same carboxyl group-containing organic compounds, hydroxyl group-containing organic compounds, phosphoric acid group-containing organic compounds, amino group-containing organic compounds, sulfo group-containing organic compounds, carbonyl group-containing organic compounds, cyano group-containing organic compounds, nitro group-containing organic compounds, aldehyde group-containing organic compounds and thiol group-containing organic compounds as those listed in the second embodiment.

The same or mutually different organic groups may be used.

In the case where mutually different organic groups are used, or in other words, the organic group contains a plurality of mutually different types of organic groups, a plurality of homologous organic groups and/or a plurality of heterologous organic groups are contained.

Examples of the homologous organic groups include the same combinations as those listed in the second embodiment.

A preferable example of the homologous organic groups is a combination of a plurality of aliphatic groups, a more preferable example is a combination of a plurality of saturated aliphatic groups, and a particularly preferable example is a combination of a saturated aliphatic group having less than 10 carbon atoms and a saturated aliphatic group having 10 or more carbon atoms. Specific examples include a combination of hexyl and decyl and a combination of octyl and decyl.

When the organic group contains a plurality of homologous organic groups, a plurality of organic groups having different sizes (lengths or/and dimensions, or in other words, the number of carbon atoms) are contained in the organic group. Accordingly, in a space between adjacent larger organic groups, a resin molecule enters a gap (pocket) formed in accordance with the smaller organic group, and the interaction between the larger organic group and the resin molecule can be enhanced. As a result, the dispersibility of the organic-inorganic composite particles can be enhanced.

Examples of the heterologous organic groups include the same combinations as those listed in the second embodiment.

As long as the organic group contains a plurality of heterologous organic groups, when the resin is prepared as a mixture of a plurality of resin components, the organic group can exert excellent compatibility with the resin molecules of the respective resin components having excellent compatibility with the organic groups of the respective groups. Accordingly, the interaction between the organic groups and the resin molecules of the resin components can be enhanced. As a result, the dispersibility of the organic-inorganic composite particles can be enhanced.

The organic groups are present on the surface of inorganic particles in the organic-inorganic composite particles. Specifically, the organic groups are bound to the surface of inorganic particles via a binding group. Also, the organic groups extend from the surface of inorganic particles toward the outside of the inorganic particles via a binding group.

The organic-inorganic composite particles are prepared by subjecting an inorganic material and an organic compound to a reaction treatment, preferably to a high temperature treatment.

The high temperature treatment is carried out in a solvent. As the solvent, for example, water and any above-listed organic compounds can be used.

Specifically, the organic-inorganic composite particles are obtained by subjecting an inorganic material and an organic compound to a high temperature treatment in water under high pressure conditions (hydrothermal synthesis: hydrothermal reaction), or subjecting an inorganic material to a high temperature treatment in an organic compound (high temperature treatment in an organic compound). In other words, the organic-inorganic composite particles are obtained by surface-treating the surface of inorganic particles formed by an inorganic material with (or in the presence of) an organic compound.

In the hydrothermal synthesis, for example, the inorganic material and the organic compound are reacted under high-temperature and high-pressure conditions in the presence of water (first hydrothermal synthesis).

The inorganic material subjected to the first hydrothermal synthesis is preferably an inorganic compound, and more preferably a carbonate or a sulfate.

Specifically, first, a reaction system is prepared under high-temperature and high-pressure conditions by placing an inorganic material, an organic compound and water in a pressure-resistant airtight container and heating them.

The proportions of respective components per 100 parts by mass of the inorganic material are as follows: the proportion of the organic compound is, for example, 1 to 1500 parts by mass, preferably 5 to 500 parts by mass and more preferably 5 to 250 parts by mass; and the proportion of water is, for example, 50 to 8000 parts by mass, preferably 80 to 6600 parts by mass and more preferably 100 to 4500 parts by mass.

The density of the organic compound is usually 0.8 to 1.1 g/mL, and thus the proportion of the organic compound is, for example, 1 to 1500 mL, preferably 5 to 500 mL and more preferably 5 to 250 mL per 100 g of the inorganic material.

Also, the number of moles of the organic compound can be, for example, 0.01 to 1000 mol, preferably 0.02 to 50 mol, and more preferably 0.1 to 10 mol per mol of the inorganic material.

In the case where the organic compound contain a plurality of (for example, two) different types of organic groups, specifically, the molar ratio between an organic compound containing one type of organic group and an organic compound containing the other type of organic group is, for example, 10:90 to 99.9:0.1, and preferably 20:80 to 99:1.

Also, the density of water is usually approximately 1 g/mL, and thus the proportion of water is, for example, 50 to 8000 mL, preferably 80 to 6600 mL, and more preferably 100 to 4500 mL per 100 g of the inorganic material.

The reaction conditions for the hydrothermal reaction are the same reaction conditions as those shown in the second embodiment.

In the above reaction, if necessary, an aqueous pH adjusting solution such as an aqueous ammonia solution or an aqueous solution of potassium hydroxide can be added in an appropriate proportion.

The reaction product obtained by the above reaction includes a precipitate that mostly precipitates in water and a deposit that adheres to the inner wall of the airtight container.

The precipitate is obtained by, for example, sedimentation separation in which the reaction product is settled by gravity or a centrifugal field. Preferably, the precipitate is obtained as a precipitate of the reaction product by centrifugal sedimentation (centrifugal separation) in which the reaction product is settled by a centrifugal field.

The deposit is recovered by, for example, a scraper (spatula) or the like.

The reaction product can also be recovered (separated) by adding a solvent to wash away an unreacted organic compound (or in other words, dissolving the organic compound in the solvent) and thereafter removing the solvent (recovering step).

The solvent can be, for example, an alcohol (hydroxyl group-containing aliphatic hydrocarbon) such as methanol, ethanol, propanol or isopropanol; a ketone (carbonyl group-containing aliphatic hydrocarbon) such as acetone, methyl ethyl ketone, cyclohexanone or cyclopentanone; an aliphatic hydrocarbon such as pentane, hexane or heptane; a halogenated aliphatic hydrocarbon such as dichloromethane, chloroform or trichloroethane; a halogenated aromatic hydrocarbon such as chlorobenzene or dichlorobenzene; an ether such as tetrahydrofuran; an aromatic hydrocarbon such as benzene, toluene or xylene; an aqueous pH adjusting solution described above; or the like.

The washed reaction product is separated from the solvent (supernatant liquid) by, for example, filtration, decantation or the like, and recovered. After that, the reaction product is dried by, for example, application of heat, an air stream or the like if necessary.

In this manner, the organic-inorganic composite particles containing inorganic particles and an organic group that binds to the surface of the inorganic particles are obtained.

Note that in the first hydrothermal synthesis, the inorganic material before reaction and the inorganic particles after reaction have the same composition.

Alternatively, the organic-inorganic composite particles containing inorganic particles formed of an inorganic substance that is different from the inorganic material serving as a starting material can also be obtained by subjecting an inorganic material (starting material) and an organic compound to a hydrothermal synthesis (second hydrothermal synthesis).

The inorganic material subjected to the second hydrothermal synthesis can be, for example, a hydroxide, an acetate, a complex or the like.

In the hydroxide, the element (element that constitutes a cation that combines with a hydroxyl ion ($OH^-$)) contained in the hydroxide can be the same as the element that combines with oxygen in an oxide listed above.

Specifically, the hydroxide can be, for example, titanium hydroxide ($Ti(OH)_4$) or cerium hydroxide ($Ce(OH)_4$).

In the acetate, the element contained in the acetate that combine with an acetic acid ion ($CH_3COO^-$) can be a group IIB element, preferably Zn, Cd or the like.

Specifically, the acetate is preferably an acetate containing a group IIB element, and specific examples of such an acetate include zinc acetate, cadmium acetate and the like. These acetates can be used singly or in a combination of two or more.

The complex contains a central atom and/or a central ion and a ligand that coordinates thereto.

Examples of the central atom include the same metal elements as those listed above. A group IVA element is preferable, and Ti is more preferable.

Examples of the central ion include cations of the metal elements listed above.

Examples of the ligand include coordinating compounds such as carboxylic acid, hydroxycarboxylic acid and acetylacetone; coordinating ions such as cations and hydroxide ions in the above coordinating compounds; and the like.

Examples of the carboxylic acid include dicarboxylic acids such as oxalic acid, succinic acid and phthalic acid, and the like.

Examples of the hydroxycarboxylic acid include monohydroxymonocarboxylic acid (specifically, α-monohydroxycarboxylic acids) such as 2-hydroxyoctanoic acid, lactic acid and glycolic acid; monohydroxydicarboxylic acids such as malic acid; monohydroxytricarboxylic acids such as citric acid; and the like.

The coordination number is, for example, 1 to 6 and preferably 1 to 3.

The complex can be obtained by preparation from a metal element and a ligand described above.

The complex can also be formed (prepared) as a salt and/or a hydrate. Examples of the salt include salts with cations such as ammonium ions.

As the organic compound, for example, the same organic compounds as those that can be used in the first hydrothermal synthesis described above can be used.

In the second hydrothermal synthesis, the inorganic material and the organic compound are reacted under high-temperature and high-pressure conditions in the presence of water.

The proportions of respective components per 100 parts by mass of the inorganic compound are as follows: the proportion of the organic compound is, for example, 1 to 1500 parts by mass, preferably 5 to 500 parts by mass and more preferably 5 to 250 parts by mass; and the proportion of water is, for example, 50 to 8000 parts by mass, preferably 80 to 6600 parts by mass and more preferably 80 to 4500 parts by mass.

Also, the proportion of the organic compound is, for example, 0.9 to 1880 mL, preferably 4.5 to 630 mL and more preferably 4.5 to 320 mL per 100 g of the hydroxide, and the number of moles of the organic compound can be, for example, 0.01 to 10000 mol and preferably 0.1 to 10 mol per mol of the hydroxide.

Also, the proportion of water is, for example, 50 to 8000 mL, preferably 80 to 6600 mL and more preferably 100 to 4500 mL per 100 g of the hydroxide.

The reaction conditions for the second hydrothermal synthesis are the same as those for the first hydrothermal synthesis described above.

In this manner, the organic-inorganic composite particles containing inorganic particles formed of an inorganic substance having a different composition as that of the starting inorganic material and an organic group that binds to the surface of the inorganic particles are obtained.

In the high temperature treatment in an organic compound, an inorganic material and an organic compound are blended and heated, for example, under normal atmospheric pressure conditions. The organic compound is subjected to the high temperature treatment while serving as an organic group-introducing compound as well as a solvent for dispersing or dissolving the inorganic material.

The proportion of the organic compound is, for example, 10 to 10000 parts by mass and preferably 100 to 1000 parts by mass per 100 parts by mass of the inorganic material. The proportion of the organic compound in terms of volume is, for example, 10 to 10000 mL and preferably 100 to 1000 mL per 100 g of the inorganic material.

The heating temperature is the same as those shown in the second embodiment. The heating time is the same as those shown in the second embodiment.

There is no particular limitation on the configuration of the organic-inorganic composite particles (primary particles) obtained in the above-described manner, and for example the organic-inorganic composite particles may be anisotropic or isotropic, with an average particle size (average maximum length in the case where they are anisotropic) of, for example, 400 nm or less, preferably 200 nm or less and more preferably 100 nm or less, and usually, for example, 1 nm or greater and preferably 3 nm or greater.

As will be described in detail in the examples given below, the average particle size of the organic-inorganic composite particles is determined by measurement by dynamic light scattering (DLS) and/or calculated from a transmission electron microscopic (TEM) or scanning electron microscopic (SEM) image analysis.

If the average particle size of the organic-inorganic composite particles exceeds the above range, the micropores (described later) will be too large, and the clarity of the resin molded article (porous film, described later) will be low. Also, the organic-inorganic composite particles may be crushed when mixed with the resin or the like. If the average particle size exceeds the above range, the organic-inorganic composite particles may be crushed when mixed with the resin or the like.

If, on the other hand, the average particle size of the organic-inorganic composite particles is below the above range, the proportion of the volume of the organic group relative to the surface of the organic-inorganic composite particles will be high, and the function of the inorganic particles is unlikely to be obtained.

The organic-inorganic composite particles thus obtained are unlikely to coagulate in a dry state, and even if the organic-inorganic composite particles appear coagulated in a dry state, the coagulation between inorganic particles is prevented in a particle-containing resin composition and a particle-containing resin molded article.

In other words, the organic-inorganic composite particles have at least a configuration that does not allow the inorganic particles to contact with each other by steric hindrance of the organic group.

The organic-inorganic composite particles are also particles that can be easily re-dispersed by simply adding a solvent (described later) even if they are once dried.

In the organic-inorganic composite particles, the proportion of the surface area of the organic group relative to the surface area of the inorganic particles, or in other words, the surface coverage by the organic group in the organic-inorganic composite particles (=(surface area of organic group/surface area of inorganic particles)×100) is, for example, 30% or greater and preferably 60% or greater and usually 200% or less.

The surface coverage is determined by the same method as that described in the second embodiment.

In the case where at least the surface coverage is high and the organic group of the organic-inorganic composite particles has a length sufficient to cancel the electric charge of the inorganic particles, the type of solvent (medium) for dispersing the organic-inorganic composite particles can be controlled (designed or managed) according to the type of organic group.

The organic-inorganic composite particles obtained in the above-described manner can be subjected to wet classification.

As the wet classification, the same wet classification as that shown in the second embodiment is used.

With the wet classification, organic-inorganic composite particles having a small average particles size can be obtained.

With the wet classification, the average particle size of the resulting organic-inorganic composite particles can be adjusted to, for example, 400 nm or less, preferably 200 nm or less and more preferably 100 nm or less, and usually, for example, 0.1 nm or greater, and preferably 0.3 nm or greater.

It is also possible to select the resin and the organic-inorganic composite particles such that the solubility parameters (SP values) thereof satisfy a predetermined relationship.

Specifically, the resin and the organic-inorganic composite particles are selected so as to attain a predetermined SP difference (ASP, specifically, the absolute value of the difference between the solubility parameter of resin ($SP_{RESIN}$ value) and the solubility parameter of organic-inorganic composite particles ($SP_{PARTICLE}$ value)).

Preferable hydrophilic groups included in both the functional group and the organic group are a carboxyl group and a hydroxyl group, and preferable hydrophobic groups included in both the functional group and the organic group are a hydrocarbon group and the like. The affinity between the organic-inorganic composite particles and the resin can be enhanced as a result of both the functional group and the organic group having any of the above groups having the same property (hydrophilicity or hydrophobicity).

In order to obtain the resin molded article of the present invention, first, a particle-containing resin composition is prepared by blending a resin and organic-inorganic composite particles described above.

In the prepared particle-containing resin composition, the existing (dispersed) state of organic-inorganic composite particles in the particle-containing resin composition varies depending on the composition of organic group contained in the organic-inorganic composite particles. Accordingly, the existing (dispersed) state of organic-inorganic composite particles in the particle-containing resin composition is not limited to the proportion of resin to organic-inorganic composite particles (described later).

To prepare a particle-containing resin composition, the same solution preparation as that described in the second embodiment is used.

As the solvent, the same solvents as those listed in the second embodiment can be used. These solvents can be used singly or in a combination of two or more. The solvent is preferably a halogenated aliphatic hydrocarbon.

Specifically, in order to prepare a particle-containing resin composition, first, a solvent and a resin described above are blended so as to dissolve the resin in the solvent to prepare a resin solution. After that, the resin solution is blended with organic-inorganic composite particles, and the resulting mixture is stirred to prepare a particle-containing resin composition (first preparation method).

The proportion of resin relative to the resin solution is the same as those (in terms of mass, volume, mol, and the like) shown in the second embodiment.

The proportion of the organic-inorganic composite particles is, for example, 1 to 5000 parts by mass, preferably 5 to 3000 parts by mass and more preferably 10 to 300 parts by mass per 100 parts by mass of the solids content (resin) of the resin solution.

In particular, for example, in order to disperse (described later) the organic-inorganic composite particles as primary particles in the resin, the proportion of the organic-inorganic composite particles is set to be relatively low (or in other words, the organic-inorganic composite particles are blended at a low concentration). Specifically, the proportion of the organic-inorganic composite particles is set to, for example, less than 1000 parts by mass, preferably 500 parts by mass or less, and more preferably 300 parts by mass or less, and for example, 1 part by mass or greater per 100 parts by mass of the solids content (resin) of the resin solution.

On the other hand, in order to cause the organic-inorganic composite particles to phase separate (described later) from the resin phase, the proportion of the organic-inorganic composite particles is set to be relatively high (or in other words, the organic-inorganic composite particles are blended at a high concentration). In particular, in order to form the particle-containing resin molded article so as to have a bicontinuous structure (described later), the proportion of the organic-inorganic composite particles is set to, for example, 5 parts by mass or greater, preferably 10 parts by mass or greater, more preferably 20 parts by mass or greater and usually, for example, 5000 parts by mass or less per 100 parts by mass of the solids content (resin) of the resin solution.

Also, in order to form the particle-containing resin molded article so as to have a two-phase separated structure (sea-island structure, described later), the proportion of the organic-inorganic composite particles is, for example, 50 to 500% and preferably 80 to 400% of that when the particle-containing resin molded article is formed so as to have a bicontinuous structure.

Also, the particle-containing resin composition can also be prepared by blending a solvent and organic-inorganic composite particles to disperse the organic-inorganic composite particles in the solvent to prepare a particle dispersion, and then blending the particle dispersion with a resin and stirring the resulting mixture (second preparation method).

In the particle dispersion, the organic-inorganic composite particles are dispersed as primary particles in the solvent.

The proportion of the organic-inorganic composite particles is, for example, 0.1 to 80 parts by mass, preferably 0.2 to 60 parts by mass and more preferably 0.5 to 50 parts by mass per 100 parts by mass of the particle dispersion.

The proportion of resin relative to the solids content (organic-inorganic composite particles) of the particle dispersion is the same as those (in terms of mass, volume, mol, and the like) shown in the second embodiment.

In particular, in order to disperse (described later) the organic-inorganic composite particles as primary particles in the resin, the proportion of resin is set to be relatively high (or in other words, the resin is blended at a high concentration). Specifically, the proportion of resin is, for example, 1 part by mass or greater, preferably 10 parts by mass or greater, more preferably 20 parts by mass or greater, particularly preferably 40 parts by mass or greater, and for example, 10000 parts by mass or less per 100 parts by mass of the solids content (organic-inorganic composite particles) of the particle dispersion.

On the other hand, in order to cause the organic-inorganic composite particles to phase separate (described later) from the resin phase, the proportion of resin is set to be relatively low (or in other words, the resin is blended at a low concentration). Specifically, in order to form the particle-containing resin molded article so as to have a bicontinuous structure (described later), the proportion of resin is set to, for example, less than 2000 parts by mass, preferably 1000 parts by mass or less, more preferably 500 parts by mass or less, and for example, 1 part by mass or greater per 100 parts by mass of the solids content (organic-inorganic composite particles) of the particle dispersion.

Also, in order to form the particle-containing resin molded article so as to have a two-phase separated structure (sea-island structure), the proportion of resin is, for example, 10 to 300% and preferably 20 to 200% of that when the particle-containing resin molded article is formed so as to have a bicontinuous structure.

Furthermore, the particle-containing resin composition can also be prepared by, for example, blending a solvent, organic-inorganic composite particles and a resin simultaneously and stirring the resulting mixture (third preparation method).

The proportions of respective components per 100 parts by mass of the total amount of the organic-inorganic composite particles and the resin are as follows: the proportion of the organic-inorganic composite particles is, for example, 0.1 to 99.9 parts by mass, preferably 1 to 99 parts by mass and more preferably 3 to 95 parts by mass; and the proportion of resin is 0.1 to 99.9 parts by mass, preferably 1 to 99 parts by mass and more preferably 5 to 97 parts by mass.

Also, the proportion of the solvent is, for example, 1 to 10000 parts by mass and preferably 10 to 5000 parts by mass per 100 parts by mass of the total amount of the organic-inorganic composite particles and the resin.

In particular, in order to disperse (described later) the organic-inorganic composite particles as primary particles in the resin, the proportion of the organic-inorganic composite particles is set to be relatively low (or in other words, the organic-inorganic composite particles are blended at a low concentration). Specifically, the proportion of the organic-inorganic composite particles is set to, for example, less than 99 parts by mass, preferably 90 parts by mass or less, more preferably 80 parts by mass or less, particularly preferably 70 parts by mass or less and for example, 0.1 parts by mass or greater per 100 parts by mass of the total amount of the organic-inorganic composite particles and the resin.

On the other hand, in order to cause the organic-inorganic composite particles to phase separate from the resin phase, the proportion of the organic-inorganic composite particles is set to be relatively high (or in other words, the organic-inorganic composite particles are blended at a high concentration). In particular, in order to form the particle-containing resin molded article so as to have a bicontinuous structure, the proportion of the organic-inorganic composite particles is set to, for example, 5 parts by mass or greater, preferably 10 parts by mass or greater, more preferably 20 parts by mass or greater and for example, 99 parts by mass or less per 100 parts by mass of the total amount of the organic-inorganic composite particles and the resin.

Also, in order to form the particle-containing resin molded article so as to have a two-phase separated structure (sea-island structure), the proportion of the organic-inorganic composite particles is, for example, 50 to 500% and preferably 80 to 400% of that when the particle-containing resin molded article is formed so as to have a bicontinuous structure.

Also, the particle-containing resin composition can also be prepared by, first, preparing a resin solution and a particle dispersion in a separate manner, and then blending and stirring the resin solution and the particle dispersion (fourth preparation method).

The proportion of resin in the resin solution is the same as those shown in the first preparation method described above.

The proportion of the organic-inorganic composite particles in the particle dispersion is the same as those shown in the second preparation method described above.

The resin solution and the particle dispersion are blended such that the proportion of the organic-inorganic composite particles is, for example, 0.1 to 99.9 parts by mass, preferably 1 to 99 parts by mass and more preferably 3 to 95 parts by mass per 100 parts by mass of the total amount of the organic-inorganic composite particles and the resin.

In particular, in order to disperse (described later) the organic-inorganic composite particles as primary particles in the resin, the resin solution and the particle dispersion are blended such that the proportion of the organic-inorganic composite particles is relatively low (or in other words, the concentration of the organic-inorganic composite particles is low). Specifically, the resin solution and the particle dispersion are blended such that the proportion of the organic-inorganic composite particles is, for example, less than 99 parts by mass, preferably 90 parts by mass or less, more preferably 80 parts by mass or less, particularly preferably 70 parts by mass or less and for example, 0.1 parts by mass or greater per 100 parts by mass of the total amount of the organic-inorganic composite particles and the resin.

On the other hand, in order to cause the organic-inorganic composite particles to phase separate (described later) from the resin phase, the resin solution and the particle dispersion are blended such that the proportion of the organic-inorganic composite particles is relatively high (or in other words, the concentration of the organic-inorganic composite particles is high). In particular, in order to form the particle-containing resin molded article so as to have a bicontinuous structure, the resin solution and the particle dispersion are blended such that the proportion of the organic-inorganic composite particles is, for example, less than 99.9 parts by mass, preferably 99 parts by mass or less, more preferably 95 parts by mass or less, particularly preferably 90 parts by mass or less, for example, 5 parts by mass or greater, preferably 10 parts by mass or greater, and more preferably 20 parts by mass or greater per 100 parts by mass of the total amount of the organic-inorganic composite particles and the resin.

Also, in order to form the particle-containing resin molded article so as to have a two-phase separated structure (sea-island structure), the proportion of the organic-inorganic composite particles is, for example, 50 to 500% and preferably 80 to 400% of that when the particle-containing resin molded article is formed so as to have a bicontinuous structure.

Furthermore, the particle-containing resin composition can also be prepared by without the use of a solvent by, for example, melting a resin by application of heat and blending the resin with organic-inorganic composite particles (fifth preparation method).

The thus-prepared particle-containing resin composition is a melt of the particle-containing resin composition without a solvent.

The heating temperature is the same as those shown in the second embodiment.

The proportion of resin is, for example, 1 to 90 parts by mass, preferably 5 to 80 parts by mass and more preferably 10 to 70 parts by mass per 100 parts by mass of the total amount of the resin and the organic-inorganic composite particles.

In particular, in order to disperse (described later) the organic-inorganic composite particles as primary particles in the resin, the proportion of the organic-inorganic composite particles is set to be relatively low (or in other words, the organic-inorganic composite particles are blended at a low concentration). Specifically, the proportion of the organic-inorganic composite particles is, for example, less than 99 parts by mass, preferably 90 parts by mass or less, more preferably 80 parts by mass or less, particularly preferably 70 parts by mass or less, for example, 0.01 parts by mass or greater, preferably 0.1 parts by mass or greater, and more preferably 1 part by mass or greater per 100 parts by mass of the total amount of the resin and the organic-inorganic composite particles.

On the other hand, in order to cause the organic-inorganic composite particles to phase separate (described later) from the resin, the proportion of the organic-inorganic composite particles is set to be relatively high (or in other words, the organic-inorganic composite particles are blended at a high concentration). In particular, in order to form the particle-containing resin molded article so as to have a bicontinuous structure, the proportion of the organic-inorganic composite particles is set to, for example, 5 parts by mass or greater, preferably 10 parts by mass or greater, more preferably 20 parts by mass or greater and for example, 99 parts by mass or less per 100 parts by mass of the total amount of the organic-inorganic composite particles and the resin.

Also, in order to form the particle-containing resin molded article so as to have a two-phase separated structure (sea-island structure), the proportion of the organic-inorganic composite particles is, for example, 50 to 500% and preferably 80 to 400% of that when the particle-containing resin molded article is formed so as to have a bicontinuous structure.

The particle-containing resin composition obtained by any of the above-described preparation methods has a configuration that does not allow the inorganic particles to contact with each other by steric hindrance of the organic group, and therefore coagulation of the inorganic particles is prevented.

Next, in order to obtain the resin molded article of the present invention, a particle-containing resin molded article is formed from the particle-containing resin composition prepared above.

To form a particle-containing resin molded article, the particle-containing resin composition is applied to, for example, a substrate to form a coating, and the coating is dried, whereby a particle-containing resin molded article as a film (particle-containing resin film) is molded. After that, the film is peeled off from the substrate.

The substrate is made of a material that is not dissolved in an extraction liquid, which will be described later. Specific examples include polyester films such as a polyethylene terephthalate film (PET); olefin films such as a polyethylene film and a polypropylene film; polyvinyl chloride films; polyimide films; polyamide films such as a nylon film; and synthetic resin films such as a rayon film. Other examples of the substrate include paper substrates such as fine quality paper, Japanese paper, kraft paper, glassine paper, synthetic paper and top-coat paper. Furthermore, other examples of the substrate include a glass plate, a copper plate, an aluminum plate, and an inorganic substrate such as stainless steel (SUS).

The thickness of the substrate is, for example, 2 to 1500 µm.

The particle-containing resin composition is applied by using, for example, a known application method such as spin coating or bar coating. Simultaneously with or immediately after application of the particle-containing resin composition, the solvent is removed by volatilization. If necessary, the solvent can be dried by application of heat after application of the particle-containing resin composition.

The thickness of the obtained film can be set as appropriate according to the use and purpose, and the thickness is, for example, 0.1 to 2000 µm, preferably 0.2 to 1000 µm and more preferably 0.3 to 500 µm.

The particle-containing resin molded article as a film can also be molded by a melt molding method in which the particle-containing resin composition is extruded by an extruding machine or the like.

The particle-containing resin molded article can also be molded as a block (mass) by injecting the particle-containing resin composition into a metal mold or the like and thereafter subjecting the resultant to, for example, heat molding such as heat pressing, In any of the particle-containing resin molded articles molded in the above-described manner, the organic-inorganic composite particles are dispersed as primary particles in the resin in the case where the organic-inorganic composite particles are blended at a low concentration. In other words, in the particle-containing resin molded article, the organic-inorganic composite particles are prevented from coagulating and forming secondary particles.

On the other hand, in the case where the organic-inorganic composite particles are blended at a high concentration, the particle-containing resin molded article has a phase separated structure formed of a resin phase composed of resin and a particle phase composed of organic-inorganic composite particles. The particle phase is phase-separated from the resin phase.

The phase separated structure can be, for example, a two-phase separated structure (sea-island structure) in which the particle phase is dispersed in the resin phase.

Also, the phase separated structure can be, for example, a bicontinuous phase separated structure in which the particle phase is three-dimensionally continuous. In the bicontinuous phase separated structure, because the particle phase is three-dimensionally continuous, the organic-inorganic composite particles in the particle phase can be extracted continuously (described later).

Other examples of the phase separated structure include a honeycomb structure, a columnar structure and the like.

After that, the organic-inorganic composite particles are removed from the particle-containing resin molded article, whereby the resin molded article of the present invention can be obtained.

In order to remove the organic-inorganic composite particles, for example, an extraction method is used in which an extraction solvent is brought into contact with the particle-containing resin molded article. With the extraction method, specifically, the particle-containing resin molded article is immersed in an extraction liquid.

The extraction liquid can be, for example, a solvent that dissolves organic-inorganic composite particles and permeates through resin without corroding (damaging) the resin. Examples of such a solvent include an acid and an alkali.

Examples of the acid include inorganic acids such as nitric acid, hydrochloric acid, sulfuric acid, carbonic acid and phosphoric acid; organic acids such as formic acid and acetic acid; and the like.

Examples of the alkali include inorganic alkalis such as sodium hydroxide, potassium hydroxide; and organic alkalis such as ammonia.

An acid is preferable, and an inorganic acid is more preferable.

The extraction liquid can be, for example, diluted with a diluent such as water, an alcohol (ethanol or the like), an aliphatic hydrocarbon (hexane or the like), and the concentration of the extraction liquid is, for example, 1 mass % or greater and less than 100 mass % of the total mass of the extraction liquid and the diluent.

In the case where a solvent is used as the extraction liquid, regardless of the level of the concentration of the organic-inorganic composite particles (or in other words, the structure of the organic-inorganic composite particles or particle phase in the particle-containing resin molded article), the organic-inorganic composite particles can be dissolved. A solvent is preferably used particularly when in the particle-containing resin molded article, the organic-inorganic composite particles are blended at a low concentration and the organic-inorganic composite particles are dispersed as primary particles in the resin. In this case, the solvent permeates through the resin and also dissolves the organic-inorganic composite particles dispersed as primary particles in the resin.

There is no particular limitation on the extraction liquid, and, for example, it can be a dispersing medium that disperses organic-inorganic composite particles, does not corrode (damage) resin and does not permeate through resin. Examples of the dispersing medium include the same dispersing media as the solvents used in the washing step described above. Specific examples include water, an aqueous pH adjusting solution, a hydroxyl group-containing aliphatic hydrocarbon, a carbonyl group-containing aliphatic hydrocarbon, an aliphatic hydrocarbon, a halogenated aliphatic hydrocarbon, a halogenated aromatic hydrocarbon, an ether, an aromatic hydrocarbon and the like. The dispersing medium is preferably an aliphatic hydrocarbon.

In the case where a dispersing medium is used as the extraction liquid, the organic-inorganic composite particles are blended at a high concentration in the particle-containing resin molded article and the particle phase composed of the organic-inorganic composite particles is three-dimensionally continuous and exposed at the surface of the particle-containing resin molded article, so that the organic-inorganic composite particles can be dispersed (extracted) into the dispersing medium by continuously withdrawing the organic-inorganic composite particles from the exposed surface.

The extraction temperature is, for example, 0 to 150° C. and preferably 10 to 100° C. If the extraction temperature is below the above range, the extraction time exceeds the desired limit, which will be described next, and the producing cost may increase. If, on the other hand, the extraction temperature exceeds the above range, the resin may be degraded or the producing cost may increase.

The extraction time is, for example, 30 seconds to 5 hours and preferably 1 minute to 3 hours.

If the extraction time is below the above range, the extraction efficiency will be low. If the extraction time exceeds the above range, the producing cost may increase.

By removing the organic-inorganic composite particles, micropores are formed in the particle-containing resin molded article.

The micropores are formed as openings (gaps) separated by the resin around the organic-inorganic composite particles.

The shape and dimension (pore size) of micropores are substantially the same outer shape and dimension as those of the organic-inorganic composite particles that have been removed from the resin.

Specifically, in the case where in the particle-containing resin molded article, the organic-inorganic composite particles are blended in the resin at a relatively low concentration and the organic-inorganic composite particles are dispersed as primary particles, the micropores are formed as independent pores (closed-cells) dispersed uniformly in the resin.

As a result, a resin molded article in which micropores are formed, or in other words, a porous molded article can be obtained. In the case where the resin molded article is formed as a film, a porous film is obtained.

With the above described method, in the particle-containing resin molded article, the organic-inorganic composite particles are dispersed as primary particles, and the resin molded article having micropores formed by removing the organic-inorganic composite particles has excellent clarity and excellent mechanical strength.

Accordingly, the resin molded article can be used in, for example, optical applications including optical films such as a low-refractive film and an antireflective film, as well as electrical and electronic applications including electrical and electronic substrates such as a low-dielectric substrate.

Moreover, the resin molded article has independent pores (micropores) formed by removing the organic-inorganic composite particles having an average particle size within the above range, and it is thus possible to further enhance clarity.

In the case where the resin molded article is used as a low-refractive film, for example, the refractive index of the low-refractive film for light having a wavelength of 633 nm is reduced to, for example, 99% or less of the refractive index of the resin for light having a wavelength of 633 nm, preferably reduced to 95% or less, more preferably reduced to 90% or less. Specifically, the refractive index is, for example, 1 to 3, preferably 1.05 to 2.5 and more preferably 1.1 to 2.

In the case where the resin molded article is used as an antireflective film (low-reflection film), the reflectivity of the antireflective film for light having a wavelength of 550 nm is reduced to, for example, 99% or less of the reflectivity of the resin for light having a wavelength of 550 nm, and preferably reduced to 95% or less. Specifically, the reflectivity of the antireflective film for light having a wavelength of 550 nm is, for example, 9% or less, preferably 1 to 8% and more preferably 1.5 to 7%.

In the case where the resin molded article is used as a low-dielectric substrate, the dielectric constant of the low-dielectric substrate is reduced to, for example, 99% or less of the dielectric constant of the resin, preferably reduced to 95% or less, and more preferably reduced to 90% or less. Specifically, the dielectric constant of the low-dielectric substrate is, for example, 1 to 1000, preferably 1.2 to 100, and more preferably 1.5 to 100.

On the other hand, with the particle-containing resin molded article, in the case where the particle-containing resin molded article has a phase separated structure formed of a particle phase and a resin phase, more specifically, a bicontinuous phase separated structure in which the particle phase is three-dimensionally continuous, the micropores are formed as communicating pores in the resin.

In this case, the resin molded article has communicating pores (micropores) formed by removing the organic-inorganic composite particles, and thus has excellent mechanical strength and can be widely used as a porous film (porous molded article) having paths (passages) formed by communicating pores extending in the thickness direction (front-back surface direction) in various applications such as a sizing filter, a molecular separation membrane, an adsorptive separation filter and an electrolyte membrane.

In the removal (extraction) of organic-inorganic composite particles described above, the organic-inorganic composite particles can be partially left by adjusting the conditions therefor.

In order to partially leave the organic-inorganic composite particles in the resin molded article, the extraction time is set to, for example, 80% or less, preferably 65% or less and more preferably 50% or less of the extraction time when the organic-inorganic composite particles are fully extracted. Specifically, the extraction time is, for example, less than 60 minutes, preferably 30 minutes or less, and for example, 1 second or greater.

In the resin molded article obtained by extraction performed for the extraction time, the proportion of remaining organic-inorganic composite particles increases toward one side of the resin molded article, specifically, increases from the surface of the resin molded article toward the interior (inside). In other words, the proportion of existing micropores in the resin molded article increases from the interior to the surface of the resin molded article.

In the resin molded article, the concentration distribution in the thickness direction of the micropores is in a range of, for example, 0 to 90 volume %, preferably a range of 0 to 60 volume % and more preferably a range of 0 to 40 volume %. Specifically, for example, the concentration of micropores in the surface of the porous film is 90 volume % (preferably 65 volume %), the concentration of micropores in the center portion in the thickness direction of the porous film is 0 volume %, and a concentration gradient is formed therebetween.

In the case where the particle-containing resin molded article is formed as a film on the top surface of a substrate, the substrate is laminated on one side of the film, and the resultant (laminate) can be immersed in an extraction liquid. After that, the laminate is removed from the extraction liquid and dried. Then, the film is peeled off from the substrate.

In the porous film obtained by immersing a laminate of a film and a substrate in an extraction liquid, the proportion of remaining organic-inorganic composite particles increases toward the back surface (one side in the thickness direction, substrate-side surface). In other words, the proportion of existing micropores increases toward the surface of the porous film (the other side in the thickness direction, the exposed surface on which the substrate is not laminated).

In the porous film in which the organic-inorganic composite particles partially remain, the concentration distribution in the thickness direction of micropores is in a range of, for example, 0 to 90 volume %, preferably a range of 0 to 65 volume % and more preferably a range of 0 to 40 volume %. Specifically, for example, the concentration of micropores in the surface of the porous film is 90 volume % (preferably 65 volume %), the concentration of micropores in the back surface of the porous film is 0 volume %, and a concentration gradient is formed in the thickness direction.

The proportion of remaining organic-inorganic composite particles and the proportion of existing micropores are measured by SEM or TEM.

The porous film (resin molded article) can be used as a refractive-index distribution optical film, a dielectric distribution substrate or the like because the organic-inorganic composite particles are partially left and the proportion of existing micropores varies in the thickness direction of the porous film.

Fifth Embodiment

Embodiment corresponding to the inventions of a titanium complex, titanium oxide particles and a producing method therefor, which are included in the fifth group of inventions The titanium complex of the present invention contains a titanium atom as a central atom and a hydroxycarboxylic acid having a total of 7 or more carbon atoms as a ligand.

The titanium atom is a transition element having an atomic number of 22 and can be, for example, a tetravalent titanium atom.

The hydroxycarboxylic acid is an organic compound that has a total of 7 or more carbon atoms and contains a carboxyl group and a hydroxyl group, and it can be, for example, a saturated or unsaturated hydroxycarboxylic acid having a total of 7 or more carbon atoms such as hydroxyalkanoic acid, hydroxyalkenoic acid or hydroxyalkynoic acid.

The total number of carbon atoms of such a hydroxycarboxylic acid is preferably 8 or greater, for example, 16 or less, and preferably 13 or less.

The number of carboxyl groups contained in the hydroxycarboxylic acid is, for example, 1 to 3 and preferably 1, and the number of hydroxyl groups is, for example, 1 to 3 and preferably 1.

Among the hydroxycarboxylic acids listed above, a hydroxymonocarboxylic acid and a monohydroxycarboxylic acid are preferable, and a monohydroxymonocarboxylic acid is preferable.

Also, among the hydroxycarboxylic acids listed above, a saturated hydroxyalkanoic acid is preferable. Specific examples include linear hydroxyalkanoic acids having 7 to 16 carbon atoms such as hydroxyheptanoic acid, hydroxyoctanoic acid, hydroxynonanoic acid, hydroxydecanoic acid, hydroxyundecanoic acid, hydroxydodecanoic acid, hydroxytridecanoic acid, hydroxytetradecanoic acid, hydroxypentadecanoic acid and hydroxyhexadecanoic acid; branched hydroxyalkanoic acids having 7 to 16 carbon atoms such as hydroxy 3-ethylhexanoic acid, hydroxy 4-ethylheptoic acid and hydroxy 3-ethyloctanoic acid; and the like. Among the hydroxyalkanoic acids listed above, linear hydroxyalkanoic acids are preferable.

That is, among the hydroxycarboxylic acids listed above, monohydroxymonoalkanoic acids having a total of 7 to 13 carbon atoms such as a 2-hydroxyalkanoic acid ($\alpha$-hydroxyalkanoic acid) and a 3-hydroxyalkanoic acid ($\beta$-hydroxyalkanoic acid) are particularly preferable. Specific examples include 2-hydroxyoctanoic acid and 3-hydroxydecanoic acid.

Such monohydroxymonoalkanoic acids having a total of 7 to 13 carbon atoms can be used as a ligand constituting a titanium complex. Furthermore, titanium complexes containing such a monohydroxymonoalkanoic acid as a ligand can enhance heat resistance (180° C. or higher) as compared to titanium complexes containing a hydroxycarboxylic acid having a total of 6 or fewer carbon atoms as a ligand.

Such a titanium complex is prepared by reacting a hydroxycarboxylic acid having a total of 7 or more carbon atoms with a titanium atom.

In order to prepare such a titanium complex, first, a substance containing a titanium atom is dissolved in a mixed solution of a hydrogen peroxide solution and an aqueous alkali solution so as to give an unstable aqueous solution of peroxotitanium complex.

The substance containing a titanium atom is not particularly limited, and can be, for example, titanium particles, titanium powders or the like.

The size (average particle size) of titanium particles or titanium powders is not particularly limited.

The titanium particles can be, for example, commercially available titanium particles (available from Wako Pure Chemical Industries, Ltd.).

The hydrogen peroxide solution is a solution in which hydrogen peroxide ($H_2O_2$) is dissolved in water, and has a concentration of, for example, 10 to 50 volume % and preferably 20 to 40 volume %.

The aqueous alkali solution can be, for example, aqueous ammonia in which ammonia ($NH_3$) is dissolved in water; an aqueous organic base solution in which a basic organic compound such as an amine is dissolved in water; an aqueous inorganic base solution in which a basic inorganic compound such as sodium hydrogencarbonate is dissolved in water; or the like.

These aqueous alkali solutions can be used singly or in combination.

Among the aqueous alkali solutions, aqueous ammonia is preferable. The concentration of aqueous ammonia is, for example, 1 to 45 mass %, preferably 5 to 40 mass % and more preferably 10 to 35 mass %.

The proportion (hydrogen peroxide solution:aqueous alkali solution) of the mixed solution of a hydrogen peroxide solution and an aqueous alkali solution is, for example, 3:7 to 9:1, preferably 5:5 to 9:1 and more preferably 6:4 to 9:1.

The pH of the mixed solution is, for example, 6 or greater, preferably 7 to 14 and more preferably 9 to 14.

In order to dissolve the substance containing a titanium atom in the mixed solution, for example, the substance containing a titanium atom is added to the mixed solution and, and the resulting mixture is stirred for a predetermined period of time.

The proportion of the substance containing a titanium atom is, for example, 0.5 to 5 g and preferably 1 to 3 g per 100 mL of the hydrogen peroxide solution, and is, for example, 0.5 to 5 g and preferably 1 to 2 g per 100 mL of the mixed solution.

Stirring conditions are as follows: the temperature is, for example, −15 to 80° C., preferably −10 to 50° C. and more preferably −5 to 25° C.; and the time is, for example, 0.1 to 24 hours, preferably 1 to 10 hours and more preferably 1 to 5 hours.

In the above-described manner, the substance containing a titanium atom is dissolved in the mixed solution, and an aqueous solution of peroxotitanium complex is prepared.

Specifically, the aqueous solution of peroxotitanium complex contains a peroxotitanium complex formed by reaction of a titanium atom and hydrogen peroxide ($H_2O_2$).

Next, any one of the hydroxycarboxylic acids having a total of 7 or more carbon atoms is mixed with the aqueous solution of peroxotitanium complex so as to prepare a titanium complex-containing solution.

In order to mix the hydroxycarboxylic acid with the aqueous solution of peroxotitanium complex, for example, the hydroxycarboxylic acid is dissolved in a solvent so as to prepare a hydroxycarboxylic acid solution, and the hydroxycarboxylic acid solution and the aqueous solution of peroxotitanium complex are mixed and stirred. After stirring, if necessary, the mixture is allowed to stand still for, for example, 10 to 40 hours.

There is no particular limitation on the solvent as long as the hydroxycarboxylic acid can be dissolved. Examples include water, alcohols such as methanol and ethanol, ketones such as acetone and methyl ethyl ketone, and the like.

These solvents can be used singly or in combination.

Among the solvents, alcohols are preferable.

The concentration of the hydroxycarboxylic acid solution is, for example, 0.1 to 80 mass %, preferably 1 to 50 mass % and more preferably 5 to 30 mass %.

The proportion of the hydroxycarboxylic acid solution is, for example, 10 to 100 mL, preferably 20 to 80 mL and more preferably 30 to 60 mL per 100 mL of the aqueous solution of peroxotitanium complex.

The proportion of hydroxycarboxylic acid is, for example, 1 to 6 mol, preferably 1 to 5 mol, and more preferably 1 to 4 mol per mol of the substance containing a titanium atom.

If the proportion of hydroxycarboxylic acid is less than 1 mol per mol of the substance containing a titanium atom, a titanium complex cannot be formed due to the shortage of ligand, and so a by-product containing a ligand (hydroxycarboxylic acid) and titanium atoms that do not form the complex may be left, and the desired titanium oxide particles may not be obtained from the titanium complex containing the by-product. If, on the other hand, the proportion of hydroxycarboxylic acid exceeds 6 mol per mol of the substance containing a titanium atom, the amount of hydroxycarboxylic acid will be excessive and wasted, and thus it may be inappropriate in terms of cost. Also, in this case, it is necessary to remove excessive hydroxycarboxylic acid left after the titanium oxide particle producing step, which makes the producing process complex. If, on the other hand, the proportion of hydroxycarboxylic acid is within the above range, the efficiency of titanium oxide particle producing can be enhanced.

Stirring conditions are as follows: the temperature is, for example, 0 to 80° C., preferably 5 to 70° C. and more preferably 10 to 60° C.; and the time is, for example, 0.1 to 24 hours, preferably 0.5 to 10 hours and more preferably 1 to 5 hours. After stirring, if necessary, the mixture is allowed to stand still for, for example, 10 to 40 hours.

By mixing and stirring a hydroxycarboxylic acid and an aqueous solution of peroxotitanium complex as described above, the hydroxycarboxylic acid is reacted with the peroxotitanium complex contained in the aqueous solution of peroxotitanium complex, as a result of which a titanium complex is formed. Accordingly, a titanium complex-containing solution that contains a titanium complex is prepared.

Next, the obtained titanium complex-containing solution is dried to prepare a titanium complex.

There is no particular limitation on the drying method, and known methods such as vacuum drying, spray drying and freeze drying can be used. For example, the solvent is dried by increasing the temperature with a drier or the like to prepare a titanium complex.

There is no particular limitation on the drying conditions as long as the solvent can be removed. The temperatures is, for example, 50 to 100° C. and preferably 60 to 90° C., and the time is 0.1 to 48 hours, preferably 0.5 to 24 hours and more preferably 1 to 10 hours.

In the above-described manner, a titanium complex is prepared.

The coordination number of the titanium complex is, for example, 1 to 6 preferably 2 to 4 per titanium atom. The coordination number can be analyzed with, for example, a mass spectrometer such as a matrix assisted laser desorption ionization (MALDI)—time-of-flight (TOF) mass spectrometer (MS), or the like The yield of the titanium complex is, for example, 60 to 100 mol % and preferably 80 to 100 mol % relative to the substance containing a titanium atom used.

There is no limitation on the applications of the titanium complex prepared in this manner. For example, the titanium complex is subjected to thermal decomposition to produce titanium oxide particles. Specifically, for example, the titanium complex is subjected to a high-temperature and high-pressure treatment (hydrothermal synthesis) in water to produce titanium oxide particles.

To produce titanium oxide particles, first, the titanium complex and water are introduced into a reactor.

The proportion of the titanium complex is, for example, 5 to 40 parts by mass, preferably 10 to 30 parts by mass per 100 parts by mass of water.

The reactor can be a known high-pressure reactor (autoclave) or continuous high-pressure reactor.

An example of such a high-pressure reactor (autoclave) is a commercially available high-pressure reactor (available from AKICO Corporation). Another example of a continuous high-pressure reactor is a commercially available continuous high-pressure reactor (available from ITEC Co. Ltd.).

Then, the reactor is brought to high-temperature and high-pressure conditions, whereby titanium oxide particles are produced (hydrothermal synthesis).

Reaction conditions for the hydrothermal synthesis are the same as those for the hydrothermal synthesis (first hydrothermal synthesis) illustrated in the third embodiment.

The reaction product obtained by the above hydrothermal synthesis includes a precipitate that mostly precipitates in water and a deposit that adheres to the inner wall of the airtight container.

There is no particular limitation on the method for separating and recovering a precipitate, and it is possible to use known methods that use a separating funnel, a filter, centrifugal separation and the like. The precipitate can be separated and recovered by using any of the methods. The precipitate is obtained by, for example, sedimentation separation in which the reaction product is settled by gravity or a centrifugal field. Preferably, the precipitate is obtained as a precipitate of the reaction product by centrifugal sedimentation (centrifugal separation) in which the reaction product is settled by a centrifugal field.

The deposit is recovered by, for example, a scraper (spatula) or the like.

The reaction product can also be recovered (separated) by adding a solvent to wash away unreacted hydroxycarboxylic acid (or in other words, dissolving the hydroxycarboxylic acid in the solvent) and thereafter removing the solvent.

The solvent can be, for example, any of the solvents listed above.

These solvents can be used singly or in combination.

Among the solvents, an alcohol is preferable.

The washed reaction product is separated from the solvent (supernatant liquid) by, for example, filtration, decantation or the like, and recovered. After that, the reaction product is dried by, for example, application of heat, an air stream or the like if necessary.

In the manner described above, titanium oxide particles are prepared from the titanium complex.

The titanium oxide particles have a crystal structure of, for example, anatase (tetragonal crystal), rutile (tetragonal crystal) or brookite (orthorhombic crystal). The crystal structure can be determined by electron diffraction such as XRD (X-ray diffraction) or TEM (transmission electron microscope).

There is no particular limitation on the crystal structure, and the crystal structure can be selected as appropriate by changing the type of ligand and the conditions for synthesizing titanium oxide. For example, the crystal structure is preferably rutile when used as an optical material having a high refractive index, and is preferably anatase when used as a catalyst material that exerts photocatalytic function.

As described above, the titanium oxide particles of the present invention are prepared by treating a titanium complex containing a hydroxyl carboxylic acid having a total of 7 or more carbon atoms as a ligand in hot high pressure water.

At this time, because the ligand of the titanium complex is a hydroxyl carboxylic acid having a total of 7 or more carbon atoms, decomposition of the ligand is suppressed even in hot high pressure water, as a result of which coloring of the resulting titanium oxide particles can be reduced.

Therefore, according to the present invention, reduction of coloring of the titanium oxide particles can be achieved while achieving reduction of the environmental load.

The applications of the titanium oxide particles of the present invention can be, for example, various industrial products, and optical applications and the like are preferable because coloring is reduced.

EXAMPLES

Hereinafter, examples and the like that correspond to the first to fifth groups of inventions that are included in the present invention and related to each other will be described in sequence.

Examples, Comparative Examples, Preparation Examples and Producing Examples Corresponding to the First Group of Inventions The first group of inventions will be described in further detail by showing Examples, Comparative Examples, Preparation Examples and Producing Examples corresponding to the first group of inventions, but the first group of inventions is not limited thereto.

The following is a description of evaluation methods for obtained particles, particle dispersions and resin molded articles (including optical films).
(1) X-Ray Diffractometry (XRD)
Particles were loaded into a glass holder and subjected to X-ray diffractometry under the following conditions. After that, from the obtained peaks, the components of the primary particles were assigned by database search.
X-ray diffractometer: D8 DISCOVER with GADDS, available from Bruker AXS
(Optical system on incident side)
X-ray source: CuKα ($\lambda$=1.542 Å), 45 kV, 360 mA
Spectroscope (monochromator): multilayer mirror
Collimator diameter: 300 μm
(Optical system on light-receiving side)
Counter: two-dimensional PSPC (Hi-STAR)
Distance between particles and counter: 15 cm
$2\theta$=20, 50, 80 degrees, $\omega$=10, 25, 40 degrees, Phi=0 degrees, Psi=0 degrees
Measurement time: 10 minutes
Assignment (semiquantitation software): FPM EVA, available from Bruker AXS
(2) Fourier Transform Infrared Spectrophotometry (FT-IR)
Fourier transform infrared spectrophotometry was carried out according to the KBr method using the following apparatus.
Fourier transform infrared spectrophotometer: FT/IRplus, available from JASCO Corporation
(3) Observation with Field Emission-Scanning Electron Microscope (FE-SEM)
(a) Observation of Particle Surface and Measurement of Lengthwise Length (Maximum Length) LL and Sideways Length (Minimum Length) SL
A sample was produced by dispersing particles on a sample stage and coating the particles with osmium. Next, the prepared sample was photographed with the following field emission-scanning electron microscope (FE-SEM).
In the obtained FE-SEM micrograph, the lengthwise length (maximum length) LL and sideways length (minimum length) SL of each particle were measured, and then the lengthwise length LL and sideways length SL of the entire particles were calculated from the arithmetic mean of the measured values.
FE-SEM: JSM-7500F, available from JEOL Ltd.
Acceleration voltage: 2 kV
(b) Observation of Cross-Section of Resin Molded Articles (Including Optical Films)
A sample was produced by machining a resin molded article (including an optical film) with a cross section polisher (SM-08010, available from JEOL Ltd.). After that, the prepared sample was coated with osmium, and a cross section of the sample was observed with the following field emission-scanning electron microscope (FE-SEM).

FE-SEM: JSM-7001F, available from JEOL Ltd.
Acceleration voltage: 5 kV (4) Observation with Transmission Electron Microscope (TEM)

Particles were dispersed on a Cu mesh having a microgrid support film, and the particles were observed with a transmission electron microscope (TEM).

TEM: HF-2000, available from Hitachi High-Tech Manufacturing & Service Corporation
Acceleration voltage: 200 kV (5) Particle Size Distribution Measurement A particle dispersion was placed in a quartz cell, and particle size distribution was measured with the following particle size distribution measuring apparatus.

Particle size distribution measuring apparatus: Zetasizer Nano-Zs, available from Marvern Instruments Example 1-1

Strontium hydroxide octahydrate (available from Wako Pure Chemical Industries, Ltd.) in an amount of 0.5 g, formic acid (available from Wako Pure Chemical Industries, Ltd.) in an amount of 0.0896 mL, decanoic acid (available from Wako Pure Chemical Industries, Ltd.) in an amount of 0.2332 mL and pure water in an amount of 2.032 mL were introduced into a 5 mL high-pressure reactor (available from AKICO Corporation).

Next, the high-pressure reactor was closed with a cover, heated to 400° C. in a shaking furnace (available from AKICO Corporation) so as to pressurize the inside of the high-pressure reactor to 40 MPa, and then shaken for 10 minutes for hydrothermal synthesis.

After that, the high-pressure reactor was plunged into cold water for quenching.

Next, because decanoic acid dissolves in ethanol, ethanol (available from Wako Pure Chemical Industries, Ltd.) was added, and the mixture was stirred and subjected to centrifugal separation performed in a centrifuge (trade name: MX-301, available from Tomy Seiko Co., Ltd.) at 12000 G for 10 minutes to separate a precipitate (reaction product) from a supernatant (washing step). This washing operation was repeated 5 times so as to remove the remaining decanoic acid, and thereby particles were obtained.

After that, the obtained particles were evaluated by (1) XRD, (2) FT-IR and (3) FE-SEM.

The formulation of respective components and the evaluation results in Example 1-1 are presented in Table 1, and an image-processed FE-SEM micrograph in Example 1-1 is shown in FIG. 1.

As a result, (1) XDR confirmed that the inorganic compound forming the inorganic particles was $SrCO_3$.

(2) FT-IR confirmed C—H stretching vibrations from 2800 to 3000 $cm^{-1}$ and the presence of C—H bonds on the surface of the inorganic particles.

(3) FE-SEM confirmed that the primary particles had an acicular shape with a sideways length SL of approximately 0.1 to 0.5 μm and a lengthwise length LL of approximately 0.8 to 6 μm with reference to FIG. 1. It was also confirmed that the aspect ratio of the primary particles was 8 to 60 as a result of calculation from FIG. 1.

Examples 1-2 to 1-16

Particles were obtained in the same manner as in Example 1-1 according to the formulation and treatment conditions presented in Table 1, and then subjected to evaluation in the same manner as in Example 1-1. The results are presented in Table 1.

Comparative Example 1-1

Strontium hydroxide octahydrate (available from Wako Pure Chemical Industries, Ltd.) in an amount of 0.5 g and pure water in an amount of 2.355 mL were introduced into a 5 mL high-pressure reactor (available from AKICO Corporation).

Next, the high-pressure reactor was closed with a cover, heated to 400° C. in a shaking furnace (available from AKICO Corporation) so as to pressurize the inside of the high-pressure reactor to 40 MPa, and then shaken for 10 minutes for hydrothermal synthesis.

After that, the high-pressure reactor was plunged into cold water for quenching.

Next, pure water was added, and the mixture was stirred and subjected to centrifugal separation performed in a centrifuge (trade name: MX-301, available from Tomy Seiko Co., Ltd.) at 12000 G for 10 minutes, and thereby a precipitate was separated from a supernatant and dried to give particles.

After that, the obtained particles were evaluated by (1) XRD described above.

The formulation of respective components and the evaluation results in Comparative Example 1-1 are presented in Table 1.

(1) XDR confirmed that the inorganic compound forming the inorganic particles was $SrCO_3$.

Comparative Example 1-2

Strontium hydroxide octahydrate (available from Wako Pure Chemical Industries, Ltd.) in an amount of 0.5 g, formic acid (available from Wako Pure Chemical Industries, Ltd.) in an amount of 0.0896 mL and pure water in an amount of 2.265 mL were introduced into a 5 mL high-pressure reactor (available from AKICO Corporation).

Next, the high-pressure reactor was closed with a cover, heated to 400° C. in a shaking furnace (available from AKICO Corporation) so as to pressurize the inside of the high-pressure reactor to 40 MPa, and then shaken for 10 minutes for hydrothermal synthesis.

After that, the high-pressure reactor was plunged into cold water for quenching.

Next, ethanol (available from Wako Pure Chemical Industries, Ltd.) was added, and the mixture was stirred and subjected to centrifugal separation performed in a centrifuge (trade name: MX-301, available from Tomy Seiko Co., Ltd.) at 12000 G for 10 minutes to separate a precipitate (reaction product) from a supernatant (washing step). This washing operation was repeated 5 times, and thereby particles were obtained.

After that, the obtained particles were evaluated by (1) XRD, (2) FT-IR and (3) FE-SEM.

Figure 2:
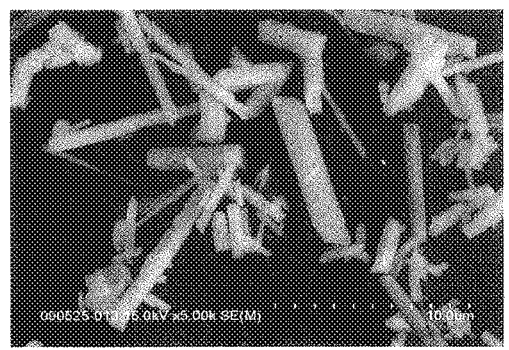
FIG. 2 shows an image-processed FE-SEM micrograph obtained in Comparative Example 1-2.

The formulation of respective components and the evaluation results in Comparative Example 1-2 are presented in Table 1, and an image-processed FE-SEM micrograph in Comparative Example 1-2 is shown in FIG. 2.

(1) XDR confirmed that the inorganic compound forming the inorganic particles was $SrCO_3$.

(2) FT-IR confirmed no C—H stretching vibrations from 2800 to 3000 $cm^{-1}$.

(3) FE-SEM confirmed that the primary particles had an acicular shape with a sideways length SL of approximately 200 nm to 1 μm and a lengthwise length LL of approximately 0.8 to 7.5 μm with reference to FIG. 2. It was also confirmed that the aspect ratio of the primary particles was 4 to 37 as a result of calculation from FIG. 2.

TABLE 1

| | | Formulations | | | | | | | |
|---|---|---|---|---|---|---|---|---|---|
| | | Inorganic compound | | | Organic compound | | Carbonic acid source | | pH adjusting agent |
| Ex. Comp. Ex. | Composition of inorganic particles *1 | Type | Amount (g) | Hydrophobic/ hydrophilic | Type | Amount (mL) | Type | Amount (mL) | Type (pH of reaction system) Amount (mL) |
| Ex. 1-1  | $SrCO_3$ | $Sr(OH)_2 \cdot 8H_2O$ | 0.5   | Hydrophobic | Decanoic acid | 0.2332  | Formic acid | 0.0896  | — |
| Ex. 1-2  | $SrCO_3$ | $Sr(OH)_2 \cdot 8H_2O$ | 0.5   | Hydrophobic | Decanoic acid | 0.9326  | Formic acid | 0.0299  | |
| Ex. 1-3  | $SrCO_3$ | $Sr(OH)_2 \cdot 8H_2O$ | 0.1   | Hydrophobic | Decanoic acid | 0.259   | Formic acid | 0.0896  | |
| Ex. 1-4  | $SrCO_3$ | $Sr(OH)_2 \cdot 8H_2O$ | 0.5   | Hydrophobic | Decanoic acid | 0.04664 | Formic acid | 0.0896  | |
| Ex. 1-5  | $SrCO_3$ | $Sr(OH)_2 \cdot 8H_2O$ | 0.5   | Hydrophobic | Decanoic acid | 0.2332  | Formic acid | 0.1792  | |
| Ex. 1-6  | $SrCO_3$ | $Sr(OH)_2 \cdot 8H_2O$ | 0.17  | Hydrophobic | Decanoic acid | 0.088   | Formic acid | 0.0338  | |
| Ex. 1-7  | $SrCO_3$ | $Sr(OH)_2 \cdot 8H_2O$ | 0.342 | Hydrophobic | Decanoic acid | 0.1768  | Formic acid | 0.0679  | |
| Ex. 1-8  | $SrCO_3$ | $Sr(OH)_2 \cdot 8H_2O$ | 0.5   | Hydrophobic | Decanoic acid | 0.2332  | Formic acid | 0.0896  | |
| Ex. 1-9  | $SrCO_3$ | $Sr(OH)_2 \cdot 8H_2O$ | 0.5   | Hydrophobic | Decanoic acid | 0.2332  | Formic acid | 0.08955 | |
| Ex. 1-10 | $SrCO_3$ | $Sr(OH)_2 \cdot 8H_2O$ | 1     | Hydrophobic | Decanoic acid | 0.2332  | Formic acid | 0.1592  | |
| Ex. 1-11 | $SrCO_3$ | $Sr(OH)_2 \cdot 8H_2O$ | 0.5   | Hydrophobic | Diethyl dodecylphosphonate | 0.3278 | Formic acid | 0.0896 | |
| Ex. 1-12 | $SrCO_3$ | $Sr(OH)_2 \cdot 8H_2O$ | 0.5   | Hydrophobic | Hexanoic acid | 0.1475  | Formic acid | 0.0896  | |
| Ex. 1-13 | $SrCO_3$ | $Sr(OH)_2 \cdot 8H_2O$ | 0.5   | Hydrophobic | Lauric acid | 0.2359    | Formic acid | 0.0896  | |
| Ex. 1-14 | $SrCO_3$ | $Sr(OH)_2 \cdot 8H_2O$ | 0.5   | Hydrophobic | 6-Phenylhexanoic acid | 0.2198 | Formic acid | 0.0896 | |
| Ex. 1-15 | $SrCO_3$ | $Sr(OH)_2 \cdot 8H_2O$ | 0.5   | Hydrophobic | Decylamine | 0.1948     | Formic acid | 0.0896  | |
| Ex. 1-16 | $SrCO_3$ | $Sr(OH)_2 \cdot 8H_2O$ | 0.5   | Hydrophobic | Decanoic acid Hexanoic acid | 0.2332 / 0.1475 | Formic acid | 0.0896 | |
| Comp. Ex. 1-1 | $SrCO_3$ | $Sr(OH)_2 \cdot 8H_2O$ | 0.5 | | — | | — | | |
| Comp. Ex. 1-2 | $SrCO_3$ | $Sr(OH)_2 \cdot 8H_2O$ | 0.5 | | — | | Formic acid | 0.0896 | |

| | Formulations | Treatment conditions | | | Primary particles Particle size | | Evaluation Dispersibility | | | |
|---|---|---|---|---|---|---|---|---|---|---|
| | | | | | SL: Sideways length | | Solvent of particle dispersion *2 | | | |
| Ex. Comp. Ex. | Pure water Amount (mL) | Temp. °C. | Pressure MPa | Time Min. | LL: Lengthwise length | Aspect ratio | Chloroform | Cyclohexane | Resin molded article *3 | Optical film *4 |
| Ex. 1-1  | 2.032 | 400 | 40 | 10  | SL: 0.1-0.5 μm / LL: 0.8-6 μm     | 8-60   | Dispersed as primary particles | — | Dispersed as primary particles | Dispersed as primary particles |
| Ex. 1-2  | 1.333 | 400 | 40 | 10  | SL: 3-4 μm / LL: 4-12.5 μm        | 15-5   | Dispersed as primary particles | Dispersed as primary particles | Dispersed as primary particles | Dispersed as primary particles |
| Ex. 1-3  | 2.328 | 400 | 40 | 10  | SL: 1-25 μm / LL: 3-6 μm          | 3-6    | Dispersed as primary particles | Dispersed as primary particles | Dispersed as primary particles | Dispersed as primary particles |
| Ex. 1-4  | 2.219 | 400 | 40 | 10  | SL: 0.2-0.6 μm / LL: 0.6-7 μm     | 3-35   | Dispersed as primary particles | Dispersed as primary particles | Dispersed as primary particles | Dispersed as primary particles |
| Ex. 1-5  | 1.942 | 400 | 40 | 10  | SL: 0.2-1.8 μm / LL: 0.6-5 μm     | 3-25   | Dispersed as primary particles | Dispersed as primary particles | Dispersed as primary particles | Dispersed as primary particles |
| Ex. 1-6  | 0.767 | 500 | 40 | 10  | SL: 0.2-0.75 μm / LL: 0.6-5.5 μm  | 3-27   | Dispersed as primary particles | Dispersed as primary particles | Dispersed as primary particles | Dispersed as primary particles |
| Ex. 1-7  | 1.542 | 400 | 30 | 10  | SL: 0.4-0.6 μm / LL: 1-6 μm       | 25-15  | Dispersed as primary particles | Dispersed as primary particles | Dispersed as primary particles | Dispersed as primary particles |
| Ex. 1-8  | 2.032 | 350 | 17 | 3   | SL: 0.1-0.5 μm / LL: 0.5-3 μm     | 5-30   | Dispersed as primary particles | Dispersed as primary particles | Dispersed as primary particles | Dispersed as primary particles |
| Ex. 1-9  | 2.032 | 400 | 40 | 120 | SL: 0.1-0.4 μm / LL: 0.2-5 μm     | 2-50   | Dispersed as primary particles | Dispersed as primary particles | Dispersed as primary particles | Dispersed as primary particles |
| Ex. 1-10 | 1.962 | 400 | 40 | 120 | SL: 0.4-0.8 μm / LL: 0.3-40 μm    | 1-100  | Dispersed as primary particles | Dispersed as primary particles | Dispersed as primary particles | Dispersed as primary particles |
| Ex. 1-11 | 1.937 | 400 | 40 | 10  | SL: 0.5-0.8 μm / LL: 5-18 μm      | 10-36  | Dispersed as primary particles | Dispersed as primary particles | Dispersed as primary particles | Dispersed as primary particles |
| Ex. 1-12 | 2.118 | 400 | 40 | 10  | SL: 0.1-0.5 μm / LL: 0.8-7.5 μm   | 8-75   | Dispersed as primary particles | Dispersed as primary particles | Dispersed as primary particles | Dispersed as primary particles |
| Ex. 1-13 | 2.029 | 400 | 40 | 10  | SL: 0.1-0.6 μm / LL: 0.5-2 μm     | 5-20   | Dispersed as primary particles | Dispersed as primary particles | Dispersed as primary particles | Dispersed as primary particles |
| Ex. 1-14 | 2.045 | 400 | 40 | 10  | SL: 0.1-0.55 μm / LL: 0.6-5.5 μm  | 6-55   | Dispersed as primary particles | Dispersed as primary particles | Dispersed as primary particles | Dispersed as primary particles |

TABLE 1-continued

| | | | | | | | | | |
|---|---|---|---|---|---|---|---|---|---|
| Ex. 1-15 | 2.07 | 400 | 40 | 10 | SL: 0.2-1 μm LL: 1-4 μm | 5-20 | Dispersed as primary particles | Dispersed as primary particles | Dispersed as primary particles |
| Ex. 1-16 | 1.885 | 400 | 40 | 10 | SL: 0.5-0.8 μm LL: 7-15 μm | 14-30 | Dispersed as primary particles | Dispersed as primary particles | Dispersed as primary particles |
| Comp. Ex. 1-1 | 2.355 | 400 | 40 | 10 | — | — | — | — | — |
| Comp. Ex. 1-2 | 2.265 | 400 | 40 | 10 | SL: 0.2-1 μm LL: 0.8-7.5 μm | 4-37 | Coagulated | Coagulated | Coagulated |

*1: Negative birefringence
*2: Preparation Example 1-1
*3: Production Example 1-1, Size: diameter of 10 mm, thickness of 5 mm
*4: Production Example 1-2, Size: thickness of 20 μm Example 1-17

Strontium hydroxide octahydrate (available from Wako Pure Chemical Industries, Ltd.) in an amount of 0.5 g, formic acid (available from Wako Pure Chemical Industries, Ltd.) in an amount of 0.0896 mL, oleic acid (available from Wako Pure Chemical Industries, Ltd.) in an amount of 0.3737 mL and aqueous ammonia in an amount of 1.892 mL were introduced into a 5 mL high-pressure reactor (available from AKICO Corporation). The amount of aqueous ammonia was adjusted such that the resulting reaction system had a pH of 10.

Next, the high-pressure reactor was closed with a cover, heated to 400° C. in a shaking furnace (available from AKICO Corporation) so as to pressurize the inside of the high-pressure reactor to 40 MPa, and then shaken for 10 minutes for hydrothermal synthesis.

After that, the high-pressure reactor was plunged into cold water for quenching.

Next, because oleic acid dissolves in ethanol, ethanol (available from Wako Pure Chemical Industries, Ltd.) was added, and the mixture was stirred and subjected to centrifugal separation performed in a centrifuge (trade name: MX-301, available from Tomy Seiko Co., Ltd.) at 12000 G for 10 minutes to separate a precipitate (reaction product) from a supernatant (washing step). This washing operation was repeated 5 times so as to remove the remaining oleic acid, and thereby particles were obtained.

After that, the obtained particles were evaluated by (1) XRD, (2) FT-IR and (4) TEM described above.

Figure 3:
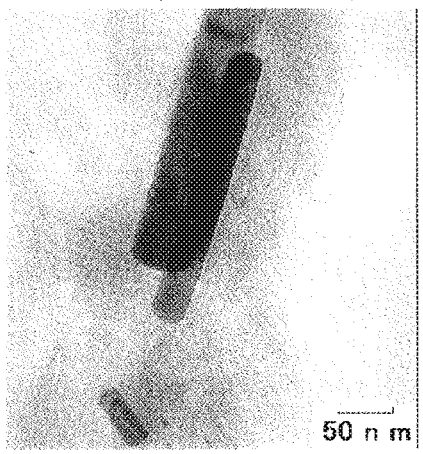
FIG. 3 shows an image-processed TEM micrograph obtained in Example 1-17.

The formulation of respective components and the evaluation results in Example 1-17 are presented in Table 2, and an image-processed TEM micrograph is shown in FIG. 3.

(1) XDR confirmed that the inorganic compound forming the inorganic particles was $SrCO_3$.

(2) FT-IR confirmed C—H stretching vibrations from 2800 to 3000 $cm^{-1}$ and the presence of C—H bonds on the surface of the inorganic particles.

(4) TEM confirmed that the primary particles had an acicular shape with a sideways length SL of approximately 20 to 100 nm and a lengthwise length LL of approximately 60 to 280 nm with reference to FIG. 3. It was also confirmed that the aspect ratio of the primary particles was 3 to 14 as a result of calculation from FIG. 3.

Examples 1-18 to 1-28

Particles were obtained in the same manner as in Example 1-17 according to the formulation and treatment conditions presented in Table 2, and then subjected to evaluation in the same manner as in Example 1-17. The results are presented in Table 2.

TABLE 2

| | | Formulations | | | | | | | |
|---|---|---|---|---|---|---|---|---|---|
| | | Inorganic compound | | Organic compound | | Carbonic acid source | | pH adjusting agent | |
| Ex. | Composition of inorganic particles *1 | Type | Amount (g) | Hydrophobic/ hydrophilic | Type | Amount (mL) | Type | Amount (mL) | Type (pH of reaction system) | Amount (mL) |
| Ex. 1-17 | $SrCO_3$ | $Sr(OH)_2 \cdot 8H_2O$ | 0.5 | Hydrophobic | Oleic acid | 0.3737 | Formic acid | 0.0896 | Aqueous ammonia (pH = 10) | 1.89 |
| Ex. 1-18 | $SrCO_3$ | $Sr(OH)_2 \cdot 8H_2O$ | 0.5 | Hydrophobic | Decanoic acid | 0.2332 | Formic acid | 0.0896 | Aqueous ammonia (pH = 10) | 2.03 |
| Ex. 1-19 | $SrCO_3$ | $Sr(OH)_2 \cdot 8H_2O$ | 0.5 | Hydrophobic | Decanoic acid | 0.2332 | Formic acid | 0.0896 | Aqueous ammonia (pH = 11) | 2.03 |
| Ex. 1-20 | $SrCO_3$ | $Sr(OH)_2 \cdot 8H_2O$ | 0.3 | Hydrophobic | Decanoic acid | 0.5181 | Formic acid | 0.0995 | Aqueous ammonia (pH = 12) | 2 |
| Ex. 1-21 | $SrCO_3$ | $Sr(OH)_2 \cdot 8H_2O$ | 0.5 | Hydrophobic | Decanoic acid | 0.5181 | Formic acid | 0.0995 | Aqueous ammonia (pH = 12) | 2 |
| Ex. 1-22 | $SrCO_3$ | $Sr(OH)_2 \cdot 8H_2O$ | 0.5 | Hydrophobic | Decanoic acid | 0.2332 | Formic acid | 0.0896 | Aqueous ammonia (pH = 8) | 2.03 |

TABLE 2-continued

| Ex. | | | | | | | | | | |
|---|---|---|---|---|---|---|---|---|---|---|
| Ex. 1-23 | SrCO₃ | Sr(OH)₂·8H₂O | 0.5 | Hydrophobic | Decanoic acid | 0.2332 | Urea | 0.1414 | Aqueous ammonia (pH = 10) | 1.98 |
| Ex. 1-24 | SrCO₃ | Sr(OH)₂·8H₂O | 0.5 | Hydrophobic | Decanoic acid | 0.2332 | Formic acid | 0.0896 | Aqueous ammonia (pH = 12) | 2.03 |
| Ex. 1-25 | SrCO₃ | Sr(OH)₂·8H₂O | 0.5 | Hydrophobic | Decanoic acid | 0.2332 | Formic acid | 0.0896 | Aqueous ammonia pH = 10) | 2.03 |
| Ex. 1-26 | SrCO₃ | Sr(OH)₂·8H₂O | 0.5 | Hydrophobic | 6-Phenylhexanoic acid | 0.2198 | Formic acid | 0.0896 | Aqueous ammonia (pH = 10) | 2.05 |
| Ex. 1-27 | SrCO₃ | Sr(OH)₂·8H₂O | 0.5 | Hydrophilic | Decylamine | 0.1948 | Formic acid | 0.0896 | Aqueous ammonia (pH = 10) | 2.07 |
| Ex. 1-28 | SrCO₃ | Sr(OH)₂·8H₂O | 0.3 | Hydrophobic | Decanoic acid Hexanoic acid | 0.2591 0.164 | Formic acid | 0.0995 | Aqueous ammonia (pH = 12) | 2.09 |

| | Evaluation | | | | | |
|---|---|---|---|---|---|---|
| | Treatment conditions | | | Primary particles Particle size SL: Sideways length LL: Lengthwise | | Dispersibility | | |
| Ex. | Temp. °C. | Pressure Ma | Time Min. | length | Aspect ratio | Solvent of particle dispersion *2 Chloroform | Cyclohexane | Resin molded article *3 | Optical film *4 |
| Ex. 1-17 | 400 | 40 | 10 | SL: 0.02-0.1 μm LL: 0.06-0.28 μm | 3-14 | Dispersed as primary particles | — | Dispersed as primary particles | Dispersed as primary particles |
| Ex. 1-18 | 400 | 40 | 10 | SL: 0.05-0.25 μm LL: 0.5-2 μm | 10-40 | Dispersed as primary particles | | Dispersed as primary particles | Dispersed as primary particles |
| Ex. 1-19 | 400 | 40 | 10 | SL: 0.1-0.5 μm LL: 0.4-5 μm | 4-50 | Dispersed as primary particles | | Dispersed as primary particles | Dispersed as primary particles |
| Ex. 1-20 | 400 | 40 | 10 | SL: 0.01-0.04 μm LL: 0.05-0.2 μm | 5-20 | Dispersed as primary particles | | Dispersed as primary particles | Dispersed as primary particles |
| Ex. 1-21 | 400 | 40 | 10 | SL: 0.01-0.02 μm LL: 0.05-0.2 μm | 5-20 | Dispersed as primary particles | | Dispersed as primary particles | Dispersed as primary particles |
| Ex. 1-22 | 400 | 40 | 10 | SL: 0.04-0.25 μm LL: 0.05-2 μm | 13-50 | Dispersed as primary particles | | Dispersed as primary particles | Dispersed as primary particles |
| Ex. 1-23 | 400 | 40 | 10 | SL: 0.1-0.2 μm LL: 1-6 μm | 10-60 | Dispersed as primary particles | | Dispersed as primary particles | Dispersed as primary particles |
| Ex. 1-24 | 400 | 40 | 10 | SL: 0.17-0.3 μm LL: 1.3-4 μm | 8-23 | Dispersed as primary particles | | Dispersed as primary particles | Dispersed as primary particles |
| Ex. 1-25 | 400 | 40 | 3 | SL: 0.075-0.2 μm LL: 0.3-1.8 μm | 4-24 | Dispersed as primary particles | | Dispersed as primary particles | Dispersed as primary particles |
| Ex. 1-26 | 400 | 40 | 10 | SL: 0.07-0.18 μm LL: 0.16-2.7 μm | 23-38 | Dispersed as primary particles | | Dispersed as primary particles | Dispersed as primary particles |
| Ex. 1-27 | 400 | 40 | 10 | SL: 0.125-0.35 μm LL: 0.43-5.3 μm | 4-42 | Dispersed as primary particles | | Dispersed as primary particles | Dispersed as primary particles |
| Ex. 1-28 | 400 | 40 | 10 | SL: 0.01-0.04 μm LL: 0.02-0.2 μm | 2-20 | Dispersed as primary particles | | Dispersed as primary particles | Dispersed as primary particles |

*1: Negative birefringence
*2: Preparation Example 1-1
*3: Production Example 1-1, Size: diameter of 10 mm, thickness of 5 mm
*4: Production Example 1-2, Size: thickness of 20 μm Example 1-29

Strontium carbonate (available from Honjo Chemical Corporation) in an amount of 0.5 g, decanoic acid (available from Wako Pure Chemical Industries, Ltd.) in an amount of 0.2332 mL and pure water in an amount of 2.122 mL were introduced into a 5 mL high-pressure reactor (available from AKICO Corporation).

Next, the high-pressure reactor was closed with a cover, heated to 400° C. in a shaking furnace (available from AKICO Corporation) so as to pressurize the inside of the high-pressure reactor to 40 MPa, and then shaken for 10 minutes for hydrothermal synthesis.

After that, the high-pressure reactor was plunged into cold water for quenching.

Next, because decanoic acid dissolves in ethanol, ethanol (available from Wako Pure Chemical Industries, Ltd.) was added, and the mixture was stirred and subjected to centrifugal separation performed in a centrifuge (trade name: MX-301, available from Tomy Seiko Co., Ltd.) at 12000 G for 10 minutes to separate a precipitate (reaction product) from a supernatant (washing step). This washing operation was repeated 5 times so as to remove the remaining decanoic acid, and thereby particles were obtained.

After that, the obtained particles were evaluated by (1) XRD, (2) FT-IR and (3) FE-SEM described above.

Figure 4:
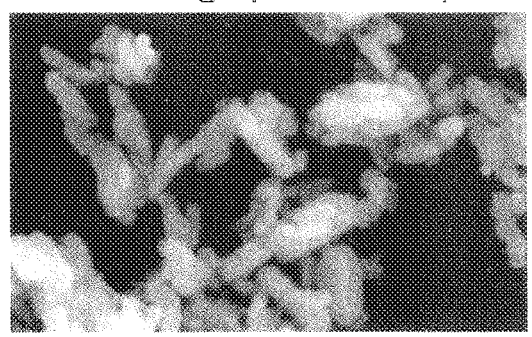
FIG. 4 shows an image-processed FE-SEM micrograph obtained in Example 1-29.

The formulation of respective components and the evaluation results in Example 1-29 are presented in Table 3, and an image-processed FE-SEM micrograph in Example 1-29 is shown in FIG. 4.

As a result, (1) XDR confirmed that the inorganic compound forming the inorganic particles was $SrCO_3$.

(2) FT-IR confirmed C—H stretching vibrations from 2800 to 3000 $cm^{-1}$ and the presence of C—H bonds on the surface of the inorganic particles.

(3) FE-SEM confirmed that the primary particles had an acicular shape with a sideways length SL of approximately 140 to 210 nm and a lengthwise length LL of approximately 400 nm to 1 μm with reference to the image-processed micrograph shown in FIG. 4. It was also confirmed that the aspect ratio of the primary particles was 3 to 5 as a result of calculation from the image-processed micrograph shown in FIG. 4.

Examples 1-30 to 1-46

Particles were obtained in the same manner as in Example 1-29 according to the formulation and treatment conditions presented in Table 3, and then subjected to evaluation in the same manner as in Example 1-29. The results are presented in Table 3.

Comparative Example 1-3

Strontium carbonate (available from Honjo Chemical Corporation) in an amount of 0.5 g and pure water in an amount of 2.355 mL were introduced into a 5 mL high-pressure reactor (available from AKICO Corporation).

Next, the high-pressure reactor was closed with a cover, heated to 400° C. in a shaking furnace (available from AKICO Corporation) so as to pressurize the inside of the high-pressure reactor to 40 MPa, and then shaken for 10 minutes for hydrothermal synthesis.

After that, the high-pressure reactor was plunged into cold water for quenching.

Next, a reaction product was recovered using ethanol (available from Wako Pure Chemical Industries, Ltd.) and subjected to centrifugal separation performed in a centrifuge (trade name: MX-301, available from Tomy Seiko Co., Ltd.) at 12000 G for 10 minutes, and thereafter a precipitate was separated from a supernatant and dried to give particles.

After that, the obtained particles were evaluated by (1) XRD, (2) FT-IR and (3) FE-SEM described above.

Figure 5:
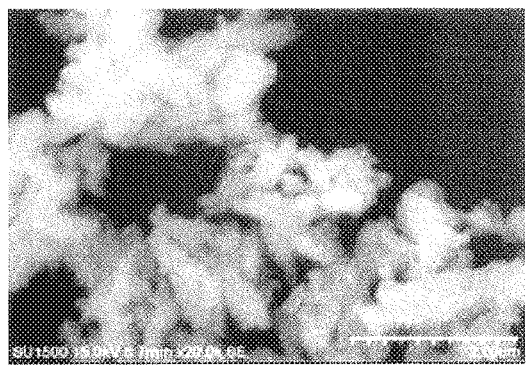
FIG. 5 shows an image-processed FE-SEM micrograph obtained in Comparative Example 1-3.

The formulation of respective components and the evaluation results in Comparative Example 1-3 are presented in Table 3, and an image-processed FE-SEM micrograph in Comparative Example 1-3 is shown in FIG. 5.

(1) XDR confirmed that the inorganic compound forming the inorganic particles was $SrCO_3$.

(2) FT-IR confirmed no C—H stretching vibrations from 2800 to 3000 $cm^{-1}$.

(3) FE-SEM confirmed that the primary particles had an acicular shape with a sideways length SL of approximately 140 to 210 nm and a lengthwise length LL of approximately 400 nm to 1 μm with reference to FIG. 5. It was also confirmed that the aspect ratio of the primary particles was 3 to 5 as a result of calculation from FIG. 5.

TABLE 3

| | | Formulations | | | | | | | |
|---|---|---|---|---|---|---|---|---|---|
| | | Inorganic compound | | | Organic compound | | Carbonic acid source | | pH adjusting agent | Pure water |
| Ex. Comp. Ex. | Composition of inorganic particles *1 | Type | Amount (g) | Hydrophobic/ hydrophilic | Type | Amount (mL) | Type | Amount (mL) | Type (pH of reaction system) | Amount (mL) | Amount (mL) |
| Ex. 1-29 | $SrCO_3$ | $SrCO_3$ | 0.5 | Hydrophobic | Decanoic acid | 0.2332 | — | | — | | 2.122 |
| Ex. 1-30 | $SrCO_3$ | $SrCO_3$ | 0.5 | Hydrophobic | Decanoic acid | 0.3406 | | | | | 3.099 |
| Ex. 1-31 | $SrCO_3$ | $SrCO_3$ | 0.5 | Hydrophobic | Decanoic acid | 0.3716 | | | | | 3.382 |
| Ex. 1-32 | $SrCO_3$ | $SrCO_3$ | 0.5 | Hydrophobic | Decylamine | 0.2845 | | | | | 3.155 |
| Ex. 1-33 | $SrCO_3$ | $SrCO_3$ | 0.5 | Hydrophobic | 6-Phenylhexanoic acid | 0.3503 | | | | | 3.403 |
| Ex. 1-34 | $SrCO_3$ | $SrCO_3$ | 0.5 | Hydrophobic | Decylphosphonic acid | 0.3823 | | | | | 3.057 |
| Ex. 1-35 | $SrCO_3$ | $SrCO_3$ | 0.5 | Hydrophobic | Decylphosphonic acid | 0.2617 | | | | | 3.057 |
| Ex. 1-36 | $SrCO_3$ | $SrCO_3$ | 0.5 | Hydrophobic | Cyclohexanepentanoic acid | 0.2511 | | | | | 2.365 |
| Ex. 1-37 | $SrCO_3$ | $SrCO_3$ | 0.5 | Hydrophobic | Norbornene decanoic acid | 0.5 | | | | | 3.253 |
| Ex. 1-38 | $SrCO_3$ | $SrCO_3$ | 0.5 | Hydrophobic | Tricoctylphosphin oxide | 0.7255 | | | | | 3.028 |
| Ex. 1-39 | $SrCO_3$ | $SrCO_3$ | 0.5 | Hydrophobic | 10-Undecenoic acid | 0.3458 | | | | | 3.407 |
| Ex. 1-40 | $SrCO_3$ $SrCO_3$ | $SrCO_3$ $SrCO_3$ | 0.5 | Hydrophobic | Decanoic acid Hexanoic acid | 0.1858 0.1176 | | | | | 3.45 |
| Ex. 1-41 | $SrCO_3$ $SrCO_3$ | $SrCO_3$ $SrCO_3$ | 0.5 | Hydrophobic | Norbornene decanoic acid Hexanoic acid | 0.25 0.1176 | | | | | 3.386 |
| Ex. 1-42 | $SrCO_3$ $SrCO_3$ | $SrCO_3$ $SrCO_3$ | 0.5 | Hydrophobic | Cyclopentanedecanoic acid Hexanoic acid | 0.2255 0.1176 | | | | | 3.41 |
| Ex. 1-43 | $SrCO_3$ | $SrCO_3$ | 0.5 | Hydrophilic | Ethyl 6-hydroxy- hexanoate | 0.2332 | | | | | 2.122 |
| Ex. 1-44 | $SrCO_3$ | $SrCO_3$ | 0.5 | Hydrophilic | 4-Oxovaleric acid | 0.2332 | | | | | 2.122 |
| Ex. 1-45 | $SrCO_3$ | $SrCO_3$ | 0.5 | Hydrophilic | 4-Hydroxyphenylacetic acid | 0.2332 | | | | | 2.122 |
| Ex. 1-46 | $SrCO_3$ | $SrCO_3$ | 0.5 | Hydrophilic | 3-(4-hydroxy- phenyl)propionic acid | 0.2332 | | | | | 2.122 |

TABLE 3-continued

| Comp. Ex. 1-3 | SrCO$_3$ | SrCO$_3$ | 0.5 | — | 2.355 |
|---|---|---|---|---|---|

| | Treatment conditions | | | Primary particles | | Evaluation | | |
|---|---|---|---|---|---|---|---|---|
| | | | | | | | Dispersibility | |
| | | | | | | Solvent of particle dispersion *2 | Resin molded article *3 | Optical film *4 |
| Ex. Comp. Ex. | Temp. ° C. | Pressure MPa | Time Min. | Particle size | Aspect ratio | Chloroform / Cyclohexane | | |
| Ex. 1-29 | 400 | 40 | 10 | SL: 0.14-0.21 µm LL: 0.4-1 µm | 3-5 | Dispersed as primary particles / — | Dispersed as primary particles | Dispersed as primary particles |
| Ex. 1-30 | 300 | 40 | 10 | | | Dispersed as primary particles | Dispersed as primary particles | Dispersed as primary particles |
| Ex. 1-31 | 300 | 30 | 10 | | | Dispersed as primary particles | Dispersed as primary particles | Dispersed as primary particles |
| Ex. 1-32 | 300 | 40 | 10 | | | Dispersed as primary particles | Dispersed as primary particles | Dispersed as primary particles |
| Ex. 1-33 | 300 | 30 | 10 | | | Dispersed as primary particles | Dispersed as primary particles | Dispersed as primary particles |
| Ex. 1-34 | 300 | 40 | 10 | | | Dispersed as primary particles | Dispersed as primary particles | Dispersed as primary particles |
| Ex. 1-35 | 400 | 40 | 10 | | | Dispersed as primary particles | Dispersed as primary particles | Dispersed as primary particles |
| Ex. 1-36 | 400 | 40 | 10 | | | Dispersed as primary particles | Dispersed as primary particles | Dispersed as primary particles |
| Ex. 1-37 | 300 | 30 | 10 | | | Dispersed as primary particles | Dispersed as primary particles | Dispersed as primary particles |
| Ex. 1-38 | 300 | 30 | 10 | | | Dispersed as primary particles | Dispersed as primary particles | Dispersed as primary particles |
| Ex. 1-39 | 300 | 30 | 10 | | | Dispersed as primary particles | Dispersed as primary particles | Dispersed as primary particles |
| Ex. 1-40 | 300 | 30 | 10 | | | Dispersed as primary particles | Dispersed as primary particles | Dispersed as primary particles |
| Ex. 1-41 | 300 | 30 | 10 | | | Dispersed as primary particles | Dispersed as primary particles | Dispersed as primary particles |
| Ex. 1-42 | 300 | 30 | 10 | | | Dispersed as primary particles | Dispersed as primary particles | Dispersed as primary particles |
| Ex. 1-43 | 400 | 40 | 10 | | | Dispersed as primary particles | — | — |
| Ex. 1-44 | 400 | 40 | 10 | | | Dispersed as primary particles | — | — |
| Ex. 1-45 | 400 | 40 | 10 | | | Dispersed as primary particles | — | — |
| Ex. 1-46 | 400 | 40 | 10 | | | Dispersed as primary particles | — | — |
| Comp. Ex. 1-3 | 400 | 40 | 10 | | | Coagulated | Coagulated | Coagulated |

*1: Negative birefringence
*2: Preparation Example 1-1
*3: Production Example 1-1, Size: diameter of 10 mm, thickness of 5 mm
*4: Production Example 1-2, Size: thickness of 20 µm Example 1-47

Strontium carbonate (available from Honjo Chemical Corporation) in an amount of 0.5 g and oleic acid (available from Wako Pure Chemical Industries, Ltd.) in an amount of 3.5 mL were introduced into a 5 mL high-pressure reactor (available from AKICO Corporation).

Next, the high-pressure reactor was shaken for 15 minutes while heating to 250° C. in a shaking furnace (available from AKICO Corporation), without closing the high-pressure reactor with a cover.

After heating, the high-pressure reactor was plunged into cold water for quenching.

Next, because oleic acid dissolves in ethanol, ethanol (available from Wako Pure Chemical Industries, Ltd.) was added, and the mixture was stirred and subjected to centrifugal separation performed in a centrifuge (trade name: MX-301, available from Tomy Seiko Co., Ltd.) at 12000 G for 10 minutes to separate a precipitate (reaction product) from a supernatant (washing step). By repeating this washing step 5 times, the remaining oleic acid was removed, and thereby particles were obtained.

After that, the obtained particles were evaluated by (1) XRD, (2) FT-IR and (3) FE-SEM described above.

Figure 6:
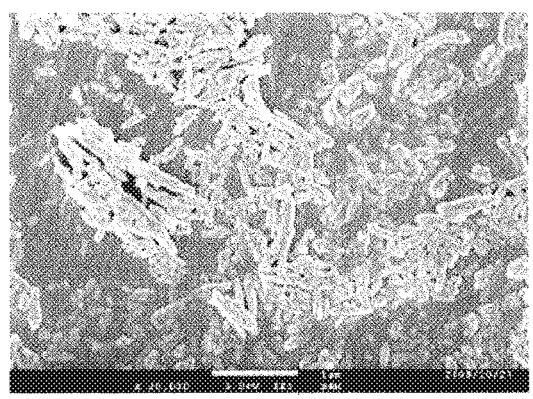
FIG. 6 shows an image-processed FE-SEM micrograph obtained in Example 1-47.

The formulation of respective components and the evaluation results in Example 1-47 are presented in Table 4, and an image-processed FE-SEM micrograph in Example 1-47 is shown in FIG. 6.

As a result, (1) XDR confirmed that the inorganic compound forming the inorganic particles was SrCO$_3$.

(2) FT-IR confirmed C—H stretching vibrations from 2800 to 3000 cm$^{-1}$ and the presence of C—H bonds on the surface of the inorganic particles.

(3) FE-SEM confirmed that the primary particles had an acicular shape with a sideways length SL of approximately 140 to 210 nm and a lengthwise length LL of approximately 400 nm to 1 μm with reference to FIG. 6. It was also confirmed that the aspect ratio of the primary particles was 3 to 5 as a result of calculation from FIG. 6.

Examples 1-48 to 1-54

Particles were obtained in the same manner as in Example 1-47 according to the formulation and treatment conditions presented in Table 4, and then subjected to evaluation in the same manner as in Example 1-47. The results are presented in Table 4.

ammonia were added to a 500 mL beaker. Furthermore, 1.5 g of titanium powder was added thereto and the mixture was stirred under ice-cold conditions for 3 hours until complete dissolution. Next, 15.5 g of 2-hydroxyoctanoic acid dissolved in 25 mL of ethanol was added and the mixture was stirred. After complete dissolution of all components, stirring was stopped and the mixture was allowed to stand still for one day. After that, the mixture was dried at 75° C. in a drier for 3 hours so as to give a water-soluble titanium complex (2-hydroxyoctanoic acid titanate).

TABLE 4

| | | | | Formulations | | | | | | |
|---|---|---|---|---|---|---|---|---|---|---|
| | Composition of | Inorganic compound | | Organic compound | | | Carbonic acid source | | pH adjusting agent | Pure water |
| Ex. Comp. Ex. | inorganic particles *1 | Type | Amount (g) | Hydrophobic/ hydrophilic | Type | Amount (mL) | Type | Amount (mL) | Type (pH of reaction system) Amount (mL) | Amount (mL) |
| Ex. 1-47 | SrCO₃ | SrCO₃ | 0.5 | Hydrophobic | Oleic acid | 3.5 | — | | — | — |
| Ex. 1-48 | SrCO₃ | SrCO₃ | 0.5 | Hydrophobic | Oleic acid | 3.5 | | | | |
| Ex. 1-49 | SrCO₃ | SrCO₃ | 0.5 | Hydrophobic | Oleic acid | 3.5 | | | | |
| Ex. 1-50 | SrCO₃ | SrCO₃ | 0.5 | Hydrophobic | Oleic acid | 3.5 | | | | |
| Ex. 1-51 | SrCO₃ | SrCO₃ | 0.5 | Hydrophobic | Oleic acid | 3.5 | | | | |
| Ex. 1-52 | SrCO₃ | SrCO₃ | 0.5 | Hydrophobic | Hexanoic acid | 3.5 | | | | |
| Ex. 1-53 | SrCO₃ | SrCO₃ | 0.5 | Hydrophobic | Octanoic acid | 3.5 | | | | |
| Ex. 1-54 | SrCO₃ | SrCO₃ | 0.5 | Hydrophobic | 3,3,5-Trimethylhexanoic acid | 3.5 | | | | |

| | Treatment conditions | | | Evaluation | | Dispersibility | | |
|---|---|---|---|---|---|---|---|---|
| | | | | Primary particles | | Solvent of particle dispersion *2 | Resin molded | Optical |
| Ex. Comp. Ex. | Temp. ° C. | Pressure MPa | Time Min. | Particle size | Aspect ratio | Chloroform / Cyclohexane | article *3 | film *4 |
| Ex. 1-47 | 250 | 0.1 | 15 | SL: 0.14-0.21 μm LL: 0.4-1 μm | 3-5 | — / Dispersed as primary particles | Dispersed as primary particles | Dispersed as primary particles |
| Ex. 1-48 | 150 | | 15 | | | Dispersed as primary particles / Dispersed as primary particles | Dispersed as primary particles | Dispersed as primary particles |
| Ex. 1-49 | 200 | | 15 | | | Dispersed as primary particles / Dispersed as primary particles | Dispersed as primary particles | Dispersed as primary particles |
| Ex. 1-50 | 250 | | 4 | | | Dispersed as primary particles / Dispersed as primary particles | Dispersed as primary particles | Dispersed as primary particles |
| Ex. 1-51 | 250 | | 8 | | | Dispersed as primary particles / Dispersed as primary particles | Dispersed as primary particles | Dispersed as primary particles |
| Ex. 1-52 | 150 | | 15 | | | Dispersed as primary particles / Dispersed as primary particles | Dispersed as primary particles | Dispersed as primary particles |
| Ex. 1-53 | 150 | | 15 | | | Dispersed as primary particles / Dispersed as primary particles | Dispersed as primary particles | Dispersed as primary particles |
| Ex. 1-54 | 150 | | 15 | | | Dispersed as primary particles / Dispersed as primary particles | Dispersed as primary particles | Dispersed as primary particles |

*1: Negative birefringence
*2: Preparation Example 1-1
*3: Production Example 1-1, Size: diameter of 10 mm, thickness of 5 mm
*4: Production Example 1-2, Size: thickness of 20 μm Example 1-55

Synthesis Example 1-1

Synthesis of Titanium Complex

Under ice-cold conditions, 100 mL of 30 volume % hydrogen peroxide solution and 25 mL of 25 wt % aqueous (Preparation of Magnesium Titanate)

Magnesium hydroxide (available from Wako Pure Chemical Industries, Ltd.) in an amount of 0.0612 g, a titanium complex (Synthesis Example 1-1) in an amount of 0.5 g, decanoic acid (available from Wako Pure Chemical Industries, Ltd.) in an amount of 0.5181 mL and pure water in an amount of 2.098 mL were introduced into a 5 mL high-pressure reactor (available from AKICO Corporation).

Next, the high-pressure reactor was closed with a cover, heated to 400° C. in a shaking furnace (available from AKICO Corporation) so as to pressurize the inside of the high-pressure reactor to 40 MPa, and then shaken for 10 minutes for hydrothermal synthesis.

After that, the high-pressure reactor was plunged into cold water for quenching.

Next, ethanol (available from Wako Pure Chemical Industries, Ltd.) was added, and the mixture was stirred and subjected to centrifugal separation performed in a centrifuge (trade name: MX-301, available from Tomy Seiko Co., Ltd.) at 12000 G for 10 minutes to separate a precipitate (reaction product) from a supernatant (washing step). By repeating this washing step 5 times, the remaining decanoic acid was removed, and thereby particles were obtained.

After that, the obtained particles were evaluated by (1) XRD, (2) FT-IR and (4) TEM described above.

Figure 7:
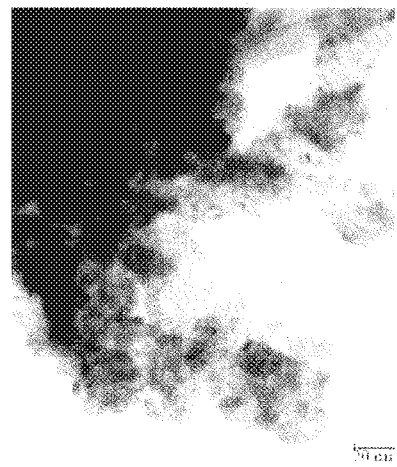
FIG. 7 shows an image-processed TEM micrograph obtained in Example 1-55.

The formulation of respective components and the evaluation results in Example 1-55 are presented in Table 5, and an image-processed TEM micrograph in Example 1-55 is shown in FIG. 7.

As a result, (1) XDR confirmed that the inorganic compound forming the inorganic particles was magnesium titanate.

(2) FT-IR confirmed C—H stretching vibrations from 2800 to 3000 $cm^{-1}$ and the presence of C—H bonds on the surface of the inorganic particles.

(4) TEM confirmed that the primary particles had an acicular shape with a sideways length SL of approximately 10 to 30 nm and a lengthwise length LL of approximately 20 to 200 nm with reference to the image-processed micrograph shown in FIG. 7. It was also confirmed that the aspect ratio of the primary particles was 2 to 20 as a result of calculation from the image-processed micrograph shown in FIG. 7.

Comparative Example 1-4

Magnesium hydroxide (available from Wako Pure Chemical Industries, Ltd.) in an amount of 0.0612 g, a titanium complex (Synthesis Example 1-1) in an amount of 0.5 g and pure water in an amount of 2.617 mL were introduced into a 5 mL high-pressure reactor (available from AKICO Corporation).

Next, the high-pressure reactor was closed with a cover, heated to 400° C. in a shaking furnace (available from AKICO Corporation) so as to pressurize the inside of the high-pressure reactor to 40 MPa, and then shaken for 10 minutes for hydrothermal synthesis.

After that, the high-pressure reactor was plunged into cold water for quenching.

Next, ethanol (available from Wako Pure Chemical Industries, Ltd.) was added, and the mixture was stirred and subjected to centrifugal separation performed in a centrifuge (trade name: MX-301, available from Tomy Seiko Co., Ltd.) at 12000 G for 10 minutes and dried to give particles.

After that, the obtained particles were evaluated by (1) XRD, (2) FT-IR and (4) TEM described above.

Figure 8:
FIG. 8 shows an image-processed TEM micrograph obtained in Comparative Example 1-4.

The formulation of respective components and the evaluation results in Comparative Example 1-4 are presented in Table 5, and an image-processed TEM micrograph in Comparative Example 1-4 is shown in FIG. 8.

As a result, (1) XDR confirmed that the inorganic compound forming the inorganic particles was magnesium titanate.

(2) FT-IR confirmed C—H stretching vibrations from 2800 to 3000 $cm^{-1}$ but the presence of no C—H bonds on the surface of the inorganic particles.

(4) TEM confirmed that the primary particles had an acicular shape with a sideways length SL of approximately 20 to 30 nm and a lengthwise length LL of approximately 30 to 200 nm. It was also confirmed that the aspect ratio of the primary particles was 1.5 to 10.

Comparative Examples 1-5 and 1-6

Particles were obtained in the same manner as in Example 1-4 according to the formulation and treatment conditions presented in Table 5, and then subjected to evaluation in the same manner as in Example 1-4. The results are presented in Table 5.

Example 1-56

The particles obtained in Example 1-26 in an amount of 0.1 g and chloroform in an amount of 30 g were introduced into a 50 mL screw vial.

Next, the mixture was stirred with a spatula and allowed to stand still for one day, and thereby separated into a supernatant and a precipitate (sedimentation separation, wet classification).

Next, the supernatant was removed therefrom and dried to give particles having a small particle size.

After that, the obtained particles were evaluated by (1) XRD, (2) FT-IR and (3) FE-SEM described above.

Figure 9:
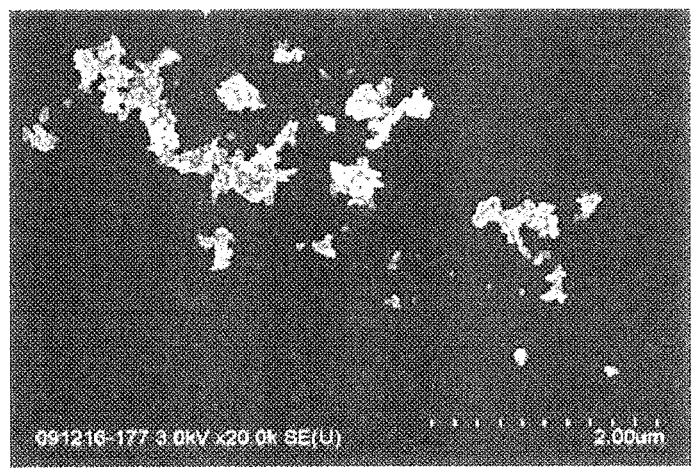
FIG. 9 shows an image-processed FE-SEM micrograph obtained in Example 1-56.

The formulation of respective components and the evaluation results in Example 1-56 are presented in Table 5, and an image-processed FE-SEM micrograph in Example 1-56 is shown in FIG. 9.

As a result, (1) XDR confirmed that the inorganic compound forming the inorganic particles was $SrCO_3$.

(2) FT-IR confirmed C—H stretching vibrations from 2800 to 3000 $cm^{-1}$ and the presence of C—H bonds on the surface of the inorganic particles.

(3) FE-SEM confirmed that the primary particles had an acicular shape with a sideways length SL of approximately 20 to 50 nm and a lengthwise length LL of approximately 30 to 200 nm with reference to FIG. 9 and were smaller than the particles of Example 1-26 (particles before wet classification). It was also confirmed that the aspect ratio of the primary particles was 1.5 to 10 as a result of calculation from FIG. 9.

TABLE 5

| | | Formulations | | | | | | | |
|---|---|---|---|---|---|---|---|---|---|
| | | Inorganic compound | | Organic compound | | Carbonic acid source | | pH adjusting agent | Pure water |
| Ex. Comp. Ex. | Composition of inorganic particles *1 | Type | Amount (g) | Hydrophobic/ hydrophilic | Type | Amount (mL) | Type | Amount (mL) | Type (pH of reaction system) | Amount (mL) | Amount (mL) |
| Ex. 1-55 | MgTiO$_3$ | Mg(OH)$_2$ Ti complex | 0.0612 0.5 | Hydrophobic | Decanoic acid | 0.5181 | — | | — | | 2.098 |
| Comp. Ex. 1-4 | MgTiO$_3$ | Mg(OH)$_2$ Ti complex | 0.0612 0.5 | | — | | | | | | 2.617 |
| Comp. Ex. 1-5 | MgTiO$_3$ | Mg(OH)$_2$ Ti complex | 0.0612 0.55 | | — | | | | | | 2.617 |
| Comp. Ex. 1-6 | MgTiO$_3$ | Mg(OH)$_2$ Ti complex | 0.0657 0.6 | | — | | | | | | 3.753 |
| Ex. 1-56 | SrCO$_3$ | | | | (From Example 1-26) | | | | | | (Wet classification) |

| | | | | Evaluation | | | |
|---|---|---|---|---|---|---|---|
| | Treatment conditions | | | Primary particles | | Dispersibility | | |
| Ex. Comp. Ex. | Temp. ° C. | Pressure MPa | Time Min. | Particle size | Aspect ratio | Solvent of particle dispersion *2 Chloroform | Cyclohexane | Resin molded article *3 | Optical film *4 |
| Ex. 1-55 | 400 | 40 | 10 | SL: 10-33 nm LL: 20-200 nm | 2-20 | Dispersed as primary particles | — | Dispersed as primary particles | Dispersed as primary particles |
| Comp. Ex. 1-4 | 400 | 40 | 10 | SL: 20-30 nm LL: 30-200 nm | 15-10 | Coagulated | Coagulated | Coagulated | Coagulated |
| Comp. Ex. 1-5 | 400 | 40 | 120 | SL: 20-30 nm LL: 30-200 nm | 15-10 | Coagulated | Coagulated | Coagulated | Coagulated |
| Comp. Ex. 1-6 | 300 | 30 | 120 | SL: 20-30 nm LL: 30-200 nm | 15-10 | Coagulated | Coagulated | Coagulated | Coagulated |
| Ex. 1-56 | (Wet classification) | | | SL: 0.02-0.05 μm LL: 0.03-0.2 μm | 15-10 | Dispersed as primary particles | | Uniformly dispersed | Uniformly dispersed |

*1: Negative birefringence
*2: Preparation Example 1-1
*3: Production Example 1-1, Size: diameter of 10 mm, thickness of 5 mm
*4: Production Example 1-2, Size: thickness of 20 μm Preparation Example 1-1

Preparation of Particle Dispersion

The particles obtained in Example 1-48 in an amount of 0.1 g and cyclohexane in an amount of 10 g were introduced into a 50 mL screw vial and stirred with a spatula to give a particle dispersion in which the particles were dispersed in cyclohexane.

This particle dispersion was subjected to (5) particle size distribution measurement.

Figure 10:
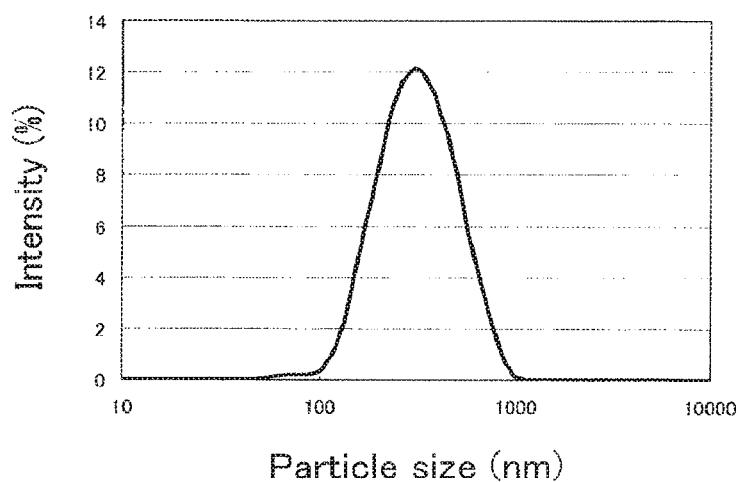
FIG. 10 shows a particle size distribution of particles in a particle dispersion obtained in Preparation Example 1-1.

The obtained particle size distribution is shown in FIG. 10.

It was found out that the particle size distribution in FIG. 10 matches the particle size distribution in Example 1-48 (or in other words, the particle size calculated from the sideways length SL and the lengthwise length LL, average particle size: 400 nm).

Accordingly, it was confirmed that in the particle dispersion obtained in Preparation Example 1-1, the particles were dispersed as primary particles in cyclohexane.

Also, the particles obtained in Examples 1-1 to 1-47, Examples 1-49 to 1-56 and Comparative Examples 1-2 to 1-6 were used to prepare particle dispersions in the same manner as described above. Next, the particle dispersions were evaluated by (5) particle size distribution measurement.

As a result, in the particle dispersions prepared using the particles obtained in Examples 1-1 to 1-47 and Examples 1-49 to 1-56, the particles were dispersed as primary particles in cyclohexane or chloroform.

On the other hand, with the particle dispersions prepared using the particles obtained in Comparative Examples 1-2 to 1-6, the particle size distribution measurement confirmed that the particles coagulated together in cyclohexane or chloroform, forming secondary particles (with an average particle size of 0.8 μm or greater).

Production Example 1-1

Production of Resin Molded Article

The particles obtained in Example 1-36 in an amount of 0.5 g and chloroform in an amount of 4.5 g were introduced into a 100 mL screw vial and stirred with a spatula to give a particle dispersion A in which the particles were dispersed in chloroform.

Next, a resin solution in which polyarylate (Mw=60,000 to 80,000, softening temperature: 200° C.) in an amount of 4.5 g was dissolved in 40.5 g of chloroform was mixed with the dispersion A to give a particle-containing resin solution, and the particle-containing resin solution was dried at 50° C. in a drier for one hour to remove chloroform, and thereby a particle-dispersed resin composition was obtained.

After that, the obtained particle-dispersed resin composition was injected into a metal mold having a diameter of 10 mm and a depth of 5 mm and then molded by vacuum pressing under conditions of 200° C. and 60 MPa to give a resin molded article.

The resin molded article was subjected to cross-section observation with the (3) field emission-scanning electron microscope (FE-SEM).

Figure 11:
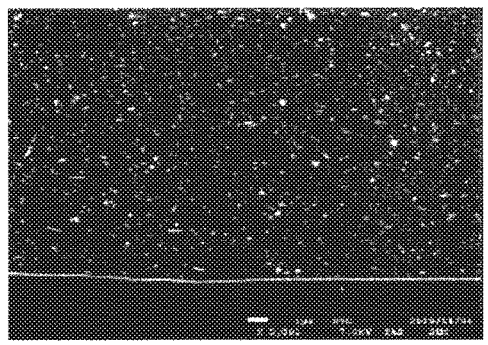
FIG. 11 shows an image-processed FE-SEM micrograph of a cross section of a resin molded article in which particles obtained in Example 1-36 are dispersed.

FIG. 11 shows an image-processed FE-SEM micrograph of a cross section of the resin molded article in which the particles of Example 1-36 are dispersed.

As can be seen from FIG. 11, it was confirmed that the particles were uniformly dispersed as primary particles in polyarylate.

The particles obtained in Examples 1-1 to 1-35, Examples 1-37 to 1-42, Examples 1-47 to 1-56 and Comparative Examples 1-2 to 1-6 were also used to produce resin molded articles in the same manner as described above. Then, the resin molded articles were subjected to cross-section observation with the (3) field emission-scanning electron microscope (FE-SEM).

Figure 12:
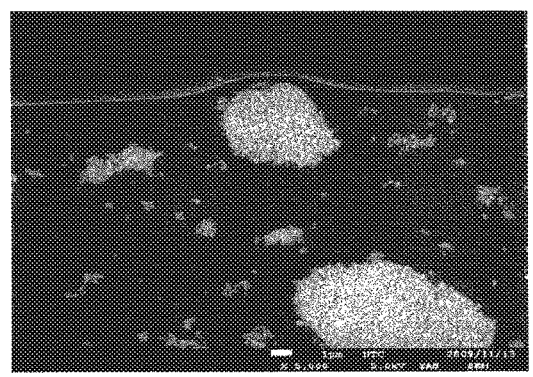
FIG. 12 shows an image-processed FE-SEM micrograph of a cross section of a resin molded article in which particles obtained in Comparative Example 1-2 are dispersed.

FIG. 12 shows an image-processed FE-SEM micrograph of a cross section of the resin molded article in which the particles of Comparative Example 1-2 are dispersed.

The result confirmed that, in the resin molded articles produced using the particles obtained in Examples 1-1 to 1-35, Examples 1-37 to 1-42, Examples 1-47 to 1-56, the particles were uniformly dispersed as primary particles in polyarylate.

On the other hand, it was confirmed that, in the resin molded articles produced using the particles of Comparative Examples 1-2 to 1-6, the particles coagulated in polyarylate, forming secondary particles.

Production Example 1-2

Production of Optical Film

The particles obtained in Example 1-36 in an amount of 0.1 g and chloroform in an amount of 0.9 g were introduced into a 100 mL screw vial and stirred with a spatula to give a particle dispersion B in which the particles were dispersed in chloroform.

Next, a resin solution in which polyarylate (Mw=60,000 to 80,000, softening temperature: 200° C.) in an amount of 0.9 g was dissolved in 8.1 g of chloroform was mixed with the dispersion B to give a particle-dispersed resin solution, and the particle-dispersed resin solution was applied to a support plate by spin coating and dried at 50° C. in a drier for one hour to remove chloroform, and thereby a coating of particle-dispersed resin composition was obtained.

Subsequently, the obtained coating was dried at 100° C. for 10 minutes to give a 20 µm thick optical film.

The optical film was subjected to cross-section observation with the (3) field emission-scanning electron microscope (FE-SEM).

Figure 13:
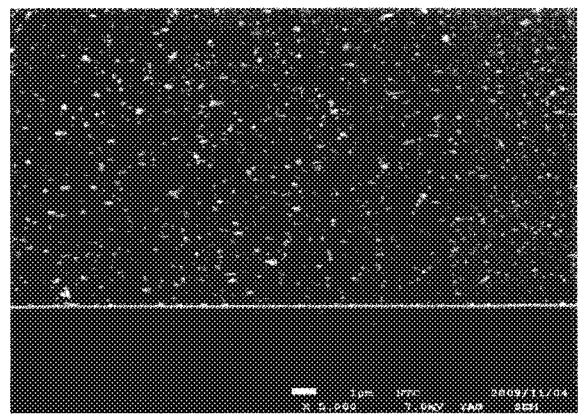
FIG. 13 shows an image-processed FE-SEM micrograph of a cross section of an optical film in which particles obtained in Example 1-36 are dispersed.

FIG. 13 shows an image-processed FE-SEM micrograph of a cross section of the optical film in which the particles of Example 1-36 are dispersed.

As can be seen from FIG. 13, it was confirmed that primary particles were uniformly dispersed in polyarylate.

Also, the particles obtained in Examples 1-1 to 1-35, Examples 1-37 to 1-42, Examples 1-47 to 1-56 and Comparative Examples 1-2 to 1-6 were used to produce optical films in the same manner as described above. Next, the optical films were subjected to cross-section observation with the (3) field emission-scanning electron microscope (FE-SEM).

Figure 14:
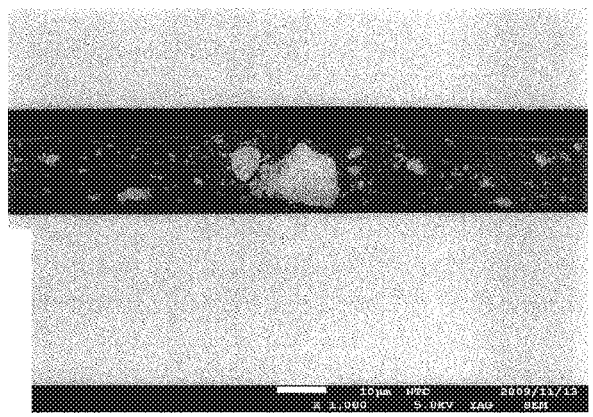
FIG. 14 shows an image-processed FE-SEM micrograph of a cross section of an optical film in which particles obtained in Comparative Example 1-2 are dispersed.

FIG. 14 shows an image-processed FE-SEM micrograph of a cross section of the optical film in which the particles of Comparative Example 1-2 were dispersed.

The result confirmed that in the optical films produced using the particles obtained in Examples 1-1 to 1-35, Examples 1-37 to 1-42 and Examples 1-47 to 1-56, the particles were uniformly dispersed as primary particles in polyarylate.

On the other hand, it was confirmed that in the optical films produced using the particles of Comparative Examples 1-2 to 1-6, the particles coagulated in polyarylate, forming secondary particles.

Preparation Examples and Examples Corresponding to the Second Group of Inventions The second group of inventions will be described in further detail by showing Preparation Examples and Examples, but the second group of inventions is not limited thereto.

Evaluation methods performed on organic-inorganic composite particles, resins, solvents and films (particle-dispersed resin molded articles) will be described below.

(1) X-Ray Diffractometry (XRD)

Organic-inorganic composite particles were loaded into a glass holder and subjected to X-ray diffractometry under the following conditions. After that, from the obtained peaks, the components of the inorganic substance were assigned by database search.

X-ray diffractometer: D8 DISCOVER with GADDS, available from Bruker AXS
(Optical system on incident side)
X-ray source: CuKα (λ=1.542 Å), 45 kV, 360 mA
Spectroscope (monochromator): multilayer mirror
Collimator diameter: 300 µm
(Optical system on light-receiving side)
Counter: two-dimensional PSPC (Hi-STAR)
Distance between organic-inorganic composite particles and counter: 15 cm
2θ=20, 50, 80 degrees, ω=10, 25, 40 degrees, Phi=0 degrees, Psi=0 degrees
Measurement time: 10 minutes
Assignment (semiquantitation software): FPM EVA, available from Bruker AXS (2) Fourier Transform Infrared Spectrophotometry (FT-IR)

Fourier transform infrared spectrophotometry was carried out on organic-inorganic composite particles according to the KBr method using the following apparatus.

Fourier transform infrared spectrophotometer: FT/IR-470Plus, available from JASCO Corporation (3) Average Particle Size Measurement by Dynamic Light Scattering (DLS)

A sample (with a concentration of solids of 1 mass % or less) was prepared by dispersing organic-inorganic composite particles in a solvent, and the average particle size of the organic-inorganic composite particles in the sample was measured with a dynamic light scattering photometer (model: ZEN 3600, available from Sysmex Corporation).

As the solvent, hexane was used in Preparation Example 2-1, chloroform was used in Preparation Examples 2-2, 2-3 and 2-5 to 2-7, aqueous ammonia having an ammonia concentration of 1 mass % was used in Preparation Example 2-4.

(4) Observation with Transmission Electron Microscope (TEM)

A film was cut, and its cross section was observed with a transmission electron microscope (TEM, H-7650, available from Hitachi High-Technologies Corporation) for the dispersed state of organic-inorganic composite particles.

Here, for a clear view of the cut surface of the film, the film was embedded in epoxy resin before cutting (machining).

Also, a particle dispersion (with a concentration of solids of 1 mass % or less) obtained by diluting organic-inorganic composite particles with a solvent was applied dropwise onto a TEM grid (collodion film, carbon support film) and dried. Then, the organic-inorganic composite particles were observed with a transmission electron microscope (TEM, H-7650, available from Hitachi High-Technologies Corporation) and the average particle size of the organic-inorganic composite particles was calculated by image analysis.

(5) Clarity

Clarity of a film was visually observed.

Preparation of Organic-Inorganic Composite Particles: Second Hydrothermal Synthesis, Wet Classification Preparation Example 2-1

Cerium hydroxide ($Ce(OH)_4$, available from Wako Pure Chemical Industries, Ltd.) as an inorganic substance, decanoic acid and hexanoic acid as organic compounds and water were introduced into a 5 mL high-pressure reactor (available from AKICO Corporation) in amounts presented in Table 6.

Next, the high-pressure reactor was closed with a cover, heated to 400° C. in a shaking furnace (available from AKICO Corporation) so as to pressurize the inside of the high-pressure reactor to 40 MPa, and then shaken for 10 minutes for hydrothermal synthesis.

After that, the high-pressure reactor was plunged into cold water for quenching.

Next, ethanol (available from Wako Pure Chemical Industries, Ltd.) was added, and the mixture was stirred and subjected to centrifugal separation performed in a centrifuge (trade name: MX-301, available from Tomy Seiko Co., Ltd.) at 12000 G for 20 minutes to separate into a precipitate (reaction product) and a supernatant (washing step). This washing operation was repeated 5 times. After that, ethanol in the precipitate was heated and dried at 80° C. to give organic-inorganic composite particles in which a decyl group and a hexyl group were present on the surface of cerium oxide ($CeO_2$).

Next, the organic-inorganic composite particles obtained above and chloroform were introduced into a 50 mL centrifuge tube and subjected to centrifugal separation in a centrifuge (trade name: MX-301, available from Tomy Seiko Co., Ltd.) at 4000 G for 5 minutes to separate into a supernatant and a precipitate (wet classification).

Next, the supernatant was removed therefrom and dried to give organic-inorganic composite particles having a small average particle size.

After that, the obtained organic-inorganic composite particles were evaluated by (1) XRD, (2) FT-IR, (3) DLS and (4) TEM described above.

As a result, (1) XDR confirmed that the inorganic substance forming the inorganic particles was $CeO_2$.

Also, (2) FT-IR confirmed that there were saturated aliphatic groups (a decyl group and a hexyl group) on the surface of the inorganic particles.

Furthermore, (3) DLS confirmed that the average particle size of the organic-inorganic composite particles was 7 nm, and (4) TEM confirmed that the average particle size of the organic-inorganic composite particles was 4 to 10 nm.

The above results are presented in Table 6.

Figure 15:
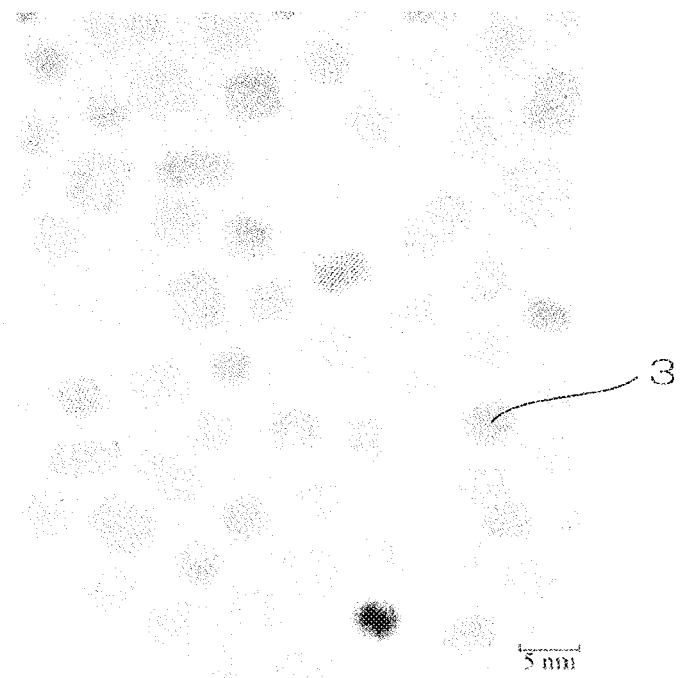
FIG. 15 shows an image-processed TEM micrograph of organic-inorganic composite particles obtained in Preparation Example 2-1.

Also, an image-processed TEM micrograph obtained by (4) TEM in Preparation Example 2-1 is shown in FIG. 15.

Preparation Examples 2-2 to 2-7

Organic-inorganic composite particles were prepared in the same manner as in Preparation Example 2-1, except that the formulation of the inorganic substance, the organic compound and water was changed to the formulations presented in Table 6, and the resulting organic-inorganic composite particles were subjected to wet classification.

After that, the obtained organic-inorganic composite particles were evaluated in the same manner as in Preparation Example 2-1. The results are presented in Table 6.

TABLE 6

| Preparation Example | Formulations | | | | | | Pure water Amount (mL) | High-temperature treatment conditions Synthesis method |
|---|---|---|---|---|---|---|---|---|
| | Inorganic substance | | Organic compound | | | | | |
| | Type | Amount (g) | Type | Amount (mL) | Type | Amount | | |
| Pre. Ex. 2-1 | $Ce(OH)_4$ | 1.09 | Decanoic acid | 0.5181 | Hexanoic acid | 0.3279 (mL) | 1.771 | Second hydrothermal synthesis |
| Pre. Ex. 2-2 | $Ce(OH)_4$ | 1.09 | 6-Phenylhexanoic acid | 0.4884 | Benzoic acid; | 0.3196 (g) | 1.809 | |
| Pre. Ex. 2-3 | $Ce(OH)_4$ | 1.09 | Decanoic acid | 1.0362 | — | | 1.01 | |
| Pre. Ex. 2-4 | Ti complex | 0.5 | 10-Carboxydecyl phosphonate | 0.44 | — | | 2.177 | |
| Pre. Ex. 2-5 | Ti complex | 0.5 | Ethyl decylphosphonate | 0.182 | Ethyl octylphosphonate | 0.1638 (mL) | 2.453 | |
| Pre. Ex. 2-6 | $SrCO_3$ | 0.5 | 6-Phenylhexanoic acid | 0.3503 | — | | 3.403 | First hydrothermal synthesis |
| Pre. Ex. 2-7 | $BaSO_4$ | 0.5 | 6-Phenylhexanoic acid | 0.3503 | — | | 3.403 | |

TABLE 6-continued

| Preparation Example | High-temperature treatment conditions | | | Organic-inorganic composite particles | | | Average particle size (nm) *3 |
|---|---|---|---|---|---|---|---|
| | Temp. ° C. | Pressure MPa | Time Min. | Compositions of inorganic particles *1 | Organic group on surface *2 | | |
| Pre. Ex. 2-1 | 400 | 40 | 10 | $CeO_2$ | Decyl group | Hexyl group | 4-10 [7] |
| Pre. Ex. 2-2 | 400 | 40 | 10 | $CeO_2$ | 6-Phenylhexyl group | Phenyl group | 4-8 |
| Pre. Ex. 2-3 | 400 | 40 | 10 | $CeO_2$ | Decyl group | — | 3-8 |
| Pre. Ex. 2-4 | 400 | 40 | 10 | $TiO_2$ | 10-Carboxydecyl group | — | 4-20 |
| Pre. Ex. 2-5 | 400 | 40 | 10 | $TiO_2$ | Decyl group | Octyl group | 4-8 |
| Pre. Ex. 2-6 | 300 | 30 | 10 | $SrCO_3$ | 6-Phenylhexyl group | — | 30-80 |
| Pre. Ex. 2-7 | 300 | 30 | 10 | $BaSO_4$ | 6-Phenylhexyl group | — | 30-80 |

*1: Confirmed by XRD
*2: Confirmed by FT-IR
*3: Measured by TEM
The value in square brackets was measured by DLS Preparation of Particle-Dispersed Resin Compositions (Fourth Preparation Method) and Production of Films Example 2-1

A resin solution having a concentration of solids of 10 mass % was prepared by blending polyetherimide resin (model: Ultem 1000, available from SABIC Innovative Plastics Japan LLC) and chloroform.

Also, a particle dispersion having a concentration of solids of 10 mass % was prepared by blending the organic-inorganic composite particles of Preparation Example 2-1 (inorganic substance: $CeO_2$, binding group: carboxyl group, organic groups: decyl group and hexyl group) and chloroform.

Next, the resin solution and the particle dispersion were blended such that the proportion of resin relative to the organic-inorganic composite particles in terms of mass was 90:10, and the organic-inorganic composite particles were dispersed in the resin solution by an ultrasonic disperser. In this manner, a clear varnish of particle-dispersed resin composition was prepared.

Next, the obtained varnish was applied to a support plate by spin coating. Chloroform was mostly volatilized during application of the varnish. After that, the applied particle-dispersed resin composition was dried at 50° C. for one hour (first drying) and then dried at 100° C. for 10 minutes (second drying) to give a 2.3 μm thick film (particle-dispersed resin molded article).

After that, the obtained film was evaluated by (4) TEM (the dispersed state and average particle size of organic-inorganic composite particles) and (5) clarity described above. The results are presented in Table 6 (average particle size) and Table 7.

Also, an image-processed TEM micrograph obtained by (4) TEM in Example 2-1 is shown in FIG. 16.

As can be seen from FIG. 16, there are gaps between organic-inorganic composite particles, and the organic-inorganic composite particles have a configuration that does not allow the inorganic particles to contact with each other by steric hindrance of the organic groups.

Examples 2-2 to 2-14

Films were produced in the same manner as in Example 2-1, except that the formulation of the resin solution and the particle dispersion was changed to the formulations presented in Table 7.

After that, the obtained films were evaluated in the same manner as in Example 2-1. The results are presented in Table 7.

Also, image-processed TEM micrographs obtained by (4) TEM in Examples 2-2 to 2-4, 2-7, 2-8, 2-11, 2-13 and 2-14 are shown in FIGS. 17 to 24, respectively.

TABLE 7

| | | | | | | | Example•Comparative Example | | | | | | | |
|---|---|---|---|---|---|---|---|---|---|---|---|---|---|---|
| | | | | | | | Ex. 2-1 | Ex. 2-2 | Ex. 2-3 | Ex. 2-4 | Ex. 2-5 | Ex. 2-6 | Ex. 2-7 | Ex. 2-8 |
| Particle dispersed-resin composition | Organic-inorganic composite particles *1 (parts by | Preparation Example Pre. Ex. 2-1 | Composition of inorganic particles $CeO_2$ | Organic group on surface Decyl group | | Hexyl group | Particle dispersion Solvent Chloroform | 10 | 10 | 10 | 30 | — | — | — | — |

TABLE 7-continued

|  |  |  | Composition of inorganic particles | Organic group on surface |  | Particle dispersion Solvent | Ex. 2-1 | Ex. 2-2 | Ex. 2-3 | Ex. 2-4 | Ex. 2-5 | Ex. 2-6 | Ex. 2-7 | Ex. 2-8 |
|---|---|---|---|---|---|---|---|---|---|---|---|---|---|---|
| (mass) | | Pre. Ex. 2-2 | $CeO_2$ | 6-Phenylhexyl group | Phenyl group | Chloroform | — | — | 10 | 20 | 10 | 10 | — | |
| | | Pre. Ex. 2-3 | $CeO_2$ | Decyl group | — | Chloroform | — | — | — | — | — | — | 10 | |
| | | Pre. Ex. 2-4 | $TiO_2$ | 10-Carboxydecyl group | — | Aqueous ammonia *3 | — | — | — | — | — | — | — | |
| | | Pre. Ex. 2-5 | $TiO_2$ | Decyl group | Octyl group | Chloroform | — | — | — | — | — | — | — | |
| | | Pre. Ex. 2-6 | $SrCO_3$ | 6-Phenylhexyl group | — | Chloroform | — | — | — | — | — | — | — | |
| | | Pre. Ex. 2-7 | $BaSO_4$ | 6-Phenylhexyl group | — | Chloroform | — | — | — | — | — | — | — | |
| | Resin *2 (parts by mass) | | Resin | | | Resin solution Solvent | | | | | | | | |
| | | Pre. Ex. 2-8 | Polyether resin | | | Chloroform | 90 | — | — | — | 80 | — | — | 90 |
| | | Pre. Ex. 2-9 | Thermoplastic fluorine-base polyimide resin | | | Chloroform | — | 90 | — | — | — | 90 | — | — |
| | | Pre. Ex. 2-10 | Polyarylate | | | Chloroform | — | — | 90 | 60 | — | — | 90 | — |
| | | Pre. Ex. 2-11 | Polyvinyl alcohol resin | | | Aqueous ammonia *3 | — | — | — | — | — | — | — | — |
| | | Preparation method | | | | | Fourth preparation method | | | | | | | |
| Resin molded article (film) | Evaluation | TEM | | | | Dispersed state of organic-inorganic particles | Uniformly dispersed as primary particles | | | | | | | |
| | | Visual inspection | | | | Clarity | Clear | | | | | | | |

Example·Comparative Example

|  |  |  | Composition of inorganic particles | Organic group on surface |  | Particle dispersion Solvent | Ex. 2-9 | Ex. 2-10 | Ex. 2-11 | Ex. 2-12 | Ex. 2-13 | Ex. 2-14 |
|---|---|---|---|---|---|---|---|---|---|---|---|---|
| Particle dispersed-resin composition | Organic-inorganic composite particles *1 (parts by mass) | Pre. Ex. 2-1 | $CeO_2$ | Decyl group | Hexyl group | Chloroform | — | — | — | — | — | — |
| | | Pre. Ex. 2-2 | $CeO_2$ | 6-Phenylhexyl group | Phenyl group | Chloroform | — | — | — | — | — | — |
| | | Pre. Ex. 2-3 | $CeO_2$ | Decyl group | — | Chloroform | 10 | 10 | — | — | — | — |
| | | Pre. Ex. 2-4 | $TiO_2$ | 10-Carboxydecyl group | — | Aqueous ammonia *3 | — | — | 10 | — | — | — |
| | | Pre. Ex. 2-5 | $TiO_2$ | Decyl group | Octyl group | Chloroform | — | — | — | 10 | — | — |
| | | Pre. Ex. 2-6 | $SrCO_3$ | 6-Phenylhexyl group | — | Chloroform | — | — | — | — | 50 | — |
| | | Pre. Ex. 2-7 | $BaSO_4$ | 6-Phenylhexyl group | — | Chloroform | — | — | — | — | — | 50 |
| | Resin *2 (parts by mass) | | Resin | | | Resin solution Solvent | | | | | | |
| | | Pre. Ex. 2-8 | Polyether resin | | | Chloroform | — | — | — | — | — | — |
| | | Pre. Ex. 2-9 | Thermoplastic fluorine-base polyimide resin | | | Chloroform | 90 | — | — | — | — | — |
| | | Pre. Ex. 2-10 | Polyarylate | | | Chloroform | — | 90 | — | 90 | 50 | 50 |
| | | Pre. Ex. 2-11 | Polyvinyl alcohol resin | | | Aqueous ammonia *3 | — | — | 90 | — | — | — |
| | | Preparation method | | | | | Fourth preparation method | | | | | |
| Resin molded article (film) | Evaluation | TEM | | | | Dispersed state of organic-inorganic particles | Uniformly dispersed as primary particles | | | | | |
| | | Visual inspection | | | | Clarity | Clear | | | | | |

*1: Blended as particle dispersion, with concentration of solids (organic-inorganic composite particles) of 10 mass %
*2: Blended as resin solution, with concentration of solids (resin) of 10 mass %
*3: Ammonia concentration of 1 mass %

In Table 7, the numerical values provided in "Organic-inorganic composite particles" and "Resin" indicate the amounts expressed in parts by mass. Also, the following gives detailed description of resins.

Polyetherimide resin: Ultem 1000, available from SABIC Innovative Plastics Japan LLC Thermoplastic fluorine-based polyimide resin: thermoplastic fluorine-based polyimide resin used in Example 1 of Japanese Unexamined Patent Publication No. 2003-315541

Polyarylate: polyarylate resin used in Example 4 of Japanese Unexamined Patent Publication No. 2009-80440

Polyvinyl alcohol resin: JC-40, available from Japan VAM & Poval Co., Ltd.

Preparation Examples, Examples, Comparative Examples and the Like Corresponding to the Third Group of Inventions The present invention will be described below in further detail by showing Preparation Examples, Examples and Comparative Examples, but the present invention is not limited thereto.

The evaluation methods for catalyst particles, catalyst solutions and films (catalyst molded articles) will be described below.

Evaluation Methods (1) X-Ray Diffractometry (XRD)

Catalyst particles were loaded into a glass holder and subjected to X-ray diffractometry under the following conditions. After that, from the obtained peaks, the components of the inorganic compound were assigned by database search.

X-ray diffractometer: D8 DISCOVER with GADDS, available from Bruker AXS
(Optical system on incident side)
X-ray source: CuKα ($\lambda$=1.542 Å), 45 kV, 360 mA
Spectroscope (monochromator): multilayer mirror
Collimator diameter: 300 μm
(Optical system on light-receiving side)
Counter: two-dimensional PSPC (Hi-STAR)
Distance between catalyst particles and counter: 15 cm
2θ=20, 50, 80 degrees, ω=10, 25, 40 degrees, Phi=0 degrees, Psi=0 degrees
Measurement time: 10 minutes
Assignment (semiquantitation software): FPM EVA, available from Bruker AXS (2) Fourier Transform Infrared Spectrophotometry (FT-IR)

Fourier transform infrared spectrophotometry was carried out on catalyst particles according to the KBr method using the following apparatus.

Fourier transform infrared spectrophotometer: FT/IR-470Plus, available from JASCO Corporation (3) Average Particle Size Measurement A. DLS (Dynamic Light Scattering)

A sample (catalyst solution with a concentration of solids of 1 mass % or less) was prepared by dispersing catalyst particles in a solvent, and the average particle size of the catalyst particles in the sample was measured with a dynamic light scattering photometer (model: ZEN 3600, available from Sysmex Corporation).

B. SEM (Scanning Electron Microscope)

A catalyst solution was applied dropwise onto a sample stage and dried. Then, the average particle size of catalyst particles was observed by observation with a scanning electron microscope (S-4800 available from Hitachi High-Technologies Corporation or JSM-7001F available from JEOL Ltd.).

C. TEM (Transmission Electron Microscope)

A sample (catalyst solution with a concentration of solids of 1 mass % or less) obtained by diluting catalyst particles with a solvent was applied dropwise onto a TEM grid (collodion film, carbon support film) and dried. Then, the catalyst particles were observed with a transmission electron microscope (TEM, H-7650, available from Hitachi High-Technologies Corporation) and the average particle size of catalyst particles was calculated by image analysis.

D. XRD

The average particle size of catalyst particles was calculated by substituting the data obtained in (1) XRD above into the following Scherrer's equation (2).

$$D=K\lambda/(\beta \cos \theta), \quad (2)$$

where D is the average crystalline particle size, K is the Scherrer constant, $\lambda$ is the wavelength of the X-ray tube, $\beta$ is the half band width, and $\theta$ is the diffraction angle.

(4) Evaluation of Catalytic Action

A. Examples 3-1 to 3-78 and Comparative Examples 3-1 to 3-5

An aqueous solution containing 0.01 mass % of rhodamine B (rhodamine B with a molecular weight of 479.01) was prepared (0.02 m mol/L).

Next, 0.01 g of catalyst particles of each of Examples 3-1 to 3-78 and Comparative Examples 3-1 to 3-5 were added to a transparent 2 mL vial and thereafter 1 g of the prepared aqueous solution of rhodamine B was added thereto.

After that, in a dark room, the vial was irradiated with black light (ultraviolet rays with a wavelength of 365 nm) at an illuminance of 1 mW/cm² for one hour.

After that, the aqueous solution of rhodamine B in the vial was subjected to ultraviolet-visible absorption spectrometry. The spectrometry was carried out with an ultraviolet-visible absorption spectrometer (U-560, available from JASCO Corporation).

Then, whether the catalyst particles exerted a catalytic action was evaluated based on the following evaluation criteria.

A circle "○" was given when a peak (wavelength: 550 nm) derived from rhodamine B disappeared.

A cross "x" was given when a peak (wavelength: 550 nm) derived from rhodamine B remained.

FIGS. 25 and 26 each show UV-visible absorption spectra at the start of irradiation and after a predetermined period of time has passed, obtained in Examples 3-10 and 3-66.

B. Examples 3-79 to 3-83 and Comparative Examples 3-6 to 3-13

One mol/L of aqueous acetaldehyde solution was prepared.

Next, 0.1 g of catalyst particles obtained in each of Examples 3-79 to 3-83 and Comparative Examples 3-6 to 3-13 was added to a vial (10 mL), and then the prepared aqueous acetaldehyde solution was added thereto in an amount of 100 μL with a syringe. After that, a septum cap was placed on the opening of the vial and the whole was stirred well.

After that, the vial was irradiated with light for 30 minutes using a 300 W xenon lamp (Cermax LX-300, available from Perkin Elmer Inc.). A cutoff filter (HOYA L42, available from HOYA) was attached to the xenon lamp to shield (shade) ultraviolet light (ultraviolet light with a wavelength of 420 nm or less).

After that, the concentration of $CO_2$ produced by decomposition of formaldehyde in the vial was measured by gas chromatography (HP 5890 Series II plus/HP5972, column: Ultra-1 (0.2 mmφ×25 m, df=0.33 um), available from Agilent Technologies, Inc.).

Then, whether the catalyst particles exerted a catalytic action was evaluated based on the following evaluation criteria.

A circle "○" was given when the $CO_2$ concentration was 10 ppm or greater.

A cross "x" was given when the $CO_2$ concentration was less than 10 ppm.

(5) Evaluation of Resin Degradation

A white film (described later) on which catalyst particles had been dispersed was heated at 80° C. in a drier for hour. After that, the film was irradiated with black light (ultraviolet rays with a wavelength of 365 nm) at an illuminance of 1 mW/cm$^2$ for 24 hours.

After that, degradation of the film was visually observed and evaluated based on the following evaluation criteria.

A circle "○" was given when the film was white.

A cross "x" was given when the film was yellow.

Preparation of Titanium Complex

Preparation Example 3-1

Preparation of Titanium Complex Containing 2-Hydroxyoctanoic Acid as Ligand

Under ice-cold conditions, 100 mL of 30 volume % hydrogen peroxide solution and 25 mL of 25 wt % aqueous ammonia were added to a 500 mL beaker. Furthermore, 1.5 g of titanium powder was added thereto and the mixture was stirred under ice-cold conditions for 3 hours until complete dissolution. Next, 15.5 g of 2-hydroxyoctanoic acid dissolved in 25 mL of ethanol was added and the mixture was stirred. After complete dissolution of all components, stirring was stopped and the mixture was allowed to stand still for one day. After that, the mixture was dried at 75° C. in a drier for 3 hours so as to give a water-soluble titanium complex.

This titanium complex was used as a complex (see Tables 8, 10 to 14 and 16) in Examples 3-8 to 3-17, 3-31 to 3-68, 3-78 and Comparative Example 3-3, which will be described later.

Preparation Example 3-2

Preparation of Titanium Complex Containing Glycolic Acid as Ligand

A water-soluble titanium complex was obtained through the same treatment as in Preparation Example 3-1, except that 3.6 g of glycolic acid was added instead of 15.5 g of 2-hydroxyoctanoic acid.

The titanium complex was used as a complex (see Table 9) in Example 3-21, which will be described later.

Preparation Example 3-3

Preparation of Titanium Complex Containing Citric Acid as Ligand

A water-soluble titanium complex was obtained through the same treatment as in Preparation Example 3-1, except that 9.1 g of citric acid was added instead of 15.5 g of 2-hydroxyoctanoic acid.

This titanium complex was used as a complex (see Table 9) in Examples 3-18 to 3-20, which will be described later.

Preparation Example 3-4

Preparation of Titanium Complex Containing Malic Acid as Ligand

A water-soluble titanium complex was obtained through the same treatment as in Preparation Example 3-1, except that 6.3 g of malic acid was added instead of 15.5 g of 2-hydroxyoctanoic acid.

This titanium complex was used as a complex (see Table 9) in Example 3-22, which will be described later.

Preparation of Catalyst Particles

Examples 3-1 to 3-83 and Comparative Examples 3-1 to 3-13

Respective components (an inorganic substance and/or a complex, an organic compound, a pH adjusting agent and water) were introduced into a 5 mL high-pressure reactor (available from AKICO Corporation) according to the formulation presented in Tables 8 to 16.

Next, the high-pressure reactor was closed with a cover and treated in a shaking furnace (available from AKICO Corporation) under the high temperature treatment conditions presented in Tables 8 to 16.

After that, the high-pressure reactor was plunged into cold water for quenching.

Next, ethanol (available from Wako Pure Chemical Industries, Ltd.) was added and the mixture was stirred. Subsequently, the mixture was subjected to centrifugal separation performed in a centrifuge (trade name: MX-301, available from Tomy Seiko Co., Ltd.) at 12000 G for 20 minutes to separate a precipitate (reaction product) from a supernatant (washing step). This washing operation was repeated 5 times.

After that, ethanol in the precipitate was heated and dried at 80° C. to give catalyst particles.

After that, the obtained catalyst particles were evaluated by (1) XRD, (2) FT-IR, (3) average particle size and (4) catalytic action described above.

As a result, (1) XRD confirmed that the primary components of the inorganic particles were $TiO_2$ (Examples 3-1 to 3-71 and Comparative Examples 3-1 to 3-5), $WO_3$ (Examples 3-72 to 3-75 and Comparative Examples 3-6 to 3-13) and $SrTiO_3$ (Examples 3-76 to 3-83).

Also, (2) FT-IR confirmed that there were organic groups that are presented in Table 8 to 16 on the surface of the inorganic particles.

(3) Average particle size measurement showed that, as is clear from Tables 8 to 16, the average particle size of catalyst particles of each of Examples 3-1 to 3-83 was 450 nm or less.

Also, it was found out, from the fact that peaks derived from rhodamine B disappeared in Examples 3-1 to 3-78 and Comparative Examples 3-1 to 3-5, and $CO_2$ was produced by decomposition of formaldehyde in Examples 3-79 to 3-83 and Comparative Examples 3-6 to 3-13, that the catalyst particles of Examples 3-1 to 3-83 and Comparative Examples 3-1 to 3-13 exerted an action of decomposing organic substances (photocatalytic action).

<Production of Catalyst Molded Articles>

A resin solution having a concentration of solids of 10 mass % was prepared by blending polyarylate (polyarylate resin used in Example 4 of Japanese Unexamined Patent Publication No. 2009-80440) with chloroform and uniformly mixing them.

Besides this, a catalyst solution having a concentration of solids of 10 mass % was prepared by blending catalyst particles of each of Examples 3-1 to 3-83 and Comparative Examples 3-1 to 3-13 with chloroform and uniformly mixing them.

Next, the resin solution and the catalyst solution were blended such that the proportion of resin relative to catalyst particles in terms of mass was 90:10 (the amount of resin expressed in parts by mass:the amount of catalyst particles expressed in parts by mass), and the catalyst particles were dispersed in the resin solution using an ultrasonic disperser. In this manner, a clear varnish of catalyst composition was prepared.

Next, the obtained varnish of catalyst composition was applied to a support plate by spin coating. Chloroform was mostly volatilized during application of the varnish. After that, the applied catalyst composition was dried at 50° C. for one hour (first drying) and then dried at 100° C. for 10 minutes (second drying) to give a film containing catalyst particles (catalyst molded article).

After that, the obtained films were evaluated by (5) resin degradation evaluation.

The results are presented in Tables 8 to 16.

As can be seen from Tables 8 to 16, the evaluation of resin degradation showed that polyarylate resin forming the films of Comparative Examples 3-1 to 3-13 degraded because the films yellowed.

On the other hand, in each of Examples 3-1 to 3-83, degradation of polyarylate resin was suppressed because the films remained white or transparent/colorless, without any discoloration.

In the tables, each numerical value within parentheses "( )" provided in "Formulation" indicates the volume expressed in mL, and other numerical values, or in other words, the numerical values without parentheses indicate the mass expressed in g.

Also, in "Average particle size" in the tables, each numerical value within square brackets "[ ]" indicates the average particle size calculated through TEM or SEM image analysis, each numerical value within angle brackets "< >" indicates the average particle size calculated with the Scherrer's equation based on the data obtained by XRD, and other numerical values, or in other words, the numerical values without brackets indicate the average particle size measured by DLS.

The following gives detailed description of $TiO_2$ used in Examples 3-1 to 3-7 and 3-30.

$TiO_2$ used in Examples 3-1 and 3-2: average particle size 7 nm, trade name CSB-M, available from Sakai Chemical Industry Co., Ltd.

$TiO_2$ used in Examples 3-3 and 3-30: average particle size 9 nm, trade name SSP-25, available from Sakai Chemical Industry Co., Ltd.

$TiO_2$ used in Examples 3-4 and 3-5: minor diameter 5 to 15 nm, major diameter 30 to 90 nm, trade name TTO-V-3, available from Ishihara Sangyo Kaisha, Ltd.

$TiO_2$ used in Example 3-6: average particle size 30 to 50 nm, TTO-55(A), available from Ishihara Sangyo Kaisha, Ltd.

$TiO_2$ used in Example 3-7: average particle size 10 to 30 nm, TTO-51(A), available from Ishihara Sangyo Kaisha, Ltd.

TABLE 8

| | Formulations | | | | | High-temperature treatment conditions | |
|---|---|---|---|---|---|---|---|
| | Inorganic substance and/or complex | | Organic compound | | Water mL | Surface treatment method | Temp. ° C. |
| | | Amount g (mL) | | Amount g (mL) | | | |
| Ex. 3-1 | $TiO_2$ | 0.5 | Decylphosphonic acid diethyl ester | 0.364 | 2.253 | First hydrothermal synthesis | 400 |
| Ex. 3-2 | | 0.5 | 10-(Diethoxy-phosphonyl)decanoic acid ethyl ester | 0.440 | 2.177 | | 400 |
| Ex. 3-3 | | 0.5 | Decylphosphonic acid diethyl ester | 0.364 | 2.253 | | 400 |
| Ex. 3-4 | | 0.04 | Decylphosphonic acid | 0.023 | 2.070 | | 400 |
| Ex. 3-5 | | 0.5 | | 0.291 | 2.326 | | 400 |
| Ex. 3-6 | | 0.5 | | 0.291 | 2.326 | | 400 |
| Ex. 3-7 | | 0.5 | Octylphosphonic acid diethyl ester | 0.328 | 2.289 | | 400 |
| Ex. 3-8 | Ti | 0.1 | 6-Phosphonohexanoic acid | 0.257 | 2.360 | Second hydrothermal synthesis | 400 |
| Ex. 3-9 | complex | 0.5 | Decylphosphonic acid | 0.197 | 4.226 | | 200 |
| Ex. 3-10 | (ligand: | 0.5 | | 0.291 | 2.326 | | 400 |
| Ex. 3-11 | 2-hydroxy- | 0.5 | Methylphosohonic acid | 0.144 | 2.473 | | 400 |
| Ex. 3-12 | octanoic | 0.5 | 3-Phosphonopropionic acid | 0.202 | 1.915 | | 400 |
| Ex. 3-13 | acid) | 0.5 | 10-(Diethoxy-phosphonyl)decanol | 0.422 | 2.195 | | 400 |
| Ex. 3-14 | | 0.5 | Decylphosphonic acid diethyl ester | 0.364 | 2.253 | | 400 |

TABLE 8-continued

| | | | | | | |
|---|---|---|---|---|---|---|
| Ex. 3-15 | | 0.5 | 10-(Diethoxy-phosphonyl)decanoic acid ethyl ester | 0.440 | 2.177 | 400 |
| Ex. 3-16 | | 0.5 | Octylphosphonic acid | 0.328 | 2.289 | 400 |
| Ex. 3-17 | | 0.6 | diethyl ester | 0.282 | 3.472 | 300 |

| | High-temperature treament conditions | | Catalyst particles | | Average particle size nm | Evaluation | |
|---|---|---|---|---|---|---|---|
| | Pressure MPa | Reaction time Min. | Inorganic particles | Organic group on surface | | Photo-catalytic action | Resin degradation |
| Ex. 3-1 | 40 | 10 | TiO$_2$ | Decyl | <7> | ○ | ○ |
| Ex. 3-2 | 40 | 10 | | 9-Carboxynonyl | <7> | ○ | ○ |
| Ex. 3-3 | 40 | 10 | | Decyl | <9> | ○ | ○ |
| Ex. 3-4 | 40 | 10 | | | [5 to 15] | ○ | ○ |
| Ex. 3-5 | 40 | 10 | | | [5 to 15] | ○ | ○ |
| Ex. 3-6 | 40 | 10 | | | [30 to 50] | ○ | ○ |
| Ex. 3-7 | 40 | 10 | | Octyl | [10 to 30] | ○ | ○ |
| Ex. 3-8 | 40 | 10 | | 5-Carboxypentyl | — | ○ | ○ |
| Ex. 3-9 | 30 | 10 | | Decyl | [1 to 10] | ○ | ○ |
| Ex. 3-10 | 40 | 10 | | | [2 to 8] | ○ | ○ |
| Ex. 3-11 | 40 | 10 | | Methyl | — | ○ | ○ |
| Ex. 3-12 | 40 | 10 | | 2-Carboxyethyl | [3 to 50] | ○ | ○ |
| Ex. 3-13 | 40 | 10 | | 10-Hydroxydecyl | [3 to 7] | ○ | ○ |
| Ex. 3-14 | 40 | 10 | | Decyl | [2 to 8] | ○ | ○ |
| Ex. 3-15 | 40 | 10 | | 9-Carboxynonyl | [4 to 20] | ○ | ○ |
| Ex. 3-16 | 40 | 10 | | Octyl | [2 to 8] | ○ | ○ |
| Ex. 3-17 | 30 | 120 | | — | | ○ | ○ |

TABLE 9

| | Formulations | | | | | | High-temperature treatment conditions |
|---|---|---|---|---|---|---|---|
| | Inorganic substance and/or complex | | Organic compound | | pH adjusting agent | | |
| | | Amount g (mL) | | Amount g (mL) | | Amount g (mL) | Water mL | Surface treatment method |
| Ex. 3-18 | Ti complex (ligand: citric acid) | 0.5 | Decylphosphonic acid | 0.556 | — | | 1.944 | Second hydrothermal synthesis |
| Ex. 3-19 | | 0.5 | 6-Phosphonohexanoic acid | 0.490 | | | 2.010 | |
| Ex. 3-20 | | 0.5 | 10-(Diethoxy-phosphonyl)decanoic acid ethyl ester | 0.841 | | | 1.659 | |
| Ex. 3-21 | Ti complex (ligand: glyolic acid) | 0.5 | Decylphosphonic acid diethyl ester | 0.440 | | | 2.177 | |
| Ex. 3-22 | Ti complex (ligand: malic acid) | 0.1 | Decylphosphonic acid | 0.291 | | | 2.326 | |
| Ex. 3-23 | 10 wt % aqueous amorphous TiO$_2$ solution | 2.2523 | Decylphosphonic acid diethyl ester | 0.364 | | | — | First hydrothermal synthesis |
| Ex. 3-24 | Titanium sulfate | 0.2093 | | 0.364 | 0.4M aqueous KOH solution | (2.044) | — | Second hydrothermal synthesis |
| Ex. 3-25 | Ammonium oxalate monohydrate | 0.5 | Octylphosphonic acid diethyl ester | 0.328 | — | | 2.289 | |
| Ex. 3-26 | 50 wt % aqueous titanium (IV) bis(ammonium lactato)dihydroxide solution | (1) | | 0.328 | | | 1.289 | |
| Ex. 3-27 | | (1) | 10-(Diethoxy-phosphonyl)decanoic acid ethyl ester | 0.733 | | | 2.622 | |
| Ex. 3-28 | | (2) | | 0.440 | | | 1.915 | |
| Ex. 3-29 | | (2) | | 0.632 | | | 0.945 | |

TABLE 9-continued

| | | High-temperature treatment conditions | | | Catalyst particles | | Average particle size nm | Evaluation | |
|---|---|---|---|---|---|---|---|---|---|
| | | Temp. ° C. | Pressure MPa | Reaction time Min. | Inorganic particles | Organic group on surface | | Photo-catalytic action | Resin degradation |
| Ex. 3-18 | | 400 | 40 | 10 | TiO$_2$ | Decyl | — | ○ | ○ |
| Ex. 3-19 | | 400 | 40 | 10 | | 5-Carboxypentyl | — | ○ | ○ |
| Ex. 3-20 | | 400 | 40 | 10 | | 9-Carboxynonyl | — | ○ | ○ |
| Ex. 3-21 | | 400 | 40 | 10 | | Decyl | [2 to 8] | ○ | ○ |
| Ex. 3-22 | | 400 | 40 | 10 | | | [8 to 40] | ○ | ○ |
| Ex. 3-23 | | 400 | 40 | 5 | | | — | ○ | ○ |
| Ex. 3-24 | | 400 | 40 | 10 | | | — | ○ | ○ |
| Ex. 3-25 | | 400 | 40 | 10 | | Octyl | [30] | ○ | ○ |
| Ex. 3-26 | | 400 | 40 | 10 | | | [5] | ○ | ○ |
| Ex. 3-27 | | 200 | 10 | 10 | | 9-Carboxynonyl | [3] | ○ | ○ |
| Ex. 3-28 | | 200 | 10 | 10 | | | [3] | ○ | ○ |
| Ex. 3-29 | | 300 | 10 | 10 | | | [5] | ○ | ○ |

TABLE 10

| | Formulations | | | | | | | | | High-temperature treatment conditions |
|---|---|---|---|---|---|---|---|---|---|---|
| | Inorganic substance and/or complex | | Organic compound | | | | | | Water mL | Surface treatment method |
| | | Amount g (mL) | | Amount g (mL) | | Amount g (mL) | | Amount g (mL) | | |
| Ex. 3-30 | TiO$_2$ | 0.5 | Octylphosphonic acid diethyl ester | 0.164 | Decylphosphonic acid diethyl ester | 0.182 | — | | 2.357 | First hydrothermal sythesis |
| Ex. 3-31 | Ti complex (ligand: 2-hydroxy-octanoic acid) | 0.1 | 3-(Diethoxy-phosphonyl)ethyl propionic acid ester | 0.156 | 6-(Diethoxy-phosphonyl)hexanoic acid ethyl ester | 0.176 | | | 2.284 | Second hydrothermal synthesis |
| Ex. 3-32 | | 0.1 | 3-Phosphono propionic acid | 0.020 | 6-Phosphonohexanoic acid | 0.026 | | | 2.571 | |
| Ex. 3-33 | | 0.1 | | 0.031 | 10-(Diethoxy-phosphonyl)decanoic acid ethyl ester | 0.044 | | | 2.541 | |
| Ex. 3-34 | | 0.1 | Octylphosphonic acid diethyl ester | 0.033 | 10-(Diethoxy-phosphonyl)decanoic acid ethyl ester | 0.044 | | | 2.540 | |
| Ex. 3-35 | | 0.1 | | 0.131 | Decylphosphonic acid diethyl ester | 0.146 | 10-(Diethoxy-phosphonyl)decanoic acid ethyl ester | 0.176 | 2.164 | |
| Ex. 3-36 | | 0.1 | Methylphosphonic acid | 0.013 | 10-(Diethoxy-phosphonyl)decanoic acid ethyl ester | 0.044 | — | | 2.560 | |
| Ex. 3-37 | | 0.1 | | 0.013 | 6-Phosphonohexanoic acid | 0.026 | | | 2.578 | |

TABLE 10-continued

| | | High-temperature treatment conditions | | | Catalyst particles | | | Average particle size nm | Evaluation | |
|---|---|---|---|---|---|---|---|---|---|---|
| | | Temp. ° C. | Pressure MPa | Reaction time Min. | Inorganic particles | Organic group on surface | | | Photocatalytic action | Resin degradation |
| Ex. 3-30 | | 400 | 40 | 10 | TiO$_2$ | Octyl | Decyl | — | <9> | ○ | ○ |
| Ex. 3-31 | | 400 | 40 | 10 | | 2-Carboxyethyl | 5-Carboxypentyl | | [2 to 10] | ○ | ○ |
| Ex. 3-32 | | 400 | 40 | 10 | | 2-Carboxyethyl | 5-Carboxypentyl | | [4 to 16] | ○ | ○ |
| Ex. 3-33 | | 400 | 40 | 10 | | | 9-Carboxynonyl | | [4 to 8] | ○ | ○ |
| Ex. 3-34 | | 400 | 40 | 10 | | Octyl | | | [4 to 15] | ○ | ○ |
| Ex. 3-35 | | 400 | 40 | 10 | | | Decyl | 9-Carboxynonyl | [2 to 10] | ○ | ○ |
| Ex. 3-36 | | 400 | 40 | 10 | | Methyl | 9-Carboxynonyl | — | [4 to 24] | ○ | ○ |
| Ex. 3-37 | | 400 | 40 | 10 | | | 5-Carboxypentyl | | [4 to 14] | ○ | ○ |

TABLE 11

| | Formulations | | | | | | | | | High-temperature treatment conditions |
|---|---|---|---|---|---|---|---|---|---|---|
| | Inorganic substance and/or complex | | Organic compound | | | | | | Water mL | Surface treatment method |
| | | Amount g (mL) | | Amount g (mL) | | Amount g (mL) | | Amount g (mL) | | |
| Ex. 3-38 | Ti complex (ligand: 2-hydroxyoctanoic acid) | 0.4 | Octylphosphonic acid diethyl ester | 0.131 | Decylphosphonic acid | 0.1164 | 10-(Diethoxyphosphonyl)decanoic acid ethyl ester | 0.088 | 2.369 | Second hydrothermal synthesis |
| Ex. 3-39 | | 0.4 | acid diethyl ester | 0.131 | acid | 0.1164 | phosphonyl)decanoic acid ethyl ester | 0.176 | 2.193 | |
| Ex. 3-40 | | 0.4 | | 0.197 | | 0.0582 | | 0.176 | 2.617 | |
| Ex. 3-41 | | 0.4 | Methylphosphonic acid | 0.072 | Octylphosphonic acid diethyl ester | 0.131 | 10-(Diethoxyphosphonyl)decanoic acid ethyl ester | 0.176 | 2.238 | |
| Ex. 3-42 | | 0.4 | | 0.115 | 3-Phosphonopropionic acid | 0.046 | — | | 2.841 | |
| Ex. 3-43 | | 0.4 | | 0.115 | 6-Phosphonohexanoic acid | 0.059 | | | 2.828 | |
| Ex. 3-44 | | 0.5 | Octylphosphonic acid diethyl ester | 0.131 | Decylphosphonic acid | 0.1164 | 10-(Diethoxyphosphonyl)decanoic acid ethyl ester | 0.088 | 2.281 | |
| Ex. 3-45 | | 0.5 | acid diethyl ester | 0.131 | acid | 0.1164 | phosphonyl)decanoic acid ethyl ester | 0.088 | 2.369 | |
| Ex. 3-46 | | 0.5 | | 0.131 | | 0.1164 | | 0.176 | 2.193 | |
| Ex. 3-47 | | 0.5 | | 0.164 | 10-(Diethoxyphosphonyl)decanoic acid ethyl ester | 0.220 | — | | 2.233 | |
| Ex. 3-48 | | 0.5 | | 0.164 | Decylphosphonic acid | 0.182 | | | 2.453 | |
| Ex. 3-49 | | 0.5 | | 0.262 | 10-(Diethoxyphosphonyl)decanoic acid ethyl ester | 0.088 | | | 2.267 | |

| | | High-temperature treatment conditions | | | Catalyst particles | | | Average particle size nm | Evaluation | |
|---|---|---|---|---|---|---|---|---|---|---|
| | | Temp. ° C. | Pressure MPa | Reaction time Min. | Inorganic particles | Organic group on surface | | | Photocatalytic action | Resin degradation |
| Ex. 3-38 | | 400 | 40 | 10 | TiO$_2$ | Octyl | Decyl | 9-Carboxynonyl | 10 | ○ | ○ |
| Ex. 3-39 | | 400 | 40 | 10 | | | | | [3 to 12] | ○ | ○ |
| Ex. 3-40 | | 400 | 40 | 10 | | | | | [2 to 14] | ○ | ○ |
| Ex. 3-41 | | 400 | 40 | 10 | | Methyl | Octyl | 9-Carboxynonyl | [3 to 40] | ○ | ○ |
| Ex. 3-42 | | 300 | 30 | 10 | | | 2-Carboxyethyl | — | [3 to 40] | ○ | ○ |

TABLE 11-continued

|  |  |  |  |  |  |  |  |  |  |
|---|---|---|---|---|---|---|---|---|---|
| Ex. 3-43 | 300 | 30 | 10 |  | 5-Carboxypentyl |  | [2 to 30] | ○ | ○ |
| Ex. 3-44 | 400 | 40 | 10 | Octyl | Decyl | 9-Carboxynonyl | 20 | ○ | ○ |
| Ex. 3-45 | 400 | 40 | 10 |  |  |  | 20 | ○ | ○ |
| Ex. 3-46 | 400 | 40 | 10 |  |  |  | [2 to 40] | ○ | ○ |
| Ex. 3-47 | 400 | 40 | 10 | 9-Carboxynonyl | — |  | — | ○ | ○ |
| Ex. 3-48 | 400 | 40 | 10 |  | Decyl |  | [4 to 8] | ○ | ○ |
| Ex. 3-49 | 400 | 40 | 10 |  | 9-Carboxynonyl |  | [4 to 8] | ○ | ○ |

TABLE 12

| | Formulations | | | | | | | |
|---|---|---|---|---|---|---|---|---|
| | Inorganic substance and/or complex | | Organic compound | | | | | Water |
| | Amount g (mL) | Amount g (mL) | | Amount g (mL) | | Amount g (mL) | Amount g (mL) | mL |
| Ex. 3-50 | Ti complex (ligand: 2-hydroxy-octanoic acid) | 0.5 | — | Octylphosphonic acid diethyl ester | 0.262 | Decylphosphonic acid | 0.0582 | 10-(Diethoxy-phosphonyl)decanoic acid ethyl ester | 0.088 | 2.296 |
| Ex. 3-51 | | 0.5 | | | 0.295 | 10-(Diethoxy-phosphonyl)decanoic acid ethyl ester | 0.044 | — | | 2.278 |
| Ex. 3-52 | | 0.5 | Pt 0.001 | | 0.295 | | | | | 2.194 |
| Ex. 3-53 | | 0.5 | — | Methylphosphonic acid | 0.072 | 10-(Diethoxy-phosphonyl)decanoic acid ethyl ester | 0.088 | Decylphosphonic acid | 0.1164 | 2.340 |
| Ex. 3-54 | | 0.5 | | | 0.144 | | 0.088 | | 0.0582 | 2.326 |
| Ex. 3-55 | | 0.5 | | | 0.144 | 3-Phosphono propionic acid | 0.040 | Octylphosphonic acid diethyl ester | 0.0655 | 2.407 |
| Ex. 3-56 | | 0.5 | | | 0.144 | 6-Phosphonohexanoic acid | 0.051 | | 0.0655 | 2.407 |
| Ex. 3-57 | | 0.1 | | 3-(Diethoxy-phosphonyl)ethyl propionic acid ester | 0.031 | 6-(Diethoxy-phosphonyl)hexanoic acid ethyl ester | 0.035 | — | | 2.550 |
| Ex. 3-58 | | 0.1 | | 3-Phosphono propionic acid | 0.020 | 6-Phosphonohexanoic acid | 0.026 | | | 2.571 |
| Ex. 3-59 | | 0.5 | | Methylphosphonic acid | 0.063 | Decylphosphonic acid | 0.146 | | | 2.560 |

| | | High-temperature treatment conditions | | | Catalyst particles | | | | Average particle size nm | Evaluation | |
|---|---|---|---|---|---|---|---|---|---|---|---|
| | Surface treatment method | Temp. °C. | Pressure MPa | Reaction time Min. | Inorganic particles | | Organic group on surface | | | Photocatalytic action | Resin degradation |
| Ex. 3-50 | Second hydrothermal synthesis | 400 | 40 | 10 | TiO$_2$ | Octyl | Decyl | 9-Carboxynonyl | [4 to 13] | ○ | ○ |
| Ex. 3-51 | | 400 | 40 | 10 | | 9-Carboxynonyl | — | | [4 to 8] | ○ | ○ |
| Ex. 3-52 | | 400 | 40 | 10 | TiO$_2$/Pt | | | | — | ○ | ○ |
| Ex. 3-53 | | 400 | 40 | 10 | TiO$_2$ | Methyl | 9-Carboxynonyl | Decyl | [4 to 12] | ○ | ○ |
| Ex. 3-54 | | 400 | 40 | 10 | | | | | — | ○ | ○ |
| Ex. 3-55 | | 400 | 40 | 10 | | | 2-Carboxyethyl | Octyl | — | ○ | ○ |
| Ex. 3-56 | | 400 | 40 | 10 | | | 5-Carboxypentyl | | — | ○ | ○ |
| Ex. 3-57 | | 400 | 40 | 10 | | 2-Carboxyethyl | 5-Carboxypentyl | — | [2 to 10] | ○ | ○ |
| Ex. 3-58 | | 400 | 40 | 10 | | 2-Carboxyethyl | 5-Carboxypentyl | | [2 to 10] | ○ | ○ |
| Ex. 3-59 | | 400 | 40 | 10 | | Methyl | Decyl | | [4 to 18] | ○ | ○ |

TABLE 13

| | Formulations | | | | | | | | | |
|---|---|---|---|---|---|---|---|---|---|---|
| | Inorganic substance and/or complex | | Organic compound | | | | | | pH adjusting agent | Water |
| | | Amount g (mL) | | Amount g (mL) | | Amount g (mL) | | Amount g (mL) | Amount g (mL) | mL |
| Ex. 3-60 | Ti complex (ligand: 2-hydroxy-octanoic acid) | 0.5 | 3-(Diethoxy-phosphonyl)ethyl propionic acid ester | 0.0623 | Decylphosphonic acid diethyl ester | 0.218 | 10-(Diethoxy-phosphonyl)decanoic acid ethyl ester | 0.088 | — | 2.248 |
| Ex. 3-61 | | 0.5 | 3-(Diethoxy-phosphonyl)ethyl propionic acid ester | 0.125 | 10-(Diethoxy-phosphonyl)decanoic acid ethyl ester | 0.176 | | | — | 2.316 |
| Ex. 3-62 | | 0.5 | Octylphosphonic acid diethyl ester | 0.6555 | Decylphosphonic acid diethyl ester | 0.073 | 10-(Diethoxy-phosphonyl)decanoic acid ethyl ester | 0.176 | | 2.302 |
| Ex. 3-63 | | 0.5 | | 0.6555 | | 0.073 | | 0.264 | | 2.214 |
| Ex. 3-64 | | 0.5 | | 0.131 | | 0.146 | | 0.176 | | 2.164 |
| Ex. 3-65 | | 0.5 | | 0.164 | Decylphosphonic acid | 0.146 | | | | 2.453 |
| Ex. 3-66 | | 0.5 | | 0.164 | Decylphosphonic acid | 0.182 | | | | 2.453 |
| Ex. 3-67 | | 0.5 | | 0.164 | diethyl ester | 0.182 | | | | 2.271 |
| Ex. 3-68 | | 0.5 | | 0.164 | | 0.182 | | | 1% Aqueous ammonia | (2.271) — |

| | High-temperature treatment conditions | | | | Catalyst particles | | | | Average particle size nm | Evaluation | |
|---|---|---|---|---|---|---|---|---|---|---|---|
| | Surface treatment method | Temp. °C. | Pressure MPa | Reaction time Min. | Inorganic particles | Organic group on surface | | | | Photocatalytic action | Resin degradation |
| Ex. 3-60 | Second hydrothermal synthesis | 400 | 40 | 10 | TiO$_2$ | 2-Carboxyethyl | Decyl | 9-Carboxynonyl | [7] | ○ | ○ |
| Ex. 3-61 | | 400 | 40 | 10 | | 9-Carboxynonyl | — | | [14] | ○ | ○ |
| Ex. 3-62 | | 400 | 40 | 10 | | Octyl | Decyl | 9-Carboxynonyl | [8] | ○ | ○ |
| Ex. 3-63 | | 400 | 40 | 10 | | | | | [8] | ○ | ○ |
| Ex. 3-64 | | 400 | 40 | 10 | | | | | [7] | ○ | ○ |
| Ex. 3-65 | | 400 | 40 | 10 | | | | — | [5] | ○ | ○ |
| Ex. 3-66 | | 400 | 40 | 10 | | | | | [5] | ○ | ○ |
| Ex. 3-67 | | 400 | 40 | 10 | | | | | [5] | ○ | ○ |
| Ex. 3-68 | | 400 | 40 | 10 | | | | | — | ○ | ○ |

TABLE 14

| | Formulations | | | | | High-temperature treatment conditions | |
|---|---|---|---|---|---|---|---|
| | Inorganic substance and/or complex | | Organic compound | | Water mL | Surface treatment method | Temp. °C. | Pressure MPa |
| | | Amount g (mL) | | Amount g (mL) | | | |
| Ex. 3-69 | Catalyst particles of Example 3-57 | 0.1 | Methanol | (3.170) | — | High-temperature methanol treatment | 300 | 40 |
| Ex. 3-70 | Catalyst particles of Example 3-61 | 0.1 | | (3.170) | | | 300 | 40 |
| Ex. 3-71 | Catalyst particles of Example 3-27 | 0.1 | | (3.170) | | | 300 | 40 |
| Comp. Ex. 3-1 | 50 wt % aqueous titanium (IV) | 1 | — | | 3.423 | Hydrothermal treatment | 200 | 30 |

TABLE 14-continued

| | | | | | | |
|---|---|---|---|---|---|---|
| Comp. Ex. 3-2 | bis(ammonium lactato) dihydroxide solution | 1 | | 1.617 | 400 | 40 |
| Comp. Ex. 3-3 | Ti complex (ligand: 2-hydroxy-octanoic acid) | 0.5 | | 2.617 | 400 | 40 |
| Comp. Ex. 3-4 | Ammonium oxalate monohydrate | 0.5 | | 4.423 | 200 | 30 |
| Comp. Ex. 3-5 | | 0.5 | | 2.617 | 400 | 40 |

| | High-temperature treatment conditions | Catalyst particles | | Average particle size nm | Evaluation | |
|---|---|---|---|---|---|---|
| | Reaction time Min. | Inorganic particles | Organic group on surface | | Photocatalytic action | Resin degradation |
| Ex. 3-69 | 180 | TiO$_2$ | 2-(Methoxy-carbonyl)ethyl | 5-(Methoxy-carbonyl)pentyl | [2 to 10] | ○ | ○ |
| Ex. 3-70 | 180 | | | 9-(Methoxy-carbonyl)nonyl | [14] | ○ | ○ |
| Ex. 3-71 | 180 | | 9-(Methoxy-carbonyl)nonyl | — | [3] | ○ | ○ |
| Comp. Ex. 3-1 | 10 | TiO$_2$ | — | | [30] | ○ | X |
| Comp. Ex. 3-2 | 10 | | | | [100] | ○ | X |
| Comp. Ex. 3-3 | 10 | | | | [10 to 140] | ○ | X |
| Comp. Ex. 3-4 | 10 | | | | [4] | ○ | X |
| Comp. Ex. 3-5 | 10 | | | | [50] | ○ | X |

TABLE 15

| | Formulations | | | | | | | High-temperature treatment conditions |
|---|---|---|---|---|---|---|---|---|
| | Inorganic substance and/or complex | | | | Organic compound | | Water mL | Surface treatment method |
| | | Amount g (mL) | | Amount g (mL) | | Amount g (mL) | | |
| Ex. 3-72 | Tungstic acid | 0.50 | — | | Decylamine | 0.2164 | 4.207 | Second hydrothermal synthesis |
| Ex. 3-73 | | 0.50 | Pd | 0.005 | | 0.2164 | 4.207 | |
| Ex. 3-74 | | 0.50 | Pt | 0.005 | | 0.2164 | 4.207 | |
| Ex. 3-75 | | 0.50 | Copper formate | 0.06 | | 0.2164 | 4.207 | |
| Comp. Ex. 3-6 | Ammoium tungstate pentahydrate | 0.50 | — | | — | | 4.423 | |
| Comp. Ex. 3-7 | | 0.50 | | | | | 2.617 | |
| Comp. Ex. 3-8 | Tungstic acid | 0.50 | | | | | 4.423 | |
| Comp. Ex. 3-9 | | 0.50 | | | | | 4.423 | |
| Comp. Ex. 3-10 | | 0.50 | | | | | 2.617 | |
| Comp. Ex. 3-11 | | 1.00 | | | | | 2.617 | |
| Comp. Ex. 3-12 | | 0.50 | Copper sulfate | 0.01 | | | 2.607 | |
| Comp. Ex. 3-13 | | 0.50 | | 0.10 | | | 2.517 | |

TABLE 15-continued

| | High-temperature treatment conditions | | | Catalyst particles | | Average particle size nm | Evaluations | |
|---|---|---|---|---|---|---|---|---|
| | Temp. °C | Pressure MPa | Reaction time Min. | Inorganic particles | Organic group on surface | | Photo-catalytic action | Resin degradation |
| Ex. 3-72 | 200 | 30 | 60 | WO₃ | Decyl | [50] | ○ | ○ |
| Ex. 3-73 | 200 | 30 | 60 | WO₃/Pd | | [50] | ○ | ○ |
| Ex. 3-74 | 200 | 30 | 60 | WO₃/Pt | | [50] | ○ | ○ |
| Ex. 3-75 | 200 | 30 | 60 | WO₃/Cu | | [50] | ○ | ○ |
| Comp. Ex. 3-6 | 200 | 30 | 10 | WO₃ | — | [5] | ○ | X |
| Comp. Ex. 3-7 | 400 | 40 | 10 | | | [100] | ○ | X |
| Comp. Ex. 3-8 | 200 | 30 | 10 | | | [20] | ○ | X |
| Comp. Ex. 3-9 | 200 | 30 | 60 | | | [60] | ○ | X |
| Comp. Ex. 3-10 | 400 | 40 | 10 | | | [100] | ○ | X |
| Comp. Ex. 3-11 | 400 | 40 | 10 | | | [100] | ○ | X |
| Comp. Ex. 3-12 | 400 | 40 | 10 | WO₃/CuO | | — | ○ | X |
| Comp. Ex. 3-13 | 400 | 40 | 10 | | | [200] | ○ | X |

TABLE 16

| | Formulations | | | | | | | | | |
|---|---|---|---|---|---|---|---|---|---|---|
| | Inorganic substance and/or complex | | | | | | Organic compound | | | Water mL |
| | | Amount g (mL) | | Amount g (mL) | | Amount g (mL) | | Amount g (mL) | Amount g (mL) | |
| Ex. 3-76 | 50 wt % aqueous titanium (IV) bis(ammonium lactato)dihydroxide solution | 0.5 | Sr(OH)₂•8H₂O | 0.5 | — | | Octylphosphonic acid diethyl ester | 0.328 | — | 2.289 |
| Ex. 3-77 | Ammonium oxalate monohydrate | 0.5 | | 0.5 | | | | 0.328 | | 2.289 |
| Ex. 3-78 | Ti complex (ligand: 2-hydroxy-octanoic acid) | 0.5 | | 0.5 | | | | 0.328 | | 2.289 |
| Ex. 3-79 | 50 wt % aqueous titanium (IV) bis(ammonium lactato)dihydroxide solution | 0.5 | | 0.5 | | | 6-Phosphonohexanoic acid | 0.488 | Octylphosphonic acid diethyl ester | 0.3275 | 1.801 |
| Ex. 3-80 | | 0.5 | | 0.5 | Nickel (II) acetate tetrahydrate | 0.065 | Octylphosphonic acid diethyl ester | 0.3275 | — | 2.289 |
| Ex. 3-81 | | 0.5 | | 0.5 | Tris(acetylacetonato)ruthenium (III) | 0.104 | | 0.3275 | | 2.289 |
| Ex. 3-82 | | 0.5 | | 0.5 | Nickel (II) acetate tetrahydrate | 0.013 | | 0.3275 | | 2.289 |
| Ex. 3-83 | | 0.5 | | 0.5 | Tris(acetylacetonato)ruthenium (III) | 0.021 | | 0.3275 | | 2.289 |

TABLE 16-continued

| | Surface treatment method | Temp. °C | Pressure MPa | Reaction time Min. | Inorganic particles | Organic group on surface | | Average particle size nm | Photocatalytic action | Resin degradation |
|---|---|---|---|---|---|---|---|---|---|---|
| Ex. 3-76 | Second | 400 | 40 | 10 | SrTiO$_3$ | Octyl | — | — | ○ | ○ |
| Ex. 3-77 | hydrothermal | 400 | 40 | 10 | | | | | ○ | ○ |
| Ex. 3-78 | synthesis | 400 | 40 | 10 | | | | | ○ | ○ |
| Ex. 3-79 | | 400 | 40 | 10 | | 6-Phenylhexyl | Octyl | | ○ | ○ |
| Ex. 3-80 | | 400 | 40 | 10 | SrTiO$_3$/NiO | Octyl | — | | ○ | ○ |
| Ex. 3-81 | | 400 | 40 | 10 | SrTiO$_3$/RuO$_2$ | | | | ○ | ○ |
| Ex. 3-82 | | 400 | 40 | 10 | SrTiO$_3$/NiO | | | | ○ | ○ |
| Ex. 3-83 | | 400 | 40 | 10 | SrTiO$_3$/RuO$_2$ | | | | ○ | ○ |

Preparation Examples, Comparative Preparation Examples, Examples and Comparative Examples Corresponding to the Fourth Group of Inventions The fourth group of inventions will be described below in further detail by showing Preparation Examples, Comparative Preparation Examples, Examples and Comparative Examples, but the fourth group of inventions is not limited thereto.

Evaluation methods performed on organic-inorganic composite particles, films (films (particle-containing resin molded articles) before extraction), and porous films (micropore resin compositions) will be described below.

(1) X-Ray Diffractometry (XRD)

Organic-inorganic composite particles were loaded into a glass holder and subjected to X-ray diffractometry under the following conditions. After that, from the obtained peaks, the components of the inorganic substance were assigned by database search.

X-ray diffractometer: D8 DISCOVER with GADDS, available from Bruker AXS
(Optical system on incident side)
  X-ray source: CuKα (λ=1.542 Å), 45 kV, 360 mA
  Spectroscope (monochromator): multilayer mirror
  Collimator diameter: 300 μm
(Optical system on light-receiving side)
  Counter: two-dimensional PSPC (Hi-STAR)
  Distance between organic-inorganic composite particles and counter: 15 cm
  2θ=20, 50, 80 degrees, ω=10, 25, 40 degrees, Phi=0 degrees, Psi=0 degrees
  Measurement time: 10 minutes
  Assignment (semiquantitation software): FPM EVA, available from Bruker AXS (2) Fourier Transform Infrared Spectrophotometry (FT-IR)

Fourier transform infrared spectrophotometry was carried out on organic-inorganic composite particles according to the KBr method using the following apparatus.

Fourier transform infrared spectrophotometer: FT/IR-470Plus, available from JASCO Corporation (3) Average Particle Size Measurement by Dynamic Light Scattering (DLS)

A particle dispersion (with a concentration of solids of 1 mass % or less) was prepared by dispersing organic-inorganic composite particles in a solvent, and the average particle size of the organic-inorganic composite particles in the particle dispersion was measured with a dynamic light scattering photometer (model: ZEN 3600, available from Sysmex Corporation).

As the solvent, hexane was used in Preparation Example 4-1, chloroform was used in Preparation Examples 4-2, 4-3, 4-5 and 4-6, and aqueous ammonia having a concentration of 1 mass % was used in Preparation Example 4-4.

(4) Observation with Transmission Electron Microscope (TEM)

A film (film (particle-containing resin molded article) before extraction) was cut, and the cut surface was observed with a transmission electron microscope (TEM, H-7650, available from Hitachi High-Technologies Corporation) for the dispersed state of organic-inorganic composite particles in the film.

Also, the concentration distribution in the thickness direction of micropores was observed.

Here, for a clear view of the cut surface of the film, the film was embedded in epoxy resin before cutting (machining).

Also, a particle dispersion (with a concentration of solids of 1 mass % or less) obtained by diluting organic-inorganic composite particles with a solvent was applied dropwise onto a TEM grid (collodion film, carbon support film) and dried. Then, the organic-inorganic composite particles were observed with a transmission electron microscope (TEM, H-7650, available from Hitachi High-Technologies Corporation) and the average particle size of the organic-inorganic composite particles was calculated by image analysis.

(5) Observation with Optical Microscope

The dispersed state of organic-inorganic composite particles in a film was observed with an optical microscope in the same manner as in the observation with TEM described above.

(6) Clarity

Clarity of a porous film was visually observed and evaluated.

(7) Refractive Index

The refractive index of a porous film was measured using a prism coupler (SPA-4000, available from Sairon Technology, Inc.).

Specifically, the porous film was placed on a silicon wafer, and measurement was carried out.

The refractive index of the film was measured using light having a wavelength of 633 nm.

(8) Reflectance

The reflectivity (wavelength: 550 nm) of a porous film was measured using Hitachi spectrophotometer U-4100 (available from Hitachi High-Technologies Corporation).

(9) Dielectric Constant

The dielectric constant of a porous film was measured using TR-100 automatic dielectric loss measurement apparatus (available from Ando Electric Co., Ltd.). The dielectric constant was measured at a frequency of 1 MHz.

(10) Elongation at Break

The elongation at break of a porous film was measured using a tensile tester (trade name, STM-T-50BP, available from Toyo Baldwin Co. Ltd.)

Specifically, a sample having a width of 5 mm and a length of 100 mm was made from the porous film, and elongation was measured using the above-mentioned tensile tester, with a chuck distance of 50 mm and a pulling speed of 5 mm/min.

Preparation of Organic-Inorganic Composite Particles

Preparation Example 4-1

Cerium hydroxide ($Ce(OH)_4$, available from Wako Pure Chemical Industries, Ltd.) as an inorganic material, decanoic acid and hexanoic acid as organic compounds and water were introduced into a 5 mL high-pressure reactor (available from AKICO Corporation) in amounts presented in Table 17.

Next, the high-pressure reactor was closed with a cover, heated to 400° C. in a shaking furnace (available from AKICO Corporation) so as to pressurize the inside of the high-pressure reactor to 40 MPa, and then shaken for 10 minutes for hydrothermal synthesis.

After that, the high-pressure reactor was plunged into cold water for quenching.

Next, ethanol (available from Wako Pure Chemical Industries, Ltd.) was added, and the mixture was stirred and subjected to centrifugal separation performed in a centrifuge (trade name: MX-301, available from Tomy Seiko Co., Ltd.) at 12000 G for 20 minutes to separate into a precipitate (reaction product) and a supernatant (washing step). This washing operation was repeated 5 times. After that, ethanol in the precipitate was heated and dried at 80° C. to give organic-inorganic composite particles in which a decyl group and a hexyl group were bound to the surface of cerium oxide ($CeO_2$).

Next, the organic-inorganic composite particles obtained above and chloroform were introduced into a 50 mL centrifuge tube, and the mixture was subjected to centrifugal separation performed in a centrifuge (trade name: MX-301, available from Tomy Seiko Co., Ltd.) at 4000 G for 5 minutes to separate into a supernatant and a precipitate (wet classification).

Next, the supernatant was removed therefrom and dried to give organic-inorganic composite particles having a small average particle size.

After that, the obtained organic-inorganic composite particles were evaluated by XRD, FT-IR, DLS and TEM described above.

As a result, XRD confirmed that the inorganic substance forming the inorganic particles was $CeO_2$.

Also, FT-IR confirmed that there were saturated aliphatic groups (a decyl group and a hexyl group) on the surface of the inorganic particles.

Furthermore, DLS showed that the organic-inorganic composite particles had an average particle size of 7 nm.

The above results are presented in Table 17.

TABLE 17

| | Formulations | | | | | | |
|---|---|---|---|---|---|---|---|
| | Inorganic substance and/or complex | | Organic compound | | | | Pure water |
| Preparation Example | | Amount g (mL) | | Amount g (mL) | | Amount g (mL) | Amount (mL) |
| Pre. Ex. 4-1 | $Ce(OH)_4$ | 1.09 | Decanoic acid | 0.5181 | Hexanoic acid | 0.3279 | 1.771 |
| Pre. Ex. 4-2 | $Ce(OH)_4$ | 1.09 | Decanoic acid | 1.0362 | — | | 1.01 |
| Pre. Ex. 4-3 | $Zn(CH_3COO)_2$ | 0.5 | Ethyl decylphosphonate | 0.182 | Ethyl octylphosphonate | 0.1638 | 2.453 [2 mol/L aqueous KOH solution] |
| Pre. Ex. 4-4 | Ti complex (ligand: 2-hydroxy-octanoic acid) | 0.5 | Ethyl decylphosphonate | 0.182 | Ethyl octylphosphonate | 0.1638 | 2.453 |
| Pre. Ex. 4-5 | $SrCO_3$ | 0.5 | 6-Phenylhexanoic acid | 0.3503 | — | | 3.403 |
| Pre. Ex. 4-6 | $BaSO_4$ | 0.5 | Decanoic acid | 0.2500 | Hexanoic acid | 0.1000 | 3.403 |

TABLE 17-continued

| Preparation Example | High-temperature treatment conditions | | | Organic-inorganic composite particles | | | |
|---|---|---|---|---|---|---|---|
| | Temp. °C. | Pressure MPa | Reaction time Min. | Composition of inorganic particles *1 | Organic group on surface *2 | | Average particle size (nm) *3 |
| Pre. Ex. 4-1 | 400 | 40 | 10 | $CeO_2$ | Decyl group | Hexyl group | 4 to 10 [7] |
| Pre. Ex. 4-2 | 400 | 40 | 10 | $CeO_2$ | Decyl group | — | 3 to 8 |
| Pre. Ex. 4-3 | 400 | 40 | 10 | ZnO | Decyl group | Octyl group | 4 to 20 |
| Pre. Ex. 4-4 | 400 | 40 | 10 | $TiO_2$ | Decyl group | Octyl group | 4 to 8 |
| Pre. Ex. 4-5 | 300 | 30 | 10 | $SrCO_3$ | 6-Phenylhexyl group | — | 30 to 80 |
| Pre. Ex. 4-6 | 300 | 30 | 10 | $BaSO_4$ | Decyl group | Hexyl group | 30 to 80 |

The matters specified by asterisks in Table 17 will be described below.
*1: The composition was confirmed by XRD.
*2: The organic groups were confirmed by FT-IR.
*3: The average particle size was measured by TEM. It should be noted that each value within parentheses "( )" indicates the result obtained from measurement by DLS.

Preparation Examples 4-2 to 4-6

Organic-inorganic composite particles were prepared in the same manner as in Preparation Example 4-1, except that the formulation (amounts) of the inorganic material, the organic compounds and water (or aqueous pH adjusting solution) was changed to the formulations presented in Table 17, and then subjected to washing and wet classification.

After that, the obtained organic-inorganic composite particles were evaluated in the same manner as in Preparation Example 4-1. The results are presented in Table 17.

Comparative Preparation Examples 4-1 to 4-6

Untreated inorganic particles (or in other words, inorganic particles that had not been subjected to a high temperature treatment) were prepared as inorganic particles for use in Comparative Preparation Examples 4-1 to 4-6, and used as inorganic particles in Comparative Examples 4-1 to 4-12, which will be described later (see Table 20).

Preparation of Particle-Containing Resin Compositions, Production of Films and Production of Porous Films Example 4-1

A resin solution having a concentration of solids of 10 mass % was prepared by blending polyetherimide resin (model: Ultem 1000, available from SABIC Innovative Plastics Japan LLC) with chloroform.

Also, a particle dispersion having a concentration of solids of 10 mass % was prepared by blending the organic-inorganic composite particles obtained in Preparation Example 4-5 (inorganic substance: $SrCO_3$, organic group: 6-phenylhexyl group) with chloroform.

Next, the resin solution and the particle dispersion were blended such that the proportion of resin relative to organic-inorganic composite particles was those presented in Table 18, and stirred with an ultrasonic disperser. In this manner, a clear varnish of particle-containing resin composition was prepared.

Next, the obtained varnish was applied to a substrate (glass substrate having a thickness of 1100 μm) by spin coating. Chloroform was mostly volatilized during application of the varnish.

After that, the applied particle-containing resin composition was dried at 50° C. for one hour (first drying) and then dried at 100° C. for 10 minutes (second drying) to give a 15 μm thick film (particle-containing resin molded article).

After that, the obtained film was evaluated by TEM described above (the dispersed state and average particle size of organic-inorganic composite particles). The results are presented in Table 17 (average particle size) and Table 18.

After that, the obtained film was peeled off from the substrate, and then the organic-inorganic composite particles were extracted from the resin under the extraction conditions shown in Table 18.

In this extraction process, a nitric acid ethanol solution serving as an extraction solvent permeated through the resin and dissolved the organic-inorganic composite particles.

As a result, micropores were formed in the resin, and a porous film (resin molded article) having the micropores was obtained.

After that, the obtained porous films were evaluated in terms of TEM (the presence of concentration distribution in the thickness direction), clarity, refractive index, reflectance, dielectric constant and elongation at break described above. The results are presented in Table 18.

Examples 4-2 to 4-15 and Comparative Examples 4-1 to 4-12

Porous films were obtained by producing films in the same manner as in Example 4-1, except that the formulation of the resin solution and the particle dispersion was changed to the formulations presented in Tables 18 to 20, and then extracting organic-inorganic composite particles under the extraction conditions presented in Tables 18 to 20.

In Examples 4-8 and 4-9, the film was immersed in the extraction solvent together with the substrate without the film being peeled off from the substrate.

In Comparative Examples 4-5 to 4-12, it was not possible to obtain self-standing porous films because the porous film was significantly damaged when peeled from the substrate and lost flexibility.

The obtained films (films (particle-containing resin molded articles) before extraction) and porous films were evaluated in the same manner described above.

Image-processed TEM micrographs obtained in Examples 4-6, 4-7 and 4-13 are shown in FIGS. 27 to 29, respectively.

TABLE 18

| | | | | | | Example | | | | |
|---|---|---|---|---|---|---|---|---|---|---|
| | | Example | | | | 4-1 | 4-2 | 4-3 | 4-4 | 4-5 |
| Particle dispersed-resin composition | Organic-inorganic composite particles *4 (parts by mass) | Preparation Example | Composition of inorganic particles | Organic group on surface | | | | | | |
| | | Preparation Example 4-1 | $CeO_2$ | Decyl group | Hexyl group | — | — | — | — | — |
| | | Preparation Example 4-2 | $CeO_2$ | Decyl group | — | — | — | — | — | — |
| | | Preparation Example 4-3 | ZnO | Decyl group | Octyl group | — | — | — | — | — |
| | | Preparation Example 4-4 | $TiO_2$ | Decyl group | Octyl group | — | — | — | — | — |
| | | Preparation Example 4-5 | $SrCO_3$ | 6-Phenylhexyl group | — | 30 | 30 | 30 | 50 | 50 |
| | | Preparation Example 4-6 | $BaSO_4$ | Decyl group | Hexyl group | — | — | — | — | — |
| | Resin *5 (parts by mass) | | Polyetherimide resin | | | 70 | — | — | — | — |
| | | | Thermoplastic fluorine-based polyimide resin | | | — | 70 | — | — | — |
| | | | Polyarylate | | | — | — | 70 | 50 | 50 |
| Extraction conditions | | | Presence of substrate | | | No | No | No | No | No |
| | | | Extraction liquid *6 | | | Nitric acid ethanol solution | | | | |
| | | | Extraction state | | | Dissolved | Dissolved | Dissolved | Dissolved | Dissolved |
| | | | Extraction temperature (° C.) | | | 60 | 60 | 60 | 80 | 60 |
| | | | Extraction time (hr) | | | 1 | 1 | 1 | 1 | 1 |
| Resin molded article (porous film) | Evaluation | TEM | State of organic-inorganic composite particles in film (particle-containing resin molded article) *9 | | | Dispersed as primary particles | | | | |
| | | | Presence of micropores | | | Yes | | | | |
| | | | Presence of concentration distribution in thickness direction of micropores | | | No | No | No | No | No |
| | | Visual inspection | Clarity *10 | | | ○ | ○ | ○ | ○ | ○ |
| | | Refractive index | Wavelength 633 nm | | | 1.56 | 1.46 | 1.44 | 1.4 | 1.4 |
| | | Reflectance | (%) Wavelength 550 nm | | | — | — | — | — | — |
| | | Dielectric constant | Measurement frequency 1 MHz | | | 3.0 | 2.6 | 2.8 | 2.6 | 2.6 |
| | | Mechanical strength | Elongation at break *11 | | | ○ | ○ | ○ | ○ | ○ |

| | | | | | | Example | | | |
|---|---|---|---|---|---|---|---|---|---|
| | | Example | | | | 4-6 | 47 | 4-8 | 49 |
| Particle dispersed-resin composition | Organic-inorganic composite particles *4 (parts by mass) | Preparation Example | Composition of inorganic particles | Organic group on surface | | | | | |
| | | Preparation Example 4-1 | $CeO_2$ | Decyl group | Hexyl group | — | — | — | — |
| | | Preparation Example 4-2 | $CeO_2$ | Decyl group | — | — | — | — | — |
| | | Preparation Example 4-3 | ZnO | Decyl group | Octyl group | — | — | — | — |
| | | Preparation Example 4-4 | $TiO_2$ | Decyl group | Octyl group | — | — | — | — |
| | | Preparation Example 4-5 | $SrCO_3$ | 6-Phenylhexyl group | — | 50 | 50 | 50 | 50 |
| | | Preparation Example 4-6 | $BaSO_4$ | Decyl group | Hexyl group | — | — | — | — |
| | Resin *5 (parts by mass) | | Polyetherimide resin | | | — | — | — | — |
| | | | Thermoplastic fluorine-based polyimide resin | | | — | — | — | — |
| | | | Polyarylate | | | 50 | 50 | 50 | 50 |
| Extraction conditions | | | Presence of substrate | | | No | No | Yes | Yes |
| | | | Extraction liquid *6 | | | Nitric acid ethanol solution | | | |

TABLE 18-continued

|  |  |  |  | | | | |
|---|---|---|---|---|---|---|---|
| | | | Extraction state | Dissolved | Dissolved | Dissolved | Dissolved |
| | | | Extraction temperature (° C.) | 20 | 20 | 20 | 20 |
| | | | Extraction time (hr) | 1 | 0.5 | 0.5 | 3 |
| Resin molded article (porous film) | Evaluation | TEM | State of organic-inorganic composite particles in film (particle-containing resin molded article) *9 | Dispersed as primary particles | | | |
| | | | Presence of micropores | | Yes | | |
| | | | Presence of concentration distribution in thickness direction of micropores | No | Yes | Yes | Yes |
| | | Visual inspection | Clarity *10 | ○ | ○ | ○ | ○ |
| | | Refractive index | Wavelength 633 nm | 1.4 | 1.39/1.49 *7 | 1.41/1.49 *8 | — |
| | | Reflectance | (%) Wavelength 550 nm | 3.5 | <3.5 | <3.5 | — |
| | | Dielectric constant | Measurement frequency 1 MHz | 2.6 | 2.7 | 2.7 | 2.6 |
| | | Mechanical strength | Elongation at break *11 | ○ | ○ | ○ | ○ |

TABLE 19

| | | | | | | Example | | |
|---|---|---|---|---|---|---|---|---|
| | | | Example | | | 4-10 | 4-11 | 4-12 |
| Particle dispersed-resin composition | Organic-inorganic composite particles *4 (parts by mass) | Preparation Example | Composition of inorganic particles | Organic group on surface | | | | |
| | | Preparation Example 4-1 | $CeO_2$ | Decyl group | Hexyl group | 80 | 80 | — |
| | | Preparation Example 4-2 | $CeO_2$ | Decyl group | — | — | — | 70 |
| | | Preparation Example 4-3 | ZnO | Decyl group | Octyl group | — | — | — |
| | | Preparation Example 4-4 | $TiO_2$ | Decyl group | Octyl group | — | — | — |
| | | Preparation Example 4-5 | $SrCO_3$ | 6-Phenylhexyl group | — | — | — | — |
| | | Preparation Example 4-6 | $BaSO_4$ | Decyl group | Hexyl group | — | — | — |
| | Resin *5 (parts by mass) | | Polyetherimide resin | | | — | — | — |
| | | | Thermoplastic fluorine-based polyimide resin | | | — | — | — |
| | | | Polyarylate | | | 20 | 20 | 30 |
| Extraction conditions | | | Presence of substrate | | | No | No | No |
| | | | Extraction liquid *6 | | | Hexane | | |
| | | | Extraction state | | | Dispersed | Dispersed | Dispersed |
| | | | Extraction temperature (° C.) | | | 20 | 60 | 60 |
| | | | Extraction time (hr) | | | 1 | 1 | 1 |
| Resin molded article (porous film) | Evaluation | TEM | State of organic-inorganic composite particles in film (particle-containing resin molded article) *9 | | | Bicontinuous phase separated structure | | |
| | | | Presence of micropores | | | | Yes | |
| | | | Presence of concentration distribution in thickness direction of micropores | | | No | No | No |
| | | Dielectric constant | Measurement frequency 1 MHz | | | 2.5 | 2.5 | 2.5 |
| | | Mechanical strength | Elongation at break *11 | | | ○ | ○ | ○ |

| | | | | | | Example | | |
|---|---|---|---|---|---|---|---|---|
| | | | Example | | | 4-13 | 4-14 | 4-15 |
| Particle dispersed-resin composition | Organic-inorganic composite particles *4 (parts by mass) | Preparation Example | Composition of inorganic particles | Organic group on surface | | | | |
| | | Preparation Example 4-1 | $CeO_2$ | Decyl group | Hexyl group | — | — | — |
| | | Preparation Example 4-2 | $CeO_2$ | Decyl group | — | | | |

TABLE 19-continued

| | | | | | | | | | |
|---|---|---|---|---|---|---|---|---|---|
| | | | Preparation Example 4-3 | ZnO | Decyl group | Octyl group | 70 | — | — |
| | | | Preparation Example 4-4 | TiO$_2$ | Decyl group | Octyl group | — | 70 | — |
| | | | Preparation Example 4-5 | SrCO$_3$ | 6-Phenylhexyl group | — | — | — | — |
| | | | Preparation Example 4-6 | BaSO$_4$ | Decyl group | Hexyl group | — | — | 80 |
| | Resin *5 (parts by mass) | | | Polyetherimide resin | | | — | — | — |
| | | | | Thermoplastic fluorine-based polyimide resin | | | — | — | — |
| | | | | Polyarylate | | | 30 | 30 | 30 |
| Extraction conditions | | | Presence of substrate | | | | No | No | No |
| | | | Extraction liquid *6 | | | | | Hexane | |
| | | | Extraction state | | | | Dispersed | Dispersed | Dispersed |
| | | | Extraction temperature (° C.) | | | | 60 | 60 | 20 |
| | | | Extraction time (hr) | | | | 1 | 1 | 1 |
| Resin molded article (porous film) | Evaluation | TEM | State of organic-inorganic composite particles in film (particle-containing resin molded article) *9 | | | | Bicontinuous phase separated structure | | |
| | | | Presence of micropores | | | | | Yes | |
| | | | Presence of concentration distribution in thickness direction of micropores | | | | No | No | No |
| | Dielectric constant | | Measurement frequency 1 MHz | | | | 2.5 | 2.5 | 2.5 |
| | Mechanical strength | | Elongation at break *11 | | | | ○ | ○ | ○ |

TABLE 20

| | | | | | | Comparative Example | | | | | |
|---|---|---|---|---|---|---|---|---|---|---|---|
| | | Comparative Example | | | | 4-1 | 4-2 | 4-3 | 4-4 | 4-5 | 4-6 |
| Particle dispersed-resin composition | Organic-inorganic composite particles *4 (parts by mass) | Comparative Preparation Example | Composition of inorganic particles | Organic group on surface | | | | | | | |
| | | Comparative Preparation Example 4-1 | CeO$_2$ | — | | — | — | — | — | — | — |
| | | Comparative Preparation Example 4-2 | ZnO | — | | — | — | — | — | — | — |
| | | Comparative Preparation Example 4-3 | TiO$_2$ | — | | — | — | — | — | — | — |
| | | Comparative Preparation Example 4-4 | SrCO$_3$ | — | | 30 | — | — | — | — | — |
| | | Comparative Preparation Example 4-5 | BaSO$_4$ | — | | — | — | — | — | — | — |
| | | Comparative Preparation Example 4-6 | Al$_2$O$_3$ | — | | — | 30 | 30 | 30 | 80 | 80 |
| | Resin *5 (parts by mass) | | Polyetherimide resin | | | — | 70 | — | — | 20 | — |
| | | | Thermoplastic fluorine-based polyimide resin | | | — | — | 70 | — | — | 20 |
| | | | Polyarylate | | | 70 | — | — | 70 | — | — |
| Extraction conditions | | | Presence of substrate | | | No | No | No | No | No | No |
| | | | Extraction liquid *6 | | | Nitric acid ethanol solution | | | Hexane | | |
| | | | Extraction state | | | Dissolved | Dispersed | Dispersed | Dispersed | Dispersed | Dispersed |
| | | | Extraction temperature (° C.) | | | 20 | 20 | 20 | 20 | 20 | 20 |
| | | | Extraction time (hr) | | | 5 | 5 | 5 | 5 | 5 | 5 |
| Resin molded article (porous film) | Evaluation | TEM | State of organic-inorganic composite particles in film (particle-containing resin molded article) *9 | | | | | Coagulated | | | |
| | | | Presence or of micropores | | | | | Yes | | | |

TABLE 20-continued

|  |  |  | Comparative Example | | | | | |
|---|---|---|---|---|---|---|---|---|
|  |  |  | 4-7 | 4-8 | 4-9 | 4-10 | 4-11 | 4-12 |
|  |  | Presence of concentration distribution in thickness direction of micropores | No | No | No | No | No | No |
|  | Visual inspection | Clarity *10 | X | X | X | X | X | X |
|  | Reflectance | (%) Wavelength 550 nm | 10 | 10 | 10 | 10 | — | — |
|  | Dielectric constant | Measurement frequency 1 MHz | 2.8 | 3.1 | 2.7 | 2.9 | — | — |
|  | Mechanical strength | Elongation at break *11 | X | X | X | X | Self-standing film was not obtained due to lack of flexibility | |

|  |  |  |  |  | Comparative Example | | | | | |
|---|---|---|---|---|---|---|---|---|---|---|
|  |  | Comparative Example | | | 4-7 | 4-8 | 4-9 | 4-10 | 4-11 | 4-12 |
| Particle dispersed-resin composition | Organic-inorganic composite particles *4 (parts by mass) | Comparative Preparation Example | Composition of inorganic particles | Organic group on surface | | | | | | |
| | | Comparative Preparation Example 4-1 | CeO₂ | — | — | 80 | — | — | — | — |
| | | Comparative Preparation Example 4-2 | ZnO | — | — | — | 80 | — | — | — |
| | | Comparative Preparation Example 4-3 | TiO₂ | — | — | — | — | 80 | — | — |
| | | Comparative Preparation Example 4-4 | SrCO₃ | — | — | — | — | — | 80 | — |
| | | Comparative Preparation Example 4-5 | BaSO₄ | — | — | — | — | — | — | 80 |
| | | Comparative Preparation Example 4-6 | Al₂O₃ | — | 80 | — | — | — | — | — |
| | Resin *5 (parts by mass) | Polyetherimide resin | | | — | — | — | — | — | — |
| | | Thermoplastic fluorine-based polyimide resin | | | — | — | — | — | — | — |
| | | Polyarylate | | | 20 | 20 | 20 | 20 | 20 | 20 |
| Extraction conditions | | Presence of substrate | | | No | No | No | No | No | No |
| | | Extraction liquid *6 | | | Hexane | | | | | |
| | | Extraction state | | | Dispersed | Dispersed | Dispersed | Dispersed | Dispersed | Dispersed |
| | | Extraction temperature (° C.) | | | 20 | 20 | 20 | 20 | 20 | 20 |
| | | Extraction time (hr) | | | 5 | 5 | 5 | 5 | 5 | 5 |
| Resin molded article (porous film) | Evaluation | TEM | State of organic-inorganic composite particles in film (particle-containing resin molded article) *9 | | | | Coagulated | | | |
| | | | Presence or of micropores | | | | Yes | | | |
| | | | Presence of concentration distribution in thickness direction of micropores | | No | No | No | No | No | No |
| | | Visual inspection | Clarity *10 | | X | X | X | X | X | X |
| | | Reflectance | (%) Wavelength 550 nm | | — | — | — | — | — | — |
| | | Dielectric constant | Measurement frequency 1 MHz | | — | — | — | — | — | — |
| | | Mechanical strength | Elongation at break *11 | | | | Self-standing film was not obtained due to lack of flexibility | | | |

In Tables 18 to 20, the numerical values provided in "Organic-inorganic composite particles" indicate the amount of organic-inorganic composite particles in a particle dispersion, expressed in parts by mass, and the numerical values provided in "Resin" indicate the amount of resin in a resin solution, expressed in parts by mass.

The following gives detailed description of resins presented in Tables 18 to 20 and inorganic particles of Comparative Preparation Examples 4-1 to 4-6 presented in Table 20, as well as description of the matters specified by asterisks.

<Resins>

Polyetherimide resin: Ultem 1000, refractive index (wavelength: 633 nm): 1.63, reflectance (wavelength: 550 nm): 7%, dielectric constant: 3.2, available from SABIC Innovative Plastics Japan LLC Thermoplastic fluorine-based polyimide resin: thermoplastic fluorine-based polyimide resin used in Example 1 of Japanese Unexamined Patent Publication No. 2003-315541, refractive index (wavelength: 633 nm): 1.52, reflectance (wavelength: 550 nm): 5%, dielectric constant: 2.8

Polyarylate: polyarylate resin used in Example 4 of Japanese Unexamined Patent Publication No. 2009-80440, refractive index (wavelength: 633 nm): 1.49, reflectance (wavelength: 550 nm): 5%, dielectric constant: 3.0

<Inorganic Particles (Comparative Preparation Examples 4-1 to 4-6)>

$CeO_2$: Comparative Preparation Example 4-1, average particle size 200 nm, available from Kojundo Chemical Lab. Co., Ltd.

ZnO: Comparative Preparation Example 4-2, average particle size 200 nm, available from Sakai Chemical Industry Co., Ltd.

$TiO_2$: Comparative Preparation Example 4-3, trade name SSP-25, average particle size 9 nm, available from Sakai Chemical Industry Co., Ltd.

$SrCO_3$: Comparative Preparation Example 4-4, average particle size 200 nm, available from Honjo Chemical Corporation $BaSO_4$: Comparative Preparation Example 4-5, trade name BF40, average particle size 10 nm, available from Sakai Chemical Industry Co., Ltd.

$AL_2O_3$: Comparative Preparation Example 4-6, trade name AEROXIDO@AluC, average particle size 15 nm, available from Nippon Aerosil Co., Ltd.

<Specified Matters (*4 to *9)>

*4: Prepared as a particle-dispersed chloroform solution having a concentration of solids of 10 mass %. The numerical value indicates the amount of solids expressed in parts by mass.

*5: Prepared as a resin solution having a concentration of solids of 10 mass %. The numerical value indicates the amount of solids expressed in parts by mass.

*6: A nitric acid ethanol solution having a concentration of 3.2 mass % prepared by mixing 50 parts by mass of 1 mol/L (6.3 wt %) aqueous nitric acid solution and 50 parts by mass of ethanol.

*7: Refractive indices obtained by calculation that indicate that the surface refractive index was 1.39 and the internal refractive index was 1.49.

*8: Refractive indices obtained by calculation that indicate that the refractive index of the exposed surface was 1.41 and the refractive index of the substrate-side surface was 1.49.

*9: Determined from TEM or optical micrographs.

*10: Visually determined based on the following criteria.

A circle "○" was given when the film was clear.

A cross "x" was given when the film was opaque.

*11: Elongation at break was determined based on the following criteria.

A circle "○" was given when the elongation was 10% or greater.

A cross "x" was given when the elongation was less than 10%

Examples and Comparative Examples Corresponding to the Fifth Group of Inventions The fifth group of inventions will be described below in further detail by showing Examples and Comparative Examples, but the fifth group of inventions is not limited thereto.

Evaluation methods performed on titanium complexes will be described below.

<Evaluation Methods>

(1) MALDI-TOF MS measurement (Measurement apparatus)

Autoflex available from Bruker Daltonics (Measurement conditions)

Laser light source: $N_2$ laser (wavelength: 337 nm)

Measurement modes: reflector mode, negative ion mode

Measured mass range (m/z): 20 to 3000

Number of scans: 1500 times

Matrix: Meso-tetrakis-(pentafluorophenyl)-porphyrin

Preparation of Titanium Complexes

Example 5-1

Preparation of Titanium Complex Containing 2-Hydroxyoctanoic Acid as Ligand

Under ice-cold conditions, 100 mL of 30 volume % hydrogen peroxide solution (available from Wako Pure Chemical Industries, Ltd.) and 25 mL of 25 mass % aqueous ammonia (available from Wako Pure Chemical Industries, Ltd.) were mixed in a 500 mL beaker. Then, 1.5 g of titanium particles (available from Wako Pure Chemical Industries, Ltd.) were added thereto and the mixture was stirred for 3 hours under ice-cold conditions until complete dissolution. Next, 15.5 g of 2-hydroxyoctanoic acid dissolved in 50 mL of ethanol (titanium particles: 2-hydroxyoctanoic acid=1:1.5 (molar ratio)) was added and the mixture was stirred. After complete dissolution of all components, stirring was stopped and the mixture was allowed to stand still for one day. After that, the mixture was dried at 75° C. in a drier for 3 hours so as to give a water-soluble titanium complex.

The obtained water-soluble titanium complex was subjected to MALDI-TOF MS measurement. As a result, the obtained titanium complex was identified as a mixture composed of two titanium complexes represented by the following chemical formulas (3) and (4).

General Formula (3):
[Chemical Formula 1]
General Formula (4):
[Chemical Formula 2]

Example 5-2

Preparation of Titanium Complex Containing 3-Hydroxydecanoic Acid as Ligand

A water-soluble titanium complex was obtained through the same treatment as in Example 5-1, except that 18.2 g of 3-hydroxydecanoic acid (titanium particles: 3-hydroxydecanoic acid=1:1.5 (molar ratio)) was added instead of 15.5 g of 2-hydroxyoctanoic acid.

Comparative Example 5-1

Preparation of Titanium Complex Containing Malic Acid as Ligand

A water-soluble titanium complex was obtained through the same treatment as in Example 5-1, except that 13.0 g of malic acid (titanium particles:malic acid=1:1.5 (molar ratio)) was added instead of 15.5 g of 2-hydroxyoctanoic acid.

Comparative Example 5-2

Preparation of Titanium Complex Containing Glycolic Acid as Ligand

A water-soluble titanium complex was obtained through the same treatment as in Example 5-1, except that 7.2 g of glycolic acid (titanium particles:glycolic acid=1:1.5 (molar ratio)) was added instead of 15.5 g of 2-hydroxyoctanoic acid.

Preparation of Titanium Oxide Particles

Example 5-3

The titanium complex prepared in Example 5-1 in an amount of 0.5 g and water in an amount of 2.3 g were introduced into a 5 mL high-pressure reactor (available from AKICO Corporation). Next, the high-pressure reactor was closed with a cover, and the titanium complex and water were treated in a shaking furnace (available from AKICO Corporation) at 400° C. and 40 MPa for 10 minutes. After that, the high-pressure reactor was plunged into cold water for quenching.

Next, ethanol (available from Wako Pure Chemical Industries, Ltd.) was added, and the mixture was stirred and subjected to centrifugal separation performed in a centrifuge (trade name: MX-301, available from Tomy Seiko Co., Ltd.) at 12000 G for 20 minutes to separate a precipitate (reaction product) from a supernatant (washing step). This washing operation was repeated 5 times.

After that, ethanol in the precipitate was heated and dried at 80° C., and thereby pale yellow white rutile titanium oxide particles ($TiO_2$) were obtained.

Example 5-4

Pale yellow white rutile titanium oxide particles ($TiO_2$) were obtained in the same manner as in Example 5-3, except that the titanium complex prepared in Example 5-2 was used instead of the titanium complex prepared in Example 5-1.

Comparative Example 5-3

Brown titanium oxide particles ($TiO_2$) were obtained in the same manner as in Example 5-3, except that the titanium complex prepared in Comparative Example 5-1 was used instead of the titanium complex prepared in Example 5-1.

Comparative Example 5-4

Brown titanium oxide particles ($TiO_2$) were obtained in the same manner as in Example 5-3, except that the titanium complex prepared in Example 5-4 was used instead of the titanium complex prepared in Example 5-1.

Comparative Example 5-5

Brown titanium oxide particles ($TiO_2$) were obtained in the same manner as in Example 5-3, except that titanium peroxo citric acid ammonium tetrahydrate (trade name: TAS-FINE, available from Furuuchi Chemical Corporation) was used instead of the titanium complex prepared in Example 5-1.

While the illustrative embodiments of the present invention are provided in the above description, they are for illustrative purposes only and not to be construed as limiting. Modification and variation of the present invention that will be obvious to those skilled in the art is to be covered by the following claims.

INDUSTRIAL APPLICABILITY

The particle-containing resin molded article has various applications including, for example, optical applications such as flexible substrates, electronic and electrical applications, mechanical applications and the like. When used in electronic and electrical applications, the particle-containing resin molded article is used as, for example, an optical fiber, an optical disc, a light guide plate, or a flexible substrate such as an optical film.

The particle-dispersed resin composition and the particle-dispersed resin molded article are used in various industrial applications including optical applications.

Also, the catalyst molded article containing catalyst particles can be used as, for example, an optical film such as a polarizing film, a retardance film, a brightness enhancing film, a viewing angle enhancing film, a high-refractive index film or a light diffusing film; or a construction material (construction) film such as an ultraviolet absorbing film, a dirt repellent film, an antimicrobial film, a deodorizing film, a super-hydrophilic film, a germicidal film, a detoxification film or a chemical substance decomposing film.

Also, the resin molded article is used as a porous film in optical applications including optical films such as a low-refractive film and an antireflective film, as well as electrical and electronic applications including electrical and electronic substrates such as a low-dielectric substrate. Alternatively, the resin molded article is used as a film having paths formed by communicating pores in various applications including sizing filters, molecular separation membrane, adsorptive separation filters and electrolyte membranes.

Also, the titanium complex is used in production of, for example, titanium oxide particles, and the titanium oxide particles are used in, for example, various industrial products for optical applications or the like.

The invention claimed is:

1. A method for producing particles that can be dispersed in a solvent and/or a resin as primary particles, the primary particles being organic-inorganic composite particles having a hydrophobic group and/or a hydrophilic group and a binding group on the surface of inorganic particles, the binding group chemically bonding the hydrophobic group and/or the hydrophilic group to the surface of the inorganic particles, the organic-inorganic composite particles having negative birefringence, comprising subjecting a metal hydroxide containing an alkaline earth metal, a carbonic acid source, and an organic compound to a hydrothermal synthesis to obtain the organic-inorganic composite particles, wherein a surface coverage by an organic group in the organic-inorganic composite particles is 30% or greater, and wherein the binding group is at least one selected from the group consisting of a carboxyl group, an amino group and a sulfo group.

2. The method for producing particles according to claim 1, wherein inorganic parts of the composite particles comprise a carbonate containing the alkaline earth metal and/or a composite oxide containing the alkaline earth metal.

3. The method for producing particles according to claim 1, wherein the primary particles are obtained by surface-treating the inorganic particles with the organic compound, and the organic compound contains a binding group capable of binding to the surface of the inorganic particles and the hydrophobic group and/or the hydrophilic group serving as the organic group.

4. The method for producing particles according to claim 1, having an aspect ratio of 1000 or less.

5. The method for producing particles according to claim 1, having a maximum length of 200 μm or less.

6. The method for producing particles according to claim 1, wherein the carbonic acid source is formic acid and/or urea.

7. The method for producing particles according to claim 1, wherein the hydrothermal synthesis is performed in the presence of a pH adjusting agent.

8. A method for producing a particle-dispersed resin composition comprising subjecting a metal hydroxide containing an alkaline earth metal, a carbonic acid source, and an organic compound to a hydrothermal synthesis to obtain the organic-inorganic composite particles, and blending a resin and particles such that the particles are dispersed as primary particles in the resin, wherein the particles are organic-inorganic composite particles having a hydrophobic group and/or a hydrophilic group and a binding group on the surface of inorganic particles, the binding group chemically bonding the hydrophobic group and/or hydrophilic group to the surface of the inorganic particles, and the organic-inorganic composite particles having negative birefringence, wherein a surface coverage by an organic group in the organic-inorganic composite particles is 30% or greater, and wherein the binding group is at least one selected from the group consisting of a carboxyl group, an amino group and a sulfo group.

9. A method for producing a resin molded article that is formed of a particle-dispersed resin composition comprising subjecting a metal hydroxide containing an alkaline earth metal, a carbonic acid source, and an organic compound to a hydrothermal synthesis to obtain the organic-inorganic composite particles, and preparing the particle-dispersed resin composition by blending a resin and particles such that the particles are dispersed as primary particles in the resin, and molding the particle-dispersed resin composition to obtain the resin molded article, wherein the particles are organic-inorganic composite particles having a hydrophobic group and/or a hydrophilic group and a binding group on the surface of inorganic particles, the binding group chemically bonding the hydrophobic group and/or hydrophilic group to the surface of the inorganic particles, and the organic-inorganic composite particles having negative birefringence, wherein a surface coverage by an organic group in the organic-inorganic composite particles is 30% or greater, and wherein the binding group is at least one selected from the group consisting of a carboxyl group, an amino group and a sulfo group.

10. A method for producing the resin molded article according to claim 9, being a method for producing an optical film.

* * * * *